US010815535B2

(12) United States Patent
Holder et al.

(10) Patent No.: US 10,815,535 B2
(45) Date of Patent: Oct. 27, 2020

(54) BACTERIOPHAGE ENGINEERING METHODS

(71) Applicant: The Charles Stark Draper Laboratory, Inc., Cambridge, MA (US)

(72) Inventors: Jason Holder, Swampscott, MA (US); Connor McBrine, Somerville, MA (US); Sarah Gruszka, Cambridge, MA (US); Miles Rogers, Boston, MA (US); Nicole Billings, Framingham, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 285 days.

(21) Appl. No.: 15/470,685

(22) Filed: Mar. 27, 2017

(65) Prior Publication Data

US 2017/0283779 A1 Oct. 5, 2017

Related U.S. Application Data

(60) Provisional application No. 62/314,163, filed on Mar. 28, 2016.

(51) Int. Cl.

| | |
|---|---|
| ***C12N 15/11*** | (2006.01) |
| ***C12Q 1/70*** | (2006.01) |
| ***C12N 15/86*** | (2006.01) |
| ***C12N 7/00*** | (2006.01) |
| ***C12N 15/66*** | (2006.01) |
| ***C12N 15/90*** | (2006.01) |
| ***B01L 3/00*** | (2006.01) |

(52) U.S. Cl.

CPC .......... *C12Q 1/70* (2013.01); *B01L 3/502753* (2013.01); *B01L 3/502761* (2013.01); *C12N 7/00* (2013.01); *C12N 15/11* (2013.01); *C12N 15/66* (2013.01); *C12N 15/86* (2013.01); *C12N 15/902* (2013.01); *C12Y 301/00* (2013.01); *B01L 2200/0652* (2013.01); *B01L 2200/10* (2013.01); *B01L 2300/0627* (2013.01); *B01L 2300/12* (2013.01); *C12N 2310/20* (2017.05); *C12N 2795/10221* (2013.01); *C12N 2795/10243* (2013.01); *C12N 2795/10251* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 7,312,085 B2 | 12/2007 | Chou et al. | |
| 2004/0191859 A1 | 9/2004 | Tabacco et al. | |
| 2014/0273180 A1 | 9/2014 | Griswold et al. | |
| 2015/0344930 A1* | 12/2015 | Koeris .................... | C12Q 1/66 435/5 |
| 2016/0010138 A1 | 1/2016 | Shamsheyeva et al. | |
| 2016/0319378 A1 | 11/2016 | Rey | |
| 2016/0348187 A1 | 12/2016 | Rey et al. | |
| 2017/0152576 A1 | 6/2017 | Rey et al. | |
| 2017/0233783 A1 | 8/2017 | De Forest et al. | |
| 2017/0321289 A1 | 11/2017 | Rey et al. | |

FOREIGN PATENT DOCUMENTS

| | | |
|---|---|---|
| WO | WO-2011/014946 A1 | 2/2011 |
| WO | WO-2016/100389 A1 | 6/2016 |

OTHER PUBLICATIONS

Scearce et al., J. Bact. 173, 2, 869-878 (Year: 1991).*

Sadowski et al., Proc. Nat. Acad. Sci. USA, 73, 3, 692-696 (Year: 1976).*

Cotta de Almeida (Genome Research 13:2190-2194, 2003) (Year: 2003).*

Shen et al. (Genetics 112:441-457, 1986 (Year: 1986).*

Box, et al., "Functional analysis of bacteriophage immunity through a type I-E CRISPR-Cas system in Vibrio cholera and its application in bacteriophage genome engineering", Journal of Bacteriology, vol. 198, No. 3, Feb. 23, 2016.

Jiang et al., Cas9-Assisted Targeting of Chromosome segments CATCH enables one-step targeted cloning of large gene clusters, Nature Communications, vol. 6, Sep. 1, 2015.

Final Office Action on U.S. Appl. No. 15/470,750 dated Dec. 31, 2018.

International Search Report and Written Opinion for PCT/US2017/024369 dated Oct. 9, 2017.

International Search Report and Written Opinion for PCT/US2017/024369 filed Oct. 9, 2017.

Jia-Wang, et al., "CRISPR/Cas9 nuclease cleavage combined with Gibson assembly for seamless cloning", Biotechniques Rapid Dispatches, vol. 58, No. 4, Apr. 1, 2015.

Kiro, et al., "Efficient engineering of a bacteriophage genome using the type I-E CRISPR-Cas system", RNA Biology, vol. 11, No. 1, Jan. 1, 2014, pp. 42-44.

Mannelli et al., "BRED: A Simple and Powerful Tool for Constructing Mutant and Recombinant Bacteriophage Genomes", PLOS ONE, vol. 3, No. 12, Dec. 17, 2008, p. e3957, XP055385275.

Martel, et al., "CRISPR-Cas: an efficient tool for genome engineering of virulent bacteriophages", Nucleic Acids Research, vol. 42, No. 14, Jul. 24, 2014.

Non-Final Office Action on U.S. Appl. No. 15/470,750 dated Jun. 15, 2018.

(Continued)

*Primary Examiner* — Nancy A Treptow

(74) *Attorney, Agent, or Firm* — Foley & Lardner LLP

(57) ABSTRACT

The present disclosure provides methods and kits for generating recombinant bacteriophage genomes.

17 Claims, 49 Drawing Sheets

Specification includes a Sequence Listing.

(56) References Cited

OTHER PUBLICATIONS

Ying-Ta Lai, et al., "In Vitro Repair of Gaps in Bacteriophage T7 DNA", Journal of Bacteriology, Dec. 1, 1998, pp. 6193-6202, XP055385229.
Ai et al., "Separation of *Escherichia coli* Bacteria from Peripheral Blood Mononuclear Cells Using Standing Surface Acoustic Waves," Analytical Chemistry 85: 9126-9134, Aug. 23, 2013, (9 pages).
Huh et al., "Microfluidics for flow cytometric analysis of cells and particles," Physiol. Meas. vol. 26, pp. R73-R98, Feb. 1, 2005 (26 pages).
Non-Final Office Action on U.S. Appl. No. 15/470,750 dated Mar. 19, 2020 (9 pages).
Wu et al., "Soft inertial microfluidics for high throughput separation of bacteria from human blood cells," Lab Chip vol. 9, pp. 1193-1199, Feb. 13, 2009 (7 pages).
Zourub et al., "Principles of Bacterial Detection: Biosensors, Recognition Receptors and Microsystems," Springer Science and Business Media, Sep. 3, 2008 (980 pages).

* cited by examiner

Figure 10

>DLPEC01_T7_cut_and_nluc_insert Enterobacteria phage T7, complete genome
(SEQ ID NO: 1)

TCTCACAGTGTACGGACCTAAAGTTCCCCCATAGGGGGTACCTAAAGCCCAGCCAATCACCTAAAGTCAACCTT
CGGTTGACCTTGAGGGTTCCCTAAGGGTTGGGGATGACCCTTGGGTTTGTCTTTGGGTGTTACCTTGAGTGTCT
CTCTGTGTCCCTATCTGTTACAGTCTCCTAAAGTATCCTCCTAAAGTCACCTCCTAACGTCCATCCTAAAGCCA
ACACCTAAAGCCTACACCTAAAGACCCATCAAGTCAACGCCTATCTTAAAGTTTAAACATAAAGACCAGACCTA
AAGACCAGACCTAAAGACACTACATAAAGACCAGACCTAAAGACGCCTTGTTGTTAGCCATAAAGTGATAACCT
TTAATCATTGTCTTTATTAATACAACTCACTATAAGGAGAGACAACTTAAAGAGACTTAAAAGATTAATTTAAA
ATTTATCAAAAAGAGTATTGACTTAAAGTCTAACCTATAGGATACTTACAGCCATCGAGAGGGACACGGCGAAT
AGCCATCCCAATCGACACCGGGGTCAACCGGATAAGTAGACAGCCTGATAAGTCGCACGAAAAACAGGTATTGA
CAACATGAAGTAACATGCAGTAAGATACAAATCGCTAGGTAACACTAGCAGCGTCAACCGGGCGCACAGTGCCT
TCTAGGTGACTTAAGCGCACCACGGCACATAAGGTGAAACAAAACGGTTGACAACATGAAGTAAACACGGTACG
ATGTACCACATGAAACGACAGTGAGTCACCACACTGAAAGGTGATGCGGTCTAACGAAACCTGACCTAAGACGC
TCTTTAACAATCTGGTAAATAGCTCTTGAGTGCATGACTAGCGGATAACTCAAGGGTATCGCAAGGTGCCCTTT
ATGATATTCACTAATAACTGCACGAGGTAACACAAGATGGCTATGTCTAACATGACTTACAACAACGTTTTCGA
CCACGCTTACGAAATGCTGAAAGAAAACATCCGTTATGATGACATCCGTGACACTGATGACCTGCACGATGCTA
TTCACATGGCTGCCGATAATGCAGTTCCGCACTACTACGCTGACATCTTTAGCGTAATGGCAAGTGAGGGCATT
GACCTTGAGTTCGAAGACTCTGGTCTGATGCCTGACACCAAGGACGTAATCCGCATCCTGCAAGCGCGTATCTA
TGAGCAATTAACGATTGACCTCTGGGAAGACGCAGAAGACTTGCTCAATGAATACTTGGAGGAAGTCGAGGAGT
ACGAGGAGGATGAAGAGTAATGTCTACTACCAACGTGCAATACGGTCTGACCGCTCAAACTGTACTTTTCTATA
GCGACATGGTGCGCTGTGGCTTTAACTGGTCACTCGCAATGGCACAGCTCAAAGAACTGTACGAAAACAACAAG
GCAATAGCTTTAGAATCTGCTGAGTGATAGACTCAAGGTCGCTCCTAGCGAGTGGCCTTTATGATTATCACTTT
ACTTATGAGGGAGTAATGTATATGCTTACTATCGGTCTACTCACCGCTCTAGGTCTAGCTGTAGGTGCATCCTT
TGGGAAGGCTTTAGGTGTAGCTGTAGGTTCCTACTTTACCGCTTGCATCATCATAGGAATCATCAAAGGGGCAC
TACGCAAATGATGAAGCACTACGTTATGCCAATCCACACGTCCAACGGGGCAACCGTATGTACACCTGATGGGT
TCGCAATGAAACAACGAATCGAACGCCTTAAGCGTGAACTCCGCATTAACCGCAAGATTAACAAGATAGGTTCC
GGCTATGACAGAACGCACTGATGGCTTAAAGAAAGGTTATATGCCCAATGGCACACTATACGCTGCAAATCGGC
GAATAGTGAGAACTTGGCGAGAGAACAACCTCGAACGCCGCAAGGACAAGAGAGGGCGGCGTGGCATAGACGAA
AGGAAAAGGTTAAAGCCAAGAAACTCGCCGCACTTGAACAGGCACTAGCCAACACACTGAACGCTATCTCATAA
CGAACATAAAGGACACAATGCAATGAACATTACCGACATCATGAACGCTATCGACGCAATCAAAGCACTGCCAA
TCTGTGAACTTGACAAGCGTCAAGGTATGCTTATCGACTTACTGGTCGAGATGGTCAACAGCGAGACGTGTGAT
GGCGAGCTAACCGAACTAAATCAGGCACTTGAGCATCAAGATTGGTGGACTACCTTGAAGTGTCTCACGGCTGA
CGCAGGGTTCAAGATGCTCGGTAATGGTCACTTCTCGGCTGCTTATAGTCACCCGCTGCTACCTAACAGAGTGA
TTAAGGTGGGCTTTAAGAAAGAGGATTCAGGCGCAGCCTATACCGCATTCTGCCGCATGTATCAGGGTCGTCCT
GGTATCCCTAACGTCTACGATGTACAGCGCCACGCTGGATGCTATACGGTGGTACTTGACGCACTTAAGGATTG
CGAGCGTTTCAACAATGATGCCCATTATAAATACGCTGAGATTGCAAGCGACATCATTGATTGCAATTCGGATG
AGCATGATGAGTTAACTGGATGGGATGGTGAGTTTGTTGAAACTTGTAAACTAATCCGCAAGTTCTTTGAGGGC
ATCGCCTCATTCGACATGCATAGCGGGAACATCATGTTCTCAAATGGAGACGTACCATACATCACCGACCCGGT
ATCATTCTCGCAGAAGAAAGACGGTGGCGCATTCAGCATCGACCCTGAGGAACTCATCAAGGAAGTCGAGGAAG
TCGCACGACAGAAAGAAATTGACCGCGCTAAGGCCCGTAAAGAACGTCACGAGGGGCGCTTAGAGGCACGCAGA
TTCAAACGTCGCAACCGCAAGGCACGTAAAGCACACAAAGCTAAGCGCGAAAGAATGCTTGCTGCGTGGCGATG
GGCTGAACGTCAAGAACGGCGTAACCATGAGGTAGCTGTAGATGTACTAGGAAGAACCAATAACGCTATGCTCT
GGGTCAACATGTTCTCTGGGGACTTTAAGGCGCTTGAGGAACGAATCGCGCTGCACTGGCGTAATGCTGACCGG
ATGGCTATCGCTAATGGTCTTACGCTCAACATTGATAAGCAACTTGACGCAATGTTAATGGGCTGATAGTCTTA
TCTTACAGGTCATCTGCGGGTGGCCTGAATAGGTACGATTTACTAACTGGAAGAGGCACTAAATGAACACGATT
AACATCGCTAAGAACGACTTCTCTGACATCGAACTGGCTGCTATCCCGTTCAACACTCTGGCTGACCATTACGG
TGAGCGTTTAGCTCGCGAACAGTTGGCCCTTGAGCATGAGTCTTACGAGATGGGTGAAGCACGCTTCCGCAAGA
TGTTTGAGCGTCAACTTAAAGCTGGTGAGGTTGCGGATAACGCTGCCGCCAAGCCTCTCATCACTACCCTACTC
CCTAAGATGATTGCACGCATCAACGACTGGTTTGAGGAAGTGAAAGCTAAGCGCGGCAAGCGCCCGACAGCCTT

Figure 10 (CONTD.)

CCAGTTCCTGCAAGAAATCAAGCCGGAAGCCGTAGCGTACATCACCATTAAGACCACTCTGGCTTGCCTAACCA
GTGCTGACAATACAACCGTTCAGGCTGTAGCAAGCGCAATCGGTCGGGCCATTGAGGACGAGGCTCGCTTCGGT
CGTATCCGTGACCTTGAAGCTAAGCACTTCAAGAAAAACGTTGAGGAACAACTCAACAAGCGCGTAGGGCACGT
CTACAAGAAAGCATTTATGCAAGTTGTCGAGGCTGACATGCTCTCTAAGGGTCTACTCGGTGGCGAGGCGTGGT
CTTCGTGGCATAAGGAAGACTCTATTCATGTAGGAGTACGCTGCATCGAGATGCTCATTGAGTCAACCGGAATG
GTTAGCTTACACCGCCAAAATGCTGGCGTAGTAGGTCAAGACTCTGAGACTATCGAACTCGCACCTGAATACGC
TGAGGCTATCGCAACCCGTGCAGGTGCGCTGGCTGGCATCTCTCCGATGTTCCAACCTTGCGTAGTTCCTCCTA
AGCCGTGGACTGGCATTACTGGTGGTGGCTATTGGGCTAACGGTCGTCGTCCTCTGGCGCTGGTGCGTACTCAC
AGTAAGAAAGCACTGATGCGCTACGAAGACGTTTACATGCCTGAGGTGTACAAAGCGATTAACATTGCGCAAAA
CACCGCATGGAAAATCAACAAGAAAGTCCTAGCGGTCGCCAACGTAATCACCAAGTGGAAGCATTGTCCGGTCG
AGGACATCCCTGCGATTGAGCGTGAAGAACTCCCGATGAAACCGGAAGACATCGACATGAATCCTGAGGCTCTC
ACCGCGTGGAAACGTGCTGCCGCTGCTGTGTACCGCAAGGACAAGGCTCGCAAGTCTCGCCGTATCAGCCTTGA
GTTCATGCTTGAGCAAGCCAATAAGTTTGCTAACCATAAGGCCATCTGGTTCCCTTACAACATGGACTGGCGCG
GTCGTGTTTACGCTGTGTCAATGTTCAACCCGCAAGGTAACGATATGACCAAAGGACTGCTTACGCTGGCGAAA
GGTAAACCAATCGGTAAGGAAGGTTACTACTGGCTGAAAATCCACGGTGCAAACTGTGCGGGTGTCGATAAGGT
TCCGTTCCCTGAGCGCATCAAGTTCATTGAGGAAAACCACGAGAACATCATGGCTTGCGCTAAGTCTCCACTGG
AGAACACTTGGTGGGCTGAGCAAGATTCTCCGTTCTGCTTCCTTGCGTTCTGCTTTGAGTACGCTGGGGTACAG
CACCACGGCCTGAGCTATAACTGCTCCCTTCCGCTGGCGTTTGACGGGTCTTGCTCTGGCATCCAGCACTTCTC
CGCGATGCTCCGAGATGAGGTAGGTGGTCGCGCGGTTAACTTGCTTCCTAGTGAAACCGTTCAGGACATCTACG
GGATTGTTGCTAAGAAAGTCAACGAGATTCTACAAGCAGACGCAATCAATGGGACCGATAACGAAGTAGTTACC
GTGACCGATGAGAACACTGGTGAAATCTCTGAGAAAGTCAAGCTGGGCACTAAGGCACTGGCTGGTCAATGGCT
GGCTTACGGTGTTACTCGCAGTGTGACTAAGCGTTCAGTCATGACGCTGGCTTACGGGTCCAAAGAGTTCGGCT
TCCGTCAACAAGTGCTGGAAGATACCATTCAGCCAGCTATTGATTCCGGCAAGGGTCTGATGTTCACTCAGCCG
AATCAGGCTGCTGGATACATGGCTAAGCTGATTTGGGAATCTGTGAGCGTGACGGTGGTAGCTGCGGTTGAAGC
AATGAACTGGCTTAAGTCTGCTGCTAAGCTGCTGGCTGCTGAGGTCAAAGATAAGAAGACTGGAGAGATTCTTC
GCAAGCGTTGCGCTGTGCATTGGGTAACTCCTGATGGTTTCCCTGTGTGGCAGGAATACAAGAAGCCTATTCAG
ACGCGCTTGAACCTGATGTTCCTCGGTCAGTTCCGCTTACAGCCTACCATTAACACCAACAAAGATAGCGAGAT
TGATGCACACAAACAGGAGTCTGGTATCGCTCCTAACTTTGTACACAGCCAAGACGGTAGCCACCTTCGTAAGA
CTGTAGTGTGGGCACACGAGAAGTACGGAATCGAATCTTTTGCACTGATTCACGACTCCTTCGGTACCATTCCG
GCTGACGCTGCGAACCTGTTCAAAGCAGTGCGCGAAACTATGGTTGACACATATGAGTCTTGTGATGTACTGGC
TGATTTCTACGACCAGTTCGCTGACCAGTTGCACGAGTCTCAATTGGACAAAATGCCAGCACTTCCGGCTAAAG
GTAACTTGAACCTCCGTGACATCTTAGAGTCGGACTTCGCGTTCGCGTAACGCCAAATCAATACGACTCACTAT
AGAGGGACAAACTCAAGGTCATTCGCAAGAGTGGCCTTTATGATTGACCTTCTTCCGGTTAATACGACTCACTA
TAGGAGAACCTTAAGGTTTAACTTTAAGACCCTTAAGTGTTAATTAGAGATTTAAGGAGATTCAACATGGTCTT
CACACTCGAAGATTTCGTTGGGGACTGGCGACAGACAGCCGGCTACAACCTGGACCAAGTCCTTGAACAGGGAG
GTGTGTCCAGTTTGTTTCAGAATCTCGGGGTGTCCGTAACTCCGATCCAAAGGATTGTCCTGAGCGGTGAAAAT
GGGCTGAAGATCGACATCCATGTCATCATCCCGTATGAAGGTCTGAGCGGCGACCAAATGGGCCAGATCGAAAA
AATTTTTAAGGTGGTGTACCCTGTGGATGATCATCACTTTAAGGTGATCCTGCACTATGGCACACTGGTAATCG
ACGGGGTTACGCCGAACATGATCGACTATTTCGGACGGCCGTATGAAGGCATCGCCGTGTTCGACGGCAAAAAG
ATCACTGTAACAGGGACCCTGTGGAACGGCAACAAAATTATCGACGAGCGCCTGATCAACCCCGACGGCTCCCT
GCTGTTCCGAGTAACCATCAACGGAGTGACCGGCTGGCGGCTGTGCGAACGCATTCTGGCGTAAAGGAGGTAAA
CATATGACCATGATTACGGATTCACTGGCCGTCGTTTTACAACGTCGTGACTGGGAAAACCCTGGCGTTACCCA
ACTTAATCGCCTTGCAGCACATCCCCCTTTCGCCAGCTGGCGTAATAGCGAAGAGGCCCGCACCGATCGCCCTT
CCCAACAGTTGCGCAGCCTGAATGGCGAATGGTAAAAATTAAAGAATTACTAAGAGAGGACTTTAAGTATGCGT
AACTTCGAAAAGATGACCAAACGTTCTAACCGTAATGCTCGTGACTTCGAGGCAACCAAAGGTCGCAAGTTGAA
TAAGACTAAGCGTGACCGCTCTCACAAGCGTAGCTGGGAGGGTCAGTAAGATGGGACGTTTATATAGTGGTAAT
CTGGCAGCATTCAAGGCAGCAACAAACAAGCTGTTCCAGTTAGACTTAGCGGTCATTTATGATGACTGGTATGA
TGCCTATACAAGAAAAGATTGCATACGGTTACGTATTGAGGACAGGAGTGGAAACCTGATTGATACTAGCACCT
TCTACCACCACGACGAGGACGTTCTGTTCAATATGTGTACTGATTGGTTGAACCATATGTATGACCAGTTGAAG
GACTGGAAGTAATACGACTCAGTATAGGGACAATGCTTAAGGTCGCTCTCTAGGAGTGGCCTTAGTCATTTAAC
CAATAGGAGATAAACATTATGATGAACATTAAGACTAACCCGTTTAAAGCCGTGTCTTTCGTAGAGTCTGCCAT
TAAGAAGGCTCTGGATAACGCTGGGTATCTTATCGCTGAAATCAAGTACGATGGTGTACGCGGGAACATCTGCG

Figure 10 (CONTD.)

TAGACAATACTGCTAACAGTTACTGGCTCTCTCGTGTATCTAAAACGATTCCGGCACTGGAGCACTTAAACGGG
TTTGATGTTCGCTGGAAGCGTCTACTGAACGATGACCGTTGCTTCTACAAAGATGGCTTTATGCTTGATGGGGA
ACTCATGGTCAAGGGCGTAGACTTTAACACAGGGTCCGGCCTACTGCGTACCAAATGGACTGACACGAAGAACC
AAGAGTTCCATGAAGAGTTATTCGTTGAACCAATCCGTAAGAAAGATAAAGTTCCCTTTAAGCTGCACACTGGA
CACCTTCACATAAAACTGTACGCTATCCTCCCGCTGCACATCGTGGAGTCTGGAGAAGACTGTGATGTCATGAC
GTTGCTCATGCAGGAACACGTTAAGAACATGCTGCCTCTGCTACAGGAATACTTCCCTGAAATCGAATGGCAAG
CGGCTGAATCTTACGAGGTCTACGATATGGTAGAACTACAGCAACTGTACGAGCAGAAGCGAGCAGAAGGCCAT
GAGGGTCTCATTGTGAAAGACCCGATGTGTATCTATAAGCGCGGTAAGAAATCTGGCTGGTGGAAAATGAAACC
TGAGAACGAAGCTGACGGTATCATTCAGGGTCTGGTATGGGGTACAAAAGGTCTGGCTAATGAAGGTAAAGTGA
TTGGTTTTGAGGTGCTTCTTGAGAGTGGTCGTTTAGTTAACGCCACGAATATCTCTCGCGCCTTAATGGATGAG
TTCACTGAGACAGTAAAAGAGGCCACCCTAAGTCAATGGGGATTCTTTAGCCCATACGGTATTGGCGACAACGA
TGCTTGTACTATTAACCCTTACGATGGCTGGGCGTGTCAAATTAGCTACATGGAGGAAACACCTGATGGCTCTT
TGCGGCACCCATCGTTCGTAATGTTCCGTGGCACCGAGGACAACCCTCAAGAGAAAATGTAATCACACTGGCTC
ACCTTCGGGTGGGCCTTTCTGCGTTTATAAGGAGACACTTTATGTTTAAGAAGGTTGGTAAATTCCTTGCGGCT
TTGGCAGCTATCCTGACGCTTGCGTATATTCTTGCGGTATACCCTCAAGTAGCACTAGTAGTAGTTGGCGCTTG
TTACTTAGCGGCAGTGTGTGCTTGCGTGTGGAGTATAGTTAACTGGTAATACGACTCACTAAAGGAGGTACACA
CCATGATGTACTTAATGCCATTACTCATCGTCATTGTAGGATGCCTTGCGCTCCACTGTAGCGATGATGATATG
CCAGATGGTCACGCTTAATACGACTCACTAAAGGAGACACTATATGTTTCGACTTCATTACAACAAAAGCGTTA
AGAATTTCACGGTTCGCCGTGCTGACCGTTCAATCGTATGTGCGAGCGAGCGCCGAGCTAAGATACCTCTTATT
GGTAACACAGTTCCTTTGGCACCGAGCGTCCACATCATTATCACCCGTGGTGACTTTGAGAAAGCAATAGACAA
GAAACGTCCGGTTCTTAGTGTGGCAGTGACCCGCTTCCCGTTCGTCCGTCTGTTACTCAAACGAATCAAGGAGG
TGTTCTGATGGGACTGTTAGATGGTGAAGCCTGGGAAAAAGAAAACCCGCCAGTACAAGCAACTGGGTGTATAG
CTTGCTTAGAGAAAGATGACCGTTATCCACACACCTGTAACAAAGGAGCTAACGATATGACCGAACGTGAACAA
GAGATGATCATTAAGTTGATAGACAATAATGAAGGTCGCCCAGATGATTTGAATGGCTGCGGTATTCTCTGCTC
CAATGTCCCTTGCCACCTCTGCCCCGCAAATAACGATCAAAAGATAACCTTAGGTGAAATCCGAGCGATGGACC
CACGTAAACCACATCTGAATAAACCTGAGGTAACTCCTACAGATGACCAGCCTTCCGCTGAGACAATCGAAGGT
GTCACTAAGCCTTCCCACTACATGCTGTTTGACGACATTGAGGCTATCGAAGTGATTGCTCGTTCAATGACCGT
TGAGCAGTTCAAGGGATACTGCTTCGGTAACATCTTAAAGTACAGACTACGTGCTGGTAAGAAGTCAGAGTTAG
CGTACTTAGAGAAAGACCTAGCGAAAGCAGACTTCTATAAAGAACTCTTTGAGAAACATAAGGATAAATGTTAT
GCATAACTTCAAGTCAACCCCACCTGCCGACAGCCTATCTGATGACTTCACATCTTGCTCAGAGTGGTGCCGAA
AGATGTGGGAAGAGACATTCGACGATGCGTACATCAAGCTGTATGAACTTTGGAAATCGAGAGGTCAATGACTA
TGTCAAACGTAAATACAGGTTCACTTAGTGTGGACAATAAGAAGTTTTGGGCTACCGTAGAGTCCTCGGAGCAT
TCCTTCGAGGTTCCAATCTACGCTGAGACCCTAGACGAAGCTCTGGAGTTAGCCGAATGGCAATACGTTCCGGC
TGGCTTTGAGGTTACTCGTGTGCGTCCTTGTGTAGCACCGAAGTAATACGACTCACTATTAGGGAAGACTCCCT
CTGAGAAACCAAACGAAACCTAAAGGAGATTAACATTATGGCTAAGAAGATTTTCACCTCTGCGCTGGGTACCG
CTGAACCTTACGCTTACATCGCCAAGCCGGACTACGGCAACGAAGAGCGTGGCTTTGGGAACCCTCGTGGTGTC
TATAAAGTTGACCTGACTATTCCCAACAAAGACCCGCGCTGCCAGCGTATGGTCGATGAAATCGTGAAGTGTCA
CGAAGAGGCTTATGCTGCTGCCGTTGAGGAATACGAAGCTAATCCACCTGCTGTAGCTCGTGGTAAGAAACCGC
TGAAACCGTATGAGGGTGACATGCCGTTCTTCGATAACGGTGACGGTACGACTACCTTTAAGTTCAAATGCTAC
GCGTCTTTCCAAGACAAGAAGACCAAAGAGACCAAGCACATCAATCTGGTTGTGGTTGACTCAAAAGGTAAGAA
GATGGAAGACGTTCCGATTATCGGTGGTGGCTCTAAGCTGAAAGTTAAATATTCTCTGGTTCCATACAAGTGGA
ACACTGCTGTAGGTGCGAGCGTTAAGCTGCAACTGGAATCCGTGATGCTGGTCGAACTGGCTACCTTTGGTGGC
GGTGAAGACGATTGGGCTGACGAAGTTGAAGAGAACGGCTATGTTGCCTCTGGTTCTGCCAAAGCGAGCAAACC
ACGCGACGAAGAAAGCTGGGACGAAGACGACGAAGAGTCCGAGGAAGCAGACGAAGACGGAGACTTCTAAGTGG
AACTGCGGGAGAAAATCCTTGAGCGAATCAAGGTGACTTCCTCTGGGTGTTGGGAGTGGCAGGGCGCTACGAAC
AATAAAGGGTACGGGCAGGTGTGGTGCAGCAATACCGGAAAGGTTGTCTACTGTCATCGCGTAATGTCTAATGC
TCCGAAAGGTTCTACCGTCCTGCACTCCTGTGATAATCCATTATGTTGTAACCCTGAACACCTATCCATAGGAA
CTCCAAAAGAGAACTCCACTGACATGGTAAATAAGGGTCGCTCACACAAGGGGTATAAACTTTCAGACGAAGAC
GTAATGGCAATCATGGAGTCCAGCGAGTCCAATGTATCCTTAGCTCGCACCTATGGTGTCTCCCAACAGACTAT
TTGTGATATACGCAAAGGGAGGCGACATGGCAGGTTACGGCGCTAAAGGAATCCGAAAGGTTGGAGCGTTTCGC
TCTGGCCTAGAGGACAAGGTTTCAAAGCAGTTGGAATCAAAAGGTATTAAATTCGAGTATGAAGAGTGGAAAGT
GCCTTATGTAATTCCGGCGAGCAATCACACTTACACTCCAGACTTCTTACTTCCAAACGGTATATTCGTTGAGA

Figure 10 (CONTD.)

CAAAGGGTCTGTGGGAAAGCGATGATAGAAAGAAGCACTTATTAATTAGGGAGCAGCACCCCGAGCTAGACATC
CGTATTGTCTTCTCAAGCTCACGTACTAAGTTATACAAAGGTTCTCCAACGTCTTATGGAGAGTTCTGCGAAAA
GCATGGTATTAAGTTCGCTGATAAACTGATACCTGCTGAGTGGATAAAGGAACCCAAGAAGGAGGTCCCCTTTG
ATAGATTAAAAAGGAAAGGAGGAAAGAAATAATGGCTCGTGTACAGTTTAAACAACGTGAATCTACTGACGCAA
TCTTTGTTCACTGCTCGGCTACCAAGCCAAGTCAGAATGTTGGTGTCCGTGAGATTCGCCAGTGGCACAAAGAG
CAGGGTTGGCTCGATGTGGGATACCACTTTATCATCAAGCGAGACGGTACTGTGGAGGCAGGACGAGATGAGAT
GGCTGTAGGCTCTCACGCTAAGGGTTACAACCACAACTCTATCGGCGTCTGCCTTGTTGGTGGTATCGACGATA
AAGGTAAGTTCGACGCTAACTTTACGCCAGCCCAAATGCAATCCCTTCGCTCACTGCTTGTCACACTGCTGGCT
AAGTACGAAGGCGCTGTGCTTCGCGCCCATCATGAGGTGGCGCCGAAGGCTTGCCCTTCGTTCGACCTTAAGCG
TTGGTGGGAGAAGAACGAACTGGTCACTTCTGACCGTGGATAATTAATTGAACTCACTAAAGGGAGACCACAGC
GGTTTCCCTTTGTTCGCATTGGAGGTCAAATAATGCGCAAGTCTTATAAACAATTCTATAAGGCTCCGAGGAGG
CATATCCAAGTGTGGGAGGCAGCCAATGGGCCTATACCAAAAGGTTATTATATAGACCACATTGACGGCAATCC
ACTCAACGACGCCTTAGACAATCTCCGTCTGGCTCTCCCAAAAGAAAACTCATGGAACATGAAGACTCCAAAGA
GCAATACCTCAGGACTAAAGGGACTGAGTTGGAGCAAGGAAAGGGAGATGTGGAGAGGCACTGTAACAGCTGAG
GGTAAACAGCATAACTTTCGTAGTAGAGATCTATTGGAAGTCGTTGCGTGGATTTATAGAACTAGGAGGGAATT
GCATGGACAATTCGCACGATTCCGATAGTGTATTTCTTTACCACATTCCTTGTGACAACTGTGGGAGTAGTGAT
GGGAACTCGCTGTTCTCTGACGGACACACGTTCTGCTACGTATGCGAGAAGTGGACTGCTGGTAATGAAGACAC
TAAAGAGAGGGCTTCAAAACGGAAACCCTCAGGAGGTAAACCAATGACTTACAACGTGTGGAACTTCGGGGAAT
CCAATGGACGCTACTCCGCGTTAACTGCGAGAGGAATCTCCAAGGAAACCTGTCAGAAGGCTGGCTACTGGATT
GCCAAAGTAGACGGTGTGATGTACCAAGTGGCTGACTATCGGGACCAGAACGGCAACATTGTGAGTCAGAAGGT
TCGAGATAAAGATAAGAACTTTAAGACCACTGGTAGTCACAAGAGTGACGCTCTGTTCGGGAAGCACTTGTGGA
ATGGTGGTAAGAAGATTGTCGTTACAGAAGGTGAAATCGACATGCTTACCGTGATGGAACTTCAAGACTGTAAG
TATCCTGTAGTGTCGTTGGGTCACGGTGCCTCTGCCGCTAAGAAGACATGCGCTGCCAACTACGAATACTTTGA
CCAGTTCGAACAGATTATCTTAATGTTCGATATGGACGAAGCAGGGCGCAAAGCAGTCGAAGAGGCTGCACAGG
TTCTACCTGCTGGTAAGGTACGAGTGGCAGTTCTTCCGTGTAAGGATGCAAACGAGTGTCACCTAAATGGTCAC
GACCGTGAAATCATGGAGCAAGTGTGGAATGCTGGTCCTTGGATTCCTGATGGTGTGGTATCGGCTCTTTCGTT
ACGTGAACGAATCCGTGAGCACCTATCGTCCGAGGAATCAGTAGGTTTACTTTTCAGTGGCTGCACTGGTATCA
ACGATAAGACCTTAGGTGCCCGTGGTGGTGAAGTCATTATGGTCACTTCCGGTTCCGGTATGGGTAAGTCAACG
TTCGTCCGTCAACAAGCTCTACAATGGGGCACAGCGATGGGCAAGAAGGTAGGCTTAGCGATGCTTGAGGAGTC
CGTTGAGGAGACCGCTGAGGACCTTATAGGTCTACACAACCGTGTCCGACTGAGACAATCCGACTCACTAAAGA
GAGAGATTATTGAGAACGGTAAGTTCGACCAATGGTTCGATGAACTGTTCGGCAACGATACGTTCCATCTATAT
GACTCATTCGCCGAGGCTGAGACGGATAGACTGCTCGCTAAGCTGGCCTACATGCGCTCAGGCTTGGGCTGTGA
CGTAATCATTCTAGACCACATCTCAATCGTCGTATCCGCTTCTGGTGAATCCGATGAGCGTAAGATGATTGACA
ACCTGATGACCAAGCTCAAAGGGTTCGCTAAGTCAACTGGGGTGGTGCTGGTCGTAATTTGTCACCTTAAGAAC
CCAGACAAAGGTAAAGCACATGAGGAAGGTCGCCCCGTTTCTATTACTGACCTACGTGGTTCTGGCGCACTACG
CCAACTATCTGATACTATTATTGCCCTTGAGCGTAATCAGCAAGGCGATATGCCTAACCTTGTCCTCGTTCGTA
TTCTCAAGTGCCGCTTTACTGGTGATACTGGTATCGCTGGCTACATGGAATACAACAAGGAAACCGGATGGCTT
GAACCATCAAGTTACTCAGGGGAAGAAGAGTCACACTCAGAGTCAACAGACTGGTCCAACGACACTGACTTCTG
ACAGGATTCTTGATGACTTTCCAGACGACTACGAGAAGTTTCGCTGGAGAGTCCCATTCTAATACGACTCACTA
AAGGAGACACACCATGTTCAAACTGATTAAGAAGTTAGGCCAACTGCTGGTTCGTATGTACAACGTGGAAGCCA
AGCGACTGAACGATGAGGCTCGTAAAGAGGCCACACAGTCACGCGCTCTGGCGATTCGCTCCAACGAACTGGCT
GACAGTGCATCCACTAAAGTTACCGAGGCTGCCCGTGTGGCAAACCAAGCTCAACAGCTTTCCAAATTCTTTGA
GTAATCAAACAGGAGAAACCATTATGTCTAACGTAGCTGAAACTATCCGTCTATCCGATACAGCTGACCAGTGG
AACCGTCGAGTCCACATCAACGTTCGCAACGGTAAGGCGACTATGGTTTACCGCTGGAAGGACTCTAAGTCCTC
TAAGAATCACACTCAGCGTATGACGTTGACAGATGAGCAAGCACTGCGTCTGGTCAATGCGCTTACCAAAGCTG
CCGTGACAGCAATTCATGAAGCTGGTCGCGTCAATGAAGCTATGGCTATCCTCGACAAGATTGATAACTAAGAG
TGGTATCCTCAAGGTCGCCAAAGTGGTGGCCTTCATGAATACTATTCGACTCACTATAGGAGATATTACCATGC
GTGACCCTAAAGTTATCCAAGCAGAAATCGCTAAACTGGAAGCTGAACTGGAGGACGTTAAGTACCATGAAGCT
AAGACTCGCTCCGCTGTTCACATCTTGAAGAACTTAGGCTGGACTTGGACAAGACAGACTGGCTGGAAGAAACC
AGAAGTTACCAAGCTGAGTCATAAGGTGTTCGATAAGGACACTATGACCCACATCAAGGCTGGTGATTGGGTTA
AGGTTGACATGGGAGTTGTTGGTGGATACGGCTACGTCCGCTCAGTTAGTGGCAAATATGCACAAGTGTCATAC
ATCACAGGTGTTACTCCACGCGGTGCAATCGTTGCCGATAAGACCAACATGATTCACACAGGTTTCTTGACAGT

Figure 10 (CONTD.)

TGTTTCATATGAAGAGATTGTTAAGTCACGATAATCAATAGGAGAAATCAATATGATCGTTTCTGACATCGAAG
CTAACGCCCTCTTAGAGAGCGTCACTAAGTTCCACTGCGGGGTTATCTACGACTACTCCACCGCTGAGTACGTA
AGCTACCGTCCGAGTGACTTCGGTGCGTATCTGGATGCGCTGGAAGCCGAGGTTGCACGAGGCGGTCTTATTGT
GTTCCACAACGGTCACAAGTATGACGTTCCTGCATTGACCAAACTGGCAAAGTTGCAATTGAACCGAGAGTTCC
ACCTTCCTCGTGAGAACTGTATTGACACCCTTGTGTTGTCACGTTTGATTCATTCCAACCTCAAGGACACCGAT
ATGGGTCTTCTGCGTTCCGGCAAGTTGCCCGGAAAACGCTTTGGGTCTCACGCTTTGGAGGCGTGGGGTTATCG
CTTAGGCGAGATGAAGGGTGAATACAAAGACGACTTTAAGCGTATGCTTGAAGAGCAGGGTGAAGAATACGTTG
ACGGAATGGAGTGGTGGAACTTCAACGAAGAGATGATGGACTATAACGTTCAGGACGTTGTGGTAACTAAAGCT
CTCCTTGAGAAGCTACTCTCTGACAAACATTACTTCCCTCCTGAGATTGACTTTACGGACGTAGGATACACTAC
GTTCTGGTCAGAATCCCTTGAGGCCGTTGACATTGAACATCGTGCTGCATGGCTGCTCGCTAAACAAGAGCGCA
ACGGGTTCCCGTTTGACACAAAAGCAATCGAAGAGTTGTACGTAGAGTTAGCTGCTCGCCGCTCTGAGTTGCTC
CGTAAATTGACCGAAACGTTCGGCTCGTGGTATCAGCCTAAAGGTGGCACTGAGATGTTCTGCCATCCGCGAAC
AGGTAAGCCACTACCTAAATACCCTCGCATTAAGACACCTAAAGTTGGTGGTATCTTTAAGAAGCCTAAGAACA
AGGCACAGCGAGAAGGCCGTGAGCCTTGCGAACTTGATACCCGCGAGTACGTTGCTGGTGCTCCTTACACCCCA
GTTGAACATGTTGTGTTTAACCCTTCGTCTCGTGACCACATTCAGAAGAAACTCCAAGAGGCTGGGTGGGTCCC
GACCAAGTACACCGATAAGGGTGCTCCTGTGGTGGACGATGAGGTACTCGAAGGAGTACGTGTAGATGACCCTG
AGAAGCAAGCCGCTATCGACCTCATTAAAGAGTACTTGATGATTCAGAAGCGAATCGGACAGTCTGCTGAGGGA
GACAAAGCATGGCTTCGTTATGTTGCTGAGGATGGTAAGATTCATGGTTCTGTTAACCCTAATGGAGCAGTTAC
GGGTCGTGCGACCCATGCGTTCCCAAACCTTGCGCAAATTCCGGGTGTACGTTCTCCTTATGGAGAGCAGTGTC
GCGCTGCTTTTGGCGCTGAGCACCATTTGGATGGGATAACTGGTAAGCCTTGGGTTCAGGCTGGCATCGACGCA
TCCGGTCTTGAGCTACGCTGCTTGGCTCACTTCATGGCTCGCTTTGATAACGGCGAGTACGCTCACGAGATTCT
TAACGGCGACATCCACACTAAGAACCAGATAGCTGCTGAACTACCTACCCGAGATAACGCTAAGACGTTCATCT
ATGGGTTCCTCTATGGTGCTGGTGATGAGAAGATTGGACAGATTGTTGGTGCTGGTAAAGAGCGCGGTAAGGAA
CTCAAGAAGAAATTCCTTGAGAACACCCCCGCGATTGCAGCACTCCGCGAGTCTATCCAACAGACACTTGTCGA
GTCCTCTCAATGGGTAGCTGGTGAGCAACAAGTCAAGTGGAAACGCCGCTGGATTAAAGGTCTGGATGGTCGTA
AGGTACACGTTCGTAGTCCTCACGCTGCCTTGAATACCCTACTGCAATCTGCTGGTGCTCTCATCTGCAAACTG
TGGATTATCAAGACCGAAGAGATGCTCGTAGAGAAAGGCTTGAAGCATGGCTGGGATGGGGACTTTGCGTACAT
GGCATGGGTACATGATGAAATCCAAGTAGGCTGCCGTACCGAAGAGATTGCTCAGGTGGTCATTGAGACCGCAC
AAGAAGCGATGCGCTGGGTTGGAGACCACTGGAACTTCCGGTGTCTTCTGGATACCGAAGGTAAGATGGGTCCT
AATTGGGCGATTTGCCACTGATACAGGAGGCTACTCATGAACGAAAGACACTTAACAGGTGCTGCTTCTGAAAT
GCTAGTAGCCTACAAATTTACCAAAGCTGGGTACACTGTCTATTACCCTATGCTGACTCAGAGTAAAGAGGACT
TGGTTGTATGTAAGGATGGTAAATTTAGTAAGGTTCAGGTTAAAACAGCCACAACGGTTCAAACCAACACAGGA
GATGCCAAGCAGGTTAGGCTAGGTGGATGCGGTAGGTCCGAATATAAGGATGGAGACTTTGACATTCTTGCGGT
TGTGGTTGACGAAGATGTGCTTATTTTCACATGGGACGAAGTAAAAGGTAAGACATCCATGTGTGTCGGCAAGA
GAAACAAAGGCATAAAACTATAGGAGAAATTATTATGGCTATGACAAAGAAATTTAAAGTGTCCTTCGACGTTA
CCGCAAAGATGTCGTCTGACGTTCAGGCAATCTTAGAGAAAGATATGCTGCATCTATGTAAGCAGGTCGGCTCA
GGTGCGATTGTCCCCAATGGTAAACAGAAGGAAATGATTGTCCAGTTCCTGACACACGGTATGGAAGGATTGAT
GACATTCGTAGTACGTACATCATTTCGTGAGGCCATTAAGGACATGCACGAAGAGTATGCAGATAAGGACTCTT
TCAAACAATCTCCTGCAACAGTACGGGAGGTGTTCTGATGTCTGACTACCTGAAAGTGCTGCAAGCAATCAAAA
GTTGCCCTAAGACTTTCCAGTCCAACTATGTACGGAACAATGCGAGCCTCGTAGCGGAGGCCGCTTCCCGTGGT
CACATCTCGTGCCTGACTACTAGTGGACGTAACGGTGGCGCTTGGGAAATCACTGCTTCCGGTACTCGCTTTCT
GAAACGAATGGGAGGATGTGTCTAATGTCTCGTGACCTTGTGACTATTCCACGCGATGTGTGGAACGATATACA
GGGCTACATCGACTCTCTGGAACGTGAGAACGATAGCCTTAAGAATCAACTAATGGAAGCTGACGAATACGTAG
CGGAACTAGAGGAGAAACTTAATGGCACTTCTTGACCTTAAACAATTCTATGAGTTACGTGAAGGCTGCGACGA
CAAGGGTATCCTTGTGATGGACGGCGACTGGCTGGTCTTCCAAGCTATGAGTGCTGCTGAGTTTGATGCCTCTT
GGGAGGAAGAGATTTGGCACCGATGCTGTGACCACGCTAAGGCCCGTCAGATTCTTGAGGATTCCATTAAGTCC
TACGAGACCCGTAAGAAGGCTTGGGCAGGTGCTCCAATTGTCCTTGCGTTCACCGATAGTGTTAACTGGCGTAA
AGAACTGGTTGACCCGAACTATAAGGCTAACCGTAAGGCCGTGAAGAAACCTGTAGGGTACTTTGAGTTCCTTG
ATGCTCTCTTTGAGCGCGAAGAGTTCTATTGCATCCGTGAGCCTATGCTTGAGGGTGATGACGTTATGGGAGTT
ATTGCTTCCAATCCGTCTGCCTTCGGTGCTCGTAAGGCTGTAATCATCTCTTGCGATAAGGACTTTAAGACCAT
CCCTAACTGTGACTTCCTGTGGTGTACCACTGGTAACATCCTGACTCAGACCGAAGAGTCCGCTGACTGGTGGC
ACCTCTTCCAGACCATCAAGGGTGACATCACTGATGGTTACTCAGGGATTGCTGGATGGGGTGATACCGCCGAG

Figure 10 (CONTD.)

GACTTCTTGAATAACCCGTTCATAACCGAGCCTAAAACGTCTGTGCTTAAGTCCGGTAAGAACAAAGGCCAAGA
GGTTACTAAATGGGTTAAACGCGACCCTGAGCCTCATGAGACGCTTTGGGACTGCATTAAGTCCATTGGCGCGA
AGGCTGGTATGACCGAAGAGGATATTATCAAGCAGGGCCAAATGGCTCGAATCCTACGGTTCAACGAGTACAAC
TTTATTGACAAGGAGATTTACCTGTGGAGACCGTAGCGTATATTGGTCTGGGTCTTTGTGTTCTCGGAGTGTGC
CTCATTTCGTGGGGCCTTTGGGACTTAGCCAGAATAATCAAGTCGTTACACGACACTAAGTGATAAACTCAAGG
TCCCTAAATTAATACGACTCACTATAGGGAGATAGGGGCCTTTACGATTATTACTTTAAGATTTAACTCTAAGA
GGAATCTTTATTATGTTAACACCTATTAACCAATTACTTAAGAACCCTAACGATATTCCAGATGTACCTCGTGC
AACCGCTGAGTATCTACAGGTTCGATTCAACTATGCGTACCTCGAAGCGTCTGGTCATATAGGACTTATGCGTG
CTAATGGTTGTAGTGAGGCCCACATCTTGGGTTTCATTCAGGGCCTACAGTATGCCTCTAACGTCATTGACGAG
ATTGAGTTACGCAAGGAACAACTAAGAGATGATGGGGAGGATTGACACTATGTGTTTCTCACCGAAAATTAAAA
CTCCGAAGATGGATACCAATCAGATTCGAGCCGTTGAGCCAGCGCCTCTGACCCAAGAAGTGTCAAGCGTGGAG
TTCGGTGGGTCTTCTGATGAGACGGATACCGAGGGCACCGAAGTGTCTGGACGCAAAGGCCTCAAGGTCGAACG
TGATGATTCCGTAGCGAAGTCTAAAGCCAGCGGCAATGGCTCCGCTCGTATGAAATCTTCCATCCGTAAGTCCG
CATTTGGAGGTAAGAAGTGATGTCTGAGTTCACATGTGTGGAGGCTAAGAGTCGCTTCCGTGCAATCCGGTGGA
CTGTGGAACACCTTGGGTTGCCTAAAGGATTCGAAGGACACTTTGTGGGCTACAGCCTCTACGTAGACGAAGTG
ATGGACATGTCTGGTTGCCGTGAAGAGTACATTCTGGACTCTACCGGAAAACATGTAGCGTACTTCGCGTGGTG
CGTAAGCTGTGACATTCACCACAAAGGAGACATTCTGGATGTAACGTCCGTTGTCATTAATCCTGAGGCAGACT
CTAAGGGCTTACAGCGATTCCTAGCGAAACGCTTTAAGTACCTTGCGGAACTCCACGATTGCGATTGGGTGTCT
CGTTGTAAGCATGAAGGCGAGACAATGCGTGTATACTTTAAGGAGGTATAAGTTATGGGTAAGAAAGTTAAGAA
GGCCGTGAAGAAAGTCACCAAGTCCGTTAAGAAAGTCGTTAAGGAAGGGGCTCGTCCGGTTAAACAGGTTGCTG
GCGGTCTAGCTGGTCTGGCTGGTGGTACTGGTGAAGCACAGATGGTGGAAGTACCACAAGCTGCCGCACAGATT
GTTGACGTACCTGAGAAAGAGGTTTCCACTGAGGACGAAGCACAGACAGAAAGCGGACGCAAGAAAGCTCGTGC
TGGCGGTAAGAAATCCTTGAGTGTAGCCCGTAGCTCCGGTGGCGGTATCAACATTTAATCAGGAGGTTATCGTG
GAAGACTGCATTGAATGGACCGGAGGTGTCAACTCTAAGGGTTATGGTCGTAAGTGGGTTAATGGTAAACTTGT
GACTCCACATAGGCACATCTATGAGGAGACATATGGTCCAGTTCCAACAGGAATTGTGGTGATGCATATCTGCG
ATAACCCTAGGTGCTATAACATAAAGCACCTTACGCTTGGAACTCCAAAGGATAATTCCGAGGACATGGTTACC
AAAGGTAGACAGGCTAAAGGAGAGGAACTAAGCAAGAAACTTACAGAGTCAGACGTTCTCGCTATACGCTCTTC
AACCTTAAGCCACCGCTCCTTAGGAGAACTGTATGGAGTCAGTCAATCAACCATAACGCGAATACTACAGCGTA
AGACATGGAGACACATTTAATGGCTGAGAAACGAACAGGACTTGCGGAGGATGGCGCAAAGTCTGTCTATGAGC
GTTTAAAGAACGACCGTGCTCCCTATGAGACACGCGCTCAGAATTGCGCTCAATATACCATCCCATCATTGTTC
CCTAAGGACTCCGATAACGCCTCTACAGATTATCAAACTCCGTGGCAAGCCGTGGGCGCTCGTGGTCTGAACAA
TCTAGCCTCTAAGCTCATGCTGGCTCTATTCCCTATGCAGACTTGGATGCGACTTACTATATCTGAATATGAAG
CAAAGCAGTTACTGAGCGACCCCGATGGACTCGCTAAGGTCGATGAGGGCCTCTCGATGGTAGAGCGTATCATC
ATGAACTACATTGAGTCTAACAGTTACCGCGTGACTCTCTTTGAGGCTCTCAAACAGTTAGTCGTAGCTGGTAA
CGTCCTGCTGTACCTACCGGAACCGGAAGGGTCAAACTATAATCCCATGAAGCTGTACCGATTGTCTTCTTATG
TGGTCCAACGAGACGCATTCGGCAACGTTCTGCAAATGGTGACTCGTGACCAGATAGCTTTTGGTGCTCTCCCT
GAGGACATCCGTAAGGCTGTAGAAGGTCAAGGTGGTGAGAAGAAAGCTGATGAGACAATCGACGTGTACACTCA
CATCTATCTGGATGAGGACTCAGGTGAATACCTCCGATACGAAGAGGTCGAGGGTATGGAAGTCCAAGGCTCCG
ATGGGACTTATCCTAAAGAGGCTTGCCCATACATCCCGATTCGGATGGTCAGACTAGATGGTGAATCCTACGGT
CGTTCGTACATTGAGGAATACTTAGGTGACTTACGGTCCCTTGAAAATCTCCAAGAGGCTATCGTCAAGATGTC
CATGATTAGCTCTAAGGTTATCGGCTTAGTGAATCCTGCTGGTATCACCCAGCCACGCCGACTGACCAAAGCTC
AGACTGGTGACTTCGTTACTGGTCGTCCAGAAGACATCTCGTTCCTCCAACTGGAGAAGCAAGCAGACTTTACT
GTAGCTAAAGCCGTAAGTGACGCTATCGAGGCTCGCCTTTCGTTTGCCTTTATGTTGAACTCTGCGGTTCAGCG
TACAGGTGAACGTGTGACCGCCGAAGAGATTCGGTATGTAGCTTCTGAACTTGAAGATACTTTAGGTGGTGTCT
ACTCTATCCTTTCTCAAGAATTACAATTGCCTCTGGTACGAGTGCTCTTGAAGCAACTACAAGCCACGCAACAG
ATTCCTGAGTTACCTAAGGAAGCCGTAGAGCCAACCATTAGTACAGGTCTGGAAGCAATTGGTCGAGGACAAGA
CCTTGATAAGCTGGAGCGGTGTGTCACTGCGTGGGCTGCACTGGCACCTATGCGGGACGACCCTGATATTAACC
TTGCGATGATTAAGTTACGTATTGCCAACGCTATCGGTATTGACACTTCTGGTATTCTACTCACCGAAGAACAG
AAGCAACAGAAGATGGCCCAACAGTCTATGCAAATGGGTATGGATAATGGTGCTGCTGCGCTGGCTCAAGGTAT
GGCTGCACAAGCTACAGCTTCACCTGAGGCTATGGCTGCTGCCGCTGATTCCGTAGGTTTACAGCCGGGAATTT
AATACGACTCACTATAGGGAGACCTCATCTTTGAAATGAGCGATGACAAGAGGTTGGAGTCCTCGGTCTTCCTG
TAGTTCAACTTTAAGGAGACAATAATAATGGCTGAATCTAATGCAGACGTATATGCATCTTTTGGCGTGAACTC

Figure 10 (CONTD.)

CGCTGTGATGTCTGGTGGTTCCGTTGAGGAACATGAGCAGAACATGCTGGCTCTTGATGTTGCTGCCCGTGATG
GCGATGATGCAATCGAGTTAGCGTCAGACGAAGTGGAAACAGAACGTGACCTGTATGACAACTCTGACCCGTTC
GGTCAAGAGGATGACGAAGGCCGCATTCAGGTTCGTATCGGTGATGGCTCTGAGCCGACCGATGTGGACACTGG
AGAAGAAGGCGTTGAGGGCACCGAAGGTTCCGAAGAGTTTACCCCACTGGGCGAGACTCCAGAAGAACTGGTAG
CTGCCTCTGAGCAACTTGGTGAGCACGAAGAGGGCTTCCAAGAGATGATTAACATTGCTGCTGAGCGTGGCATG
AGTGTCGAGACCATTGAGGCTATCCAGCGTGAGTACGAGGAGAACGAAGAGTTGTCCGCCGAGTCCTACGCTAA
GCTGGCTGAAATTGGCTACACGAAGGCTTTCATTGACTCGTATATCCGTGGTCAAGAAGCTCTGGTGGAGCAGT
ACGTAAACAGTGTCATTGAGTACGCTGGTGGTCGTGAACGTTTTGATGCACTGTATAACCACCTTGAGACGCAC
AACCCTGAGGCTGCACAGTCGCTGGATAATGCGTTGACCAATCGTGACTTAGCGACCGTTAAGGCTATCATCAA
CTTGGCTGGTGAGTCTCGCGCTAAGGCGTTCGGTCGTAAGCCAACTCGTAGTGTGACTAATCGTGCTATTCCGG
CTAAACCTCAGGCTACCAAGCGTGAAGGCTTTGCGGACCGTAGCGAGATGATTAAAGCTATGAGTGACCCTCGG
TATCGCACAGATGCCAACTATCGTCGTCAAGTCGAACAGAAAGTAATCGATTCGAACTTCTGATAGACTTCGAA
ATTAATACGACTCACTATAGGGAGACCACAACGGTTTCCCTCTAGAAATAATTTTGTTTAACTTTAAGAAGGAG
ATATACATATGGCTAGCATGACTGGTGGACAGCAAATGGGTACTAACCAAGGTAAAGGTGTAGTTGCTGCTGGA
GATAAACTGGCGTTGTTCTTGAAGGTATTTGGCGGTGAAGTCCTGACTGCGTTCGCTCGTACCTCCGTGACCAC
TTCTCGCCACATGGTACGTTCCATCTCCAGCGGTAAATCCGCTCAGTTCCCTGTTCTGGGTCGCACTCAGGCAG
CGTATCTGGCTCCGGGCGAGAACCTCGACGATAAACGTAAGGACATCAAACACACCGAGAAGGTAATCACCATT
GACGGTCTCCTGACGGCTGACGTTCTGATTTATGATATTGAGGACGCGATGAACCACTACGACGTTCGCTCTGA
GTATACCTCTCAGTTGGGTGAATCTCTGGCGATGGCTGCGGATGGTGCGGTTCTGGCTGAGATTGCCGGTCTGT
GTAACGTGGAAAGCAAATATAATGAGAACATCGAGGGCTTAGGTACTGCTACCGTAATTGAGACCACTCAGAAC
AAGGCCGCACTTACCGACCAAGTTGCGCTGGGTAAGGAGATTATTGCGGCTCTGACTAAGGCTCGTGCGGCTCT
GACCAAGAACTATGTTCCGGCTGCTGACCGTGTGTTCTACTGTGACCCAGATAGCTACTCTGCGATTCTGGCAG
CACTGATGCCGAACGCAGCAAACTACGCTGCTCTGATTGACCCTGAGAAGGGTTCTATCCGCAACGTTATGGGC
TTTGAGGTTGTAGAAGTTCCGCACCTCACCGCTGGTGGTGCTGGTACCGCTCGTGAGGGCACTACTGGTCAGAA
GCACGTCTTCCCTGCCAATAAAGGTGAGGGTAATGTCAAGGTTGCTAAGGACAACGTTATCGGCCTGTTCATGC
ACCGCTCTGCGGTAGGTACTGTTAAGCTGCGTGACTTGGCTCTGGAGCGCGCTCGCCGTGCTAACTTCCAAGCG
GACCAGATTATCGCTAAGTACGCAATGGGCCACGGTGGTCTTCGCCCAGAAGCTGCTGGTGCAGTGGTTTTCAA
AGTGGAGTAATGCTGGGGGTGGCCTCAACGGTCGCTGCTAGTCCCGAAGAGGCGAGTGTTACTTCAACAGAAGA
AACCTTAACGCCAGCACAGGAGGCCGCACGCACCCGCGCTGCTAACAAAGCCCGAAAGGAAGCTGAGTTGGCTG
CTGCCACCGCTGAGCAATAACTAGCATAACCCCTTGGGGCCTCTAAACGGGTCTTGAGGGGTTTTTTGCTGAAA
GGAGGAACTATATGCGCTCATACGATATGAACGTTGAGACTGCCGCTGAGTTATCAGCTGTGAACGACATTCTG
GCGTCTATCGGTGAACCTCCGGTATCAACGCTGGAAGGTGACGCTAACGCAGATGCAGCGAACGCTCGGCGTAT
TCTCAACAAGATTAACCGACAGATTCAATCTCGTGGATGGACGTTCAACATTGAGGAAGGCATAACGCTACTAC
CTGATGTTTACTCCAACCTGATTGTATACAGTGACGACTATTTATCCCTAATGTCTACTTCCGGTCAATCCATC
TACGTTAACCGAGGTGGCTATGTGTATGACCGAACGAGTCAATCAGACCGCTTTGACTCTGGTATTACTGTGAA
CATTATTCGTCTCCGCGACTACGATGAGATGCCTGAGTGCTTCCGTTACTGGATTGTCACCAAGGCTTCCCGTC
AGTTCAACAACCGATTCTTTGGGGCACCGGAAGTAGAGGGTGTACTCCAAGAAGAGGAAGATGAGGCTAGACGT
CTCTGCATGGAGTATGAGATGGACTACGGTGGGTACAATATGCTGGATGGAGATGCGTTCACTTCTGGTCTACT
GACTCGCTAACATTAATAAATAAGGAGGCTCTAATGGCACTCATTAGCCAATCAATCAAGAACTTGAAGGGTGG
TATCAGCCAACAGCCTGACATCCTTCGTTATCCAGACCAAGGGTCACGCCAAGTTAACGGTTGGTCTTCGGAGA
CCGAGGGCCTCCAAAAGCGTCCACCTCTTGTTTTCTTAAATACACTTGGAGACAACGGTGCGTTAGGTCAAGCT
CCGTACATCCACCTGATTAACCGAGATGAGCACGAACAGTATTACGCTGTGTTCACTGGTAGCGGAATCCGAGT
GTTCGACCTTTCTGGTAACGAGAAGCAAGTTAGGTATCCTAACGGTTCCAACTACATCAAGACCGCTAATCCAC
GTAACGACCTGCGAATGGTTACTGTAGCAGACTATACGTTCATCGTTAACCGTAACGTTGTTGCACAGAAGAAC
ACAAAGTCTGTCAACTTACCGAATTACAACCCTAATCAAGACGGATTGATTAACGTTCGTGGTGGTCAGTATGG
TAGGGAACTAATTGTACACATTAACGGTAAAGACGTTGCGAAGTATAAGATACCAGATGGTAGTCAACCTGAAC
ACGTAAACAATACGGATGCCCAATGGTTAGCTGAAGAGTTAGCCAAGCAGATGCGCACTAACTTGTCTGATTGG
ACTGTAAATGTAGGGCAAGGGTTCATCCATGTGACCGCACCTAGTGGTCAACAGATTGACTCCTTCACGACTAA
AGATGGCTACGCAGACCAGTTGATTAACCCTGTGACCCACTACGCTCAGTCGTTCTCTAAGCTGCCACCTAATG
CTCCTAACGGCTACATGGTGAAAATCGTAGGGGACGCCTCTAAGTCTGCCGACCAGTATTACGTTCGGTATGAC
GCTGAGCGGAAAGTTTGGACTGAGACTTTAGGTTGGAACACTGAGGACCAAGTTCTATGGGAAACCATGCCACA
CGCTCTTGTGCGAGCCGCTGACGGTAATTTCGACTTCAAGTGGCTTGAGTGGTCTCCTAAGTCTTGTGGTGACG

Figure 10 (CONTD.)

TTGACACCAACCCTTGGCCTTCTTTTGTTGGTTCAAGTATTAACGATGTGTTCTTCTTCCGTAACCGCTTAGGA
TTCCTTAGTGGGGAGAACATCATATTGAGTCGTACAGCCAAATACTTCAACTTCTACCCTGCGTCCATTGCGAA
CCTTAGTGATGACGACCCTATAGACGTAGCTGTGAGTACCAACCGAATAGCAATCCTTAAGTACGCCGTTCCGT
TCTCAGAAGAGTTACTCATCTGGTCCGATGAAGCACAATTCGTCCTGACTGCCTCGGGTACTCTCACATCTAAG
TCGGTTGAGTTGAACCTAACGACCCAGTTTGACGTACAGGACCGAGCGAGACCTTTTGGGATTGGGCGTAATGT
CTACTTTGCTAGTCCGAGGTCCAGCTTCACGTCCATCCACAGGTACTACGCTGTGCAGGATGTCAGTTCCGTTA
AGAATGCTGAGGACATTACATCACACGTTCCTAACTACATCCCTAATGGTGTGTTCAGTATTTGCGGAAGTGGT
ACGGAAAACTTCTGTTCGGTACTATCTCACGGGGACCCTAGTAAAATCTTCATGTACAAATTCCTGTACCTGAA
CGAAGAGTTAAGGCAACAGTCGTGGTCTCATTGGGACTTTGGGGAAAACGTACAGGTTCTAGCTTGTCAGAGTA
TCAGCTCAGATATGTATGTGATTCTTCGCAATGAGTTCAATACGTTCCTAGCTAGAATCTCTTTCACTAAGAAC
GCCATTGACTTACAGGGAGAACCCTATCGTGCCTTTATGGACATGAAGATTCGATACACGATTCCTAGTGGAAC
ATACAACGATGACACATTCACTACCTCTATTCATATTCCAACAATTTATGGTGCAAACTTCGGGAGGGGCAAAA
TCACTGTATTGGAGCCTGATGGTAAGATAACCGTGTTTGAGCAACCTACGGCTGGGTGGAATAGCGACCCTTGG
CTGAGACTCAGCGGTAACTTGGAGGGACGCATGGTGTACATTGGGTTCAACATTAACTTCGTATATGAGTTCTC
TAAGTTCCTCATCAAGCAGACTGCCGACGACGGGTCTACCTCCACGGAAGACATTGGGCGCTTACAGTTACGCC
GAGCGTGGGTTAACTACGAGAACTCTGGTACGTTTGACATTTATGTTGAGAACCAATCGTCTAACTGGAAGTAC
ACAATGGCTGGTGCCCGATTAGGCTCTAACACTCTGAGGGCTGGGAGACTGAACTTAGGGACCGGACAATATCG
ATTCCCTGTGGTTGGTAACGCCAAGTTCAACACTGTATACATCTTGTCAGATGAGACTACCCCTCTGAACATCA
TTGGGTGTGGCTGGGAAGGTAACTACTTACGGAGAAGTTCCGGTATTTAATTAAATATTCTCCCTGTGGTGGCT
CGAAATTAATACGACTCACTATAGGGAGAACAATACGACTACGGGAGGGTTTTCTTATGATGACTATAAGACCT
ACTAAAAGTACAGACTTTGAGGTATTCACTCCGGCTCACCATGACATTCTTGAAGCTAAGGCTGCTGGTATTGA
GCCGAGTTTCCCTGATGCTTCCGAGTGTGTCACGTTGAGCCTCTATGGGTTCCCTCTAGCTATCGGTGGTAACT
GCGGGGACCAGTGCTGGTTCGTTACGAGCGACCAAGTGTGGCGACTTAGTGGAAAGGCTAAGCGAAAGTTCCGT
AAGTTAATCATGGAGTATCGCGATAAGATGCTTGAGAAGTATGATACTCTTTGGAATTACGTATGGGTAGGCAA
TACGTCCCACATTCGTTTCCTCAAGACTATCGGTGCGGTATTCCATGAAGAGTACACACGAGATGGTCAATTTC
AGTTATTTACAATCACGAAAGGAGGATAACCATATGTGTTGGGCAGCCGCAATACCTATCGCTATATCTGGCGC
TCAGGCTATCAGTGGTCAGAACGCTCAGGCCAAAATGATTGCCGCTCAGACCGCTGCTGGTCGTCGTCAAGCTA
TGGAAATCATGAGGCAGACGAACATCCAGAATGCTGACCTATCGTTGCAAGCTCGAAGTAAACTTGAGGAAGCG
TCCGCCGAGTTGACCTCACAGAACATGCAGAAGGTCCAAGCTATTGGGTCTATCCGAGCGGCTATCGGAGAGAG
TATGCTTGAAGGTTCCTCAATGGACCGCATTAAGCGAGTCACAGAAGGACAGTTCATTCGGGAAGCCAATATGG
TAACTGAGAACTATCGCCGTGACTACCAAGCAATCTTCGCACAGCAACTTGGTGGTACTCAAAGTGCTGCAAGT
CAGATTGACGAAATCTATAAGAGCGAACAGAAACAGAAGAGTAAGCTACAGATGGTTCTGGACCCACTGGCTAT
CATGGGGTCTTCCGCTGCGAGTGCTTACGCATCCGGTGCGTTCGACTCTAAGTCCACAACTAAGGCACCTATTG
TTGCCGCTAAAGGAACCAAGACGGGGAGGTAATGAGCTATGAGTAAAATTGAATCTGCCCTTCAAGCGGCACAA
CCGGGACTCTCTCGGTTACGTGGTGGTGCTGGAGGTATGGGCTATCGTGCAGCAACCACTCAGGCCGAACAGCC
AAGGTCAAGCCTATTGGACACCATTGGTCGGTTCGCTAAGGCTGGTGCCGATATGTATACCGCTAAGGAACAAC
GAGCACGAGACCTAGCTGATGAACGCTCTAACGAGATTATCCGTAAGCTGACCCCTGAGCAACGTCGAGAAGCT
CTCAACAACGGGACCCTTCTGTATCAGGATGACCCATACGCTATGGAAGCACTCCGAGTCAAGACTGGTCGTAA
CGCTGCGTATCTTGTGGACGATGACGTTATGCAGAAGATAAAAGAGGGTGTCTTCCGTACTCGCGAAGAGATGG
AAGAGTATCGCCATAGTCGCCTTCAAGAGGGCGCTAAGGTATACGCTGAGCAGTTCGGCATCGACCCTGAGGAC
GTTGATTATCAGCGTGGTTTCAACGGGGACATTACCGAGCGTAACATCTCGCTGTATGGTGCGCATGATAACTT
CTTGAGCCAGCAAGCTCAGAAGGGCGCTATCATGAACAGCCGAGTGGAACTCAACGGTGTCCTTCAAGACCCTG
ATATGCTGCGTCGTCCAGACTCTGCTGACTTCTTTGAGAAGTATATCGACAACGGTCTGGTTACTGGCGCAATC
CCATCTGATGCTCAAGCCACACAGCTTATAAGCCAAGCGTTCAGTGACGCTTCTAGCCGTGCTGGTGGTGCTGA
CTTCCTGATGCGAGTCGGTGACAAGAAGGTAACACTTAACGGAGCCACTACGACTTACCGAGAGTTGATTGGTG
AGGAACAGTGGAACGCTCTCATGGTCACAGCACAACGTTCTCAGTTTGAGACTGACGCGAAGCTGAACGAGCAG
TATCGCTTGAAGATTAACTCTGCGCTGAACCAAGAGGACCCAAGGACAGCTTGGGAGATGCTTCAAGGTATCAA
GGCTGAACTAGATAAGGTCCAACCTGATGAGCAGATGACACCACAACGTGAGTGGCTAATCTCCGCACAGGAAC
AAGTTCAGAATCAGATGAACGCATGGACGAAAGCTCAGGCCAAGGCTCTGGACGATTCCATGAAGTCAATGAAC
AAACTTGACGTAATCGACAAGCAATTCCAGAAGCGAATCAACGGTGAGTGGGTCTCAACGGATTTTAAGGATAT
GCCAGTCAACGAGAACACTGGTGAGTTCAAGCATAGCGATATGGTTAACTACGCCAATAAGAAGCTCGCTGAGA
TTGACAGTATGGACATTCCAGACGGTGCCAAGGATGCTATGAAGTTGAAGTACCTTCAAGCGGACTCTAAGGAC

Figure 10 (CONTD.)

GGAGCATTCCGTACAGCCATCGGAACCATGGTCACTGACGCTGGTCAAGAGTGGTCTGCCGCTGTGATTAACGG
TAAGTTACCAGAACGAACCCCAGCTATGGATGCTCTGCGCAGAATCCGCAATGCTGACCCTCAGTTGATTGCTG
CGCTATACCCAGACCAAGCTGAGCTATTCCTGACGATGGACATGATGGACAAGCAGGGTATTGACCCTCAGGTT
ATTCTTGATGCCGACCGACTGACTGTTAAGCGGTCCAAAGAGCAACGCTTTGAGGATGATAAAGCATTCGAGTC
TGCACTGAATGCATCTAAGGCTCCTGAGATTGCCCGTATGCCAGCGTCACTGCGCGAATCTGCACGTAAGATTT
ATGACTCCGTTAAGTATCGCTCGGGGAACGAAAGCATGGCTATGGAGCAGATGACCAAGTTCCTTAAGGAATCT
ACCTACACGTTCACTGGTGATGATGTTGACGGTGATACCGTTGGTGTGATTCCTAAGAATATGATGCAGGTTAA
CTCTGACCCGAAATCATGGGAGCAAGGTCGGGATATTCTGGAGGAAGCACGTAAGGGAATCATTGCGAGCAACC
CTTGGATAACCAATAAGCAACTGACCATGTATTCTCAAGGTGACTCCATTTACCTTATGGACACCACAGGTCAA
GTCAGAGTCCGATACGACAAAGAGTTACTCTCGAAGGTCTGGAGTGAGAACCAGAAGAAACTCGAAGAGAAAGC
TCGTGAGAAGGCTCTGGCTGATGTGAACAAGCGAGCACCTATAGTTGCCGCTACGAAGGCCCGTGAAGCTGCTG
CTAAACGAGTCCGAGAGAAACGTAAACAGACTCCTAAGTTCATCTACGGACGTAAGGAGTAACTAAAGGCTACA
TAAGGAGGCCCTAAATGGATAAGTACGATAAGAACGTACCAAGTGATTATGATGGTCTGTTCCAAAAGGCTGCT
GATGCCAACGGGGTCTCTTATGACCTTTTACGTAAAGTCGCTTGGACAGAATCACGATTTGTGCCTACAGCAAA
ATCTAAGACTGGACCATTAGGCATGATGCAATTTACCAAGGCAACCGCTAAGGCCCTCGGTCTGCGAGTTACCG
ATGGTCCAGACGACGACCGACTGAACCCTGAGTTAGCTATTAATGCTGCCGCTAAGCAACTTGCAGGTCTGGTA
GGGAAGTTTGATGGCGATGAACTCAAAGCTGCCCTTGCGTACAACCAAGGCGAGGGACGCTTGGGTAATCCACA
ACTTGAGGCGTACTCTAAGGGAGACTTCGCATCAATCTCTGAGGAGGGACGTAACTACATGCGTAACCTTCTGG
ATGTTGCTAAGTCACCTATGGCTGGACAGTTGGAAACTTTTGGTGGCATAACCCCAAAGGGTAAAGGCATTCCG
GCTGAGGTAGGATTGGCTGGAATTGGTCACAAGCAGAAAGTAACACAGGAACTTCCTGAGTCCACAAGTTTTGA
CGTTAAGGGTATCGAACAGGAGGCTACGGCGAAACCATTCGCCAAGGACTTTTGGGAGACCCACGGAGAAACAC
TTGACGAGTACAACAGTCGTTCAACCTTCTTCGGATTCAAAAATGCTGCCGAAGCTGAACTCTCCAACTCAGTC
GCTGGGATGGCTTTCCGTGCTGGTCGTCTCGATAATGGTTTTGATGTGTTTAAAGACACCATTACGCCGACTCG
CTGGAACTCTCACATCTGGACTCCAGAGGAGTTAGAGAAGATTCGAACAGAGGTTAAGAACCCTGCGTACATCA
ACGTTGTAACTGGTGGTTCCCCTGAGAACCTCGATGACCTCATTAAATTGGCTAACGAGAACTTTGAGAATGAC
TCCCGCGCTGCCGAGGCTGGCCTAGGTGCCAAACTGAGTGCTGGTATTATTGGTGCTGGTGTGGACCCGCTTAG
CTATGTTCCTATGGTCGGTGTCACTGGTAAGGGCTTTAAGTTAATCAATAAGGCTCTTGTAGTTGGTGCCGAAA
GTGCTGCTCTGAACGTTGCATCCGAAGGTCTCCGTACCTCCGTAGCTGGTGGTGACGCAGACTATGCGGGTGCT
GCCTTAGGTGGCTTTGTGTTTGGCGCAGGCATGTCTGCAATCAGTGACGCTGTAGCTGCTGGACTGAAACGCAG
TAAACCAGAAGCTGAGTTCGACAATGAGTTCATCGGTCCTATGATGCGATTGGAAGCCCGTGAGACAGCACGAA
ACGCCAACTCTGCGGACCTCTCTCGGATGAACACTGAGAACATGAAGTTTGAAGGTGAACATAATGGTGTCCCT
TATGAGGACTTACCAACAGAGAGAGGTGCCGTGGTGTTACATGATGGCTCCGTTCTAAGTGCAAGCAACCCAAT
CAACCCTAAGACTCTAAAAGAGTTCTCCGAGGTTGACCCTGAGAAGGCTGCGCGAGGAATCAAACTGGCTGGGT
TCACCGAGATTGGCTTGAAGACCTTGGGGTCTGACGATGCTGACATCCGTAGAGTGGCTATCGACCTCGTTCGC
TCTCCTACTGGTATGCAGTCTGGTGCCTCAGGTAAGTTCGGTGCAACAGCTTCTGACATCCATGAGAGACTTCA
TGGTACTGACCAGCGTACTTATAATGACTTGTACAAAGCAATGTCTGACGCTATGAAAGACCCTGAGTTCTCTA
CTGGCGGCGCTAAGATGTCCCGTGAAGAAACTCGATACACTATCTACCGTAGAGCGGCACTAGCTATTGAGCGT
CCAGAACTACAGAAGGCACTCACTCCGTCTGAGAGAATCGTTATGGACATCATTAAGCGTCACTTTGACACCAA
GCGTGAACTTATGGAAAACCCAGCAATATTCGGTAACACAAAGGCTGTGAGTATCTTCCCTGAGAGTCGCCACA
AAGGTACTTACGTTCCTCACGTATATGACCGTCATGCCAAGGCGCTGATGATTCAACGCTACGGTGCCGAAGGT
TTGCAGGAAGGGATTGCCCGCTCATGGATGAACAGCTACGTCTCCAGACCTGAGGTCAAGGCCAGAGTCGATGA
GATGCTTAAGGAATTACACGGGGTGAAGGAAGTAACACCAGAGATGGTAGAGAAGTACGCTATGGATAAGGCTT
ATGGTATCTCCCACTCAGACCAGTTCACCAACAGTTCCATAATAGAAGAGAACATTGAGGGCTTAGTAGGTATC
GAGAATAACTCATTCCTTGAGGCACGTAACTTGTTTGATTCGGACCTATCCATCACTATGCCAGACGGACAGCA
ATTCTCAGTGAATGACCTAAGGGACTTCGATATGTTCCGCATCATGCCAGCGTATGACCGCCGTGTCAATGGTG
ACATCGCCATCATGGGGTCTACTGGTAAAACCACTAAGGAACTTAAGGATGAGATTTTGGCTCTCAAAGCGAAA
GCTGAGGGAGACGGTAAGAAGACTGGCGAGGTACATGCTTTAATGGATACCGTTAAGATTCTTACTGGTCGTGC
TAGACGCAATCAGGACACTGTGTGGGAAACCTCACTGCGTGCCATCAATGACCTAGGGTTCTTCGCTAAGAACG
CCTACATGGGTGCTCAGAACATTACGGAGATTGCTGGGATGATTGTCACTGGTAACGTTCGTGCTCTAGGGCAT
GGTATCCCAATTCTGCGTGATACACTCTACAAGTCTAAACCAGTTTCAGCTAAGGAACTCAAGGAACTCCATGC
GTCTCTGTTCGGGAAGGAGGTGGACCAGTTGATTCGGCCTAAACGTGCTGACATTGTGCAGCGCCTAAGGGAAG
CAACTGATACCGGACCTGCCGTGGCGAACATCGTAGGGACCTTGAAGTATTCAACACAGGAACTGGCTGCTCGC

Figure 10 (CONTD.)

TCTCCGTGGACTAAGCTACTGAACGGAACCACTAACTACCTTCTGGATGCTGCGCGTCAAGGTATGCTTGGGGA
TGTTATTAGTGCCACCCTAACAGGTAAGACTACCCGCTGGGAGAAAGAAGGCTTCCTTCGTGGTGCCTCCGTAA
CTCCTGAGCAGATGGCTGGCATCAAGTCTCTCATCAAGGAACATATGGTACGCGGTGAGGACGGGAAGTTTACC
GTTAAGGACAAGCAAGCGTTCTCTATGGACCCACGGGCTATGGACTTATGGAGACTGGCTGACAAGGTAGCTGA
TGAGGCAATGCTGCGTCCACATAAGGTGTCCTTACAGGATTCCCATGCGTTCGGAGCACTAGGTAAGATGGTTA
TGCAGTTTAAGTCTTTCACTATCAAGTCCCTTAACTCTAAGTTCCTGCGAACCTTCTATGATGGATACAAGAAC
AACCGAGCGATTGACGCTGCGCTGAGCATCATCACCTCTATGGGTCTCGCTGGTGGTTTCTATGCTATGGCTGC
ACACGTCAAAGCATACGCTCTGCCTAAGGAGAAACGTAAGGAGTACTTGGAGCGTGCACTGGACCCAACCATGA
TTGCCCACGCTGCGTTATCTCGTAGTTCTCAATTGGGTGCTCCTTTGGCTATGGTTGACCTAGTTGGTGGTGTT
TTAGGGTTCGAGTCCTCCAAGATGGCTCGCTCTACGATTCTACCTAAGGACACCGTGAAGGAACGTGACCCAAA
CAAACCGTACACCTCTAGAGAGGTAATGGGCGCTATGGGTTCAAACCTTCTGGAACAGATGCCTTCGGCTGGCT
TTGTGGCTAACGTAGGGGCTACCTTAATGAATGCTGCTGGCGTGGTCAACTCACCTAATAAAGCAACCGAGCAG
GACTTCATGACTGGTCTTATGAACTCCACAAAAGAGTTAGTACCGAACGACCCATTGACTCAACAGCTTGTGTT
GAAGATTTATGAGGCGAACGGTGTTAACTTGAGGGAGCGTAGGAAATAATACGACTCACTATAGGGAGAGGCGA
AATAATCTTCTCCCTGTAGTCTCTTAGATTTACTTTAAGGAGGTCAAATGGCTAACGTAATTAAAACCGTTTTG
ACTTACCAGTTAGATGGCTCCAATCGTGATTTTAATATCCCGTTTGAGTATCTAGCCCGTAAGTTCGTAGTGGT
AACTCTTATTGGTGTAGACCGAAAGGTCCTTACGATTAATACAGACTATCGCTTTGCTACACGTACTACTATCT
CTCTGACAAAGGCTTGGGGTCCAGCCGATGGCTACACGACCATCGAGTTACGTCGAGTAACCTCCACTACCGAC
CGATTGGTTGACTTTACGGATGGTTCAATCCTCCGCGCGTATGACCTTAACGTCGCTCAGATTCAAACGATGCA
CGTAGCGGAAGAGGCCCGTGACCTCACTACGGATACTATCGGTGTCAATAACGATGGTCACTTGGATGCTCGTG
GTCGTCGAATTGTGAACCTAGCGAACGCCGTGGATGACCGCGATGCTGTTCCGTTTGGTCAACTAAAGACCATG
AACCAGAACTCATGGCAAGCACGTAATGAAGCCTTACAGTTCCGTAATGAGGCTGAGACTTTCAGAAACCAAGC
GGAGGGCTTTAAGAACGAGTCCAGTACCAACGCTACGAACACAAAGCAGTGGCGCGATGAGACCAAGGGTTTCC
GAGACGAAGCCAAGCGGTTCAAGAATACGGCTGGTCAATACGCTACATCTGCTGGGAACTCTGCTTCCGCTGCG
CATCAATCTGAGGTAAACGCTGAGAACTCTGCCACAGCATCCGCTAACTCTGCTCATTTGGCAGAACAGCAAGC
AGACCGTGCGGAACGTGAGGCAGACAAGCTGGAAAATTACAATGGATTGGCTGGTGCAATTGATAAGGTAGATG
GAACCAATGTGTACTGGAAAGGAAATATTCACGCTAACGGGCGCCTTTACATGACCACAAACGGTTTTGACTGT
GGCCAGTATCAACAGTTCTTTGGTGGTGTCACTAATCGTTACTCTGTCATGGAGTGGGGAGATGAGAACGGATG
GCTGATGTATGTTCAACGTAGAGAGTGGACAACAGCGATAGGCGGTAACATCCAGTTAGTAGTAAACGGACAGA
TCATCACCCAAGGTGGAGCCATGACCGGTCAGCTAAAATTGCAGAATGGGCATGTTCTTCAATTAGAGTCCGCA
TCCGACAAGGCGCACTATATTCTATCTAAAGATGGTAACAGGAATAACTGGTACATTGGTAGAGGGTCAGATAA
CAACAATGACTGTACCTTCCACTCCTATGTACATGGTACGACCTTAACACTCAAGCAGGACTATGCAGTAGTTA
ACAAACACTTCCACGTAGGTCAGGCCGTTGTGGCCACTGATGGTAATATTCAAGGTACTAAGTGGGGAGGTAAA
TGGCTGGATGCTTACCTACGTGACAGCTTCGTTGCGAAGTCCAAGGCGTGGACTCAGGTGTGGTCTGGTAGTGC
TGGCGGTGGGGTAAGTGTGACTGTTTCACAGGATCTCCGCTTCCGCAATATCTGGATTAAGTGTGCCAACAACT
CTTGGAACTTCTTCCGTACTGGCCCCGATGGAATCTACTTCATAGCCTCTGATGGTGGATGGTTACGATTCCAA
ATACACTCCAACGGTCTCGGATTCAAGAATATTGCAGACAGTCGTTCAGTACCTAATGCAATCATGGTGGAGAA
CGAGTAATTGGTAAATCACAAGGAAAGACGTGTAGTCCACGGATGGACTCTCAAGGAGGTACAAGGTGCTATCA
TTAGACTTTAACAACGAATTGATTAAGGCTGCTCCAATTGTTGGGACGGGTGTAGCAGATGTTAGTGCTCGACT
GTTCTTTGGGTTAAGCCTTAACGAATGGTTCTACGTTGCTGCTATCGCCTACACAGTGGTTCAGATTGGTGCCA
AGGTAGTCGATAAGATGATTGACTGGAAGAAAGCCAATAAGGAGTGATATGTATGGAAAAGGATAAGAGCCTTA
TTACATTCTTAGAGATGTTGGACACTGCGATGGCTCAGCGTATGCTTGCGGACCTTTCGGACCATGAGCGTCGC
TCTCCGCAACTCTATAATGCTATTAACAAACTGTTAGACCGCCACAAGTTCCAGATTGGTAAGTTGCAGCCGGA
TGTTCACATCTTAGGTGGCCTTGCTGGTGCTCTTGAAGAGTACAAAGAGAAAGTCGGTGATAACGGTCTTACGG
ATGATGATATTTACACATTACAGTGATATACTCAAGGCCACTACAGATAGTGGTCTTTATGGATGTCATTGTCT
ATACGAGATGCTCCTACGTGAAATCTGAAAGTTAACGGGAGGCATTATGCTAGAATTTTTACGTAAGCTAATCC
CTTGGGTTCTCGCTGGGATGCTATTCGGGTTAGGATGGCATCTAGGGTCAGACTCAATGGACGCTAAATGGAAA
CAGGAGGTACACAATGAGTACGTTAAGAGAGTTGAGGCTGCGAAGAGCACTCAAAGAGCAATCGATGCGGTATC
TGCTAAGTATCAAGAAGACCTTGCCGCGCTGGAAGGGAGCACTGATAGGATTATTTCTGATTTGCGTAGCGACA
ATAAGCGGTTGCGCGTCAGAGTCAAAACTACCGGAACCTCCGATGGTCAGTGTGGATTCGAGCCTGATGGTCGA
GCCGAACTTGACGACCGAGATGCTAAACGTATTCTCGCAGTGACCCAGAAGGGTGACGCATGGATTCGTGCGTT
ACAGGATACTATTCGTGAACTGCAACGTAAGTAGGAAATCAAGTAAGGAGGCAATGTGTCTACTCAATCCAATC

Figure 10 (CONTD.)

GTAATGCGCTCGTAGTGGCGCAACTGAAAGGAGACTTCGTGGCGTTCCTATTCGTCTTATGGAAGGCGCTAAAC
CTACCGGTGCCCACTAAGTGTCAGATTGACATGGCTAAGGTGCTGGCGAATGGAGACAACAAGAAGTTCATCTT
ACAGGCTTTCCGTGGTATCGGTAAGTCGTTCATCACATGTGCGTTCGTTGTGTGGTCCTTATGGAGAGACCCTC
AGTTGAAGATACTTATCGTATCAGCCTCTAAGGAGCGTGCAGACGCTAACTCCATCTTTATTAAGAACATCATT
GACCTGCTGCCATTCCTATCTGAGTTAAAGCCAAGACCCGGACAGCGTGACTCGGTAATCAGCTTTGATGTAGG
CCCAGCCAATCCTGACCACTCTCCTAGTGTGAAATCAGTAGGTATCACTGGTCAGTTAACTGGTAGCCGTGCTG
ACATTATCATTGCGGATGACGTTGAGATTCCGTCTAACAGCGCAACTATGGGTGCCCGTGAGAAGCTATGGACT
CTGGTTCAGGAGTTCGCTGCGTTACTTAAACCGCTGCCTTCCTCTCGCGTTATCTACCTTGGTACACCTCAGAC
AGAGATGACTCTCTATAAGGAACTTGAGGATAACCGTGGGTACACAACCATTATCTGGCCTGCTCTGTACCCAA
GGACACGTGAAGAGAACCTCTATTACTCACAGCGTCTTGCTCCTATGTTACGCGCTGAGTACGATGAGAACCCT
GAGGCACTTGCTGGGACTCCAACAGACCCAGTGCGCTTTGACCGTGATGACCTGCGCGAGCGTGAGTTGGAATA
CGGTAAGGCTGGCTTTACGCTACAGTTCATGCTTAACCCTAACCTTAGTGATGCCGAGAAGTACCCGCTGAGGC
TTCGTGACGCTATCGTAGCGGCCTTAGACTTAGAGAAGGCCCCAATGCATTACCAGTGGCTTCCGAACCGTCAG
AACATCATTGAGGACCTTCCTAACGTTGGCCTTAAGGGTGATGACCTGCATACGTACCACGATTGTTCCAACAA
CTCAGGTCAGTACCAACAGAAGATTCTGGTCATTGACCCTAGTGGTCGCGGTAAGGACGAAACAGGTTACGCTG
TGCTGTACACACTGAACGGTTACATCTACCTTATGGAAGCTGGAGGTTTCCGTGATGGCTACTCCGATAAGACC
CTTGAGTTACTCGCTAAGAAGGCAAAGCAATGGGGAGTCCAGACGGTTGTCTACGAGAGTAACTTCGGTGACGG
TATGTTCGGTAAGGTATTCAGTCCTATCCTTCTTAAACACCACAACTGTGCGATGGAAGAGATTCGTGCCCGTG
GTATGAAAGAGATGCGTATTTGCGATACCCTTGAGCCAGTCATGCAGACTCACCGCCTTGTAATTCGTGATGAG
GTCATTAGGGCCGACTACCAGTCCGCTCGTGACGTAGACGGTAAGCATGACGTTAAGTACTCGTTGTTCTACCA
GATGACCCGTATCACTCGTGAGAAAGGCGCTCTGGCTCATGATGACCGATTGGATGCCCTTGCGTTAGGCATTG
AGTATCTCCGTGAGTCCATGCAGTTGGATTCCGTTAAGGTCGAGGGTGAAGTACTTGCTGACTTCCTTGAGGAA
CACATGATGCGTCCTACGGTTGCTGCTACGCATATCATTGAGATGTCTGTGGGAGGAGTTGATGTGTACTCTGA
GGACGATGAGGGTTACGGTACGTCTTTCATTGAGTGGTGATTTATGCATTAGGACTGCATAGGGATGCACTATA
GACCACGGATGGTCAGTTCTTTAAGTTACTGAAAAGACACGATAAATTAATACGACTCACTATAGGGAGAGGAG
GGACGAAAGGTTACTATATAGATACTGAATGAATACTTATAGAGTGCATAAAGTATGCATAATGGTGTACCTAG
AGTGACCTCTAAGAATGGTGATTATATTGTATTAGTATCACCTTAACTTAAGGACCAACATAAAGGGAGGAGAC
TCATGTTCCGCTTATTGTTGAACCTACTGCGGCATAGAGTCACCTACCGATTTCTTGTGGTACTTTGTGCTGCC
CTTGGGTACGCATCTCTTACTGGAGACCTCAGTTCACTGGAGTCTGTCGTTTGCTCTATACTCACTTGTAGCGA
TTAGGGTCTTCCTGACCGACTGATGGCTCACCGAGGGATTCAGCGGTATGATTGCATCACACCACTTCATCCCT
ATAGAGTCAAGTCCTAAGGTATACCCATAAAGAGCCTCTAATGGTCTATCCTAAGGTCTATACCTAAAGATAGG
CCATCCTATCAGTGTCACCTAAAGAGGGTCTTAGAGAGGGCCTATGGAGTTCCTATAGGGTCCTTTAAAATATA
CCATAAAAATCTGAGTGACTATCTCACAGTGTACGGACCTAAAGTTCCCCCATAGGGGGTACCTAAAGCCCAGC
CAATCACCTAAAGTCAACCTTCGGTTGACCTTGAGGGTTCCCTAAGGGTTGGGGATGACCCTTGGGTTTGTCTT
TGGGTGTTACCTTGAGTGTCTCTCTGTGTCCCT

Figure 11

>DLPECO2_Double_lumi Enterobacteria phage T7, complete genome (SEQ ID NO: 2)

TCTCACAGTGTACGGACCTAAAGTTCCCCCATAGGGGGTACCTAAAGCCCAGCCAATCACCTAAAGTCAACCTT
CGGTTGACCTTGAGGGTTCCCTAAGGGTTGGGGATGACCCTTGGGTTTGTCTTTGGGTGTTACCTTGAGTGTCT
CTCTGTGTCCCTATCTGTTACAGTCTCCTAAAGTATCCTCCTAAAGTCACCTCCTAACGTCCATCCTAAAGCCA
ACACCTAAAGCCTACACCTAAAGACCCATCAAGTCAACGCCTATCTTAAAGTTTAAACATAAAGACCAGACCTA
AAGACCAGACCTAAAGACACTACATAAAGACCAGACCTAAAGACGCCTTGTTGTTAGCCATAAAGTGATAACCT
TTAATCATTGTCTTTATTAATACAACTCACTATAAGGAGAGACAACTTAAAGAGACTTAAAAGATTAATTTAAA
ATTTATCAAAAAGAGTATTGACTTAAAGTCTAACCTATAGGATACTTACAGCCATCGAGAGGGACACGGCGAAT
AGCCATCCCAATCGACACCGGGGTCAACCGGATAAGTAGACAGCCTGATAAGTCGCACGAAAAACAGGTATTGA
CAACATGAAGTAACATGCAGTAAGATACAAATCGCTAGGTAACACTAGCAGCGTCAACCGGGCGCACAGTGCCT
TCTAGGTGACTTAAGCGCACCACGGCACATAAGGTGAAACAAAACGGTTGACAACATGAAGTAAACACGGTACG
ATGTACCACATGAAACGACAGTGAGTCACCACACTGAAAGGTGATGCGGTCTAACGAAACCTGACCTAAGACGC
TCTTTAACAATCTGGTAAATAGCTCTTGAGTGCATGACTAGCGGATAACTCAAGGGTATCGCAAGGTGCCCTTT
ATGATATTCACTAATAACTGCACGAGGTAACACAAGATGGCTATGTCTAACATGACTTACAACAACGTTTTCGA
CCACGCTTACGAAATGCTGAAAGAAAACATCCGTTATGATGACATCCGTGACACTGATGACCTGCACGATGCTA
TTCACATGGCTGCCGATAATGCAGTTCCGCACTACTACGCTGACATCTTTAGCGTAATGGCAAGTGAGGGCATT
GACCTTGAGTTCGAAGACTCTGGTCTGATGCCTGACACCAAGGACGTAATCCGCATCCTGCAAGCGCGTATCTA
TGAGCAATTAACGATTGACCTCTGGGAAGACGCAGAAGACTTGCTCAATGAATACTTGGAGGAAGTCGAGGAGT
ACGAGGAGGATGAAGAGTAATGTCTACTACCAACGTGCAATACGGTCTGACCGCTCAAACTGTACTTTTCTATA
GCGACATGGTGCGCTGTGGCTTTAACTGGTCACTCGCAATGGCACAGCTCAAAGAACTGTACGAAAACAACAAG
GCAATAGCTTTAGAATCTGCTGAGTGATAGACTCAAGGTCGCTCCTAGCGAGTGGCCTTTATGATTATCACTTT
ACTTATGAGGGAGTAATGTATATGCTTACTATCGGTCTACTCACCGCTCTAGGTCTAGCTGTAGGTGCATCCTT
TGGGAAGGCTTTAGGTGTAGCTGTAGGTTCCTACTTTACCGCTTGCATCATCATAGGAATCATCAAAGGGGCAC
TACGCAAATGATGAAGCACTACGTTATGCCAATCCACACGTCCAACGGGGCAACCGTATGTACACCTGATGGGT
TCGCAATGAAACAACGAATCGAACGCCTTAAGCGTGAACTCCGCATTAACCGCAAGATTAACAAGATAGGTTCC
GGCTATGACAGAACGCACTGATGGCTTAAAGAAAGGTTATATGCCCAATGGCACACTATACGCTGCAAATCGGC
GAATAGTGAGAACTTGGCGAGAGAACAACCTCGAACGCCGCAAGGACAAGAGAGGGCGGCGTGGCATAGACGAA
AGGAAAAGGTTAAAGCCAAGAAACTCGCCGCACTTGAACAGGCACTAGCCAACACACTGAACGCTATCTCATAA
CGAACATAAAGGACACAATGCAATGAACATTACCGACATCATGAACGCTATCGACGCAATCAAAGCACTGCCAA
TCTGTGAACTTGACAAGCGTCAAGGTATGCTTATCGACTTACTGGTCGAGATGGTCAACAGCGAGACGTGTGAT
GGCGAGCTAACCGAACTAAATCAGGCACTTGAGCATCAAGATTGGTGGACTACCTTGAAGTGTCTCACGGCTGA
CGCAGGGTTCAAGATGCTCGGTAATGGTCACTTCTCGGCTGCTTATAGTCACCCGCTGCTACCTAACAGAGTGA
TTAAGGTGGGCTTTAAGAAAGAGGATTCAGGCGCAGCCTATACCGCATTCTGCCGCATGTATCAGGGTCGTCCT
GGTATCCCTAACGTCTACGATGTACAGCGCCACGCTGGATGCTATACGGTGGTACTTGACGCACTTAAGGATTG
CGAGCGTTTCAACAATGATGCCCATTATAAATACGCTGAGATTGCAAGCGACATCATTGATTGCAATTCGGATG
AGCATGATGAGTTAACTGGATGGGATGGTGAGTTTGTTGAAACTTGTAAACTAATCCGCAAGTTCTTTGAGGGC
ATCGCCTCATTCGACATGCATAGCGGGAACATCATGTTCTCAAATGGAGACGTACCATACATCACCGACCCGGT
ATCATTCTCGCAGAAGAAAGACGGTGGCGCATTCAGCATCGACCCTGAGGAACTCATCAAGGAAGTCGAGGAAG
TCGCACGACAGAAAGAAATTGACCGCGCTAAGGCCCGTAAAGAACGTCACGAGGGGCGCTTAGAGGCACGCAGA
TTCAAACGTCGCAACCGCAAGGCACGTAAAGCACACAAAGCTAAGCGCGAAAGAATGCTTGCTGCGTGGCGATG
GGCTGAACGTCAAGAACGGCGTAACCATGAGGTAGCTGTAGATGTACTAGGAAGAACCAATAACGCTATGCTCT
GGGTCAACATGTTCTCTGGGGACTTTAAGGCGCTTGAGGAACGAATCGCGCTGCACTGGCGTAATGCTGACCGG
ATGGCTATCGCTAATGGTCTTACGCTCAACATTGATAAGCAACTTGACGCAATGTTAATGGGCTGATAGTCTTA
TCTTACAGGTCATCTGCGGGTGGCCTGAATAGGTACGATTTACTAACTGGAAGAGGCACTAAATGAACACGATT
AACATCGCTAAGAACGACTTCTCTGACATCGAACTGGCTGCTATCCCGTTCAACACTCTGGCTGACCATTACGG
TGAGCGTTTAGCTCGCGAACAGTTGGCCCTTGAGCATGAGTCTTACGAGATGGGTGAAGCACGCTTCCGCAAGA
TGTTTGAGCGTCAACTTAAAGCTGGTGAGGTTGCGGATAACGCTGCCGCCAAGCCTCTCATCACTACCCTACTC
CCTAAGATGATTGCACGCATCAACGACTGGTTTGAGGAAGTGAAAGCTAAGCGCGGCAAGCGCCCGACAGCCTT

Figure 11 (CONTD.)

CCAGTTCCTGCAAGAAATCAAGCCGGAAGCCGTAGCGTACATCACCATTAAGACCACTCTGGCTTGCCTAACCA
GTGCTGACAATACAACCGTTCAGGCTGTAGCAAGCGCAATCGGTCGGGCCATTGAGGACGAGGCTCGCTTCGGT
CGTATCCGTGACCTTGAAGCTAAGCACTTCAAGAAAAACGTTGAGGAACAACTCAACAAGCGCGTAGGGCACGT
CTACAAGAAAGCATTTATGCAAGTTGTCGAGGCTGACATGCTCTCTAAGGGTCTACTCGGTGGCGAGGCGTGGT
CTTCGTGGCATAAGGAAGACTCTATTCATGTAGGAGTACGCTGCATCGAGATGCTCATTGAGTCAACCGGAATG
GTTAGCTTACACCGCCAAAATGCTGGCGTAGTAGGTCAAGACTCTGAGACTATCGAACTCGCACCTGAATACGC
TGAGGCTATCGCAACCCGTGCAGGTGCGCTGGCTGGCATCTCTCCGATGTTCCAACCTTGCGTAGTTCCTCCTA
AGCCGTGGACTGGCATTACTGGTGGTGGCTATTGGGCTAACGGTCGTCGTCCTCTGGCGCTGGTGCGTACTCAC
AGTAAGAAAGCACTGATGCGCTACGAAGACGTTTACATGCCTGAGGTGTACAAAGCGATTAACATTGCGCAAAA
CACCGCATGGAAAATCAACAAGAAAGTCCTAGCGGTCGCCAACGTAATCACCAAGTGGAAGCATTGTCCGGTCG
AGGACATCCCTGCGATTGAGCGTGAAGAACTCCCGATGAAACCGGAAGACATCGACATGAATCCTGAGGCTCTC
ACCGCGTGGAAACGTGCTGCCGCTGCTGTGTACCGCAAGGACAAGGCTCGCAAGTCTCGCCGTATCAGCCTTGA
GTTCATGCTTGAGCAAGCCAATAAGTTTGCTAACCATAAGGCCATCTGGTTCCCTTACAACATGGACTGGCGCG
GTCGTGTTTACGCTGTGTCAATGTTCAACCCGCAAGGTAACGATATGACCAAAGGACTGCTTACGCTGGCGAAA
GGTAAACCAATCGGTAAGGAAGGTTACTACTGGCTGAAAATCCACGGTGCAAACTGTGCGGGTGTCGATAAGGT
TCCGTTCCCTGAGCGCATCAAGTTCATTGAGGAAAACCACGAGAACATCATGGCTTGCGCTAAGTCTCCACTGG
AGAACACTTGGTGGGCTGAGCAAGATTCTCCGTTCTGCTTCCTTGCGTTCTGCTTTGAGTACGCTGGGGTACAG
CACCACGGCCTGAGCTATAACTGCTCCCTTCCGCTGGCGTTTGACGGGTCTTGCTCTGGCATCCAGCACTTCTC
CGCGATGCTCCGAGATGAGGTAGGTGGTCGCGCGGTTAACTTGCTTCCTAGTGAAACCGTTCAGGACATCTACG
GGATTGTTGCTAAGAAAGTCAACGAGATTCTACAAGCAGACGCAATCAATGGGACCGATAACGAAGTAGTTACC
GTGACCGATGAGAACACTGGTGAAATCTCTGAGAAAGTCAAGCTGGGCACTAAGGCACTGGCTGGTCAATGGCT
GGCTTACGGTGTTACTCGCAGTGTGACTAAGCGTTCAGTCATGACGCTGGCTTACGGGTCCAAAGAGTTCGGCT
TCCGTCAACAAGTGCTGGAAGATACCATTCAGCCAGCTATTGATTCCGGCAAGGGTCTGATGTTCACTCAGCCG
AATCAGGCTGCTGGATACATGGCTAAGCTGATTTGGGAATCTGTGAGCGTGACGGTGGTAGCTGCGGTTGAAGC
AATGAACTGGCTTAAGTCTGCTGCTAAGCTGCTGGCTGCTGAGGTCAAAGATAAGAAGACTGGAGAGATTCTTC
GCAAGCGTTGCGCTGTGCATTGGGTAACTCCTGATGGTTTCCCTGTGTGGCAGGAATACAAGAAGCCTATTCAG
ACGCGCTTGAACCTGATGTTCCTCGGTCAGTTCCGCTTACAGCCTACCATTAACACCAACAAAGATAGCGAGAT
TGATGCACACAAACAGGAGTCTGGTATCGCTCCTAACTTTGTACACAGCCAAGACGGTAGCCACCTTCGTAAGA
CTGTAGTGTGGGCACACGAGAAGTACGGAATCGAATCTTTTGCACTGATTCACGACTCCTTCGGTACCATTCCG
GCTGACGCTGCGAACCTGTTCAAAGCAGTGCGCGAAACTATGGTTGACACATATGAGTCTTGTGATGTACTGGC
TGATTTCTACGACCAGTTCGCTGACCAGTTGCACGAGTCTCAATTGGACAAAATGCCAGCACTTCCGGCTAAAG
GTAACTTGAACCTCCGTGACATCTTAGAGTCGGACTTCGCGTTCGCGTAACGCCAAATCAATACGACTCACTAT
AGAGGGACAAACTCAAGGTCATTCGCAAGAGTGGCCTTTATGATTGACCTTCTTCCGGTTAATACGACTCACTA
TAGGAGAACCTTAAGGTTTAACTTTAAGACCCTTAAGTGTTAATTAGAGATTTAGGAGATTCAACATGGTCTTC
ACACTCGAAGATTTCGTTGGGGACTGGCGACAGACAGCCGGCTACAACCTGGACCAAGTCCTTGAACAGGGAGG
TGTGTCCAGTTTGTTTCAGAATCTCGGGGTGTCCGTAACTCCGATCCAAAGGATTGTCCTGAGCGGTGAAAATG
GGCTGAAGATCGACATCCATGTCATCATCCCGTATGAAGGTCTGAGCGGCGACCAAATGGGCCAGATCGAAAAA
ATTTTTAAGGTGGTGTACCCTGTGGATGATCATCACTTTAAGGTGATCCTGCACTATGGCACACTGGTAATCGA
CGGGGTTACGCCGAACATGATCGACTATTTCGGACGGCCGTATGAAGGCATCGCCGTGTTCGACGGCAAAAAGA
TCACTGTAACAGGGACCCTGTGGAACGGCAACAAAATTATCGACGAGCGCCTGATCAACCCCGACGGCTCCCTG
CTGTTCCGAGTAACCATCAACGGAGTGACCGGCTGGCGGCTGTGCGAACGCATTCTGGCGTAAAGGAGGTAAAC
ATATGACCATGATTACGGATTCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGCACCGATCGCCCTTC
CCAACAGTTGCGCAGCCTGAATGGCGAATGGAAATTAAAGAATTACTAAGAGAGGACTTTAAGTATGCGTAACT
TCGAAAAGATGACCAAACGTTCTAACCGTAATGCTCGTGACTTCGAGGCAACCAAAGGTCGCAAGTTGAATAAG
ACTAAGCGTGACCGCTCTCACAAGCGTAGCTGGGAGGGTCAGTAAGATGGGACGTTTATATAGTGGTAATCTGG
CAGCATTCAAGGCAGCAACAAACAAGCTGTTCCAGTTAGACTTAGCGGTCATTTATGATGACTGGTATGATGCC
TATACAAGAAAAGATTGCATACGGTTACGTATTGAGGACAGGAGTGGAAACCTGATTGATACTAGCACCTTCTA
CCACCACGACGAGGACGTTCTGTTCAATATGTGTACTGATTGGTTGAACCATATGTATGACCAGTTGAAGGACT
GGAAGTAATACGACTCAGTATAGGGACAATGCTTAAGGTCGCTCTCTAGGAGTGGCCTTAGTCATTTAACCAAT
AGGAGATAAACATTATGATGAACATTAAGACTAACCCGTTTAAAGCCGTGTCTTTCGTAGAGTCTGCCATTAAG
AAGGCTCTGGATAACGCTGGGTATCTTATCGCTGAAATCAAGTACGATGGTGTACGCGGGAACATCTGCGTAGA

Figure 11 (CONTD.)

CAATACTGCTAACAGTTACTGGCTCTCTCGTGTATCTAAAACGATTCCGGCACTGGAGCACTTAAACGGGTTTG
ATGTTCGCTGGAAGCGTCTACTGAACGATGACCGTTGCTTCTACAAAGATGGCTTTATGCTTGATGGGGAACTC
ATGGTCAAGGGCGTAGACTTTAACACAGGGTCCGGCCTACTGCGTACCAAATGGACTGACACGAAGAACCAAGA
GTTCCATGAAGAGTTATTCGTTGAACCAATCCGTAAGAAAGATAAAGTTCCCTTTAAGCTGCACACTGGACACC
TTCACATAAAACTGTACGCTATCCTCCCGCTGCACATCGTGGAGTCTGGAGAAGACTGTGATGTCATGACGTTG
CTCATGCAGGAACACGTTAAGAACATGCTGCCTCTGCTACAGGAATACTTCCCTGAAATCGAATGGCAAGCGGC
TGAATCTTACGAGGTCTACGATATGGTAGAACTACAGCAACTGTACGAGCAGAAGCGAGCAGAAGGCCATGAGG
GTCTCATTGTGAAAGACCCGATGTGTATCTATAAGCGCGGTAAGAAATCTGGCTGGTGGAAAATGAAACCTGAG
AACGAAGCTGACGGTATCATTCAGGGTCTGGTATGGGGTACAAAAGGTCTGGCTAATGAAGGTAAAGTGATTGG
TTTTGAGGTGCTTCTTGAGAGTGGTCGTTTAGTTAACGCCACGAATATCTCTCGCGCCTTAATGGATGAGTTCA
CTGAGACAGTAAAAGAGGCCACCCTAAGTCAATGGGGATTCTTTAGCCCATACGGTATTGGCGACAACGATGCT
TGTACTATTAACCCTTACGATGGCTGGGCGTGTCAAATTAGCTACATGGAGGAAACACCTGATGGCTCTTTGCG
GCACCCATCGTTCGTAATGTTCCGTGGCACCGAGGACAACCCTCAAGAGAAAATGTAATCACACTGGCTCACCT
TCGGGTGGGCCTTTCTGCGTTTATAAGGAGACACTTTATGTTTAAGAAGGTTGGTAAATTCCTTGCGGCTTTGG
CAGCTATCCTGACGCTTGCGTATATTCTTGCGGTATACCCTCAAGTAGCACTAGTAGTAGTTGGCGCTTGTTAC
TTAGCGGCAGTGTGTGCTTGCGTGTGGAGTATAGTTAACTGGTAATACGACTCACTAAAGGAGGTACACACCAT
GATGTACTTAATGCCATTACTCATCGTCATTGTAGGATGCCTTGCGCTCCACTGTAGCGATGATGATATGCCAG
ATGGTCACGCTTAATACGACTCACTAAAGGAGACACTATATGTTTCGACTTCATTACAACAAAAGCGTTAAGAA
TTTCACGGTTCGCCGTGCTGACCGTTCAATCGTATGTGCGAGCGAGCGCCGAGCTAAGATACCTCTTATTGGTA
ACACAGTTCCTTTGGCACCGAGCGTCCACATCATTATCACCCGTGGTGACTTTGAGAAAGCAATAGACAAGAAA
CGTCCGGTTCTTAGTGTGGCAGTGACCCGCTTCCCGTTCGTCCGTCTGTTACTCAAACGAATCAAGGAGGTGTT
CTGATGGGACTGTTAGATGGTGAAGCCTGGGAAAAAGAAAACCCGCCAGTACAAGCAACTGGGTGTATAGCTTG
CTTAGAGAAAGATGACCGTTATCCACACACCTGTAACAAAGGAGCTAACGATATGACCGAACGTGAACAAGAGA
TGATCATTAAGTTGATAGACAATAATGAAGGTCGCCCAGATGATTTGAATGGCTGCGGTATTCTCTGCTCCAAT
GTCCCTTGCCACCTCTGCCCCGCAAATAACGATCAAAAGATAACCTTAGGTGAAATCCGAGCGATGGACCCACG
TAAACCACATCTGAATAAACCTGAGGTAACTCCTACAGATGACCAGCCTTCCGCTGAGACAATCGAAGGTGTCA
CTAAGCCTTCCCACTACATGCTGTTTGACGACATTGAGGCTATCGAAGTGATTGCTCGTTCAATGACCGTTGAG
CAGTTCAAGGGATACTGCTTCGGTAACATCTTAAAGTACAGACTACGTGCTGGTAAGAAGTCAGAGTTAGCGTA
CTTAGAGAAAGACCTAGCGAAAGCAGACTTCTATAAAGAACTCTTTGAGAAACATAAGGATAAATGTTATGCAT
AACTTCAAGTCAACCCCACCTGCCGACAGCCTATCTGATGACTTCACATCTTGCTCAGAGTGGTGCCGAAAGAT
GTGGGAAGAGACATTCGACGATGCGTACATCAAGCTGTATGAACTTTGGAAATCGAGAGGTCAATGACTATGTC
AAACGTAAATACAGGTTCACTTAGTGTGGACAATAAGAAGTTTTGGGCTACCGTAGAGTCCTCGGAGCATTCCT
TCGAGGTTCCAATCTACGCTGAGACCCTAGACGAAGCTCTGGAGTTAGCCGAATGGCAATACGTTCCGGCTGGC
TTTGAGGTTACTCGTGTGCGTCCTTGTGTAGCACCGAAGTAATACGACTCACTATTAGGGAAGACTCCCTCTGA
GAAACCAAACGAAACCTAAAGGAGATTAACATTATGGCTAAGAAGATTTTCACCTCTGCGCTGGGTACCGCTGA
ACCTTACGCTTACATCGCCAAGCCGGACTACGGCAACGAAGAGCGTGGCTTTGGGAACCCTCGTGGTGTCTATA
AAGTTGACCTGACTATTCCCAACAAAGACCCGCGCTGCCAGCGTATGGTCGATGAAATCGTGAAGTGTCACGAA
GAGGCTTATGCTGCTGCCGTTGAGGAATACGAAGCTAATCCACCTGCTGTAGCTCGTGGTAAGAAACCGCTGAA
ACCGTATGAGGGTGACATGCCGTTCTTCGATAACGGTGACGGTACGACTACCTTTAAGTTCAAATGCTACGCGT
CTTTCCAAGACAAGAAGACCAAAGAGACCAAGCACATCAATCTGGTTGTGGTTGACTCAAAAGGTAAGAAGATG
GAAGACGTTCCGATTATCGGTGGTGGCTCTAAGCTGAAAGTTAAATATTCTCTGGTTCCATACAAGTGGAACAC
TGCTGTAGGTGCGAGCGTTAAGCTGCAACTGGAATCCGTGATGCTGGTCGAACTGGCTACCTTTGGTGGCGGTG
AAGACGATTGGGCTGACGAAGTTGAAGAGAACGGCTATGTTGCCTCTGGTTCTGCCAAAGCGAGCAAACCACGC
GACGAAGAAAGCTGGGACGAAGACGACGAAGAGTCCGAGGAAGCAGACGAAGACGGAGACTTCTAAGTGGAACT
GCGGGAGAAAATCCTTGAGCGAATCAAGGTGACTTCCTCTGGGTGTTGGGAGTGGCAGGGCGCTACGAACAATA
AAGGGTACGGGCAGGTGTGGTGCAGCAATACCGGAAAGGTTGTCTACTGTCATCGCGTAATGTCTAATGCTCCG
AAAGGTTCTACCGTCCTGCACTCCTGTGATAATCCATTATGTTGTAACCCTGAACACCTATCCATAGGAACTCC
AAAAGAGAACTCCACTGACATGGTAAATAAGGGTCGCTCACACAAGGGGTATAAACTTTCAGACGAAGACGTAA
TGGCAATCATGGAGTCCAGCGAGTCCAATGTATCCTTAGCTCGCACCTATGGTGTCTCCCAACAGACTATTTGT
GATATACGCAAAGGGAGGCGACATGGCAGGTTACGGCGCTAAAGGAATCCGAAAGGTTGGAGCGTTTCGCTCTG
GCCTAGAGGACAAGGTTTCAAAGCAGTTGGAATCAAAAGGTATTAAATTCGAGTATGAAGAGTGGAAAGTGCCT
TATGTAATTCCGGCGAGCAATCACACTTACACTCCAGACTTCTTACTTCCAAACGGTATATTCGTTGAGACAAA

Figure 11 (CONTD.)

GGGTCTGTGGGAAAGCGATGATAGAAAGAAGCACTTATTAATTAGGGAGCAGCACCCCGAGCTAGACATCCGTA
TTGTCTTCTCAAGCTCACGTACTAAGTTATACAAAGGTTCTCCAACGTCTTATGGAGAGTTCTGCGAAAAGCAT
GGTATTAAGTTCGCTGATAAACTGATACCTGCTGAGTGGATAAAGGAACCCAAGAAGGAGGTCCCCTTTGATAG
ATTAAAAAGGAAAGGAGGAAAGAAATAATGGCTCGTGTACAGTTTAAACAACGTGAATCTACTGACGCAATCTT
TGTTCACTGCTCGGCTACCAAGCCAAGTCAGAATGTTGGTGTCCGTGAGATTCGCCAGTGGCACAAAGAGCAGG
GTTGGCTCGATGTGGGATACCACTTTATCATCAAGCGAGACGGTACTGTGGAGGCAGGACGAGATGAGATGGCT
GTAGGCTCTCACGCTAAGGGTTACAACCACAACTCTATCGGCGTCTGCCTTGTTGGTGGTATCGACGATAAAGG
TAAGTTCGACGCTAACTTTACGCCAGCCCAAATGCAATCCCTTCGCTCACTGCTTGTCACACTGCTGGCTAAGT
ACGAAGGCGCTGTGCTTCGCGCCCATCATGAGGTGGCGCCGAAGGCTTGCCCTTCGTTCGACCTTAAGCGTTGG
TGGGAGAAGAACGAACTGGTCACTTCTGACCGTGGATAATTAATTGAACTCACTAAAGGGAGACCACAGCGGTT
TCCCTTTGTTCGCATTGGAGGTCAAATAATGCGCAAGTCTTATAAACAATTCTATAAGGCTCCGAGGAGGCATA
TCCAAGTGTGGGAGGCAGCCAATGGGCCTATACCAAAAGGTTATTATATAGACCACATTGACGGCAATCCACTC
AACGACGCCTTAGACAATCTCCGTCTGGCTCTCCCAAAAGAAAACTCATGGAACATGAAGACTCCAAAGAGCAA
TACCTCAGGACTAAAGGGACTGAGTTGGAGCAAGGAAAGGGAGATGTGGAGAGGCACTGTAACAGCTGAGGGTA
AACAGCATAACTTTCGTAGTAGAGATCTATTGGAAGTCGTTGCGTGGATTTATAGAACTAGGAGGGAATTGCAT
GGACAATTCGCACGATTCCGATAGTGTATTTCTTTACCACATTCCTTGTGACAACTGTGGGAGTAGTGATGGGA
ACTCGCTGTTCTCTGACGGACACACGTTCTGCTACGTATGCGAGAAGTGGACTGCTGGTAATGAAGACACTAAA
GAGAGGGCTTCAAAACGGAAACCCTCAGGAGGTAAACCAATGACTTACAACGTGTGGAACTTCGGGGAATCCAA
TGGACGCTACTCCGCGTTAACTGCGAGAGGAATCTCCAAGGAAACCTGTCAGAAGGCTGGCTACTGGATTGCCA
AAGTAGACGGTGTGATGTACCAAGTGGCTGACTATCGGGACCAGAACGGCAACATTGTGAGTCAGAAGGTTCGA
GATAAAGATAAGAACTTTAAGACCACTGGTAGTCACAAGAGTGACGCTCTGTTCGGGAAGCACTTGTGGAATGG
TGGTAAGAAGATTGTCGTTACAGAAGGTGAAATCGACATGCTTACCGTGATGGAACTTCAAGACTGTAAGTATC
CTGTAGTGTCGTTGGGTCACGGTGCCTCTGCCGCTAAGAAGACATGCGCTGCCAACTACGAATACTTTGACCAG
TTCGAACAGATTATCTTAATGTTCGATATGGACGAAGCAGGGCGCAAAGCAGTCGAAGAGGCTGCACAGGTTCT
ACCTGCTGGTAAGGTACGAGTGGCAGTTCTTCCGTGTAAGGATGCAAACGAGTGTCACCTAAATGGTCACGACC
GTGAAATCATGGAGCAAGTGTGGAATGCTGGTCCTTGGATTCCTGATGGTGTGGTATCGGCTCTTTCGTTACGT
GAACGAATCCGTGAGCACCTATCGTCCGAGGAATCAGTAGGTTTACTTTTCAGTGGCTGCACTGGTATCAACGA
TAAGACCTTAGGTGCCCGTGGTGGTGAAGTCATTATGGTCACTTCCGGTTCCGGTATGGGTAAGTCAACGTTCG
TCCGTCAACAAGCTCTACAATGGGGCACAGCGATGGGCAAGAAGGTAGGCTTAGCGATGCTTGAGGAGTCCGTT
GAGGAGACCGCTGAGGACCTTATAGGTCTACACAACCGTGTCCGACTGAGACAATCCGACTCACTAAAGAGAGA
GATTATTGAGAACGGTAAGTTCGACCAATGGTTCGATGAACTGTTCGGCAACGATACGTTCCATCTATATGACT
CATTCGCCGAGGCTGAGACGGATAGACTGCTCGCTAAGCTGGCCTACATGCGCTCAGGCTTGGGCTGTGACGTA
ATCATTCTAGACCACATCTCAATCGTCGTATCCGCTTCTGGTGAATCCGATGAGCGTAAGATGATTGACAACCT
GATGACCAAGCTCAAAGGGTTCGCTAAGTCAACTGGGGTGGTGCTGGTCGTAATTTGTCACCTTAAGAACCCAG
ACAAAGGTAAAGCACATGAGGAAGGTCGCCCCGTTTCTATTACTGACCTACGTGGTTCTGGCGCACTACGCCAA
CTATCTGATACTATTATTGCCCTTGAGCGTAATCAGCAAGGCGATATGCCTAACCTTGTCCTCGTTCGTATTCT
CAAGTGCCGCTTTACTGGTGATACTGGTATCGCTGGCTACATGGAATACAACAAGGAAACCGGATGGCTTGAAC
CATCAAGTTACTCAGGGGAAGAAGAGTCACACTCAGAGTCAACAGACTGGTCCAACGACACTGACTTCTGACAG
GATTCTTGATGACTTTCCAGACGACTACGAGAAGTTTCGCTGGAGAGTCCCATTCTAATACGACTCACTAAAGG
AGACACACCATGTTCAAACTGATTAAGAAGTTAGGCCAACTGCTGGTTCGTATGTACAACGTGGAAGCCAAGCG
ACTGAACGATGAGGCTCGTAAAGAGGCCACACAGTCACGCGCTCTGGCGATTCGCTCCAACGAACTGGCTGACA
GTGCATCCACTAAAGTTACCGAGGCTGCCCGTGTGGCAAACCAAGCTCAACAGCTTTCCAAATTCTTTGAGTAA
TCAAACAGGAGAAACCATTATGTCTAACGTAGCTGAAACTATCCGTCTATCCGATACAGCTGACCAGTGGAACC
GTCGAGTCCACATCAACGTTCGCAACGGTAAGGCGACTATGGTTTACCGCTGGAAGGACTCTAAGTCCTCTAAG
AATCACACTCAGCGTATGACGTTGACAGATGAGCAAGCACTGCGTCTGGTCAATGCGCTTACCAAAGCTGCCGT
GACAGCAATTCATGAAGCTGGTCGCGTCAATGAAGCTATGGCTATCCTCGACAAGATTGATAACTAAGAGTGGT
ATCCTCAAGGTCGCCAAAGTGGTGGCCTTCATGAATACTATTCGACTCACTATAGGAGATATTACCATGCGTGA
CCCTAAAGTTATCCAAGCAGAAATCGCTAAACTGGAAGCTGAACTGGAGGACGTTAAGTACCATGAAGCTAAGA
CTCGCTCCGCTGTTCACATCTTGAAGAACTTAGGCTGGACTTGGACAAGACAGACTGGCTGGAAGAAACCAGAA
GTTACCAAGCTGAGTCATAAGGTGTTCGATAAGGACACTATGACCCACATCAAGGCTGGTGATTGGGTTAAGGT
TGACATGGGAGTTGTTGGTGGATACGGCTACGTCCGCTCAGTTAGTGGCAAATATGCACAAGTGTCATACATCA
CAGGTGTTACTCCACGCGGTGCAATCGTTGCCGATAAGACCAACATGATTCACACAGGTTTCTTGACAGTTGTT

Figure 11 (CONTD.)

TCATATGAAGAGATTGTTAAGTCACGATAATCAATAGGAGAAATCAATATGATCGTTTCTGACATCGAAGCTAA
CGCCCTCTTAGAGAGCGTCACTAAGTTCCACTGCGGGGTTATCTACGACTACTCCACCGCTGAGTACGTAAGCT
ACCGTCCGAGTGACTTCGGTGCGTATCTGGATGCGCTGGAAGCCGAGGTTGCACGAGGCGGTCTTATTGTGTTC
CACAACGGTCACAAGTATGACGTTCCTGCATTGACCAAACTGGCAAAGTTGCAATTGAACCGAGAGTTCCACCT
TCCTCGTGAGAACTGTATTGACACCCTTGTGTTGTCACGTTTGATTCATTCCAACCTCAAGGACACCGATATGG
GTCTTCTGCGTTCCGGCAAGTTGCCCGGAAAACGCTTTGGGTCTCACGCTTTGGAGGCGTGGGGTTATCGCTTA
GGCGAGATGAAGGGTGAATACAAAGACGACTTTAAGCGTATGCTTGAAGAGCAGGGTGAAGAATACGTTGACGG
AATGGAGTGGTGGAACTTCAACGAAGAGATGATGGACTATAACGTTCAGGACGTTGTGGTAACTAAAGCTCTCC
TTGAGAAGCTACTCTCTGACAAACATTACTTCCCTCCTGAGATTGACTTTACGGACGTAGGATACACTACGTTC
TGGTCAGAATCCCTTGAGGCCGTTGACATTGAACATCGTGCTGCATGGCTGCTCGCTAAACAAGAGCGCAACGG
GTTCCCGTTTGACACAAAAGCAATCGAAGAGTTGTACGTAGAGTTAGCTGCTCGCCGCTCTGAGTTGCTCCGTA
AATTGACCGAAACGTTCGGCTCGTGGTATCAGCCTAAAGGTGGCACTGAGATGTTCTGCCATCCGCGAACAGGT
AAGCCACTACCTAAATACCCTCGCATTAAGACACCTAAAGTTGGTGGTATCTTTAAGAAGCCTAAGAACAAGGC
ACAGCGAGAAGGCCGTGAGCCTTGCGAACTTGATACCCGCGAGTACGTTGCTGGTGCTCCTTACACCCCAGTTG
AACATGTTGTGTTTAACCCTTCGTCTCGTGACCACATTCAGAAGAAACTCCAAGAGGCTGGGTGGGTCCCGACC
AAGTACACCGATAAGGGTGCTCCTGTGGTGGACGATGAGGTACTCGAAGGAGTACGTGTAGATGACCCTGAGAA
GCAAGCCGCTATCGACCTCATTAAAGAGTACTTGATGATTCAGAAGCGAATCGGACAGTCTGCTGAGGGAGACA
AAGCATGGCTTCGTTATGTTGCTGAGGATGGTAAGATTCATGGTTCTGTTAACCCTAATGGAGCAGTTACGGGT
CGTGCGACCCATGCGTTCCCAAACCTTGCGCAAATTCCGGGTGTACGTTCTCCTTATGGAGAGCAGTGTCGCGC
TGCTTTTGGCGCTGAGCACCATTTGGATGGGATAACTGGTAAGCCTTGGGTTCAGGCTGGCATCGACGCATCCG
GTCTTGAGCTACGCTGCTTGGCTCACTTCATGGCTCGCTTTGATAACGGCGAGTACGCTCACGAGATTCTTAAC
GGCGACATCCACACTAAGAACCAGATAGCTGCTGAACTACCTACCCGAGATAACGCTAAGACGTTCATCTATGG
GTTCCTCTATGGTGCTGGTGATGAGAAGATTGGACAGATTGTTGGTGCTGGTAAAGAGCGCGGTAAGGAACTCA
AGAAGAAATTCCTTGAGAACACCCCCGCGATTGCAGCACTCCGCGAGTCTATCCAACAGACACTTGTCGAGTCC
TCTCAATGGGTAGCTGGTGAGCAACAAGTCAAGTGGAAACGCCGCTGGATTAAAGGTCTGGATGGTCGTAAGGT
ACACGTTCGTAGTCCTCACGCTGCCTTGAATACCCTACTGCAATCTGCTGGTGCTCTCATCTGCAAACTGTGGA
TTATCAAGACCGAAGAGATGCTCGTAGAGAAAGGCTTGAAGCATGGCTGGGATGGGGACTTTGCGTACATGGCA
TGGGTACATGATGAAATCCAAGTAGGCTGCCGTACCGAAGAGATTGCTCAGGTGGTCATTGAGACCGCACAAGA
AGCGATGCGCTGGGTTGGAGACCACTGGAACTTCCGGTGTCTTCTGGATACCGAAGGTAAGATGGGTCCTAATT
GGGCGATTTGCCACTGATACAGGAGGCTACTCATGAACGAAAGACACTTAACAGGTGCTGCTTCTGAAATGCTA
GTAGCCTACAAATTTACCAAAGCTGGGTACACTGTCTATTACCCTATGCTGACTCAGAGTAAAGAGGACTTGGT
TGTATGTAAGGATGGTAAATTTAGTAAGGTTCAGGTTAAAACAGCCACAACGGTTCAAACCAACACAGGAGATG
CCAAGCAGGTTAGGCTAGGTGGATGCGGTAGGTCCGAATATAAGGATGGAGACTTTGACATTCTTGCGGTTGTG
GTTGACGAAGATGTGCTTATTTTCACATGGGACGAAGTAAAAGGTAAGACATCCATGTGTGTCGGCAAGAGAAA
CAAAGGCATAAAACTATAGGAGAAATTATTATGGCTATGACAAAGAAATTTAAAGTGTCCTTCGACGTTACCGC
AAAGATGTCGTCTGACGTTCAGGCAATCTTAGAGAAAGATATGCTGCATCTATGTAAGCAGGTCGGCTCAGGTG
CGATTGTCCCCAATGGTAAACAGAAGGAAATGATTGTCCAGTTCCTGACACACGGTATGGAAGGATTGATGACA
TTCGTAGTACGTACATCATTTCGTGAGGCCATTAAGGACATGCACGAAGAGTATGCAGATAAGGACTCTTTCAA
ACAATCTCCTGCAACAGTACGGGAGGTGTTCTGATGTCTGACTACCTGAAAGTGCTGCAAGCAATCAAAAGTTG
CCCTAAGACTTTCCAGTCCAACTATGTACGGAACAATGCGAGCCTCGTAGCGGAGGCCGCTTCCCGTGGTCACA
TCTCGTGCCTGACTACTAGTGGACGTAACGGTGGCGCTTGGGAAATCACTGCTTCCGGTACTCGCTTTCTGAAA
CGAATGGGAGGATGTGTCTAATGTCTCGTGACCTTGTGACTATTCCACGCGATGTGTGGAACGATATACAGGGC
TACATCGACTCTCTGGAACGTGAGAACGATAGCCTTAAGAATCAACTAATGGAAGCTGACGAATACGTAGCGGA
ACTAGAGGAGAAACTTAATGGCACTTCTTGACCTTAAACAATTCTATGAGTTACGTGAAGGCTGCGACGACAAG
GGTATCCTTGTGATGGACGGCGACTGGCTGGTCTTCCAAGCTATGAGTGCTGCTGAGTTTGATGCCTCTTGGGA
GGAAGAGATTTGGCACCGATGCTGTGACCACGCTAAGGCCCGTCAGATTCTTGAGGATTCCATTAAGTCCTACG
AGACCCGTAAGAAGGCTTGGGCAGGTGCTCCAATTGTCCTTGCGTTCACCGATAGTGTTAACTGGCGTAAAGAA
CTGGTTGACCCGAACTATAAGGCTAACCGTAAGGCCGTGAAGAAACCTGTAGGGTACTTTGAGTTCCTTGATGC
TCTCTTTGAGCGCGAAGAGTTCTATTGCATCCGTGAGCCTATGCTTGAGGGTGATGACGTTATGGGAGTTATTG
CTTCCAATCCGTCTGCCTTCGGTGCTCGTAAGGCTGTAATCATCTCTTGCGATAAGGACTTTAAGACCATCCCT
AACTGTGACTTCCTGTGGTGTACCACTGGTAACATCCTGACTCAGACCGAAGAGTCCGCTGACTGGTGGCACCT
CTTCCAGACCATCAAGGGTGACATCACTGATGGTTACTCAGGGATTGCTGGATGGGGTGATACCGCCGAGGACT

Figure 11 (CONTD.)

TCTTGAATAACCCGTTCATAACCGAGCCTAAAACGTCTGTGCTTAAGTCCGGTAAGAACAAAGGCCAAGAGGTT
ACTAAATGGGTTAAACGCGACCCTGAGCCTCATGAGACGCTTTGGGACTGCATTAAGTCCATTGGCGCGAAGGC
TGGTATGACCGAAGAGGATATTATCAAGCAGGGCCAAATGGCTCGAATCCTACGGTTCAACGAGTACAACTTTA
TTGACAAGGAGATTTACCTGTGGAGACCGTAGCGTATATTGGTCTGGGTCTTTGTGTTCTCGGAGTGTGCCTCA
TTTCGTGGGGCCTTTGGGACTTAGCCAGAATAATCAAGTCGTTACACGACACTAAGTGATAAACTCAAGGTCCC
TAAATTAATACGACTCACTATAGGGAGATAGGGGCCTTTACGATTATTACTTTAAGATTTAACTCTAAGAGGAA
TCTTTATTATGTTAACACCTATTAACCAATTACTTAAGAACCCTAACGATATTCCAGATGTACCTCGTGCAACC
GCTGAGTATCTACAGGTTCGATTCAACTATGCGTACCTCGAAGCGTCTGGTCATATAGGACTTATGCGTGCTAA
TGGTTGTAGTGAGGCCCACATCTTGGGTTTCATTCAGGGCCTACAGTATGCCTCTAACGTCATTGACGAGATTG
AGTTACGCAAGGAACAACTAAGAGATGATGGGGAGGATTGACACTATGTGTTTCTCACCGAAAATTAAAACTCC
GAAGATGGATACCAATCAGATTCGAGCCGTTGAGCCAGCGCCTCTGACCCAAGAAGTGTCAAGCGTGGAGTTCG
GTGGGTCTTCTGATGAGACGGATACCGAGGGCACCGAAGTGTCTGGACGCAAAGGCCTCAAGGTCGAACGTGAT
GATTCCGTAGCGAAGTCTAAAGCCAGCGGCAATGGCTCCGCTCGTATGAAATCTTCCATCCGTAAGTCCGCATT
TGGAGGTAAGAAGTGATGTCTGAGTTCACATGTGTGGAGGCTAAGAGTCGCTTCCGTGCAATCCGGTGGACTGT
GGAACACCTTGGGTTGCCTAAAGGATTCGAAGGACACTTTGTGGGCTACAGCCTCTACGTAGACGAAGTGATGG
ACATGTCTGGTTGCCGTGAAGAGTACATTCTGGACTCTACCGGAAAACATGTAGCGTACTTCGCGTGGTGCGTA
AGCTGTGACATTCACCACAAAGGAGACATTCTGGATGTAACGTCCGTTGTCATTAATCCTGAGGCAGACTCTAA
GGGCTTACAGCGATTCCTAGCGAAACGCTTTAAGTACCTTGCGGAACTCCACGATTGCGATTGGGTGTCTCGTT
GTAAGCATGAAGGCGAGACAATGCGTGTATACTTTAAGGAGGTATAAGTTATGGGTAAGAAAGTTAAGAAGGCC
GTGAAGAAAGTCACCAAGTCCGTTAAGAAAGTCGTTAAGGAAGGGGCTCGTCCGGTTAAACAGGTTGCTGGCGG
TCTAGCTGGTCTGGCTGGTGGTACTGGTGAAGCACAGATGGTGGAAGTACCACAAGCTGCCGCACAGATTGTTG
ACGTACCTGAGAAAGAGGTTTCCACTGAGGACGAAGCACAGACAGAAAGCGGACGCAAGAAAGCTCGTGCTGGC
GGTAAGAAATCCTTGAGTGTAGCCCGTAGCTCCGGTGGCGGTATCAACATTTAATCAGGAGGTTATCGTGGAAG
ACTGCATTGAATGGACCGGAGGTGTCAACTCTAAGGGTTATGGTCGTAAGTGGGTTAATGGTAAACTTGTGACT
CCACATAGGCACATCTATGAGGAGACATATGGTCCAGTTCCAACAGGAATTGTGGTGATGCATATCTGCGATAA
CCCTAGGTGCTATAACATAAAGCACCTTACGCTTGGAACTCCAAAGGATAATTCCGAGGACATGGTTACCAAAG
GTAGACAGGCTAAAGGAGAGGAACTAAGCAAGAAACTTACAGAGTCAGACGTTCTCGCTATACGCTCTTCAACC
TTAAGCCACCGCTCCTTAGGAGAACTGTATGGAGTCAGTCAATCAACCATAACGCGAATACTACAGCGTAAGAC
ATGGAGACACATTTAATGGCTGAGAAACGAACAGGACTTGCGGAGGATGGCGCAAAGTCTGTCTATGAGCGTTT
AAAGAACGACCGTGCTCCCTATGAGACACGCGCTCAGAATTGCGCTCAATATACCATCCCATCATTGTTCCCTA
AGGACTCCGATAACGCCTCTACAGATTATCAAACTCCGTGGCAAGCCGTGGGCGCTCGTGGTCTGAACAATCTA
GCCTCTAAGCTCATGCTGGCTCTATTCCCTATGCAGACTTGGATGCGACTTACTATATCTGAATATGAAGCAAA
GCAGTTACTGAGCGACCCCGATGGACTCGCTAAGGTCGATGAGGGCCTCTCGATGGTAGAGCGTATCATCATGA
ACTACATTGAGTCTAACAGTTACCGCGTGACTCTCTTTGAGGCTCTCAAACAGTTAGTCGTAGCTGGTAACGTC
CTGCTGTACCTACCGGAACCGGAAGGGTCAAACTATAATCCCATGAAGCTGTACCGATTGTCTTCTTATGTGGT
CCAACGAGACGCATTCGGCAACGTTCTGCAAATGGTGACTCGTGACCAGATAGCTTTTGGTGCTCTCCCTGAGG
ACATCCGTAAGGCTGTAGAAGGTCAAGGTGGTGAGAAGAAAGCTGATGAGACAATCGACGTGTACACTCACATC
TATCTGGATGAGGACTCAGGTGAATACCTCCGATACGAAGAGGTCGAGGGTATGGAAGTCCAAGGCTCCGATGG
GACTTATCCTAAAGAGGCTTGCCCATACATCCCGATTCGGATGGTCAGACTAGATGGTGAATCCTACGGTCGTT
CGTACATTGAGGAATACTTAGGTGACTTACGGTCCCTTGAAAATCTCCAAGAGGCTATCGTCAAGATGTCCATG
ATTAGCTCTAAGGTTATCGGCTTAGTGAATCCTGCTGGTATCACCCAGCCACGCCGACTGACCAAAGCTCAGAC
TGGTGACTTCGTTACTGGTCGTCCAGAAGACATCTCGTTCCTCCAACTGGAGAAGCAAGCAGACTTTACTGTAG
CTAAAGCCGTAAGTGACGCTATCGAGGCTCGCCTTTCGTTTGCCTTTATGTTGAACTCTGCGGTTCAGCGTACA
GGTGAACGTGTGACCGCCGAAGAGATTCGGTATGTAGCTTCTGAACTTGAAGATACTTTAGGTGGTGTCTACTC
TATCCTTTCTCAAGAATTACAATTGCCTCTGGTACGAGTGCTCTTGAAGCAACTACAAGCCACGCAACAGATTC
CTGAGTTACCTAAGGAAGCCGTAGAGCCAACCATTAGTACAGGTCTGGAAGCAATTGGTCGAGGACAAGACCTT
GATAAGCTGGAGCGGTGTGTCACTGCGTGGGCTGCACTGGCACCTATGCGGGACGACCCTGATATTAACCTTGC
GATGATTAAGTTACGTATTGCCAACGCTATCGGTATTGACACTTCTGGTATTCTACTCACCGAAGAACAGAAGC
AACAGAAGATGGCCCAACAGTCTATGCAAATGGGTATGGATAATGGTGCTGCTGCGCTGGCTCAAGGTATGGCT
GCACAAGCTACAGCTTCACCTGAGGCTATGGCTGCTGCCGCTGATTCCGTAGGTTTACAGCCGGGAATTTAATA
CGACTCACTATAGGGAGACCTCATCTTTGAAATGAGCGATGACAAGAGGTTGGAGTCCTCGGTCTTCCTGTAGT
TCAACTTTAAGGAGACAATAATAATGGCTGAATCTAATGCAGACGTATATGCATCTTTTGGCGTGAACTCCGCT

Figure 11 (CONTD.)

GTGATGTCTGGTGGTTCCGTTGAGGAACATGAGCAGAACATGCTGGCTCTTGATGTTGCTGCCCGTGATGGCGA
TGATGCAATCGAGTTAGCGTCAGACGAAGTGGAAACAGAACGTGACCTGTATGACAACTCTGACCCGTTCGGTC
AAGAGGATGACGAAGGCCGCATTCAGGTTCGTATCGGTGATGGCTCTGAGCCGACCGATGTGGACACTGGAGAA
GAAGGCGTTGAGGGCACCGAAGGTTCCGAAGAGTTTACCCCACTGGGCGAGACTCCAGAAGAACTGGTAGCTGC
CTCTGAGCAACTTGGTGAGCACGAAGAGGGCTTCCAAGAGATGATTAACATTGCTGCTGAGCGTGGCATGAGTG
TCGAGACCATTGAGGCTATCCAGCGTGAGTACGAGGAGAACGAAGAGTTGTCCGCCGAGTCCTACGCTAAGCTG
GCTGAAATTGGCTACACGAAGGCTTTCATTGACTCGTATATCCGTGGTCAAGAAGCTCTGGTGGAGCAGTACGT
AAACAGTGTCATTGAGTACGCTGGTGGTCGTGAACGTTTTGATGCACTGTATAACCACCTTGAGACGCACAACC
CTGAGGCTGCACAGTCGCTGGATAATGCGTTGACCAATCGTGACTTAGCGACCGTTAAGGCTATCATCAACTTG
GCTGGTGAGTCTCGCGCTAAGGCGTTCGGTCGTAAGCCAACTCGTAGTGTGACTAATCGTGCTATTCCGGCTAA
ACCTCAGGCTACCAAGCGTGAAGGCTTTGCGGACCGTAGCGAGATGATTAAAGCTATGAGTGACCCTCGGTATC
GCACAGATGCCAACTATCGTCGTCAAGTCGAACAGAAAGTAATCGATTCGAACTTCTGATAGACTTCGAAATTA
ATACGACTCACTATAGGGAGACCACAACGGTTTCCCTCTAGAAATAATTTTGTTTAACTTTAAGAAGGAGATAT
ACATATGGAGGAGATTCAACATGGTCTTCACACTCGAAGATTTCGTTGGGGACTGGCGACAGACAGCCGGCTAC
AACCTGGACCAAGTCCTTGAACAGGGAGGTGTGTCCAGTTTGTTTCAGAATCTCGGGGTGTCCGTAACTCCGAT
CCAAAGGATTGTCCTGAGCGGTGAAAATGGGCTGAAGATCGACATCCATGTCATCATCCCGTATGAAGGTCTGA
GCGGCGACCAAATGGGCCAGATCGAAAAAATTTTTAAGGTGGTGTACCCTGTGGATGATCATCACTTTAAGGTG
ATCCTGCACTATGGCACACTGGTAATCGACGGGGTTACGCCGAACATGATCGACTATTTCGGACGGCCGTATGA
AGGCATCGCCGTGTTCGACGGCAAAAAGATCACTGTAACAGGGACCCTGTGGAACGGCAACAAAATTATCGACG
AGCGCCTGATCAACCCCGACGGCTCCCTGCTGTTCCGAGTAACCATCAACGGAGTGACCGGCTGGCGGCTGTGC
GAACGCATTCTGGCGTAAAGGAGGTAAACATATGACCATGATTACGGATTCACTGGCCGTCGTTTTACAACGTC
GTGACTGGGAAAACCCTGGCGTTACCCAACTTAATCGCCTTGCAGCACATCCCCCTTTCGCCAGCTGGCGTAAT
AGCGAAGAGGCCCGCACCGATCGCCCTTCCCAACAGTTGCGCAGCCTGAATGGCGAATGGCATGACTGGTGGAC
AGCAAATGGGTACTAACCAAGGTAAAGGTGTAGTTGCTGCTGGAGATAAACTGGCGTTGTTCTTGAAGGTATTT
GGCGGTGAAGTCCTGACTGCGTTCGCTCGTACCTCCGTGACCACTTCTCGCCACATGGTACGTTCCATCTCCAG
CGGTAAATCCGCTCAGTTCCCTGTTCTGGGTCGCACTCAGGCAGCGTATCTGGCTCCGGGCGAGAACCTCGACG
ATAAACGTAAGGACATCAAACACACCGAGAAGGTAATCACCATTGACGGTCTCCTGACGGCTGACGTTCTGATT
TATGATATTGAGGACGCGATGAACCACTACGACGTTCGCTCTGAGTATACCTCTCAGTTGGGTGAATCTCTGGC
GATGGCTGCGGATGGTGCGGTTCTGGCTGAGATTGCCGGTCTGTGTAACGTGGAAAGCAAATATAATGAGAACA
TCGAGGGCTTAGGTACTGCTACCGTAATTGAGACCACTCAGAACAAGGCCGCACTTACCGACCAAGTTGCGCTG
GGTAAGGAGATTATTGCGGCTCTGACTAAGGCTCGTGCGGCTCTGACCAAGAACTATGTTCCGGCTGCTGACCG
TGTGTTCTACTGTGACCCAGATAGCTACTCTGCGATTCTGGCAGCACTGATGCCGAACGCAGCAAACTACGCTG
CTCTGATTGACCCTGAGAAGGGTTCTATCCGCAACGTTATGGGCTTTGAGGTTGTAGAAGTTCCGCACCTCACC
GCTGGTGGTGCTGGTACCGCTCGTGAGGGCACTACTGGTCAGAAGCACGTCTTCCCTGCCAATAAAGGTGAGGG
TAATGTCAAGGTTGCTAAGGACAACGTTATCGGCCTGTTCATGCACCGCTCTGCGGTAGGTACTGTTAAGCTGC
GTGACTTGGCTCTGGAGCGCGCTCGCCGTGCTAACTTCCAAGCGGACCAGATTATCGCTAAGTACGCAATGGGC
CACGGTGGTCTTCGCCCAGAAGCTGCTGGTGCAGTGGTTTTCAAAGTGGAGTAATGCTGGGGGTGGCCTCAACG
GTCGCTGCTAGTCCCGAAGAGGCGAGTGTTACTTCAACAGAAGAAACCTTAACGCCAGCACAGGAGGCCGCACG
CACCCGCGCTGCTAACAAAGCCCGAAAGGAAGCTGAGTTGGCTGCTGCCACCGCTGAGCAATAACTAGCATAAC
CCCTTGGGGCCTCTAAACGGGTCTTGAGGGGTTTTTTGCTGAAAGGAGGAACTATATGCGCTCATACGATATGA
ACGTTGAGACTGCCGCTGAGTTATCAGCTGTGAACGACATTCTGGCGTCTATCGGTGAACCTCCGGTATCAACG
CTGGAAGGTGACGCTAACGCAGATGCAGCGAACGCTCGGCGTATTCTCAACAAGATTAACCGACAGATTCAATC
TCGTGGATGGACGTTCAACATTGAGGAAGGCATAACGCTACTACCTGATGTTTACTCCAACCTGATTGTATACA
GTGACGACTATTTATCCCTAATGTCTACTTCCGGTCAATCCATCTACGTTAACCGAGGTGGCTATGTGTATGAC
CGAACGAGTCAATCAGACCGCTTTGACTCTGGTATTACTGTGAACATTATTCGTCTCCGCGACTACGATGAGAT
GCCTGAGTGCTTCCGTTACTGGATTGTCACCAAGGCTTCCCGTCAGTTCAACAACCGATTCTTTGGGGCACCGG
AAGTAGAGGGTGTACTCCAAGAAGAGGAAGATGAGGCTAGACGTCTCTGCATGGAGTATGAGATGGACTACGGT
GGGTACAATATGCTGGATGGAGATGCGTTCACTTCTGGTCTACTGACTCGCTAACATTAATAAATAAGGAGGCT
CTAATGGCACTCATTAGCCAATCAATCAAGAACTTGAAGGGTGGTATCAGCCAACAGCCTGACATCCTTCGTTA
TCCAGACCAAGGGTCACGCCAAGTTAACGGTTGGTCTTCGGAGACCGAGGGCCTCCAAAAGCGTCCACCTCTTG
TTTTCTTAAATACACTTGGAGACAACGGTGCGTTAGGTCAAGCTCCGTACATCCACCTGATTAACCGAGATGAG
CACGAACAGTATTACGCTGTGTTCACTGGTAGCGGAATCCGAGTGTTCGACCTTTCTGGTAACGAGAAGCAAGT

Figure 11 (CONTD.)

TAGGTATCCTAACGGTTCCAACTACATCAAGACCGCTAATCCACGTAACGACCTGCGAATGGTTACTGTAGCAG
ACTATACGTTCATCGTTAACCGTAACGTTGTTGCACAGAAGAACACAAAGTCTGTCAACTTACCGAATTACAAC
CCTAATCAAGACGGATTGATTAACGTTCGTGGTGGTCAGTATGGTAGGGAACTAATTGTACACATTAACGGTAA
AGACGTTGCGAAGTATAAGATACCAGATGGTAGTCAACCTGAACACGTAAACAATACGGATGCCCAATGGTTAG
CTGAAGAGTTAGCCAAGCAGATGCGCACTAACTTGTCTGATTGGACTGTAAATGTAGGGCAAGGGTTCATCCAT
GTGACCGCACCTAGTGGTCAACAGATTGACTCCTTCACGACTAAAGATGGCTACGCAGACCAGTTGATTAACCC
TGTGACCCACTACGCTCAGTCGTTCTCTAAGCTGCCACCTAATGCTCCTAACGGCTACATGGTGAAAATCGTAG
GGGACGCCTCTAAGTCTGCCGACCAGTATTACGTTCGGTATGACGCTGAGCGGAAAGTTTGGACTGAGACTTTA
GGTTGGAACACTGAGGACCAAGTTCTATGGGAAACCATGCCACACGCTCTTGTGCGAGCCGCTGACGGTAATTT
CGACTTCAAGTGGCTTGAGTGGTCTCCTAAGTCTTGTGGTGACGTTGACACCAACCCTTGGCCTTCTTTTGTTG
GTTCAAGTATTAACGATGTGTTCTTCTTCCGTAACCGCTTAGGATTCCTTAGTGGGGAGAACATCATATTGAGT
CGTACAGCCAAATACTTCAACTTCTACCCTGCGTCCATTGCGAACCTTAGTGATGACGACCCTATAGACGTAGC
TGTGAGTACCAACCGAATAGCAATCCTTAAGTACGCCGTTCCGTTCTCAGAAGAGTTACTCATCTGGTCCGATG
AAGCACAATTCGTCCTGACTGCCTCGGGTACTCTCACATCTAAGTCGGTTGAGTTGAACCTAACGACCCAGTTT
GACGTACAGGACCGAGCGAGACCTTTTGGGATTGGGCGTAATGTCTACTTTGCTAGTCCGAGGTCCAGCTTCAC
GTCCATCCACAGGTACTACGCTGTGCAGGATGTCAGTTCCGTTAAGAATGCTGAGGACATTACATCACACGTTC
CTAACTACATCCCTAATGGTGTGTTCAGTATTTGCGGAAGTGGTACGGAAAACTTCTGTTCGGTACTATCTCAC
GGGGACCCTAGTAAAATCTTCATGTACAAATTCCTGTACCTGAACGAAGAGTTAAGGCAACAGTCGTGGTCTCA
TTGGGACTTTGGGGAAAACGTACAGGTTCTAGCTTGTCAGAGTATCAGCTCAGATATGTATGTGATTCTTCGCA
ATGAGTTCAATACGTTCCTAGCTAGAATCTCTTTCACTAAGAACGCCATTGACTTACAGGGAGAACCCTATCGT
GCCTTTATGGACATGAAGATTCGATACACGATTCCTAGTGGAACATACAACGATGACACATTCACTACCTCTAT
TCATATTCCAACAATTTATGGTGCAAACTTCGGGAGGGGCAAAATCACTGTATTGGAGCCTGATGGTAAGATAA
CCGTGTTTGAGCAACCTACGGCTGGGTGGAATAGCGACCCTTGGCTGAGACTCAGCGGTAACTTGGAGGGACGC
ATGGTGTACATTGGGTTCAACATTAACTTCGTATATGAGTTCTCTAAGTTCCTCATCAAGCAGACTGCCGACGA
CGGGTCTACCTCCACGGAAGACATTGGGCGCTTACAGTTACGCCGAGCGTGGGTTAACTACGAGAACTCTGGTA
CGTTTGACATTTATGTTGAGAACCAATCGTCTAACTGGAAGTACACAATGGCTGGTGCCCGATTAGGCTCTAAC
ACTCTGAGGGCTGGGAGACTGAACTTAGGGACCGGACAATATCGATTCCCTGTGGTTGGTAACGCCAAGTTCAA
CACTGTATACATCTTGTCAGATGAGACTACCCCTCTGAACATCATTGGGTGTGGCTGGGAAGGTAACTACTTAC
GGAGAAGTTCCGGTATTTAATTAAATATTCTCCCTGTGGTGGCTCGAAATTAATACGACTCACTATAGGGAGAA
CAATACGACTACGGGAGGGTTTTCTTATGATGACTATAAGACCTACTAAAAGTACAGACTTTGAGGTATTCACT
CCGGCTCACCATGACATTCTTGAAGCTAAGGCTGCTGGTATTGAGCCGAGTTTCCCTGATGCTTCCGAGTGTGT
CACGTTGAGCCTCTATGGGTTCCCTCTAGCTATCGGTGGTAACTGCGGGGACCAGTGCTGGTTCGTTACGAGCG
ACCAAGTGTGGCGACTTAGTGGAAAGGCTAAGCGAAAGTTCCGTAAGTTAATCATGGAGTATCGCGATAAGATG
CTTGAGAAGTATGATACTCTTTGGAATTACGTATGGGTAGGCAATACGTCCCACATTCGTTTCCTCAAGACTAT
CGGTGCGGTATTCCATGAAGAGTACACACGAGATGGTCAATTTCAGTTATTTACAATCACGAAAGGAGGATAAC
CATATGTGTTGGGCAGCCGCAATACCTATCGCTATATCTGGCGCTCAGGCTATCAGTGGTCAGAACGCTCAGGC
CAAAATGATTGCCGCTCAGACCGCTGCTGGTCGTCGTCAAGCTATGGAAATCATGAGGCAGACGAACATCCAGA
ATGCTGACCTATCGTTGCAAGCTCGAAGTAAACTTGAGGAAGCGTCCGCCGAGTTGACCTCACAGAACATGCAG
AAGGTCCAAGCTATTGGGTCTATCCGAGCGGCTATCGGAGAGAGTATGCTTGAAGGTTCCTCAATGGACCGCAT
TAAGCGAGTCACAGAAGGACAGTTCATTCGGGAAGCCAATATGGTAACTGAGAACTATCGCCGTGACTACCAAG
CAATCTTCGCACAGCAACTTGGTGGTACTCAAAGTGCTGCAAGTCAGATTGACGAAATCTATAAGAGCGAACAG
AAACAGAAGAGTAAGCTACAGATGGTTCTGGACCCACTGGCTATCATGGGGTCTTCCGCTGCGAGTGCTTACGC
ATCCGGTGCGTTCGACTCTAAGTCCACAACTAAGGCACCTATTGTTGCCGCTAAAGGAACCAAGACGGGGAGGT
AATGAGCTATGAGTAAAATTGAATCTGCCCTTCAAGCGGCACAACCGGGACTCTCTCGGTTACGTGGTGGTGCT
GGAGGTATGGGCTATCGTGCAGCAACCACTCAGGCCGAACAGCCAAGGTCAAGCCTATTGGACACCATTGGTCG
GTTCGCTAAGGCTGGTGCCGATATGTATACCGCTAAGGAACAACGAGCACGAGACCTAGCTGATGAACGCTCTA
ACGAGATTATCCGTAAGCTGACCCCTGAGCAACGTCGAGAAGCTCTCAACAACGGGACCCTTCTGTATCAGGAT
GACCCATACGCTATGGAAGCACTCCGAGTCAAGACTGGTCGTAACGCTGCGTATCTTGTGGACGATGACGTTAT
GCAGAAGATAAAAGAGGGTGTCTTCCGTACTCGCGAAGAGATGGAAGAGTATCGCCATAGTCGCCTTCAAGAGG
GCGCTAAGGTATACGCTGAGCAGTTCGGCATCGACCCTGAGGACGTTGATTATCAGCGTGGTTTCAACGGGGAC
ATTACCGAGCGTAACATCTCGCTGTATGGTGCGCATGATAACTTCTTGAGCCAGCAAGCTCAGAAGGGCGCTAT
CATGAACAGCCGAGTGGAACTCAACGGTGTCCTTCAAGACCCTGATATGCTGCGTCGTCCAGACTCTGCTGACT

Figure 11 (CONTD.)

TCTTTGAGAAGTATATCGACAACGGTCTGGTTACTGGCGCAATCCCATCTGATGCTCAAGCCACACAGCTTATA
AGCCAAGCGTTCAGTGACGCTTCTAGCCGTGCTGGTGGTGCTGACTTCCTGATGCGAGTCGGTGACAAGAAGGT
AACACTTAACGGAGCCACTACGACTTACCGAGAGTTGATTGGTGAGGAACAGTGGAACGCTCTCATGGTCACAG
CACAACGTTCTCAGTTTGAGACTGACGCGAAGCTGAACGAGCAGTATCGCTTGAAGATTAACTCTGCGCTGAAC
CAAGAGGACCCAAGGACAGCTTGGGAGATGCTTCAAGGTATCAAGGCTGAACTAGATAAGGTCCAACCTGATGA
GCAGATGACACCACAACGTGAGTGGCTAATCTCCGCACAGGAACAAGTTCAGAATCAGATGAACGCATGGACGA
AAGCTCAGGCCAAGGCTCTGGACGATTCCATGAAGTCAATGAACAAACTTGACGTAATCGACAAGCAATTCCAG
AAGCGAATCAACGGTGAGTGGGTCTCAACGGATTTTAAGGATATGCCAGTCAACGAGAACACTGGTGAGTTCAA
GCATAGCGATATGGTTAACTACGCCAATAAGAAGCTCGCTGAGATTGACAGTATGGACATTCCAGACGGTGCCA
AGGATGCTATGAAGTTGAAGTACCTTCAAGCGGACTCTAAGGACGGAGCATTCCGTACAGCCATCGGAACCATG
GTCACTGACGCTGGTCAAGAGTGGTCTGCCGCTGTGATTAACGGTAAGTTACCAGAACGAACCCCAGCTATGGA
TGCTCTGCGCAGAATCCGCAATGCTGACCCTCAGTTGATTGCTGCGCTATACCCAGACCAAGCTGAGCTATTCC
TGACGATGGACATGATGGACAAGCAGGGTATTGACCCTCAGGTTATTCTTGATGCCGACCGACTGACTGTTAAG
CGGTCCAAAGAGCAACGCTTTGAGGATGATAAAGCATTCGAGTCTGCACTGAATGCATCTAAGGCTCCTGAGAT
TGCCCGTATGCCAGCGTCACTGCGCGAATCTGCACGTAAGATTTATGACTCCGTTAAGTATCGCTCGGGGAACG
AAAGCATGGCTATGGAGCAGATGACCAAGTTCCTTAAGGAATCTACCTACACGTTCACTGGTGATGATGTTGAC
GGTGATACCGTTGGTGTGATTCCTAAGAATATGATGCAGGTTAACTCTGACCCGAAATCATGGGAGCAAGGTCG
GGATATTCTGGAGGAAGCACGTAAGGGAATCATTGCGAGCAACCCTTGGATAACCAATAAGCAACTGACCATGT
ATTCTCAAGGTGACTCCATTTACCTTATGGACACCACAGGTCAAGTCAGAGTCCGATACGACAAAGAGTTACTC
TCGAAGGTCTGGAGTGAGAACCAGAAGAAACTCGAAGAGAAAGCTCGTGAGAAGGCTCTGGCTGATGTGAACAA
GCGAGCACCTATAGTTGCCGCTACGAAGGCCCGTGAAGCTGCTGCTAAACGAGTCCGAGAGAAACGTAAACAGA
CTCCTAAGTTCATCTACGGACGTAAGGAGTAACTAAAGGCTACATAAGGAGGCCCTAAATGGATAAGTACGATA
AGAACGTACCAAGTGATTATGATGGTCTGTTCCAAAAGGCTGCTGATGCCAACGGGGTCTCTTATGACCTTTTA
CGTAAAGTCGCTTGGACAGAATCACGATTTGTGCCTACAGCAAAATCTAAGACTGGACCATTAGGCATGATGCA
ATTTACCAAGGCAACCGCTAAGGCCCTCGGTCTGCGAGTTACCGATGGTCCAGACGACGACCGACTGAACCCTG
AGTTAGCTATTAATGCTGCCGCTAAGCAACTTGCAGGTCTGGTAGGGAAGTTTGATGGCGATGAACTCAAAGCT
GCCCTTGCGTACAACCAAGGCGAGGGACGCTTGGGTAATCCACAACTTGAGGCGTACTCTAAGGGAGACTTCGC
ATCAATCTCTGAGGAGGGACGTAACTACATGCGTAACCTTCTGGATGTTGCTAAGTCACCTATGGCTGGACAGT
TGGAAACTTTTGGTGGCATAACCCCAAAGGGTAAAGGCATTCCGGCTGAGGTAGGATTGGCTGGAATTGGTCAC
AAGCAGAAAGTAACACAGGAACTTCCTGAGTCCACAAGTTTTGACGTTAAGGGTATCGAACAGGAGGCTACGGC
GAAACCATTCGCCAAGGACTTTTGGGAGACCCACGGAGAAACACTTGACGAGTACAACAGTCGTTCAACCTTCT
TCGGATTCAAAAATGCTGCCGAAGCTGAACTCTCCAACTCAGTCGCTGGGATGGCTTTCCGTGCTGGTCGTCTC
GATAATGGTTTTGATGTGTTTAAAGACACCATTACGCCGACTCGCTGGAACTCTCACATCTGGACTCCAGAGGA
GTTAGAGAAGATTCGAACAGAGGTTAAGAACCCTGCGTACATCAACGTTGTAACTGGTGGTTCCCCTGAGAACC
TCGATGACCTCATTAAATTGGCTAACGAGAACTTTGAGAATGACTCCCGCGCTGCCGAGGCTGGCCTAGGTGCC
AAACTGAGTGCTGGTATTATTGGTGCTGGTGTGGACCCGCTTAGCTATGTTCCTATGGTCGGTGTCACTGGTAA
GGGCTTTAAGTTAATCAATAAGGCTCTTGTAGTTGGTGCCGAAAGTGCTGCTCTGAACGTTGCATCCGAAGGTC
TCCGTACCTCCGTAGCTGGTGGTGACGCAGACTATGCGGGTGCTGCCTTAGGTGGCTTTGTGTTTGGCGCAGGC
ATGTCTGCAATCAGTGACGCTGTAGCTGCTGGACTGAAACGCAGTAAACCAGAAGCTGAGTTCGACAATGAGTT
CATCGGTCCTATGATGCGATTGGAAGCCCGTGAGACAGCACGAAACGCCAACTCTGCGGACCTCTCTCGGATGA
ACACTGAGAACATGAAGTTTGAAGGTGAACATAATGGTGTCCCTTATGAGGACTTACCAACAGAGAGAGGTGCC
GTGGTGTTACATGATGGCTCCGTTCTAAGTGCAAGCAACCCAATCAACCCTAAGACTCTAAAAGAGTTCTCCGA
GGTTGACCCTGAGAAGGCTGCGCGAGGAATCAAACTGGCTGGGTTCACCGAGATTGGCTTGAAGACCTTGGGGT
CTGACGATGCTGACATCCGTAGAGTGGCTATCGACCTCGTTCGCTCTCCTACTGGTATGCAGTCTGGTGCCTCA
GGTAAGTTCGGTGCAACAGCTTCTGACATCCATGAGAGACTTCATGGTACTGACCAGCGTACTTATAATGACTT
GTACAAAGCAATGTCTGACGCTATGAAAGACCCTGAGTTCTCTACTGGCGGCGCTAAGATGTCCCGTGAAGAAA
CTCGATACACTATCTACCGTAGAGCGGCACTAGCTATTGAGCGTCCAGAACTACAGAAGGCACTCACTCCGTCT
GAGAGAATCGTTATGGACATCATTAAGCGTCACTTTGACACCAAGCGTGAACTTATGGAAAACCCAGCAATATT
CGGTAACACAAAGGCTGTGAGTATCTTCCCTGAGAGTCGCCACAAAGGTACTTACGTTCCTCACGTATATGACC
GTCATGCCAAGGCGCTGATGATTCAACGCTACGGTGCCGAAGGTTTGCAGGAAGGGATTGCCCGCTCATGGATG
AACAGCTACGTCTCCAGACCTGAGGTCAAGGCCAGAGTCGATGAGATGCTTAAGGAATTACACGGGGTGAAGGA
AGTAACACCAGAGATGGTAGAGAAGTACGCTATGGATAAGGCTTATGGTATCTCCCACTCAGACCAGTTCACCA

Figure 11 (CONTD.)

ACAGTTCCATAATAGAAGAGAACATTGAGGGCTTAGTAGGTATCGAGAATAACTCATTCCTTGAGGCACGTAAC
TTGTTTGATTCGGACCTATCCATCACTATGCCAGACGGACAGCAATTCTCAGTGAATGACCTAAGGGACTTCGA
TATGTTCCGCATCATGCCAGCGTATGACCGCCGTGTCAATGGTGACATCGCCATCATGGGGTCTACTGGTAAAA
CCACTAAGGAACTTAAGGATGAGATTTTGGCTCTCAAAGCGAAAGCTGAGGGAGACGGTAAGAAGACTGGCGAG
GTACATGCTTTAATGGATACCGTTAAGATTCTTACTGGTCGTGCTAGACGCAATCAGGACACTGTGTGGGAAAC
CTCACTGCGTGCCATCAATGACCTAGGGTTCTTCGCTAAGAACGCCTACATGGGTGCTCAGAACATTACGGAGA
TTGCTGGGATGATTGTCACTGGTAACGTTCGTGCTCTAGGGCATGGTATCCCAATTCTGCGTGATACACTCTAC
AAGTCTAAACCAGTTTCAGCTAAGGAACTCAAGGAACTCCATGCGTCTCTGTTCGGGAAGGAGGTGGACCAGTT
GATTCGGCCTAAACGTGCTGACATTGTGCAGCGCCTAAGGGAAGCAACTGATACCGGACCTGCCGTGGCGAACA
TCGTAGGGACCTTGAAGTATTCAACACAGGAACTGGCTGCTCGCTCTCCGTGGACTAAGCTACTGAACGGAACC
ACTAACTACCTTCTGGATGCTGCGCGTCAAGGTATGCTTGGGGATGTTATTAGTGCCACCCTAACAGGTAAGAC
TACCCGCTGGGAGAAAGAAGGCTTCCTTCGTGGTGCCTCCGTAACTCCTGAGCAGATGGCTGGCATCAAGTCTC
TCATCAAGGAACATATGGTACGCGGTGAGGACGGGAAGTTTACCGTTAAGGACAAGCAAGCGTTCTCTATGGAC
CCACGGGCTATGGACTTATGGAGACTGGCTGACAAGGTAGCTGATGAGGCAATGCTGCGTCCACATAAGGTGTC
CTTACAGGATTCCCATGCGTTCGGAGCACTAGGTAAGATGGTTATGCAGTTTAAGTCTTTCACTATCAAGTCCC
TTAACTCTAAGTTCCTGCGAACCTTCTATGATGGATACAAGAACAACCGAGCGATTGACGCTGCGCTGAGCATC
ATCACCTCTATGGGTCTCGCTGGTGGTTTCTATGCTATGGCTGCACACGTCAAAGCATACGCTCTGCCTAAGGA
GAAACGTAAGGAGTACTTGGAGCGTGCACTGGACCCAACCATGATTGCCCACGCTGCGTTATCTCGTAGTTCTC
AATTGGGTGCTCCTTTGGCTATGGTTGACCTAGTTGGTGGTGTTTTAGGGTTCGAGTCCTCCAAGATGGCTCGC
TCTACGATTCTACCTAAGGACACCGTGAAGGAACGTGACCCAAACAAACCGTACACCTCTAGAGAGGTAATGGG
CGCTATGGGTTCAAACCTTCTGGAACAGATGCCTTCGGCTGGCTTTGTGGCTAACGTAGGGGCTACCTTAATGA
ATGCTGCTGGCGTGGTCAACTCACCTAATAAAGCAACCGAGCAGGACTTCATGACTGGTCTTATGAACTCCACA
AAAGAGTTAGTACCGAACGACCCATTGACTCAACAGCTTGTGTTGAAGATTTATGAGGCGAACGGTGTTAACTT
GAGGGAGCGTAGGAAATAATACGACTCACTATAGGGAGAGGCGAAATAATCTTCTCCCTGTAGTCTCTTAGATT
TACTTTAAGGAGGTCAAATGGCTAACGTAATTAAAACCGTTTTGACTTACCAGTTAGATGGCTCCAATCGTGAT
TTTAATATCCCGTTTGAGTATCTAGCCCGTAAGTTCGTAGTGGTAACTCTTATTGGTGTAGACCGAAAGGTCCT
TACGATTAATACAGACTATCGCTTTGCTACACGTACTACTATCTCTCTGACAAAGGCTTGGGGTCCAGCCGATG
GCTACACGACCATCGAGTTACGTCGAGTAACCTCCACTACCGACCGATTGGTTGACTTTACGGATGGTTCAATC
CTCCGCGCGTATGACCTTAACGTCGCTCAGATTCAAACGATGCACGTAGCGGAAGAGGCCCGTGACCTCACTAC
GGATACTATCGGTGTCAATAACGATGGTCACTTGGATGCTCGTGGTCGTCGAATTGTGAACCTAGCGAACGCCG
TGGATGACCGCGATGCTGTTCCGTTTGGTCAACTAAAGACCATGAACCAGAACTCATGGCAAGCACGTAATGAA
GCCTTACAGTTCCGTAATGAGGCTGAGACTTTCAGAAACCAAGCGGAGGGCTTTAAGAACGAGTCCAGTACCAA
CGCTACGAACACAAAGCAGTGGCGCGATGAGACCAAGGGTTTCCGAGACGAAGCCAAGCGGTTCAAGAATACGG
CTGGTCAATACGCTACATCTGCTGGGAACTCTGCTTCCGCTGCGCATCAATCTGAGGTAAACGCTGAGAACTCT
GCCACAGCATCCGCTAACTCTGCTCATTTGGCAGAACAGCAAGCAGACCGTGCGGAACGTGAGGCAGACAAGCT
GGAAAATTACAATGGATTGGCTGGTGCAATTGATAAGGTAGATGGAACCAATGTGTACTGGAAAGGAAATATTC
ACGCTAACGGGCGCCTTTACATGACCACAAACGGTTTTGACTGTGGCCAGTATCAACAGTTCTTTGGTGGTGTC
ACTAATCGTTACTCTGTCATGGAGTGGGGAGATGAGAACGGATGGCTGATGTATGTTCAACGTAGAGAGTGGAC
AACAGCGATAGGCGGTAACATCCAGTTAGTAGTAAACGGACAGATCATCACCCAAGGTGGAGCCATGACCGGTC
AGCTAAAATTGCAGAATGGGCATGTTCTTCAATTAGAGTCCGCATCCGACAAGGCGCACTATATTCTATCTAAA
GATGGTAACAGGAATAACTGGTACATTGGTAGAGGGTCAGATAACAACAATGACTGTACCTTCCACTCCTATGT
ACATGGTACGACCTTAACACTCAAGCAGGACTATGCAGTAGTTAACAAACACTTCCACGTAGGTCAGGCCGTTG
TGGCCACTGATGGTAATATTCAAGGTACTAAGTGGGGAGGTAAATGGCTGGATGCTTACCTACGTGACAGCTTC
GTTGCGAAGTCCAAGGCGTGGACTCAGGTGTGGTCTGGTAGTGCTGGCGGTGGGGTAAGTGTGACTGTTTCACA
GGATCTCCGCTTCCGCAATATCTGGATTAAGTGTGCCAACAACTCTTGGAACTTCTTCCGTACTGGCCCCGATG
GAATCTACTTCATAGCCTCTGATGGTGGATGGTTACGATTCCAAATACACTCCAACGGTCTCGGATTCAAGAAT
ATTGCAGACAGTCGTTCAGTACCTAATGCAATCATGGTGGAGAACGAGTAATTGGTAAATCACAAGGAAAGACG
TGTAGTCCACGGATGGACTCTCAAGGAGGTACAAGGTGCTATCATTAGACTTTAACAACGAATTGATTAAGGCT
GCTCCAATTGTTGGGACGGGTGTAGCAGATGTTAGTGCTCGACTGTTCTTTGGGTTAAGCCTTAACGAATGGTT
CTACGTTGCTGCTATCGCCTACACAGTGGTTCAGATTGGTGCCAAGGTAGTCGATAAGATGATTGACTGGAAGA
AAGCCAATAAGGAGTGATATGTATGGAAAAGGATAAGAGCCTTATTACATTCTTAGAGATGTTGGACACTGCGA
TGGCTCAGCGTATGCTTGCGGACCTTTCGGACCATGAGCGTCGCTCTCCGCAACTCTATAATGCTATTAACAAA

Figure 11 (CONTD.)

CTGTTAGACCGCCACAAGTTCCAGATTGGTAAGTTGCAGCCGGATGTTCACATCTTAGGTGGCCTTGCTGGTGC
TCTTGAAGAGTACAAAGAGAAAGTCGGTGATAACGGTCTTACGGATGATGATATTTACACATTACAGTGATATA
CTCAAGGCCACTACAGATAGTGGTCTTTATGGATGTCATTGTCTATACGAGATGCTCCTACGTGAAATCTGAAA
GTTAACGGGAGGCATTATGCTAGAATTTTTACGTAAGCTAATCCCTTGGGTTCTCGCTGGGATGCTATTCGGGT
TAGGATGGCATCTAGGGTCAGACTCAATGGACGCTAAATGGAAACAGGAGGTACACAATGAGTACGTTAAGAGA
GTTGAGGCTGCGAAGAGCACTCAAAGAGCAATCGATGCGGTATCTGCTAAGTATCAAGAAGACCTTGCCGCGCT
GGAAGGGAGCACTGATAGGATTATTTCTGATTTGCGTAGCGACAATAAGCGGTTGCGCGTCAGAGTCAAAACTA
CCGGAACCTCCGATGGTCAGTGTGGATTCGAGCCTGATGGTCGAGCCGAACTTGACGACCGAGATGCTAAACGT
ATTCTCGCAGTGACCCAGAAGGGTGACGCATGGATTCGTGCGTTACAGGATACTATTCGTGAACTGCAACGTAA
GTAGGAAATCAAGTAAGGAGGCAATGTGTCTACTCAATCCAATCGTAATGCGCTCGTAGTGGCGCAACTGAAAG
GAGACTTCGTGGCGTTCCTATTCGTCTTATGGAAGGCGCTAAACCTACCGGTGCCCACTAAGTGTCAGATTGAC
ATGGCTAAGGTGCTGGCGAATGGAGACAACAAGAAGTTCATCTTACAGGCTTTCCGTGGTATCGGTAAGTCGTT
CATCACATGTGCGTTCGTTGTGTGGTCCTTATGGAGAGACCCTCAGTTGAAGATACTTATCGTATCAGCCTCTA
AGGAGCGTGCAGACGCTAACTCCATCTTTATTAAGAACATCATTGACCTGCTGCCATTCCTATCTGAGTTAAAG
CCAAGACCCGGACAGCGTGACTCGGTAATCAGCTTTGATGTAGGCCCAGCCAATCCTGACCACTCTCCTAGTGT
GAAATCAGTAGGTATCACTGGTCAGTTAACTGGTAGCCGTGCTGACATTATCATTGCGGATGACGTTGAGATTC
CGTCTAACAGCGCAACTATGGGTGCCCGTGAGAAGCTATGGACTCTGGTTCAGGAGTTCGCTGCGTTACTTAAA
CCGCTGCCTTCCTCTCGCGTTATCTACCTTGGTACACCTCAGACAGAGATGACTCTCTATAAGGAACTTGAGGA
TAACCGTGGGTACACAACCATTATCTGGCCTGCTCTGTACCCAAGGACACGTGAAGAGAACCTCTATTACTCAC
AGCGTCTTGCTCCTATGTTACGCGCTGAGTACGATGAGAACCCTGAGGCACTTGCTGGGACTCCAACAGACCCA
GTGCGCTTTGACCGTGATGACCTGCGCGAGCGTGAGTTGGAATACGGTAAGGCTGGCTTTACGCTACAGTTCAT
GCTTAACCCTAACCTTAGTGATGCCGAGAAGTACCCGCTGAGGCTTCGTGACGCTATCGTAGCGGCCTTAGACT
TAGAGAAGGCCCCAATGCATTACCAGTGGCTTCCGAACCGTCAGAACATCATTGAGGACCTTCCTAACGTTGGC
CTTAAGGGTGATGACCTGCATACGTACCACGATTGTTCCAACAACTCAGGTCAGTACCAACAGAAGATTCTGGT
CATTGACCCTAGTGGTCGCGGTAAGGACGAAACAGGTTACGCTGTGCTGTACACACTGAACGGTTACATCTACC
TTATGGAAGCTGGAGGTTTCCGTGATGGCTACTCCGATAAGACCCTTGAGTTACTCGCTAAGAAGGCAAAGCAA
TGGGGAGTCCAGACGGTTGTCTACGAGAGTAACTTCGGTGACGGTATGTTCGGTAAGGTATTCAGTCCTATCCT
TCTTAAACACCACAACTGTGCGATGGAAGAGATTCGTGCCCGTGGTATGAAAGAGATGCGTATTTGCGATACCC
TTGAGCCAGTCATGCAGACTCACCGCCTTGTAATTCGTGATGAGGTCATTAGGGCCGACTACCAGTCCGCTCGT
GACGTAGACGGTAAGCATGACGTTAAGTACTCGTTGTTCTACCAGATGACCCGTATCACTCGTGAGAAAGGCGC
TCTGGCTCATGATGACCGATTGGATGCCCTTGCGTTAGGCATTGAGTATCTCCGTGAGTCCATGCAGTTGGATT
CCGTTAAGGTCGAGGGTGAAGTACTTGCTGACTTCCTTGAGGAACACATGATGCGTCCTACGGTTGCTGCTACG
CATATCATTGAGATGTCTGTGGGAGGAGTTGATGTGTACTCTGAGGACGATGAGGGTTACGGTACGTCTTTCAT
TGAGTGGTGATTTATGCATTAGGACTGCATAGGGATGCACTATAGACCACGGATGGTCAGTTCTTTAAGTTACT
GAAAAGACACGATAAATTAATACGACTCACTATAGGGAGAGGAGGGACGAAAGGTTACTATATAGATACTGAAT
GAATACTTATAGAGTGCATAAAGTATGCATAATGGTGTACCTAGAGTGACCTCTAAGAATGGTGATTATATTGT
ATTAGTATCACCTTAACTTAAGGACCAACATAAAGGGAGGAGACTCATGTTCCGCTTATTGTTGAACCTACTGC
GGCATAGAGTCACCTACCGATTTCTTGTGGTACTTTGTGCTGCCCTTGGGTACGCATCTCTTACTGGAGACCTC
AGTTCACTGGAGTCTGTCGTTTGCTCTATACTCACTTGTAGCGATTAGGGTCTTCCTGACCGACTGATGGCTCA
CCGAGGGATTCAGCGGTATGATTGCATCACACCACTTCATCCCTATAGAGTCAAGTCCTAAGGTATACCCATAA
AGAGCCTCTAATGGTCTATCCTAAGGTCTATACCTAAAGATAGGCCATCCTATCAGTGTCACCTAAAGAGGGTC
TTAGAGAGGGCCTATGGAGTTCCTATAGGGTCCTTTAAAATATACCATAAAAATCTGAGTGACTATCTCACAGT
GTACGGACCTAAAGTTCCCCCATAGGGGGTACCTAAAGCCCAGCCAATCACCTAAAGTCAACCTTCGGTTGACC
TTGAGGGTTCCCTAAGGGTTGGGGATGACCCTTGGGTTTGTCTTTGGGTGTTACCTTGAGTGTCTCTCTGTGTC
CCT

Figure 15

>K1-5 BAR 3.0 Insert DNA (SEQ ID NO: 3)

CAACGTCGTGCCATGAAGAAACCTTCTGCATCTTCTGCGTAAAGAGGAGATATACAATGGTCTTCACACTCGAAGA
TTTCGTTGGGGACTGGCGACAGACAGCCGGCTACAACCTGGACCAAGTCCTTGAACAGGGAGGTGTGTCCAGTTT
GTTTCAGAATCTCGGGGTGTCCGTAACTCCGATCCAAAGGATTGTCCTGAGCGGTGAAAATGGGCTGAAGATCGA
CATCCATGTCATCATCCCGTATGAAGGTCTGAGCGGCGACCAAATGGGCCAGATCGAAAAAATTTTTAAGGTGGT
GTACCCTGTGGATGATCATCACTTTAAGGTGATCCTGCACTATGGCACACTGGTAATCGACGGGGTTACGCCGAAC
ATGATCGACTATTTCGGACGGCCGTATGAAGGCATCGCCGTGTTCGACGGCAAAAAGATCACTGTAACAGGGACC
CTGTGGAACGGCAACAAAATTATCGACGAGCGCCTGATCAACCCCGACGGCTCCCTGCTGTTCCGAGTAACCATCA
ACGGAGTGACCGGCTGGCGGCTGTGCGAACGCATTCTGGCGTAAGCAGGTTAATATCTTAGTATAAACAAGGGCA
GACTTAGGTTTGTCCTTAGTGTATTCCAAAGGAGGTAACATGCTGAAAGATGGTTGGGTTTCATATGACCCTACAG
ACCCTAAGAATTGGCTACAGGTTATCGCTATAGCTTGTGCAGGTAGCCTATTGGCTGCCCTGATGTATTCATTATGG
ATGTACACAAAGTAACCAAAGTCAAAATTTTGATGTAGGCGTGTGTCAGCTCTCTCGCCCTCGCCCTCGCCGGGTT
GTCCCCATAGGGTGGCCTGAGGGAATCCGTCTTCGACGGGCAGGGCTGATGTACTCCTTGTCTAGTACAAGGGAG
GCGGAGGGAACGCCTAGGGAGGCCTAGGAATGGCTTAGTGGTGGACAAGGTGATTACCTTAGTGAAGCCTCTTA
GTGCATTCCTGAGGCCATTCAGGGCGTTTATGAGGGATTGACAGGGTGTGAGGGCGTGGGCTA

Figure 16

>K1-5 BAR 3.0_(SEQ ID NO:4)

TCGCCCTCGCCCTCGCCGGGTTGTCCCCATAGGGTGGCCTGAGGGAATCCGTCTTCGACGGGCAGGGCTGATGTACTCCTTGTCTAGTACAA
GGGAGGCGGAGGGAACGCCTAGGGAGGCCTAGGAATGGCTTAGTGGTGGACAAGGTGATTACCTTAGTGAAGCCTCTTAGTGCATTCCTGA
GGCCATTCAGGGCGTTTATGAGGGATTGACAGGGTGTGAGGGCGTGGGCTATCTGTTCCTTTGCTCCTCACTTCGTTCGTCGCTGCGGTAGCC
TGATGTGTACCTTAGGTTATTCCTTGATGGATAGCTTAGGTTAGCCTTAGTGGATTACCTTAGTTAAAGCCTTAGTGCTTCACTTAGTATCAGCT
TAGTAGTGTACCTTAGTAAGTCTTAGTGTCTTCTCTTAGTGATTGCACATGCAAGCATGTAAGATGCTAATAGGTCGCGGTCGGCAGACCGCT
AAAGAAAGAGAATGGTAATAAGATGCAGTAGGAGGAACACCAGAAGCCTAGCCAACCTAAGCTATCCTAGCTCTATATCTATTGCTTTTCCTT
AGTCTAACACGTTAGACAACCTATCTTATTCTTAGTGATGGTAACTTAGTGTTGACAAGATAATCTTAGTGTAATACTATGCATCACGTAGGCG
GTGCTGAGGCACCTAGTAGCCAGCTAGTAAGGCATACGAAGAGACTAGCGCTTACATTGCTCTTTAACAATTTGCTTAGTGTAACCTATGTAT
GCCGTGGTTAACTACTTATTGAATGAGGTATTAACTATGACATTAAATAACCGTGAACTGTCCGTTCTCTTCACTCTGTTGTGCTACATGATTCG
TAACAACGAATTACTTACAGATGATGAGTTAGCCTTGTATCACCGCTTTCTTAACGAAGGTTGGACCGATACAGTTAATCAATACCGTAACATG
ATAGATGAGTTGAGGGAGGGTAAATAATGTATCAACATGAGGTATTCTTTGAATCAGCTAGCGAAGCTATTCGCTTCCGTGATGATATGATG
CAAGCTGGTGTAGGCGTTGATGTGTATCACTATTTGATAGATTACGACACTGAATATCACCGAGTTACCTTAGTATCTGAGTATGACAACCAA
GTCATTACTGAGTATCTAGGCAGTGAAGATTACGATTACGATGAAGTAATCACGACAAATCTCTAAATTAACTGTTGACAGCCACGGCATACA
AGGTTACATTAAGCATCAAGACGGCGACGTCTTTAAACATCCCGCTCTTTAACAATACGGTTTGTGTCTTGATAGGCTAACTAACTAACTAAGG
TAATTATCATGAAAGGGTTAATTTGTGTAGAACGTATGGTCAATGGTAAACTTGAAATATTACCACTGGAAAACCAATCTAGCTTCAAAGAGT
GGTATGGCTGTTTCTCACTGATTTAAGGTAAAGGCTGGCACTAGTCAGCCTATCAAGGCGCAAACCAAGCTCTTTAACAATTTGGATGGTAGC
TTCTTAGTCTGGATAGGTTAAACCTAGGAGATTCTCTTGAGTCTCCTATAATGTAACCTAACTAACTAAATGAGGATTAAATCATGGAACGCAA
TGCTAACGCTTACTACAACCTTCTGGCTGCAACTGTTGAAGCATTCAACGAGCGTATTCAGTTTGATGAGATTCGCGAAGGTGATGATTACTCT
GATGCACTACATGAGGTTGTAGACAGCAATGTTCCAGTTTATTACAGCGAAATCTTTACAGTGATGGCTGCTGATGGTATTGATGTTGATTTT
GAGGATGCTGGTTTGATTCCTGACACGAAGGATGTAACCAAGATTCTACAAGCTCGCATCTATGAAGCTCTTTATAATGATGTACCAAATGAC
AGCGATGTAGTTTGGTGTGAAGGCGAAGAAGAGGAAGAATAAGGATGGAAAAGCAATATAACTTTATCTTTTCAGACGGTGTAACCCTGAA
GTGTTCCCTACGATTCGCACAAATTCGTGAGGAAGTACTAGGCACTACATACAAACTATTTAGCTGACACTATAAGAGAAGGCTTAACAAGGC
GTTACTAAGGTAGCGCCTGATTAAACTTTCACTTACTAGGAGTTGAGATTATGAAAACCTTGATTGGATGCTTCTTGTTGGCTTCTCTTGCTCT
GGCATTTACCGCTAAAGCTGGTTATGACGCTTATAAAGTAGAACAAGCCCAGCAAGACTGGGCCAAAAAAAAGTTCAACTTGTGCAGCAAGA
GCAACACCTACGAGTACTGCAACAAAACACTAAGACACTTATGGAAAGAGTAACTAGCCTATAGCCCACCTGAGTGGGCTATGTGATATTTAC
TTAACACTATATAAGGTGATTACTATGACTACTGAAAACACCCTCGTGTCTGTCCGTGAAGCTGCAACCGCTGAAATCAAGCAACATTTAGAC
AATATCGGCACTTCTTACATCAAAGTAGGGGCTTGTCTGAATGAGTTACGCGGAGACTTTGAAGGTCAAAAAGAGTTTTTAGCCTATGTTGAA
GCAGAGTTTGCCATTAAGAAGGCACAATGTTACAAGCTGATGAGTGTAGCCCGTGTCTTTGAAGGCGATGATCGCTTTAAAGGCGTGGCGAT
GCGTGTAATGCTGGCGCTTGTTCCTTTCGCTGATGAAAATATAATCATGGAGAAGGCCGCAGAACTCGCCGCAAATGGCAAGCTGGACACTA
ATGCCGTAAACGCCCTGATTGAACCTAAGAAAGAGTCAAAGGCCGAAACGGTACAATCTAAGGCTGAGACAGTAAAACCGCAGGAGAACGC
GACTGAGTCCGCAGAATCACATGAAATGCAAGCGCCGCAGGTAGTGCCACCCGCGAGCGAGCAGGAGTCCGACGAATCAGCACCTTGGGAA
GAGGAAAGCAAACCGGAAGCGCCAAAGGCAGCTCCGATGGATAACACGGCTAATACTGAGAATGCCGCTATTGCTGGTCTGCTGGCACAAA
TTAAAGCACTGACTGAGCAATTACAGGCAGCCAATGACCGCATCGCCTCCTTAAGTAGCGCACGCGAAAGCAAGAAGGCATCCGCACCTATG
CTGCCGCAGTTCAAATCTTCCTGCTTCTACGCTCGCTTAGGCTTGAGCGCGGAGGAGGCAACGAAGAAAACAGCAGTTAACAAGGCACGCCG
CGAACTGGTTAAGCTGGGATACGGTGAAGGCCATGAGGCATGGCCCTTAATCTCTGAGGCAGTAGAAGAGTTGACTAAGTAACCTTATCGGT
GGCATCTTCTTAGGTGTCACCTATTAAGGTTTCTTTCACTAGGAGTAAACAAGATGCAAGGCCTACACGCTATTCAACTTCAACTTGAAGAAGA
AATGTTTAACGGCGGTATCCGTCGCTTTGAAGCGGACCAACAACGCCAGATTGCATCCGGTAATGAATCAGACACGGCATGGAATCGCCGCT
TATTGTCCGAGTTAATCGCGCCAATGGCTGAAGGTATTCAGGCATACAAGGAAGAGTATGAAGGTAAAAGAGGCCGTGCACCGCGTGCATT
AGCTTTCATTAACTGCGTAGAAAACGAAGTGGCAGCATATATCACGATGAAAATCGTTATGGATATGCTGAACACGGATGTAACCTTGCAGG
CTATAGCCATGAATGTAGCTGACCGCATTGAGGACCAAGTACGTTTTAGCAAGCTGGAAGGTCACGCCGCCAAATACTTTGAAAAAGTTAAG
AAGTCACTTAAGGCAAGTAAGACTAAATCATATCGCCATGCGCACAACGTAGCGGTAGTGGCTGAGAAGTCAGTAGCTGACCGTGACGCTGA
TTTCTCCCGCTGGGAGGCATGGCCTAAAGACACCTTGCTGCAAATTGGGATGACCTTGCTTGAAATCTTAGAGAATAGCGTATTCTTCAACGG
GCAACCTGTCTTCCTCCGCACCTTGCGCACTAATGGCGGCAAACATGGTGTTTACTACCTACAGACTAGTGAACACGTAGGTGAGTGGATAAC
TGCATTCAAAGAGCACGTAGCGCAACTGAGTCCTGCCTATGCTCCTTGCGTCATCCCTCCGCGTCCGTGGGTATCACCTTTTAACGGCGGTTTC
CACACTGAGAAAGTAGCAAGCCGTATTCGTCTGGTAAAAGGAAACCGCGAACACGTCCGCAAGCTGACCAAAAAGCAAATGCCAGAGGTTT
ACAAGGCTGTTAACGCGTTGCAGGCGACTAAATGGCAGGTTAACAAGGAAGTTTTACAGGTTGTGGAAGACGTCATCCGTCTAGACCTAGGT
TATGGTGTACCTTCCTTTAAACCACTCATTGACCGCGAGAACAAGCCAGCTAATCCAGTGCCGCTAGAATTTCAGCACCTACGGGGCCGTGAA
CTGAAAGAAATGCTTACGCCGGAACAATGGCAAGCCTTTATCAACTGGAAAGGTGAATGTACTAAGCTGTACACCGCTGAAACTAAGCGCGG
AAGCAAATCGGCGGCAACCGTTCGCATGGTTGGTCAGGCCCGTAAATATAGCCAGTTCGACGCAATCTACTTCGTGTATGCACTGGACAGCC

Figure 16 (CONTD.)

GCAGCCGCGTCTACGCGCAATCTAGCACACTCTCACCGCAATCAAATGACTTGGGCAAGGCCTTGCTCCGTTTTACCGAAGGGCAGCGTCTTG
ATAGCGCTGAGGCGCTTAAGTGGTTTTTGGTGAACGGGGCTAATAACTGGGGTTGGGATAAGAAAACTTTTGACGTGCGCACCGCTAACGTG
CTGGATAGTGAATTTCAAGACATGTGCCGCGACATTGCAGCGGATCCGCTGACCTTCACTCAATGGGTAAATGCCGACTCCCCTTACGGCTTC
CTTGCATGGTGCTTTGAATATGCGCGTTATCTGGATGCACTGGATGAAGGCACGCAAGACCAATTCATGACGCACCTCCCAGTCCATCAAGAT
GGTAGTTGTTCTGGTATCCAGCACTACAGTGCTATGCTACGCGATGCAGTAGGTGCGAAAGCAGTAAACCTTAAGCCCTCTGACTCTCCTCAA
GATATTTATGGTGCCGTTGCGCAGGTAGTAATTCAGAAGAATTATGCATACATGAATGCAGAGGATGCGGAAACCTTCACTTCTGGCAGCGT
GACTTTAACAGGTGCGGAGCTGCGTAGTATGGCTAGTGCGTGGGATATGATAGGAATCACTCGCGGCCTGACCAAAAAGCCCGTAATGACA
CTACCTTATGGCAGCACACGTCTAACCTGCCGTGAGTCAGTGATTGATTATATCGTTGATTTAGAAGAAAAAGAGGCCCAACGGGCTATTGCG
GAAGGGCGTACCGCCAATCCTGTACACCCTTTTGATAATGACCGTAAAGACAGCCTGACACCTAGCGCAGCTTATAACTATATGACAGCTTTA
ATCTGGCCTTCTATTTCGGAAGTGGTTAAAGCCCCTATAGTGGCAATGAAAATGATTCGTCAGCTTGCCCGTTTCGCAGCTAAAAGGAATGAA
GGCTTAGAGTATACCCTGCCTACTGGCTTCATCTTGCAACAAAAGATTATGGCTACTGATATGCTCCGCGTATCTACTTGCTTGATGGGAGAAA
TCAAGATGAGTCTACAGATTGAAACAGACGTAGTGGATGAAACGGCAATGATGGGCGCTGCTGCTCCTAACTTTGTGCATGGTCATGATGCC
AGCCACCTTATCTTAACAGTCTGCGACCTTGTTGATAAAGGGATTACATCTATCGCAGTTATTCATGACTCTTTTGGCACTCATGCAGGCCGTA
CAGCCGACCTTCGTGATAGCTTAAGGGCAGAAATGGTGAAGATGTATCAAGGCCGTAATGCACTGCAAAGCCTGCTAGATGAGCACGAAGA
ACGCTGGTTAGTTGATACCGGAATACAAGTACCAGAGCAAGGGGAGTTTGACCTTAACGAAATCTTAGTTTCAGACTATTGCTTCGCATAATA
TTAATAGGCCATTCCTTCGGGAGTGGCCTTTCTTTTACCTACTACCTGTAACATTTCATTAACATAAAAGTGTCTCACATGTGAGACTTATTTAC
CGGACACTATAGGATAGCCGTCGGAGACGGGAAAGAAAGGGAAGATAAAGGATATAAAGGAAGTAATAGGTATTAAAGGTTATATAGGTT
ATCTAGGAATACCTATTACCTTCTTCCTTCCTCTTATTACCACTCAGAGGAAGGGCAGACCTAGGTTGTCTCACATGTGAGACTTCGTATTTACC
GGACAGTATAGATAAGATTAACTCACTTTGGAGATTTAACCATGCGCAACTTTGAGAAGATGGCCCGTAAAGCTAACCGTTTTGACATGGAA
GAGGGGCAGAAGAAAGGCAAGAAGCTGAATAAGCCTGTCCGTGACCGTGCATCTAAACGCGCTGCGTGGGAGTTCTAAGTTATGGCTATTA
TTCAGAATGTACCGTGTCCTGCCTGTCAAAAGAATGGACATGATATTACTGGCAACCATCTCATGATATTTGATGATGGTGCCGGCTACTGTA
ATCGTGGACACTTTCATGATAATGGTAGACCTTACTATCACAAGCCGGAAGGTGGCATCGAGATAACCGAGTTATCTATTACTGGCAATATCA
AATATACACCTTCTCAATTCAAAGAAATGGAGAAGGAAGGGAAGATAAGCGACCCTAAATTACGTGCCATCGCACTTGGTGGTATGCGTATG
AAAGACCGTTGGGAGGTCATGAATGAACAAGAAAGGGCAGAGCAAGAAGCAGAGTGGAAACTTGATGTTGAATGGTTCCTCACGCTTAAGC
GTAAGAACCTTGTTTCCAGGCACATTCGCGGCGACATTTGCGCATTGTATGATGTACGTGTTGGGCACGATGAAGAGGGTAGAGTCTCACGG
CATTACTATCCGCGCTTCGAAAAAGGTGAGCTAGTAGGCGCTAAGTGTCGCACATTACCTAAAGATTTTAAGTTTGGTCATTTAGGTAAACTCT
TTGGTATGCAAGATCTTTTCGGTATGAATACTTTGTCTCACGTGTTAGACAAGGGAAGACGAAAGGATTGCTTGCTCATTGTCGGCGGCGAAC
TGGATGCACTAGCAGCGCAGCAGATGCTCCTTGATTCTGCCAAGGGTACTAAGTGGGAAGGCCAGCCATACCATGTATGGTCTGTCAACAAA
GGCGAGTCTTGCCTTGAAGAGATAGTGCAGAACCGTGAGCATATCGCCCAATTCAAGAAGATTATATGGGGTTTTGATGGAGATGAGGTAG
GGCAGAAGCAGAATCAGCAAGCGGCTCGCCTGTTTCCTGGTAAATCCTATATCCTTGAATACCCCTCTGGTTGCAAAGATGCTAACAAGGCAT
TGATGGCTGGCAAGGCTAAAGAATTTGTAGATGCATGGTTTAATGCCAAGTCATCTGATGAAGTCTTTGGTAGCCAGATTAAATCTATCGCAT
CTCAAAGGGATAAGCTCAAGGCTGCACGTCCAGAGCAAGGACTGTCATGGCCTTGGCCTAAGCTGAACAAGGTAACGCTAGGTATTCGTAAG
AACCAGCTTATCATTGTAGGTGCAGGGTCTGGTGTAGGTAAGACTGAGTTCCTTCGTGAAGTAGTTAAGCACCTCATTGAAGAACACGGTGA
ATCTGTAGGCATCATTTCTACAGAAGACCCGATGGTCAAGGTGTCCCGTGCTTTTATCGGCAAGTGGATTGATAAGCGTATTGAGTTACCTCC
AACCAACGACCCGAAAGAAGACGGATACCGTGAGGTGTTCGACTATACCGAGGAAGAAGCTAACGCCGCCATTGATTATGTAGCTGATACA
GGTAAGCTGTTTGTAGCTGACCTAGAGGGTGACTATTCGATGGAAAAGGTAGAGCAAACTTGCCTAGAGTTTGAGGCTATGGGTATTTCTAA
TATCATCATTGATAACTTAACGGGGATTAAATTAGATGAGCGTGCTTTTGGTGGGAAGGTTGGTGCACTTGATGAATGCGTCAAGCGGATTG
GTACTATCAAAGACCGACACCCGGTTACTATATTCCTTGTATCACACCTTACACGTCCTCCGGCAAACCGTACCCAACACGAAGAAGGTGGCG
AAGTTATCCTTTCTGACTTCCGAGGCTCAGGCGCTATCGGATTCTGGGCATCTTACGCCTTGGGGATTGAGCGTAATACAAGAGCTGAAACGC
TTGACGAAAGGACTACCACGTACATCTCATGTGTCAAAGACCGCGACCAAGGTATCTACACTGGAACCAAGGTCATGCTTAAGGGTGACATT
CAAACCGGACGTTTAATGGAACCACAAGCCCGTACTAAGTCATTTGATACAGGTGAAGCAAGGCAACAAGAAGTACCAGATTTACCGGATAC
TATAGAAGAGACTACCTTCGATGAAGAAAGTGAGTTCTGATTAGTGTATTTATCAGGCTTGTCTCACATGTGAGACAGGCTCTTATTAAGTAC
ATTAAATAACTGGAGATTGATTATGTATAACTTAGTGTTGAATGTAGGTGACTTTGTACGCAACATCAAGAAAGATTCAAGTCGCTATCTTTGC
CGTGGTGTTGTAACCTTTGTAGGTGAGAACCTGTATTATGTAGAATATCGCAGTGGTGTTAAGCAATATTACCACAAGAAGACAGCACATAAA
TATCTTGAAAAGATTGTAGAGATAAACAATCAATGTAAGTGCATACATGATGAGGTTTGCGATAAATGTGCTCGCCAGATGCTTAAGAATTTC
CTAGCTCCTCTTTATTATGGTGCTGGTCCTCAAACACTAGCAGAGTGCATGGCAGAAAAGAAAACCACACTCAAGAAAGAGCGTCGCAATGT
AATCACTGGTAAGACTCAAAGTGAGATGATTAAGCAATGTGGCACTGCATTAGGTGTTACACAGTTTAATACTCGTGCATTGGGTAAATCCAC
AGGACAAGCTATGGTAAAGATTGGAGAAGCCATGATGCATCCAAATGTACCTGTGCGAATCATGGATGTTGACCATGCAATCACAGAACAAG
GTACGCAACGACGTGTAATTAATAAGCATTTTGCCGACACTATAGAAGGCATTATTCGTAAGCAAGGGTTGAAAGGTCTTCACATCTTAAATG
GTGAAGAATTACTGTACCTACCTATCGTTACTGAAGAAACATACGTGAATATCTAAGGAGTTAATCATGACTAAGGTATTAATTTATATGCGT
GGACCTCATAAATGCTATGCAGTTGTAGCACCAAATGGTGTTAAGCCTTATCGTACTTCAAAAAGATTGGCATTAATAGGTGCTAGTAGTAGT
GCAAGTTTCCAAATGGAACTTTTTGGTCATTGGACTGAAAGGCAATTCCGTGAGGATTTTAAAGTCATTGGCAGCTTCATGGTGAAATATGCA

Figure 16 (CONTD.)

GAATAAACATAGTCTTAGAATGTTCGATGGTCATGAAAACCTGCAAGCCAAGATTACTAACCAAGCCTTCCTGTTCGCACAGTTAACTATGGC
TGAGGCTAAGAAGAATAGTCTCACTCGTGAACAGGTTATCAAGGAGGCCACTTGGGAACCACACCAAGGTAAATATATGGGCCACAAATTAA
CTGTAACACGCAGTCGATAAGTCAAGGGTTGTCCAACGTGTTGGACAGCCTTTCATCATATTGATTGGGAGGTATTAAATGACTAAGTTTACT
ATGCAAGACCTCATTAAATTACGTGATGAAATAGAATCACCGGAAGTTAATACAGAGTTTCACTACATTGATCCACGAGATAAACGAGAGATT
CCTGATTATCAGATTGAGACGGAGTTAATGTATGAAGATTATTGATTGGAAGAAGGAAGCAGAAGGCCGTATCCTAGTGATGGATGCGGAG
GCTAAAGGCCTGCTGGGTGCTATCCGCTACGGTCATCGTGAAGATGTACACATTATTTGCTGCATGGACTTGCTCACCACTGAGGAGTTCCTC
TTCTTCGACCCATATGAGATGCGTGACCCTGAAGCAAGGGAACACTTGAAAGAGTGGGAAGGCCATCAAGATGGGACCTTGGTTGATGGTG
TTAACTTCCTAAAGCACTGTGAAGCCATCGTCTCACAGAACTTCCTAGGCTATGACGGGCTTCTCTTTGAGAAAGCCTTCCCTGACATCTGGAA
GGGATTTAACTACACCGAGAGGCGCGGCAAGGGCAGACTACGTGCTGACTTGTGTCCGGTACGCGTCATGGATACGCTGGTCATGAGTCGC
CTGTTAAACCCAGATAGACGCCTTCCTCCGCAAGCATATGCCAAAGGTATGGGTAACGTTGCCCCTCACTCAATTGAGGCGCACGGCATTCGT
ATAGGCCGTTATAAGCCGGAGAACGAGGATTGGTCTAAACTAACTGACCACATGGTACATCGTGTACGCGAGGACGTGGCGATAGGCCGTG
ACCTATTCCTCTGGCTATTTAACGGAGAATGGACGGAGCACAAACGCCGTGGCGTGAATAAACGCACTGGCCTAGGTATTGAGACAGCCTTC
CACATGGAGTCCATTGTGACGCTGGAGATGAGCCGTCAGGCCGAGCGTGGATTCCGTCTGGATATAGATAAAGCATTAGCACGATGCGAGG
AATTGGACGCTAAGATTGATGAGACAGTCGCAGCGTTCCGTCCGCACATGCCTATGCGTATCAAGTCTAAACCTTTTAAACCGGAAGAAAAG
AATGAAGTATGCCAACGCGCAAATGAGTATGGAGCTAGCAACAATATACCTACTGTCCTTGACCCCTCTCACTTTCTTCACGCAGAGAGACGA
GGAGATCGCAAGACAGTATGGAGTGTCACTACTAAGTCTGGTGATTGGTCGGCTAGCGTCAAGAAAGACTTTCCTCACCTTAGAGGAAACCG
TAATGACACGCCAAGTGTCAAGTGGATTGGCGCTTACTCGCCTGTTACTTTCGAAGAGATTCCCTTGGGTAACAGGGATACAGTTAAGCAAGT
GCTCTATGATTATGGATGGAAAGGTGTTGAATTTAACGATACCGAGCAAGCGCATCTCGATGAGCATGGCGTATTACCCAAGCCTTGGAGTG
GGAAGATAAATGAAAAGTCCCTTACTTTATGGCAAGAGAGAGCCGCACGTGAAGGTAAAACAGTCCCTGATTGGTGCTTGGGTATCGCTGCA
TGGTACATACTCGTATCCCGTCGTGGTCAGATCCTCAACCGTGGTGACGTTGAAGCCTTCGACCAGAAGGGGGTGTGGCCTTCGCAAGCTGG
TATACGAAAGTGTCGCGGCCTTGTACCTGTAGCATTTAACAAGGAGTTAGGAATCAATGCGCAGCAATACTACGAAAGGTACGGATGCTGGC
CTACGTCAGACAAGGATGACGGAGAATGGCGTGTGCCAGCTATTGCTATTAGTATTGGAACTTCTACGTTCCGTATGCGTCATCGTAACGTGG
TTAATATTCCTGCCCGTGGCTTGTATCCTTTACGTGATTTATTCATAGCAGGGAAAGGCAAGCTAATCCTTGGTTGTGACGGTGCAGGTCTTGA
ACTGCGTGTCCTGTCTCACTTCATGAATGACCCTGAGTACCAAGAGATTGTACTGCACGGTGATATTCATACGCATAACCAGATGAAGGCTGG
TCTTCCTAAGCGTGATATGGCGAAGACATTTATATATGCCTTCCTATATGGGTCTGGTATAGCTAACCTTGCAGCAGTATGTGGTGTTACTGAG
GAAGAAATGGAGGAAGTTGTGGCAAGATTTGAGGTTGAACTACCATCTCTTGCACGTCTTCGTGAGAATGTTATCGCACAAGGTAACAAGTT
TGGCTACCTACAAGCACCTGATGGTCATTGGGGTCGCATCCGTATGTCTGGTGGTGAACTTAAAGAACACACTATGCTTAACGTACTACTCCA
GATGACTGGTTCTCTGTGTATGAAATACGCATTGGTCAGAGCGTTTGCAGTGATGCGCAAGGAAGGTGTGGCCTTAGATAGCATGGGAAACC
CTTGCGGTATAGCTAACGTGCACGATGAAATCCAGATGGAAGTCCCTGAAGATGAGGTCTTGTATCTCAACTACGACTTGCCTTTCACCTTAG
AAGGGTTCGAAACAGAGAAGGCTGCTGTGAAAGCAGTGTTCGATGCAGAGGAGAAACGTGTTCATGTGGATTCTGAAGGACGTATGTGGTC
TGCTGCAAATCTCGTTAGTGTTGATGCTGGTGTACTTCATTGCCAGCGTCGTTATCACCGTGCAGGGCATATCATTGCCGACGCAATGACCTG
GGCGGGTCAGTACCTGAAGATGCGTTGTCCGATGGCAGGTGAGTATAAGATTGGTGCAAGTTGGAAGGAAACACACTGATGGACAGGTTTG
ATATTGTTTGCCTATTCTCTACCTTCTTTCTTATATTCCTTATGCTTGCTTGCTATGGAAGTATGCGATTAGATATACCTGATGAAGAGGAGGGT
TACGATTGATGCAGGCATCTTTTATTATTCTTGGAGTCATATTATTTATGGTAGTATTCTGGGCTTTCTCTGGCATTGACCCAGATTGTGATGGT
AACTACGACTGAGTTATACTCAAGGTCACTTACGAGTGGCCTTTATGAATAACTTATTCCTACTTATTTTGTCTAACATGATTTACTGGACACTA
TAGAAGGAAAGCATAGGTAATCTAGGTTTATAAGGTAGTATAGGTAATTAAGTAAATATAGGAGATATAAATATGTCTATGGTAACTACTCTG
GTATTCGTGGCTCAATACTTTCGTGGTCTTGCTAATAAGTTCAAGTCCAAGGCTATCAAAGCTATTGAGGCTCGCATCGAAGCAGTACAGGCA
GAGCAAGTTAAAGTTGAAGAACATCGTAGTTCTCAAATGATTGACTGTCATAACCGCTACTATGCATCTCGTGATGAACTAAATGCACGTCAA
GTCAAAGAGGTAGAAGATATGCTGGCACGTCACCAGCAAGAGCGTGACAGCCTGAAAGCTGAATTTGAAGAGAACAAGGCATCAATTGCTC
TTGTACATCAAGCTGCATCTGACAGTCTGAAGAAAGAGATTGTTATGCTGGAAATCGAACTGGATAACCTGACCAAATAAGGGGGGGTTATG
ATGGAAGAAGTAATTCAAGCTAAACATGTAGGTATTATCTTTCGCGATCTAGAGCAGCGTAAAGTTGCAGGTCATACTCGTCTGGCTAAAGA
GGAAGACACCGCAATCACTACTGTAGAACAAGCAGATGCCTATCGTGGACCAGAGTTCACTCAAGGTGAAACTTGTCACCAATTGAGCCTAT
CAATTTGTGACACTATGGCTATTGTAAATGTGCAAGAAGTCGAAGAGGGTGAGTGTGTCAGTTACATCTACCCTTTAGATACTATTGCACGCA
TTAAGGTAATCCATAAGTAATTACTAGACACTATAGAACAATAGGTCGGCTTAGTTCGGCCTATGATTGTAAAGTGTTGTTGATGTTGAACCA
TTGTGCATCTTGCACAACCCGATACCGTATAGGGCTTTCTAGTGAGTACATGCTTGTGCTCAGTACAAAGCTAACTGACAATAGGAGACTAAA
TAAATGGCACGTGGTGATTTTGATTTTGGTGCTCAGGTTACTAAATCTGAAGGTAAAGTCTTTAAGAATCCAGAAGTAGGTGATCATGAAGCA
GTAATCTCTGGCATCATTCATGTTGGTTCCTTCCAAGACATCTTTAAGAAAGGTAATACCACTGAAGTTAAGAAGCCAGCAAACTTTGTTCTGG
TTAAGATTGTCCTGATGGGTGACGATGACAAGAACGAAGATGGTTCTCGCATGGAACAATGGATGGCTGTGCCTCTGAAGTCTGGTGATAAG
GCAACACTGACTAAGTTCCTGAATGCAGTTGACCCTAAAGAGTTGCTGGGTGGCTTCGATGATTTCATTGGTGAATGCCTGACTGCAACGATG
GTCGGTTCTGGTGATAAGAATGACGATGGCTCATTCAAGTATGTTAACTGGAAGGGATTTGGTGGTATGCCGGACAAGCTGAAGAAACTGGT
CATTGCTCAGGTTGAAGAGGAAGGTCTGTCTATGACAGGTCACATTACCTTCGACAAGCTGACCAAAGAAATCCTTGATGACATCCCAGCCAA
CTTGGTGCGTCAATACTTCCTGAACGAGACGCCTCGTGGTAAGAACCTGTCTGTTGCTGGTTCTCACGTAGAAGCAATCATTAAAGCTGCTCG

Figure 16 (CONTD.)

TGAAGAAGACCCAGAATGGAAGAAGGCTAAGAAGAAAGACGAGGAAGATGCTACCCCAGCTAATCGTAAATCTCTGGATACTGGTGAGTCT
GTTCCACAGGAAGTACCTGAAGCAGAAGATACTCCTGCACCGGAGATGGATGAGGACGCGGAATATTAAGGAGAAAGGATGAAAGTACAA
ATCGTAACCCTGCACTGCAAGAAAGGAATTACAACTCTTGGCGGCAACACTTTTCACTCCTTCTCTGAAGGGGACACATATGCCGACCTGCAC
TACATCTGGCGCGACGGACAGCACGTGGTGAACTACAGCGACCCAGCTACGGGGAAACGCCACGGCGTATCGCTTCCGGCGCATGACATTG
CTCAGGTGAACACAGTTTTATAAAGTCTCACGTGTGAGACAAATCGGTGTCCGGTATTTACTGGACACTATAGAAGAGAAGAATTTTAATCGG
CGATAATGCCATAACCAACAAAAGGAGAATTTAATATGTTCAAGATTGAAACTATCGTAAACCGTGTTGTTAAAGGTGCTGCTCTGGTATCCG
TTGAGTCTTTCATTATCGTCGATGAAACTGATCAACTGGTAGCTGGTACTAAGGCTTACGATACCCGTGAAGAAGCTCAGGCTAAGATTGACA
GCATGGGTAACTTCGCTGCTGGTCTGGAGTTCGCTCGTGCTTGCTTCCCTGAGCAGGCTGACAAAGCTCAGATTGGTAAGGCTAATATCGTAG
CTGAATATCTGGATTGGGTTGCTGCTGGTAAACCAGTGAAAGAAGTTAAGGCTGCTGAAGAAGCTGAAGCTCCAGCAGAAGAAGTAGCTGC
ACCGGAAACTCCGGTAAGTGAAGAGGAAGAATTTTGATAATAGCAGGTGTTGCCTCTGTTAGTCCTAGCTGACTATCACGCTCACCTCATCTA
ATGCCCTGTCTGCCTTAGTGTAGGCAGGGTCTTTTGCGTAATAGTTATTGGAGAATGAATTATGCCGACTATTGAATCTCGAATTGAACTGGA
CATTAGCTACAATGCAATCACCAGACAGTATATTGGGGTTGCCTATGATTACAAAACTGGTGAGAAGCTAGTGGAGGTGAGACAATGGGATG
ACTATTGGTTAAGACAGAACCTCCATGATGCGGTGTCCTCCTTCCTGAAGGAGTGGCCTACATGCGACCAAACTTCGACTTCGGAGCTACAGT
ATCGGAAGACAATAACCTGTTGCTGTGGCCAACTGAAGGTAATCGAATCGCTTTAATAGATGCTGATATGTTACCTTACATCATAGGGTATAC
AATCAGTGATATGACTTATGTACGAGCCACAACTCGTGTTAAGTCAGGGCAAGTCCCCTCAATCAAAGATACACCTGAGTGTAAGCAAGCGT
GTGACCGTGTGAACTCCTTGCTTAACTCTTGGGTGTATGCAGCAGAATGTGATGCAGCTAAGTTGTTCATGACGAAATCAGAAGCTAACTTCC
GTGTCCGCCTAGCATTCACCAAGCCTTATAAAGGTCAACGTAAGACCGAGAAGCCTCCATTCTTCTATGAATTGCGAGAGCATCTCTTAGAGG
TTCACGGTGCAATCTTGGCAGATGGAGAGGAAGCAGATGACCTCATGAGTATCGCACAATGGGACAGCCACCGCCGCTTCCAGCAAGATACA
GGTAACGAGTTCCCTATCGGTAGTCCAGAGCATAAAGCATTCTCTGATACTTGCATCGTTTCCTTGGATAAGGATTTGATGATTGTTCCCGGTT
GGCATCTACAGCCGGGTCAAGAGAAGAAATGGGTAGAGCCTATGGGTTGGCTTGAGCTACGCCGTAAGGCTAATGGGCAAGTCAAAGATCT
AAAAGGTGCTGGCCTCATGTTCCACTATGCACAGATGATTATCGGTGATGATATTGATAACTATGCTGGCATACCAGGTCGTGGTGCTAAATA
TGCCTATGATCTTCTCAAAGATTGTAAGACAGAGAAAGAGTTGTACATGGCAGTGCTGGGTGCTTACAAGGCTAAGTTCGGGCATGGACAAG
TTAAAATTAAGAATTACCGAGGTGGTTATCGTATCGGCAAAGCCTTTGACCTAATGCTTGAGTGTGGTCGCTTATCTCACATGGCAAGATTCA
AGGGTGATATATGGCGAGCCGATAAGAACCCAATCTTGTGGGGAGATGATGCGGAATGGTTAGCAAATTAAAATCATCGGAGGTGGCAGCT
TATAAGAAGGAATTGCTAGATAAGCAAGGATGGAAATGCCCTCTGTGTGGCGGCAGTCTCAAAGCTGTCACACCTGTAAACCGTGTACTTGA
CCATGACCATGAGACAGGATTCTGCCGCGCTGTTGTATGCCGAGGCTGCAATGGTGCGGAAGGGAAGATTAAGGGTGTTATCTCTGGTTATG
GTAAGGCTGGTAACAACCGTTACTTCCAGCTTCAATGGTTAGAGCGACTATATGAATACTGGAAGTTACATAGTACGCCTCAGACAGATAAGT
TATATCACAAACATCAAACGGAGGCAGAGAAGCGCGAGGCTAAGAACCGTAAGGCACGCCTTGCTTATGCAAGAAAGAAGGAGGTTAAAGT
TGGGTAAGCTGCGCAGCTTGTACAAAGACTCCGAGGTACTTGATGCAATCGAGCAAGCTACCGACGAGAAAGGTAATGTTAACTACAATGAG
ATGGCACGTGTATTATCGTGTCATACTGTGGGTAAGAAGATTACCCGCCAGTTGGCTCGATACTGGCATGGTCAATTCAAGAAGACCAAGAA
GAATGGTGATTACTACCAGACCCTTCTGCAAGAAGATAAGCGTATCAAAGAAGAGCGTAAGCTCAGGACTCCTGACCGCTACGAGGATTTGG
CTATTGTGCCATTGCCTGACTCGCCTCATCGAAGTGTACTGGTGATCCCTGATACTCATGCACCTTATGAGCACCCAGATACCCTAGAGTTCCT
TGCAGCCGTGGCAGCACGTTACCGTCCAGACACAGTGGTACACCTAGGAGATGAGGCAGACAAACATGCCCTGTCATTCCACGATTCGGACC
CAAATCTGGATAGTGCTGGCATGGAGTTAGAGAAGGCTCGTATCTTCATGCACAAATTGCACAAGATGTTCCCTGTGATGCGCCTGTGTCACT
CTAACCACGGCTCTATGCACTTCCGTAAGGCAAGCGCCAAAGGCATCCCTGTGCAATACCTGCGCACCTATCGTGAAGTCTTCTTCCCGCAGG
GAGGTGGCGACCAGTGGGATTGGCAACATACGCACGTCCTTGAGTTGCCGAATGGTGAACAAGTGGCATTCAAGCATCAACCTGCTGGCTCT
GTCCTAGCAGATGCAGCGCATGAGCGTATGAACCTTGTGTGTGGTCACTTGCACGGTAAGATGTCTGTGGAGTACGCACGTAATACACATGA
ACAGTATTGGGCTGTGCAAGGTGGCTGCTTAATTGATGAGTCATCCCGTGCATTTGCCTATGGTCGTGAGTCTAAATACAAGCCAGCATTAGG
TTGTGTGGTCATTCTGGAGGGTGTGCCTCACATTGTCCCGATGCAAACCAATAGCGACAACCGTTGGATTGGCAAGATTTAGTTGACACTATA
GAACAAAGGGCTAGGTAAGACTTTATCGGCTGGCGTATCCAAATGATATTGCACTAGCCCTTGATTGTATAGTGAATGGAGGATTCAATATGT
CACACTATGAATGTAAGAAGTGTCATAAGCGTTATGATTACTGTACTTGTGGTCAAGAGAAAACATCTTTTAAAGTTGGAGACAAGGTATTTC
GTAATGAAAAAGATTCGATTCCTTGGAATCAATACTGCAAAGAAGCTGGTATTGACCCTGATAGCCCTGTAACCATAGATGATATTGATGGCA
TTAACTTGTGCTTTCGTGAGGTGAGGGGTACAGGTTGGGATTCCAAAAAATTCAAACTTGCATCTGATAAGTTAGACAACAATATGGTAATTA
AGCCTAAGCACTACGAGTTCTTTGATGGCGTAGAGGCAATCACTATCATTGCCCGCAGTATGACCGAGAAGCAATTCGCTGGCTATTGCATGG
GTAATGCTTTGAAGTACCGTCTACGTGCAGGTAAGAAGTTCAACACTGAAGAAGACCTGAAGAAAGCAGATTACTACAAAGAGTTATTCCAG
AAGCATCGTCACGAATGTATTGATGAGGATATTTGATATGAATATCTTTGAGTTCCTAGGTCTTCCAGAAGACCACCGCAATCACCCATTCATG
CTGGTGAAGCATCGCGGTGAAGTTCCTGAGAAGAAATTAACTTTTCCATGTTATGCACAGGTGAAACGAGATGGTATCTTTTCTGCTGTTGTT
GTTCGCACTGATGGTGTCGTTGGCATTTTTGGTCGCACTGGTAAGAAATTGGCAAACACTGAAGGACTCGAACAAGCCTTTGCTACCTTTCCG
GTTGGCATTTATCTTGGTGAGCTTCAGTCTATGGCCATTGATATCTACCTTGAGGCAATCTCTGGGGTTGTGAACCCCAATCGCACTGAGCCAC
TTGATTTCATAGGCCAGCAGATTAAAGACAACCTGTATATCGACTTCTTCGATATGTTAACTATTAAGGCATTCCATGATGGATTCACTGATGT
TTCTTATCTCAAACGTTACGATGCTTTACATCGTCGTATCGGCGCTCATCTTAGCGGGTGCAACGCTATCCTTCCTATCACTCCTTGCCATAATG
AGCGAGAAGTTGAAGCGTTTGCGCAAGAGCAAATAGATGCAGGACGTGAGGGTGCTGTATTCAAACTGGACTGCGATTATGAAGCAGGACA

Figure 16 (CONTD.)

CAAAGGTTATCGTCAGACTAAAGAAGTCCGTAAGGTAACCTATGACCTTACTTGTATTGGCTTTGAAGAAGGTAAAGGCAAATACAAAGGTA
AGGTAGCTAACCTCATTTTCAAATGGAAAGGAGGCAAGACAATCAAAGCTATGTTAGGTAAGGGGTGGACTCATGCAGATGCAGAGCAGAT
GTTCCACGACATTAAACATGGTGGACGATTGAATGTCATTGGTAAAATCTTTGAAGTCAAAGGTCTTCAGGATTCAAGCAAGGGCAACATTCG
TCTGCCCAAAGCGGGAGAATTAAGACATGACAAAGATGAACCAGATTTCTTTTGATAGCATGAAGGCAACTCGTGCAGTTGAGGTAGCAGAA
GCTATCTTCGAAACTTTATCCTGTGGCATGGAAGTGCCATATACTTTACTTGCTGATGCAGAAGAACTTGGTCTTTCTGTAGAAGCTATCCAAG
AGAAGGTTGACGAATTATATGGTACAGACGAAGAAGAAACCGACGATTTCATTTGAAGGAATGGAGATGCTTGAGATGATTCTCAAGCCTTC
TTCTCCTAAGGTGACTAAGACTCATGAAGAGTTAATCGTTGATGAAGTTAAGCGTTACATCATGGATTGTGTCAGAGCACAACTGGTGGTCCA
ATGATACGTCCAGCCTCCTTCCTAGATATTCCTGAGATTATAAACCTTGGGAATAAATATGTGGAAGAGGAAGTCAAGGTTGTAGCCCACCAC
TCAGCCTCATGGAATGCAGAACAAAGTGCCATAACCTTTGTGCATCTCTTAATAGAGACCCACCACTCAGCCTCATGGAATGCAGAACAAAGT
GCACATAACCTTTGTGCATCTCTTAGTAGAGAAGATTTATCCCTATGGGTTGCTGTAGATGAAGGGCAGATTGTAGGGTTCCTGTGGGCTGGC
TATCACGAGTTGGCCCCTTGGACACCTGTAAGAGTTGCCTCTGACATTCTCTTTTATATTATACCAGAGAGGCGAGGAACACTACTTGGTATGC
GTCTCATCAAAGCCCTAAAGCAATGGGCTAGTGATAATGAATGCTCTGAGGTTCGCCTGTCTATCGCCTCTGGTATTAATGAAGAACGTGTCG
GACGTATGTATAAGCGACTTGGCTTTGAACCGTTTGGCACTGTGTATAACCTGAAGTTCTAAGGAGATAACATGGGTGTTGTAAAGAAAGCA
TTTAAGGCTATCGGTCTTGCTCAAGATGCACCACGTATTGAAGCCAAAGTCCCAGCACAGCAGCTTGAGCGTAAGCCTGAGACTGAAGCTGA
AGATATTCAAATTGGTGCAGGGGATGATGCTACTGCATCTGCAAAAGGTAAGCGTGGCCTTGTCCGTCCGGTAGCTTCTAGCTTGAAGGTGT
AATATGAAACAGAGCATAGATTTGGAGTATGGAGGTAAGCGGTCTAAGATACCTAAGCTATGGGAGAAGTTCTCCAATAAACGTAGCTCTTT
CCTTGATAGGGCGAAGCATTACTCCAAATTAACCTTGCCCTATCTGATGAATGACAAAGGTGATAACGAGACTTCGCAGAATGGATGGCAAG
GTGTAGGTGCTCAGGCAACCAACCATCTAGCCAACAAGCTAGCGCAAGTACTATTCCCTGCACAGCGTTCCTTCTTCCGTGTAGACTTAACTGC
ACAAGGTGAGAAGGTTCTTAATCAGCGTGGCCTGAAGAAGACAGAGCTAGCTACCATCTTCGCTCAAGTGGAAACACGGGCAATGAAAGAG
TTAGAGCAACGTCAATTCCGGCCTGCTGTAGTAGAAGCATTTAAGCATCTTATTGTTGCTGGCAGCTGTATGCTATACAAGCCGAGCAAAGGT
GCAATCAGTGCTATCCCAATGCATCACTACGTAGTTAACCGTGATACCAATGGCGACCTGTTAGACATTATCTTGCTACAAGAGAAAGCCTTAC
GTACCTTTGACCCAGCTACACGTGCGGTAGTAGAGGTTGGCCTGAAAGGTAAGAAGTGCAAGGAAGATGACAGCGTTAAGCTGTACACACA
TGCTAAGTATCTTGGTGATGGATTTTGGGAACTCAAGCAATCTGCTGATGATATCCCTGTGGGTAAGGTGAGTAAAATCAAATCAGAAAAGC
TACCTTTCATCCCATTAACTTGGAAGCGAAGCTATGGTGAGGATTGGGGTCGACCTCTTGCAGAGGATTACTCCGGTGATTTATTCGTTATCCA
ATTCTTATCTGAAGCGGTTGCCCGTGGTGCTGCGCTGATGGCAGATATCAAGTACCTGATTCGTCCTGGTGCTCAAACTGATGTTGACCACTTT
GTTAACTCTGGCACTGGTGAGGTTGTCACTGGTGTAGAAGAAGACATCCATATTGTACAGTTAGGTAAGTACGCAGACCTCACACCTATTAGC
GCGGTTCTAGAGGTATACACTCGCCGTATCGGTGTTGTCTTCATGATGGAGACAATGACACGCCGTGACGCCGAACGTGTTACTGCTGTAGA
AATCCAGCGAGATGCGTTAGAGATTGAGCAGAACATGGGTGGTGTATACTCCCTCTTTGCTACTACTATGCAATCGCCAGTAGCGATGTGGG
GTCTGCTGGAGGCAGGGGAGTCCTTCACTAGTGACTTAGTGGACCCTGTGATTATCACAGGTATTGAAGCTTTAGGACGCATGGCTGAGTTG
GATAAACTGGCTAACTTTGCTCAGTATATGTCACTGCCATTACAATGGCCTGAGCCTGTCCTAGCTGCTGTGAAATGGCCTGACTATATGGATT
GGGTGCGTGGTCAAATCTCTGCTGAACTGCCGTTCCTTAAATCGGCTGAAGAGATGGCACAAGAACAGGAAGCACAGATGCAAGCACAGCA
AGCACAGATGCTTGAAGAAGGTGTGGCTAAGGCCGTGCCGGGTGTAATTCAACAAGAACTTAAGGAGGCGTAATGTCTTTCTCATTTACTGA
ACCGTCAACCACTCACCCTACTGCTGAAGAGGGTCCGGTAGAAACCAAGGAGGTAACAACTGATGCTGCTACTACTGATGCTCCTGCTGACG
CTGGCACTTCTGTACAAGATGACAATGCTGGTGCACAACCTACTGAAGACACCGGAGGAGAAGCTTCTGGACAGCCTTCAGAAAAAGGAGA
CAATGGCGGAGAGAATGGTGAACCTAAGCCAGATGATACCGCGACCGACACTGAGGAAGTGCAATACTTCTTCGGAGAACATGAAGTAACA
GTAGACATCCCACAGGATGTAACTGACAGCCTTAAAGAGAAAGGCATTGATGCCAAGCAGGTTGCCAAGGAACTCTATTCCAAAGGTGGCAA
GTTTGAACTGTCAGATGCAACCAAGCAGAAATTGTATGATGCTTTTGGCAAGTTTGCGGTAGATGCTTACCTATCAGGTCTAAAGGCTCAAAA
TGAAGCCTTCTTCCTGAAAGAAGCCAACGCAGCTAAAGAGTTGGAAGCAGCTAACACCCAACGCTTCTCTGATGTTTCTAAGGAAATTGGTGG
CGAAGAAGGTTGGTCCCGTCTTGAGGAGTGGGCACTTGAAGCGCTGTCTGATGACGAACTAATGGCATTCAATGCGGTGATGGAATCTGGC
AACCAGTACCTGCAACAATATGCTGTTCGTGAACTGGAGGGTCGTCGTAAGCAGGCACAGGGGGATGATAAGCCATCCCTGATTGAGCCATC
AGCACCTGCTAAGGCTAATGAAGAGAATGGCCCACTGACGCGAGATCAGTACGTTCAAGCAATCGCAACTCTTAGCCAGAAGTACGGCAATG
ACCGTAAAGCTATGGCAGAAGCTCAGGCTAAACTGGACGCCCGTCGCCGTGCTGGCATGGCTCGCGGTATCTAATTCAGTATTTACTGGACA
CTATAGAAGGGAGAAAAGTTCTCCCTAGTTATCAATTTGATTTATAAGGAGATTATAATACATGTCTACACCGAATACTCTGACTAACGTTGCT
GTATCTGCGTCCGGTGAGGTTGACAGCCTTCTCATTGAGAAGTTTAATGGTAAGGTCAATGAGCAGTACCTGAAAGGTGAGAACATTCTGTC
CTACTTTGATGTACAAACTGTTACTGGCACTAACACAGTGAGCAACAAATATTTGGGCGAAACTGAGTTGCAGGTGCTAGCACCGGGTCAGT
CCCCTAATGCCACCCCTACTCAGGCGGATAAAAACCAGTTGGTAATTGATACCACTGTCATTGCTCGTAACACTGTGGCTCACATCCACGATGT
ACAAGGTGACATCGATAGCCTGAAACCAAAACTGGCTATGAACCAAGCCAAGCAACTGAAACGTCTGGAAGACCAGATGGCAATTCAGCAG
ATGCTGTTAGGCGGTATTGCTAACACCAAGGCCGAACGTAACAAGCCGCGTGTTAAAGGGCATGGCTTCTCTATCAACGTTAACGTAACTGA
GAGTGAAGCACTGGCTAACCCTCAGTATGTTATGGCTGCGGTAGAGTATGCTCTGGAGCAACAGCTTGAGCAGGAAGTGGACATCTCTGATG
TAGCTATCATGATGCCGTGGAAGTTCTTCAATGCTTTGCGTGATGCAGACCGAATTGTAGATAAGACTTACACTATCAGCCAGTCTGGTGCAA
CCATTAATGGCTTCGTTCTCTCTTCTTATAACTGCCCTGTGATCCCGTCTAACCGATTCCCTACCTTCGCTCAGGATCAGGCTCACCACCTGTTGT
CTAATGAAGATAACGGCTATCGTTATGACCCTATCGCAGAGATGAATGGTGCAGTTGCTGTTCTGTTCACTTCCGACGCACTGCTGGTGGGTC

Figure 16 (CONTD.)

GTACCATTGAAGTGACTGGTGACATCTTCTATGAGAAGAAAGAGAAGACTTATTACATTGACACCTTCATGGCTGAGGGTGCAATCCCTGACC
GTTGGGAAGCAGTGTCTGTAGTTACCACTAAACGTGATGCAACTACTGGTGATGCTGGAGGTCCTGGTGATGATCACGCAACCGTACTGGCT
CGTGCACAGCGTAAGGCTGTATATGTCAAAACCGAAGGTGCTGCGGCTGCATTCTCTGCTGCCCCAGCAGGTATCCAAGCGGAAGACCTTGT
AGCGGCGGTACGTGCTGTAATGGCAAATGACATTAAGCCGACTGCAATGAAACCTACTGAGTAACACCTATGCCCTATCTACCTTGCGTAGGT
AGGGTTCTTTTTGTTAGGAGGATTCATGCCTGTAATTAGACAAACCAGTAAATTAGGACATATGATGGAAGATGTGGCCTTCCAGATTATTGA
TAGTAAGCTGGAAGCGGTAAACTTGTGTATGCGAGCTATTGGTCGTGAGGGTGTGGATTCCCTCGACTCAGGGGACTTGGACGCAGAAGAT
GCAAGCAAAATGATCGACATCGTATCCCAGCGGTTCCAGTACAACAAAGGAGGTGGCTGGTGGTTCAATCGTGAACCAAACTGGCAACTTGC
ACCAGACACTAACGGTGAAGTTAATTTACCTAACAACTGCCTAGCAGTATTGCAGTGTTATGCTTTAGGTGAAAAGAAAGTACCTATGACTAT
GCGAGCAGGTAAGCTCTACTCTACTTGGAGTCACACCTTTGATATGCGTAAGCATGTTAATGCTAATGGTATGATTCGTCTTACCTTACTCACC
TTACTACCCTACGAGCATCTACCTACAAGTGTAATGCAGGCTATTGCCTATCAAGCTGCTGTAGAGTTTATTGTGTCTAAGGATGCAGATCAGA
CTAAGCTAGCCACTGCGCAGCAGATAGCCACTCAGCTTCTTATGGATGTACAATCTGAGCAAATGTCACAGAAGCGATTAAACATGCTGGTAC
ATAACCCTACTCAGCGTCAGTTTGGTATCATGGCTGGTGGCTCTCAGAATGTACCTGCTTACTCTCATTCACCTTATGAGAGTTGGGCGCTCCG
TCCGTGGGAGGATCGTTAATGGAAGTACAAGGTTCATTAGGTAGACAAATCCAAGGGATTAGCCAGCAGCCGCCAGCGGTACGCTTGGATG
GTCAGTGCACAGCTATGGTTAATATGATACCTGATGTAGTGAATGGTACTCAATCACGCATGGGTACAACTCATATTGCAAAGATACTTGATG
CGGGGACTGATGACATGGCTACTCATCATTATCGCAGAGGTGATGGTGATGAAGAGTATTTCTTCACGTTGAAGAAAGGACAAGTTCCTGAG
ATATTTGATAAGTATGGGCGCAAATGTAATGTGACTTCACAAGATGCACCTATGACCTACCTCTCTGAGGTTGTTAATCCAAGGGAAGATGTG
CAATTCATGACGATAGCTGATGTTACTTTCATGCTTAATCGTAGGAAAGTAGTTAAAGCTAGTAGCAGGAAGTCACCTAAAGTTGGAAACAAA
GCCATTGTGTTTTGTGCGTATGGTCAATATGGTACATCTTATTCCATTGTAATTAATGGGGCCAACGCTGCTAGTTTTAAAACACCGGATGGTG
GAAGTGCAGACCATGTTGAACAAATTCGAACTGAACGTATCACTTCTGAATTGTACTCTAAGTTGCAGCAATGGAGCGGTGTGAGTGACTAT
GAAATACAAAGAGACGGTACTAGTATATTTATCGAGAGACGGGATGGTGCTAGCTTTACAATAACAACCACCGATGGTGCAAAAGGTAAGG
ACTTAGTGGCTATCAAGAATAAAGTTAGCTCTACTGACCTACTCCCTTCTCGTGCGCCTGCTGGTTATAAAGTACAAGTGTGGCCTACTGGCAG
CAAACCTGAGTCTCGTTACTGGCTGCAAGCTGAGCCTAAAGAGGGAAACCTTGTGTCTTGGAAAGAAACAATAGCTGCTGATGTATTACTTG
GGTTTGATAAAGGCACAATGCCTTACATTATTGAACGTACAGATATCATCAACGGCATAGCTCAATTCAAGATAAGACAAGGTGATTGGGAA
GATCGTAAAGTAGGGGATGACTTGACTAACCCTATGCCCTCTTTTATTGATGAGGAAGTACCCCAGACAATAGGTGGAATGTTCATGGTGCA
GAACCGCCTATGCTTTACAGCAGGTGAAGCGGTTATTGCTTCTCGTACATCATACTTCTTCGATTTCTTTCGTTATACGGTTATCTCTGCATTGG
CAACTGACCCCTTTGATATTTTCTCAGATGCTAGTGAAGTCTACCAGCTAAAACATGCAGTGACCTTAGATGGCGCTACCGTGTTGTTCTCTGA
TAAGTCACAATTCATACTGCCAGGCGATAAGCCTTTAGAGAAGTCAAATGCACTGCTTAAGCCTGTTACAACATTTGAAGTGAACAATAAAGT
GAAGCCAGTAGTAACTGGTGAATCGGTAATGTTTGCCACTAATGATGGTTCTTACTCTGGTGTACGAGAGTTCTATACAGACTCTTATAGTGA
CACTAAGAAGGCACAAGCAATCACAAGTCATGTGAATAAACTCATCGAAGGTAACATTACCAACATGGCAGCAAGCACCAATGTCAACAGGT
TACTTGTCACTACCGATAAGTATCGTAACATAATCTACTGCTACGATTGGTTATGGCAAGGAACAGACCGTGTACAATCAGCATGGCATGTAT
GGAAGTGGCCTATAGGTACAAAGGTGCGAGGTATGTTTTATTCTGGTGAATTACTTTACCTGCTCCTTGAGCGAGGAGATGGCGTGTATCTG
GAGAAGATGGACATGGGTGATGCACTAACCTACGGTTTGAATGACCGCATCAGAATGGATAGGCAAGCAGAGTTAGTCTTCAAGCATTTCAA
AGCAGAAGATGAATGGGTATCTGAGCCGCTCCCTTGGGTTCCTACTAACCCAGAACTTTTAGATTGCATCTTAATCGAGGGTTGGGATTCATA
TATTGGCGGCTCTTTCTTATTCAAGTACAACCCTAGTGACAATACTTTGTCTACAACCTTTGATATGTATGATGACAGCCATGTAAAAGCGAAG
GTTATTGTTGGTCAGATTTACCCTCAAGAGTTTGAACCTACGCCTGTGGTTATCAGAGACAATCAAGACCGTGTATCCTACATTGATGTACCAG
TTGTAGGATTGGTTCACCTTAATCTTGACATGTACCCCGATTTCTCCGTAGAAGTTAAGAATGTGAAGAGTGGTAAAGTACGTAGAGTATTAG
CGTCAAACCGTATAGGTGGTGCTCTCAATAATACAGTAGGCTATGTTGAACCGAGAGAAGGTGTCTTCAGATTTCCACTGAGAGCTAAGAGC
ACGGATGTTGTTTATCGTATTATTGTAGAGTCACCTCACACATTCCAGCTTCGTGATATTGAGTGGGAAGGGAGCTACAATCCAACCAAAAGG
AGGGTCTAATGGCTATAGGTTCAGCCGTTATGGCTGGTATGTCTTCTATTGGTAGCATGTTTGCAGGCAGTGGTGCAGCAGCCGCTGCTGGA
GGTGCTGCCGCAGGTGGCGGAGGTTTGCTAGGTTCACTAGGTGGATTCCTAAGTGGCTCTACTGCTGGTTTCTCTAATGCTGGCCTTCTTGGT
GCTGGCCTTCAAGGGTTAGGCTTGATTGGTGATCTATTTGGTGGAAGTGATGAAGCCAAGGCGATGAAGAAAGCACAAGAAGAGCAATGGC
GGCAGCAGCTTATTGCTACACAAGAGGCGTACAAGACAGTGGCAGACGCAGAACGTTCTGCTGCTAAACAATATCATGCAGATGCAATCAGT
AATCAGGCTTCACTGCTACAGCAGCGAGCACAGGTTGCATTACTTGCTGGGGCTACTGGTACTGGTGGTAATTCTGTGTCCTCTATGCTTAAT
GACTTAGCAGCAGATGGCGGCAGGAACCAGAGTACTATCATTGATAACTATGAGAATCAGAAGATTAATTTCACCAACCAGCTTAAGTCTATC
CAACGTGGTGGTCAGATGCAGATGCGTGAGTTTAAGAAGCCTTCTGCTATGAATACCTTGGTTAAAGGTATTCCAAGTCTGGCATCTGCCTAT
GTAACTGGTAGTAAGTCTGGCAAGGCATTGGGTAAAGCCTTAACTGATTCTCGCACATATTCATCTGGAACAAGAGGTATTTAATGGCAATTG
AGCGACAAGCAGTACAAGGTCTGCCACAAGTGCAGGCCACTTCTCCTAATGTCATGACCTTTGCACCTCAACAAGTGGGAGGTGTGGAGGCT
GGCGTGGCTTCTACCTCCGGTAGTAGGTTTATCGAAGACCTTATTCGTGCAGCAAGCAGCGTGGCTGATGTTACCACTGGTATCCTTAATCAG
AAGATTGAGGAAGATAAGGTTGTTCAAATGGAACGGGCATATAACGGATTAATGCCTTCTGAGGATGCAACTCGTGGTGGCGCTCGTGCTAA
CATGCTTGTCAAAGCTCAACTGCTAGCTAATGATGAAGCAGCACGAATGAAAGACATGGCTACTCGTTTCCAAGGAACGGATGACGAATGGA
CACAACTTATGGTTGACTCTCGTAATGAGATGCAGAATAAGCTGTTCCAGCAATACCCTGAGTTGCAAGGTGACAAAGATACTATGCGTATGG
TCACTAATGTCTTCCAAGAACAGCAGCCTCAGATTTGGGCTACACGAACCCAGCATAAACTTGACCGTGAACAAGCAGACCGTGAGGATACCT

Figure 16 (CONTD.)

TTGACGGGCGAGTGGCTTCTACTTGGGATTCTAATATTGACCCTGAAGCCTCTGGCTATGCTTTACAGGAACGAATCCGCGAAGGTCTTACTC
AAGGATTACTACCTGAACAGATGTACAAGAAGTTAGTCCAGCGAGCAATTTCACTTGCACAAGGCGGTGATGTTAGCATGGCTGAAGCCCTG
AAGTATGTGAAGGACGATAAGGGTGTTTCTGTTTATGCTAAGAATCCACAGCTTATCACAGCCATCACTAGTGGTAATGCAGTTTGGGCTAGG
AATAATGTAGCTGATGTAACTCGTATGTCTTTCGAAGTTAAAGAATCCTACCTTGCAGGTGATTTAACTGATGAAGAATTGTTGGAACGAGCA
CAGCACATTAATAATCTGACAGGTAACTCTGTCTTCTCTAATCCAGAACTAGAGGCACTGATGCGCCAACGGGCTAAGCAGAATGCAGAGCTA
GGTGCAATGCAGGATATGCGACGTGAGCTTTACTCCGACCGCCTGACTGGCTTCCAAGGTAAGACTGATAAAGAGAAGAAGGCTTACATTGA
TGTTATCAAACAGGATAGCCAACTTTATGCAGACCAGCAAATCAAACAACGTGGCTTGGACCCTTACAGTCAAGAGGCTGAAGCTATTCGTG
GTGCAGTGGAAGTGCAGCGCCTGCAATTCATGAACTCCAAAGGCTTAGTGGATGATACCTTTGAGTCTCGTATCAAAGCCATGGAATCTATGC
TATCGCCTGAGCACTTTGCCAAGGGCGAACCACAGGAGTTGATGACTATTCGCCAGTTGTGGGAACAGTTACCAGAAGAGAGCCGAGGTGT
CTTTGGTGACACGGTGAATGGCTACATGGATAACTACAACACTGCACTACAAATGGGAGAGACACCTTTGCAGGCTGCAAGGTTTGCGCGTA
AAGCACAGCAGAAATTCTCTCGTACTGAGAAGGAAACCAAGAAGTTCAACTCAGCTATTGGAGATGCACTGGATGAGGTATCTGGTGCTGGC
TGGTTTGATGGTAAAACCGAAGTGTCAGACTTAGGTAAAGCTATTGCGGAAGAAGAGTTACGAGCTAAGGCCAATATGTTGTGGTCTAGTGG
TATGCGTAACATGGATTCCATCAAGAAGGCTTTAATTACTTGGGGCAATAAACGCTACACTCAATCAGAGGATGCAAAGACTTCCGGTGGCTA
TTTCATTAAAGGTGATTACACTTCTGCATCTGATATGCTTATGTCAGTTGGGAAAGGCGTAAACCCTACCGATGTACCTCTGGCGCTTGGTAGG
TATGTAGAAACACAGATGCCAGAATTGAAGAAGGAGCTTCAAGAGGGGGAAACTAAAGATGATATATACATTGATTACAATGAACAGAAAG
GTACTTTCGTGATTCGTGCTGGTGCAGCAGGTCGCCCTCTTTCTGGAGTAATCCCTGTAACCTCTTTAGATACCACTTCACTACTAGATTCTGCC
TATCAGAAGAAAGTAGAGGAACGAGATAAAGGCGAGTATGTTCACCCGTATCGTACAGATATTGGTGCACAAGAGCCTATGCCAGCTAAACC
AACTGCCAAAGATATTGGTAAATTTGGACTAGCTAACTTCCTCATGTCTTCTGCTTTTGCTTCTGGTGAGAATCTGCCTTCTAACTTCGAGATTA
ACTATCGAGGTAATATGCAACAATTCTATGACAAGCTAGCTATGGATGAGAATAAAGATAAAGTTGGCTTTAATAAGGCAACTGGAACCTTTA
CTCCATATAAAGACGCTCACGGTGAGTCTATCGGTTACGGTCATTTCTTAACGGAAGAAGAGAAGCGAAACGGGTATATTAAGATTGGCGAT
GAACTAGTTCCCTATCGAGGGTCTATGTCTCAGCTTACAGAGAGCAAGGCTCGCGCTCTTATGGAGCAAGATGCTAAGAAGCATGTGCCTCCT
ACTCGTGACTGGAAGATTCCGTTTGACCAGATGCACCCTGCACAGCAACGTGGCTTGATGGATTTAAGCTACAATTTAGGTAAAGGTGGAAT
CCAGAACTCACCGCGTGCTCTTGCTGCATTCAAAGCTGGTAAGCTTACGGAGGGCTTTATCGAAATGCTGGGCACTGCATCAAGTGAAGGTA
AGCGTATTCCTGGCCTACTGAAGCGACGCGCTGAGGCATACAATATGGCATCTGCTGGTGGTGTGCCTAAGATTACCGAAGTGGAGACTCGT
GAAGATGGCTCCATGTGGGTTAGGTTTGGTGGACCTATGCCAGCAGGTTCTGTCTCGGCATGGACTCATAAACGTATTGGCGCGGATGGTTG
GTATCAGGTTTATGAGGCTGCACCTACCAAGTTAGCTAAAGATTCTAAGGTAGGTAAAGTTAAGTTGTAGTACCTAACTCAAGGCTTGTCTCA
CATGTGAGACAGGTCTTTATGATAGGCACTATGGAGGAATTATGGAACAAGACATTAAGACTAATTGGGCTGGATATGTCCAGTCTACTCCT
GAGCCGTTTTCTATTGAGGCGGCTCCGGTATCGGCTCCTACGATACGCCAGCGTAATGAGTTACAAGAGCAAGTTCTTGAAGCTAAAGCTGA
CGCTGATATCTTAGGTGCTGTAGGTGCTGCCTTCCAGAATGAGTGGTTGGCATTCGGAGGCAAGCGGTGGTATGACCGTGCCACTGCTGATT
TCACACCTCAACCAGACTTTGAGATACAACCTGAGCAACGTGAAGCACTACGTTTCAAATATGGTACGGATATGATGCAGACAATCACTGAGG
GTGTTCGTTCTGAGGATGAATTGAACTTCCGTATTCAGAATGCGGATGAAGACCTTGAGCGCAATAAGCGCATTGCTCAGGCTGGCTGGGTT
GGCTCTGTGGCGACGATTGGCGCTGCTGTGCTTGACCCTGTGGGATGGGTTGCCTCTATTCCAACCGGTGGTGCCGCTAAAGTTGGACTCGT
AGGCCGTGCTGTGCGTGGCGCTATCGCCGCTGGCGTGAGTAATGCCGCTATTGAATCCGTATTGGTCCAAGGTGACATGACTCGTGATTTAG
ATGACATTATGGTAGCACTGGGTTCCGGTATGGCTATGGGTGGCGTTATTGGCGCTGTAGCGCGTGGTAGGGCCACTAAGCTCAGTGAGCAA
GGTGATGACAGGGCTGCTAGCATTGTGCGCAGTGCAGACGCAGGGGACCGCTATGTTCGTGCTGTTGCCGATGACAGTATCGGTGCGATGC
GTGTTAAGGGCGCAGAGGTTCTCACTGAGGGTGTATTCGATATCTCCAGTAAGAGTGAAGACCTACTGAAAACCTTGCAACGAGAAGGTAAT
GCGATTGATATGACACCTCGCCGTTGGGCTGGAACTATGTCTGCCCTCGGTACTGTCGTGCACTCATCTAAAGATGCAAGTATCCGAGGCCTT
GGTGCTCGTCTGTTTGAATCCCCACAAGGTCTAGGTATGCAGAAGGCATCTGCTAGTCTTATGCAGAATACTAACTTAAATCGCCTGAAATCT
GCTGATATGAACCGCTTCAATGATGGGTTTGATTTGTGGCTTAAAGAGAATAATATCAATCCAGTAGCAGGGCATACCAACTCTCATTATGTA
CAGCAATACAATGAAAAGGTGTGGGAGGCAGTGCGTATTGGCATGGATGAGTCTACACCTAAATCTATCCGCATGGCTGCTGAGGGACAAC
AGGCTATGTACAGAGAGGCGCTGGCTTTACGTCAACGTTCTGGTGAAGCGGGATTTGAAAAGGTAAAAGCCGACAACAAATATATGCCTGAT
ATCTTTGATAGTATGAAAGCCAGACGTCAATTCGATATGCACGATAAAGAAGACATCATCGAACTTTTCTCTCGTGCCTACCAGAATGGCGCT
CGTAAGATTCCAAAGGAAGCAGCAGATGAGATTGCACGAGCACAGGTAAATCGCGTTGCTGATGCTACCTTAACTGGAAAGCTTAGTTTTGA
AAAGGCAATGTCAGGTCAGACTAAGGCAGAGTATGAAGCTATCATGCGTAAGGCAGGCTTCAGTGATGAAGAAATTGAAAAGATGATAGAA
GCTCTGGATAACAAAGAAACCAGAGATAACATCTCTAACCGAGCTAAAATGAGTTTAGGATTAGATGTTACTCAAGAATACAATGGCATTCGT
ATGCGTGACTTCATGAATACCAACGTGGAAGAGCTAACAGATAACTATATGAAGGAAGCAGCAGGTGGCGCTGCATTGGCTCGCCAAGGCTT
CTCTACCTATCAGGCTGCACTTAATGCAATTGACCTTGTAGAGCGAAATGCACGAAACGCGGCTAAGGATAGCAAGGCTAGTTTGGCATTAG
ATGAAGAGATTCGTCAGATGCGAGAAGGTCTTCGCCTGATTATGGGCAAGTCGATTGATGCAGACCCACAGGCTATATCTACTAAGATGATG
CGTCGTGGTCGTGATATCACAGGTGTGCTTCGCTTAGGTCAAATGGGCTTCGCACAGCTAGGTGAACTTGCCAACTTTATGGGTGAATTTGGT
ATTGCTGCAACTACTATGGCTTTAGGTAAGCAATTCCGCTTCACCTCTAAGGCGTTGCGTAATGGCGATGGCTTCTTCCGAGATAAGAACTTA
GCTGAGGTTGAGAGAATGGTGGGGTACATTGGTGAGGATAACTGGCTAACAACTAAGGGTGCACGTCCTGATGAATTTGGTGATGTAACCA
CAGTAAGAGGGATGATGGCTCACTTTGACCAATCCATGAACTCAATACGTCGTGCTCAAACCAACCTATCACTCTTCCGCATGGCACAGGGTT

Figure 16 (CONTD.)

CTCTGGAGCGAATGACTAATAGGCAAATAGCTTTGTCTTTCATTGACCACCTTGAAGGCAAGAAGATTATTCCTCAGAAGAAACTGGAGGAAC
TTGGTCTTACTCAGGAGTTCATGACTAACCTACAGAAGCACTATGATGCTAACTCTAAAGGTTCTGGCTTGCTTGGCTTTGATACAATGCCTTA
TGCCATGGGTGAAACTTTAGCTAATGCTATTCGTCGTAAGTCAGGTCTAATCATCCAACGTAACTTCATTGGTGATGAAGGTATCTGGATGAA
CAAAGCACTAGGTAAGACATTTGCACAGCTTAAGTCATTCTCTCTTGTATCTGGTGAGAAGCAATTTGGTCGAGGGATTCGCCACGATAAAAT
TGGTCTTGCTAAGAAGACAGCTTACGGGTTTGCTTTGGGTTCAATAGTGTATGCGGCAAAAGCCTATGTGAACTCTATTGGGCGAGAAGACC
AAGATGAATATTTGGAAGAGAAGTTATCGCCTAAAGGGTTGGCCTTTGGTGCAATGGGTATGATGAGTACAACTGCTGTATTTAGTCTAGGT
GGAGATTTCTTAGGTGGCCTAGGTGTTCTACCTTCCGAACTCATTCAATCACGCTATGAAGCAGGTTTCCAAAGTAAGGGTCTGATTGACCAA
ATACCTCTGGTTGGCGTTGGTGCAGATGCAGTAAATCTGGCTAACTCAATCAAGAAGTATGCAGAAGGTGACACAGAAGGTGTAGATATCGC
TAAGCGAGCACTCCGTCTTGTGCCACTTACCAATATAATAGGTGTCCAAAACGCATTGCGTTATGGCTTAGATGAACTGGAGGATTGATGAGT
TATACTTTCACAGAACATACAGCCAATGGTACGCAAGTCACCTATCCTTTTAGCTTTGCTGGTAGGGATAAAGGTTATCTTCGTGCCTCAGATG
TGATAGTGGAGTCTCTTCAAGGTAACACTTGGATTGAAGTTACATCTGGCTGGCAACTAACTGGCACGCACCAGATTACTTTTGATGTAGCAC
CAGTTGCAGGTTTGAAGTTCCGTATTCGAAGGGAAGTACAAAAAGAATATCCATACGCTGAGTTTGACCGTGGTGTTACCTTGGATATGAAG
TCTTTAAATGGTTCTTTCATTCATATACTGGAGATTACACAGGAGTTACTTGACGGGTTTTATCCAGAAGGATACTTCATTAAACAGAATGTAA
GCTGGGGCGGCAATAAGATTACTGATTTGGCTGATGGCACAAATCCGGGAGATGCAGTAAATAAAGGGCAGCTTGATGCCATCGACAAGAA
GCATACAGATTGGAACGCCAAACAGGACATTGAGATTGCTGGCCTTAAGGCTGGTATGACTTCTGGTATTGCGCACAGAACTGTTCCTTGGTA
CACGATAGCCCAAGGTGGTGAGATTTCCGTAAAACCACCTTATGAATTTCAAGATGCACTAGTTTTCCTTAATGGGGTATTGCAGCACCAAAT
TGTAGGCGCATACTCTATAAGCAACAACACTATCACTTTCGCAGAGCCGCTTGTGGCTGGTACAGAGGTGTATGTGCTGATTGGTAGTCGTGT
GGCTACATCTGAACCTAATATTCAGTTGGAGTTGAACTTTGACTTAGTAGAAGGCCAACAAGTAGTACAGATTGGCTCTGCATTTAAGTACAT
TGAGGTCTACCTTGATGGATTATTACAACCTAAACTTGCTTATCAGGTAGACGGTGACATTGTTACTTTCTCAGAAAGAGTACCAGAATGCCG
GATGACTGCTAAGATTATCACAGCATAAGGAGGTGGGATGATTAACTCCGAACTGGTAGATAGTGGTGTGAAGCTTGCGCCACCTGCACTCA
TATCAGGTGGGTACTTCCTCGGTATCAGTTGGGATAATTGGGTGTTAATAGCAACATTCATTTATACCGTGTTGCAAATTGGGGACTGGTTTT
ATAATAAGTTCAAGATTTGGAGGGAGAAGCGTGAGCGTACACAATAAACATGCAGCTACAGAGGACGAGGTTGGCATTCTGCATGGTGCTA
TTACCAAAATCTTCAATAAGAAAGCACAGGCAATACTGGACACTATAGAAGAAGACCCTGATGCAGCATTACATTTAGTGTCTGGTAAGGATA
TTGGTGCGATGTGTAAGTGGGTTCTTGATAACGGCATTACCGCCACACCTGCTGCACAGCAGGAAGAGTCCAAGTTATCTAAGCGCCTCAAG
GCTATCCGAGAGGCATCCAGTGGTAAGATAATTCAATTCACTAAGGAGGATTGATGGCTAAGGCAAGAGAATCACAAGCGGAGGCTCTTGC
CAGATGGGAGATGCTACAGGAGTTACAGCAGACCTTTCCTTACACCGCGGAAGGTTTGCTTCTCTTTGCAGATACAGTTATTCATAACTTAATT
GCAGGCAACCCTCATCTGATTCGTATGCAGGCGGATATCTTGAAGTTCCTATTTTACGGACACAAGTACCGCCTCATCGAAGCGCCTCGTGGT
ATCGCTAAGACAACACTATCAGCAATCTATACGGTATTCCGTATTATTCATGAACCGCATAAGCGTATCATGGTTGTGTCCCAAAACGCCAAGC
GAGCAGAGGAAATCGCAGGTTGGGTAGTTAAAATCTTCCGTGGCTTAGACTTTCTTGAGTTTATGCTGCCGGATATCTACGCTGGGGACCGT
GCATCCGTTAAGGCGTTTGAGATTCATTACACCCTACGTGGTAGTGATAAGTCTCCTTCTGTATCCTGTTACTCAATCGAAGCAGGTATGCAGG
GTGCTCGTGCTGATATTATTCTAGCGGATGACGTAGAGTCGATGCAGAATGCTCGTACGGCAGCGGGCCGTGCCTTGCTTGAGGAGCTGACT
AAGGAGTTTGAATCTATCAACCAGTTTGGGGATATCATTTACCTTGGTACACCTCAGAACGTAAACTCTATCTACAACAACCTACCTGCTCGTG
GTTACTCTGTTCGTATCTGGACTGCGCGTTACCCTTCAGTAGAGCAAGAGCAATGTTATGGCGACTTCCTTGCACCTATGATTGTTCAAGATAT
GAAGGACAACCCAGCACTTCGCTCAGGGTACGGGTTGGATGGTAATAGTGGTGCACCTTGTGCCCCTGAAATGTATGATGATGAAGTCCTGA
TTGAGAAGGAAATCTCTCAGGGTGCTGCTAAGTTCCAGCTTCAGTTCATGCTTAACACTCGCATGATGGATGCTGACAGATACCCATTACGCC
TGAACAATCTAATCTTCACCTCGTTTGGTACAGAGGAAGTCCCTGTGATGCCTACGTGGAGTAATGATTCCATAAACATCATTGGTGATGCAC
CTAAGTATGGTAACAAGCCTACGGATTTCATGTACAGACCTGTAGCTCGCCCATATGAATGGGGTGCTGTCTCCCGCAAGATTATGTATATTG
ACCCTGCGGGTGGTGGTAAGAACGGAGATGAGACGGGTGTAGCCATCGTATTCCTGCACGGCACATTCATTTATGTGTATCAGTGCTTTGGT
GTACCTGGCGGATACCGAGAGTCGTCCCTGAATCGCATTGTGCAGGCCGCAAAGCAGGCGGGTGTTAAAGAGGTATTCATTGAGAAGAACT
TTGGTCATGGCGCGTTTGAGGCGGTAATTAAGCCGTACTTTGAACGAGAGTGGCCTGTAACTCTGGAAGAGGATTACGCCACCGGACAGAA
AGAGTTGCGTATCATTGAGACGCTGGAGCCGCTCATGGCAGCCCATAGGCTTATCTTCAATGCAGAGATGGTGAAGTCAGACTTTGAGTCGG
TACAGCACTATCCGCTTGAACTACGCATGTCCTACAGTCTTTTCAATCAAATGTCGAACATAACGATTGAGAAGAACAGCCTCCGGCACGATG
ACCGCCTAGACGCCCTGTATGGCGCTATACGGCAATTAACTTCTCAGATAGACTATGACGAGGTTACACGGATTAATCGCCTCAGAGCGCAG
GAGATGCGCGATTACATCCATGCTATGAACACACCTCATCTACGCAGGGCAATGCTATATGGAGATTACGGTACTGAGCGAAGAGTGACCAA
CACTTCCGTAGCGATGCAGCAGCGAGTTTACGGGCAGAACTACCGAAATAAATCGGCAAGCAGAAATACACTTTCTGCAAGGATTTCAAGGA
CTTATTAATTACTGGACACTATAGAAGGAAGGCCCAGATAATAAGAGAAAATAATAGGTAATATATATATAGGTTAACCTAGGTTATATAGGT
ATGCCTTAGTATGGGTGTACTCCTGTACACCCTATTCCTTACTACCTTACTATATTTACATAATAGGAGAGAGACAATGGCTAATGATTATAGT
AGTCAACCATTAACAGGTAAGTCTAAGAGAAAGCAGGTACAACCTGTAAGTGAAGAACTAATGCTTCCGGTGCTCAAAAAAGAGGAAGTTA
GTAAGAAAAGCAATGTTATTAATGATGCCACCAAATCAGGTAAACAGAAAGGGGCCATGGTGTGCCTTGAAGTGAAAGGTGGTGTATTGAA
GATTGCTATCGCGGTTGATGGCAAAGAAGATTCAGAGTGGAAGTTAGTAACAGTGGAACCAACTGTTAACCCAGTTTAAGATAAGGAGGAA
GATTACATGGCTAAATATGGTACTACAGGTTCTGTTACTGGTCAGGCTTTTCGAGTAAAAGCAGTACAAACTATTGCAACGGCAATCCCGATG
CCTGTTGTTAAAGAAGAAGACCTTAAGAGTAAAGACCACCCTATCAACATCAAACATTTATCAGGTAAACAGAAAGGTGCAATGGTTGCTCTT

Figure 16 (CONTD.)

GAGAAAGGTGACACAACCTTACATATTGCTGTTGCACGTGGTAGTGAACCCACAGACCCTTGGGATGTAACTGGTATGGAAAAGGACGCTGT
TACTCCAGCAGGGGTATAATAATGCTTAATAAATACTTCAAGCGTAAAGAGTTTGCTTGCCGTTGTGGGTGCGGTACATCCACTGTTGATGCT
GAATTACTACAGGTAGTCACAGATGTGCGTGAGCACTTTGGTTCTCCTGTAGTTATCACTTCGGGTCATCGCTGTGCTAAGCACAATGCCAAT
GTAGGTGGCGCTAAGAACTCCATGCATCTTACTGGTAAGGCTGCTGACATTAAAGTGTCTGGCATATTACCTTCTGAAGTGCATAAGTATCTT
ACTAGCAAATACCAAGGCAAGTATGGTATAGGTAAGTATAACTCCTTCACTCACATCGATGTACGGGATGGTTGTGCGCGATGGTAAGATGT
GTTGAATGGTGTGAGCGTATGGTTGCCCAAGCTGCCGAGGATGGCAACTATGATGACTGGAAGAACTACTCTGACTTGTTAGCTCAATGGAA
AGGGAGATGCAATGAAAAAGCTGTTTAAGTCTAAGAAGGTTGTAGGTGCACTGGTTGCACTTGTTATTGCTCTTGTTTCTGTAGGTCTTGGTG
TAGACCTTGGCTCTGGCACGGAATCCTCTGTGACAGATGTGGTCTGCCAAGTGATCACCTGTGAATAAGTTTCTAGAAGTTCTGGCAGGTCTT
ATTGGCCTGCTTGTCTCTGCTAAGAAGAAACAAGAAGAGAAGGAGGCACAAAGTGAAGCGAATCATGTTAGTGACAACCCTTCTGATTGGTT
CGCTGACCACTTCCGGGTGTCAGCAGGCGTTACCAGAGAAAGCAATGGTGAAACCTCTGAGGCCGACGCTGACGGCAGTTTACGAGGTAGA
CGATAAGGTCTGCTTTAGTAAGCCTGACGCTACAAAACTTGGTTTGTACATTCTCTCGCTAGAACGCGGATACAATTAATACATAGCTTTATGT
ATCAGTGTCTTACGATTTACTGGACACTATAGAAGAGGTAAGATAGCGCCGTTCTTTTGAGCGGCCTATTACTAGCCAATCTTCATAGGGAGG
GTTGGAAAGTAATAGGAGATAGCATGGCTAAATTAACCAAACCTAATACTGAAGGAATCTTGCATAAAGGACAATCTTTGTATGAGTACCTTG
ATGCGAGAGTTTTAACATCAAAGCCGTTTGGTGCTGCAGGTGACGCCACTACTGATGATACGGAGGTTATAGCTGCTTCATTAAACTCTCAGA
AAGCTGTCACAGTCTCAGATGGTGTATTCTCTAGCTCTGGTATTAACAGTAATTACTGTAACTTAGACGGCAGGGGTAGTGGCGTGCTAAGTC
ACCGTTCAAGTACAGGTAACTACTTAGTATTTAACAATCTACGTGCAGGTCGCTTAAGTAATATTACGGTAGAAAGTAATAAGGCGACTGATA
CAACTCAGGGACAGCAGGTATCCCTTGCTGGTGGAAGTGATGTTACTGTAAGTGACGTTAACTTCTCAAACGTTAAAGGTACTGGTTTCAGTT
TAATCGCATACCCTAATGATGCGCCACCTGATGGACTTATGATTAAAGGCATTCGAGGTAGCTATTCCGGCTATGCTACTAATAAGGCAGCCG
GATGCGTACTTGCTGATTCCTCAGTTAACTCCCTCATAGATAACGTCATTGCTAAGAACTACCCTCAGTTCGGAGCAGTAGAGTTGAAAGGTA
CAGCCAGTTACAACATAGTCAGTAATGTTATAGGGACAGATTGCCAGCATGTAACTTACAACGGCACTGAAGGGCCAATAGCTCCTTCTAATA
ACCTTATCAAGGGGGTGATGGCTAATAACCCTAAGTATGCAGCGGTTGTTGCAGGCAAAGGAAGTACGAACTTAATCTCAGACGTGCTCGTA
GATTACTCAACTTCTGATGCTAGGCAGGCTCATGGTGTTACAGTAGAGGGTTCTGATAACGTCATAAATAATGTGCTTATGTCAGGATGTGAT
GGTACTAACTCTTTAGGACAAGGGCAGACTGCTACAATTGCACGCTTTATAGGTACAGCTAATAACAACTATGCGTCTGTATTTCCTAGCTACA
GTGCTACAGGTGTTATTACTTTCGAATCCGGCTCTACCCGTAACTTCGTAGAGGTAAAGCACCCTGGCAGGAGAAACGACCTTCTCAGTTCTG
CTAGTACTATTGACGGTGCAGCTACTATTGACGGCACTAGTAATAGTAACGTAGTGCACGCACCTGCCTTAGGGCAGTACATAGGTAGTATGT
CAGGTAGGTTCGAATGGCGGATTAAGTCCATGTCACTCCCTTCAGGCGTTCTTACTTCTGCTGATAAGTACAGAATGCTTGGAGATGGTGCTG
TGTCATTAGCTGTAGGTGGGGGCACTTCTTCTCAAGTTCGCCTATTTACTTCTGATGGTACTTCTCGGACAGTGTCCCTCACCAACGGTAACGT
GCGTCTTTCTACCAGTAGCACAGGCTTTTTGCAGTTAGGTGCTGATGCAATGACCCCAGACAGTACTGGTACATACGCATTAGGTTCCGCCAG
CCGAGCATGGTCTGGCGGTTTTACTCAAGCAGCATTCACTGTTACCTCAGATGCTCGGTGTAAAACAGAACCTCTTACTATCTCAGATGCCTTA
CTGGATGCTTGGTCTGAAGTTGACTTTGTGCAGTTTCAGTATTTGGATCGTGTTGAGGAGAAGGGTGCAGACTCAGCTAGATGGCACTTCGG
TATCATCGCTCAGCGAGCTAAGGAGGCTTTCGAACGTCACGGTATAGATGCACATCGCTATGGCTTCTTGTGCTTCGACAGTTGGGATGATGT
ATACGAGGAAGATGCCAATGGCTCTCGTAAACTGATTACACCAGCAGGTTCCCGCTACGGTATTCGTTACGAGGAAGTACTGATATTAGAGG
CTGCGTTGATGCGGCGGACTATTAAGCGTATGCAGGAAGCACTAGCTTCCCTGCCTAAGTAAGCAACAGGCAGTGCGTAAGCACTGCTTTTA
GCGCAACTTTTCTTAAAGGTTATCACGGTGGTAGCCTTTCAGAAAAGGAGGTTACATGATTCAAAGACTAGGTTCTTCATTAGTTAAATTCAA
GAGTAAAATAGCAGGTGCAATCTGGCGTAACTTGGATGACAAGCTCACCGAGGTTGTATCGCTTAAAGATTTTGGAGCCAAAGGTGATGGTA
AGACAAACGACCAAGATGCAGTAAATGCAGCGATGGCTTCAGGTAAGAGAATTGACGGTGCTGGTGCTACTTACAAAGTATCATCTTTACCT
GATATGGAGCGATTCTATAACACCCGCTTCGTATGGGAACGTTTAGCAGGTCAACCTCTTTACTATGTGAGTAAAGGTTTTATCAATGGTGAA
CTATATAAAATCACGGATAACCCTTATTACAATGCTTGGCCTCAAGACAAAGCGTTTGTATATGAGAACGTGATATATGCACCTTACATGGGTA
GTGACCGTCATGGTGTTAGTCGTCTGCATGTATCATGGGTTAAGTCTGGTGACGATGGTCAAACATGGTCTACTCCAGAGTGGTTAACTGATC
TGCATCCAGATTACCCTACAGTGAACTATCATTGTATGAGTATGGGTGTATGTCGCAACCGTCTGTTTGCCATGATTGAAACACGTACTTTAGC
CAAGAACAAACTAACCAATTGTGCATTGTGGGATCGCCCTATGTCTCGTAGTCTGCATCTTACTGGTGGTATCACTAAGGCTGCAAATCAGCA
ATATGCAACAATACATGTACCAGATCACGGACTATTCGTGGGCGATTTTGTTAACTTCTCTAATTCTGCGGTAACAGGTGTATCAGGTGATATG
ACTGTTGCAACGGTAATAGATAAGGACAACTTCACGGTTCTTACACCTAACCAGCAGACTTCAGATTTGAATAACGCTGGAAAGAGTTGGCAC
ATGGGTACTTCTTTCCATAAGTCTCCATGGCGTAAGACAGATCTTGGTCTAATCCCTAGTGTCACAGAGGTGCATAGCTTTGCTACTATTGATA
ACAATGGCTTTGTTATGGGCTATCATCAAGGTGATGTAGCTCCACGAGAAGTTGGTCTTTTCTACTTCCCTGATGCTTTCAATAGCCCATCTAAT
TATGTTCGTCGTCAGATACCATCTGAGTATGAACCAGATGCGTCAGAGCCATGCATCAAGTACTATGACGGTGTATTATACCTTATCACTCGTG
GCACTCTTGGTGACAGACTTGGAAGCTCTTTGCATCGTAGTAGAGATATAGGTCAGACTTGGGAGTCACTGAGATTTCCACATAATGTTCATC
ATACTACCCTACCTTTTGCTAAAGTAGGAGATGACCTTATTATGTTTGGTTCAGAACGTGCAGAAAATGAATGGGAAGCAGGTGCACCAGAT
GATCGTTACAAGGCATCTTATCCTCGTACCTTCTATGCACGATTGAATGTAAACAATTGGAATGCAGATGATATTGAATGGGTTAACATCACA
GACCAAATCTATCAAGGTGACATTGTGAACTCTAGTGTAGGTGTAGGTTCGGTAGTAGTTAAAGACAGCTACATTTACTATATCTTTGGTGGC
GAAAACCATTTCAACCCAATGACTTATGGTGACAACAAAGGTAAAGACCCATTTAAAGGTCATGGACACCCTACTGATATATACTGCTATAAG
ATGCAGATTGCAAATGACAATCGTGTATCTCGTAAGTTTACATATGGTGCAACTCCGGGTCAAGCTATACCTACTTTCATGGGTACTGATGGA

Figure 16 (CONTD.)

ATACGAAATATCCCTGCACCTTTGTATTTCTCAGATAACATTGTTACAGAGGATACTAAAGTTGGACACTTAACACTTAAAGCAAGCACAAGTT
CCAATATACGATCTGAAGTGCAGATGGAAGGTGAATATGGCTTTATTGGCAAGTCTGTTCCAAAGGACAACCCAACTGGTCAACGTTTGATTA
TTTGTGGTGGAGAAGAGACTTCGTCCTCTTCAGGTGCACAGATAACTTTGCACGGCTCTAATTCAAGTAAGGCTAATCGTATCACTTATAACG
GAAATGAGCACCTATTCCAAGGTGCACCAATCATGCCTGCTGTAGATAACCAGTTTGCTGCTGGTGGACCTAGTAACCGATTCACTACCATCT
ACCTAGGTAGTGACCCTGTTACAACTTCAGATGCTGACCACAAGTACAGTATCTCTAGTATTAATACCAAGGTGTTAAAGGCTTGGAGCAGGG
TTGGTTTTAAACAGTATGGTTTGAATAGTGAAGCAGAGAGGGACCTTGATAGCATACACTTCGGTGTCTTGGCTCAGGATATTGTAGCTGCTT
TTGAAGCTGAAGGGTTGGATGCCATTAAGTATGGAATTGTGTCCTTCGAAGAAGGTAGGTACGGTGTGAGGTATAGTGAAGTTCTAATACTA
GAGGCTGCTTATACTCGTTATCGTTTAGACAAGTTAGAGGAGATGTATGCCACTAATAAAATCAGTTAAGCAAGCTGCTGTACTCCAGAACAC
AGAAGAGCTTATTCAATCAGGACGTGACCCTAAGCAGGCTTATGCCATTGCCAAGGATGTTCAACGTCGTGCCATGAAGAAACCTTCTGCATC
TTCTGCGTAAAGAGGAGATATACAATGGTCTTCACACTCGAAGATTTCGTTGGGGACTGGCGACAGACAGCCGGCTACAACCTGGACCAAGT
CCTTGAACAGGGAGGTGTGTCCAGTTTGTTTCAGAATCTCGGGGTGTCCGTAACTCCGATCCAAAGGATTGTCCTGAGCGGTGAAAATGGGC
TGAAGATCGACATCCATGTCATCATCCCGTATGAAGGTCTGAGCGGCGACCAAATGGGCCAGATCGAAAAAATTTTTAAGGTGGTGTACCCT
GTGGATGATCATCACTTTAAGGTGATCCTGCACTATGGCACACTGGTAATCGACGGGGTTACGCCGAACATGATCGACTATTTCGGACGGCC
GTATGAAGGCATCGCCGTGTTCGACGGCAAAAAGATCACTGTAACAGGGACCCTGTGGAACGGCAACAAAATTATCGACGAGCGCCTGATC
AACCCCGACGGCTCCCTGCTGTTCCGAGTAACCATCAACGGAGTGACCGGCTGGCGGCTGTGCGAACGCATTCTGGCGTAAGCAGGTTAATA
TCTTAGTATAAACAAGGGCAGACTTAGGTTTGTCCTTAGTGTATTCCAAAGGAGGTAACATGCTGAAAGATGGTTGGGTTTCATATGACCCTA
CAGACCCTAAGAATTGGCTACAGGTTATCGCTATAGCTTGTGCAGGTAGCCTATTGGCTGCCCTGATGTATTCATTATGGATGTACACAAAGT
AACCAAAGTCAAAATTTTGATGTAGGCGTGTGTCAGCTCTCTCGCCCTCGCCCTCGCCGGGTTGTCCCCATAGGGTGGCCTGAGGGAATCCGT
CTTCGACGGGCAGGGCTGATGTACTCCTTGTCTAGTACAAGGGAGGCGGAGGGAACGCCTAGGGAGGCCTAGGAATGGCTTAGTGGTGGA
CAAGGTGATTACCTTAGTGAAGCCTCTTAGTGCATTCCTGAGGCCATTCAGGGCGTTTATGAGGGATTGACAGGGTGTGAGGGCGTGGGCTA

Figure 17

T7_10A_NheI_Nluc_LacZa_ phage T7, (SEQ ID NO: 6)

CCTCTAGAAATAATTTTGTTTAACTTTAAGAAGGAGATATACATATGGTCTTCACAC
TCGAAGATTTCGTTGGGGACTGGCGACAGACAGCCGGCTACAACCTGGACCAAGTC
CTTGAACAGGGAGGTGTGTCCAGTTTGTTTCAGAATCTCGGGGTGTCCGTAACTCCG
ATCCAAAGGATTGTCCTGAGCGGTGAAAATGGGCTGAAGATCGACATCCATGTCAT
CATCCCGTATGAAGGTCTGAGCGGCGACCAAATGGGCCAGATCGAAAAAATTTTTA
AGGTGGTGTACCCTGTGGATGATCATCACTTTAAGGTGATCCTGCACTATGGCACAC
TGGTAATCGACGGGGTTACGCCGAACATGATCGACTATTTCGGACGGCCGTATGAA
GGCATCGCCGTGTTCGACGGCAAAAAGATCACTGTAACAGGGACCCTGTGGAACGG
CAACAAAATTATCGACGAGCGCCTGATCAACCCCGACGGCTCCCTGCTGTTCCGAGT
AACCATCAACGGAGTGACCGGCTGGCGGCTGTGCGAACGCATTCTGGCGTAAAGGA
GGTAAACATATGACCATGATTACGGATTCACTGGCCGTCGTTTTACAACGTCGTGAC
TGGGAAAACCCTGGCGTTACCCAACTTAATCGCCTTGCAGCACATCCCCCTTTCGCC
AGCTGGCGTAATAGCGAAGAGGCCCGCACCGATCGCCCTTCCCAACAGTTGCGCAG
CCTGAATGGCGAATGGTAAAAAGAGGAGGTATACAATGGCTAGCATGACTGGTGGA
CAGCAAATGGGTACTAACCAAGGT

Figure 18

T7_SwaI_Nanoluc_Insert_sequence Enterobacteria phage T7, (SEQ ID NO: 7)

CTTTAAGACCCTTAAGTGTTAATTAGAGATTTAAGGAGATTCAACATGGTCTTCACA
CTCGAAGATTTCGTTGGGGACTGGCGACAGACAGCCGGCTACAACCTGGACCAAGT
CCTTGAACAGGGAGGTGTGTCCAGTTTGTTTCAGAATCTCGGGGTGTCCGTAACTCC
GATCCAAAGGATTGTCCTGAGCGGTGAAAATGGGCTGAAGATCGACATCCATGTCA
TCATCCCGTATGAAGGTCTGAGCGGCGACCAAATGGGCCAGATCGAAAAAATTTTT
AAGGTGGTGTACCCTGTGGATGATCATCACTTTAAGGTGATCCTGCACTATGGCACA
CTGGTAATCGACGGGGTTACGCCGAACATGATCGACTATTTCGGACGGCCGTATGAA
GGCATCGCCGTGTTCGACGGCAAAAAGATCACTGTAACAGGGACCCTGTGGAACGG
CAACAAAATTATCGACGAGCGCCTGATCAACCCCGACGGCTCCCTGCTGTTCCGAGT
AACCATCAACGGAGTGACCGGCTGGCGGCTGTGCGAACGCATTCTGGCGTAAAGGA
GGTAAACATATGACCATGATTACGGATTCACTGGCCGTCGTTTTACAACGTCGTGAC
TGGGAAAACCCTGGCGTTACCCAACTTAATCGCCTTGCAGCACATCCCCCTTTCGCC
AGCTGGCGTAATAGCGAAGAGGCCCGCACCGATCGCCCTTCCCAACAGTTGCGCAG
CCTGAATGGCGAATGGTAAAAATTAAAGAATTACTAAGAGAGGACTTTAAGTATGC
GTAAC

SEQUENCE LISTING

```
<160> NUMBER OF SEQ ID NOS: 9

<210> SEQ ID NO 1
<211> LENGTH: 40659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

tctcacagtg tacggaccta aagttccccc atagggggta cctaaagccc agccaatcac      60
```

-continued

```
ctaaagtcaa ccttcggttg accttgaggg ttccctaagg gttggggatg acccttgggt    120
ttgtctttgg gtgttacctt gagtgtctct ctgtgtccct atctgttaca gtctcctaaa    180
gtatcctcct aaagtcacct cctaacgtcc atcctaaagc caacacctaa agcctacacc    240
taaagaccca tcaagtcaac gcctatctta aagtttaaac ataaagacca gacctaaaga    300
ccagacctaa agacactaca taaagaccag acctaaagac gccttgttgt tagccataaa    360
gtgataacct ttaatcattg tctttattaa tacaactcac tataaggaga gacaacttaa    420
agagacttaa aagattaatt taaaatttat caaaaagagt attgacttaa agtctaacct    480
ataggatact tacagccatc gagagggaca cggcgaatag ccatcccaat cgacaccggg    540
gtcaaccgga taagtagaca gcctgataag tcgcacgaaa aacaggtatt gacaacatga    600
agtaacatgc agtaagatac aaatcgctag gtaacactag cagcgtcaac cgggcgcaca    660
gtgccttcta ggtgacttaa gcgcaccacg gcacataagg tgaaacaaaa cggttgacaa    720
catgaagtaa acacggtacg atgtaccaca tgaaacgaca gtgagtcacc acactgaaag    780
gtgatgcggt ctaacgaaac ctgacctaag acgctcttta acaatctggt aaatagctct    840
tgagtgcatg actagcggat aactcaaggg tatcgcaagg tgccctttat gatattcact    900
aataactgca cgaggtaaca caagatggct atgtctaaca tgacttacaa caacgttttc    960
gaccacgctt acgaaatgct gaaagaaaac atccgttatg atgacatccg tgacactgat   1020
gacctgcacg atgctattca catggctgcc gataatgcag ttccgcacta ctacgctgac   1080
atctttagcg taatggcaag tgagggcatt gaccttgagt tcgaagactc tggtctgatg   1140
cctgacacca aggacgtaat ccgcatcctg caagcgcgta tctatgagca attaacgatt   1200
gacctctggg aagacgcaga agacttgctc aatgaatact tggaggaagt cgaggagtac   1260
gaggaggatg aagagtaatg tctactacca acgtgcaata cggtctgacc gctcaaactg   1320
tacttttcta tagcgacatg gtgcgctgtg gctttaactg gtcactcgca atggcacagc   1380
tcaaagaact gtacgaaaac aacaaggcaa tagctttaga atctgctgag tgatagactc   1440
aaggtcgctc ctagcgagtg gcctttatga ttatcacttt acttatgagg gagtaatgta   1500
tatgcttact atcggtctac tcaccgctct aggtctagct gtaggtgcat cctttgggaa   1560
ggctttaggt gtagctgtag gttcctactt taccgcttgc atcatcatag gaatcatcaa   1620
aggggcacta cgcaaatgat gaagcactac gttatgccaa tccacacgtc caacggggca   1680
accgtatgta cacctgatgg gttcgcaatg aaacaacgaa tcgaacgcct taagcgtgaa   1740
ctccgcatta accgcaagat taacaagata ggttccggct atgacagaac gcactgatgg   1800
cttaaagaaa ggttatatgc ccaatggcac actatacgct gcaaatcggc gaatagtgag   1860
aacttggcga gagaacaacc tcgaacgccg caaggacaag agagggcggc gtggcataga   1920
cgaaaggaaa aggttaaagc caagaaactc gccgcacttg aacaggcact agccaacaca   1980
ctgaacgcta tctcataacg aacataaagg acacaatgca atgaacatta ccgacatcat   2040
gaacgctatc gacgcaatca aagcactgcc aatctgtgaa cttgacaagc gtcaaggtat   2100
gcttatcgac ttactggtcg agatggtcaa cagcgagacg tgtgatggcg agctaaccga   2160
actaaatcag gcacttgagc atcaagattg gtggactacc ttgaagtgtc tcacggctga   2220
cgcagggttc aagatgctcg gtaatggtca cttctcggct gcttatagtc acccgctgct   2280
acctaacaga gtgattaagg tgggctttaa gaaagaggat tcaggcgcag cctataccgc   2340
attctgccgc atgtatcagg gtcgtcctgg tatccctaac gtctacgatg tacagcgcca   2400
```

-continued

```
cgctggatgc tatacggtgg tacttgacgc acttaaggat tgcgagcgtt tcaacaatga   2460
tgcccattat aaatacgctg agattgcaag cgacatcatt gattgcaatt cggatgagca   2520
tgatgagtta actggatggg atggtgagtt tgttgaaact tgtaaactaa tccgcaagtt   2580
ctttgagggc atcgcctcat tcgacatgca tagcgggaac atcatgttct caaatggaga   2640
cgtaccatac atcaccgacc cggtatcatt ctcgcagaag aaagacggtg gcgcattcag   2700
catcgaccct gaggaactca tcaaggaagt cgaggaagtc gcacgacaga aagaaattga   2760
ccgcgctaag gcccgtaaag aacgtcacga ggggcgctta gaggcacgca gattcaaacg   2820
tcgcaaccgc aaggcacgta aagcacacaa agctaagcgc gaaagaatgc ttgctgcgtg   2880
gcgatgggct gaacgtcaag aacggcgtaa ccatgaggta gctgtagatg tactaggaag   2940
aaccaataac gctatgctct gggtcaacat gttctctggg gactttaagg cgcttgagga   3000
acgaatcgcg ctgcactggc gtaatgctga ccggatggct atcgctaatg gtcttacgct   3060
caacattgat aagcaacttg acgcaatgtt aatgggctga tagtcttatc ttacaggtca   3120
tctgcgggtg gcctgaatag gtacgattta ctaactggaa gaggcactaa atgaacacga   3180
ttaacatcgc taagaacgac ttctctgaca tcgaactggc tgctatcccg ttcaacactc   3240
tggctgacca ttacggtgag cgtttagctc gcgaacagtt ggcccttgag catgagtctt   3300
acgagatggg tgaagcacgc ttccgcaaga tgtttgagcg tcaacttaaa gctggtgagg   3360
ttgcggataa cgctgccgcc aagcctctca tcactaccct actccctaag atgattgcac   3420
gcatcaacga ctggtttgag gaagtgaaag ctaagcgcgg caagcgcccg acagccttcc   3480
agttcctgca agaaatcaag ccggaagccg tagcgtacat caccattaag accactctgg   3540
cttgcctaac cagtgctgac aatacaaccg ttcaggctgt agcaagcgca atcggtcggg   3600
ccattgagga cgaggctcgc ttcggtcgta tccgtgacct tgaagctaag cacttcaaga   3660
aaaacgttga ggaacaactc aacaagcgcg tagggcacgt ctacaagaaa gcatttatgc   3720
aagttgtcga ggctgacatg ctctctaagg gtctactcgg tggcgaggcg tggtcttcgt   3780
ggcataagga agactctatt catgtaggag tacgctgcat cgagatgctc attgagtcaa   3840
ccggaatggt tagcttacac cgccaaaatg ctggcgtagt aggtcaagac tctgagacta   3900
tcgaactcgc acctgaatac gctgaggcta tcgcaacccg tgcaggtgcg ctggctggca   3960
tctctccgat gttccaacct tgcgtagttc ctcctaagcc gtggactggc attactggtg   4020
gtggctattg ggctaacggt cgtcgtcctc tggcgctggt gcgtactcac agtaagaaag   4080
cactgatgcg ctacgaagac gtttacatgc ctgaggtgta caaagcgatt aacattgcgc   4140
aaaacaccgc atggaaaatc aacaagaaag tcctagcggt cgccaacgta atcaccaagt   4200
ggaagcattg tccggtcgag gacatccctg cgattgagcg tgaagaactc ccgatgaaac   4260
cggaagacat cgacatgaat cctgaggctc tcaccgcgtg gaaacgtgct gccgctgctg   4320
tgtaccgcaa ggacaaggct cgcaagtctc gccgtatcag ccttgagttc atgcttgagc   4380
aagccaataa gtttgctaac cataaggcca tctggttccc ttacaacatg gactggcgcg   4440
gtcgtgttta cgctgtgtca atgttcaacc cgcaaggtaa cgatatgacc aaaggactgc   4500
ttacgctggc gaaaggtaaa ccaatcggta aggaaggtta ctactggctg aaaatccacg   4560
gtgcaaactg tgcgggtgtc gataaggttc cgttccctga gcgcatcaag ttcattgagg   4620
aaaaccacga gaacatcatg gcttgcgcta agtctccact ggagaacact tggtgggctg   4680
agcaagattc tccgttctgc ttccttgcgt tctgctttga gtacgctggg gtacagcacc   4740
acggcctgag ctataactgc tcccttccgc tggcgtttga cgggtcttgc tctggcatcc   4800
```

-continued

```
agcacttctc cgcgatgctc cgagatgagg taggtggtcg cgcggttaac ttgcttccta   4860
gtgaaaccgt tcaggacatc tacgggattg ttgctaagaa agtcaacgag attctacaag   4920
cagacgcaat caatgggacc gataacgaag tagttaccgt gaccgatgag aacactggtg   4980
aaatctctga gaaagtcaag ctgggcacta aggcactggc tggtcaatgg ctggcttacg   5040
gtgttactcg cagtgtgact aagcgttcag tcatgacgct ggcttacggg tccaaagagt   5100
tcggcttccg tcaacaagtg ctggaagata ccattcagcc agctattgat tccggcaagg   5160
gtctgatgtt cactcagccg aatcaggctg ctggatacat ggctaagctg atttgggaat   5220
ctgtgagcgt gacggtggta gctgcggttg aagcaatgaa ctggcttaag tctgctgcta   5280
agctgctggc tgctgaggtc aaagataaga agactggaga gattcttcgc aagcgttgcg   5340
ctgtgcattg ggtaactcct gatggtttcc ctgtgtggca ggaatacaag aagcctattc   5400
agacgcgctt gaacctgatg ttcctcggtc agttccgctt acagcctacc attaacacca   5460
acaaagatag cgagattgat gcacacaaac aggagtctgg tatcgctcct aactttgtac   5520
acagccaaga cggtagccac cttcgtaaga ctgtagtgtg ggcacacgag aagtacggaa   5580
tcgaatcttt tgcactgatt cacgactcct tcggtaccat tccggctgac gctgcgaacc   5640
tgttcaaagc agtgcgcgaa actatggttg acacatatga gtcttgtgat gtactggctg   5700
atttctacga ccagttcgct gaccagttgc acgagtctca attggacaaa atgccagcac   5760
ttccggctaa aggtaacttg aacctccgtg acatcttaga gtcggacttc gcgttcgcgt   5820
aacgccaaat caatacgact cactatagag ggacaaactc aaggtcattc gcaagagtgg   5880
cctttatgat tgaccttctt ccggttaata cgactcacta taggagaacc ttaaggttta   5940
actttaagac ccttaagtgt taattagaga tttaaggaga ttcaacatgg tcttcacact   6000
cgaagatttc gttggggact ggcgacagac agccggctac aacctggacc aagtccttga   6060
acagggaggt gtgtccagtt tgtttcagaa tctcggggtg tccgtaactc cgatccaaag   6120
gattgtcctg agcggtgaaa atgggctgaa gatcgacatc catgtcatca tcccgtatga   6180
aggtctgagc ggcgaccaaa tgggccagat cgaaaaaatt tttaaggtgg tgtaccctgt   6240
ggatgatcat cactttaagg tgatcctgca ctatggcaca ctggtaatcg acggggttac   6300
gccgaacatg atcgactatt tcggacggcc gtatgaaggc atcgccgtgt tcgacggcaa   6360
aaagatcact gtaacaggga ccctgtggaa cggcaacaaa attatcgacg agcgcctgat   6420
caaccccgac ggctccctgc tgttccgagt aaccatcaac ggagtgaccg gctggcggct   6480
gtgcgaacgc attctggcgt aaaggaggta aacatatgac catgattacg gattcactgg   6540
ccgtcgtttt acaacgtcgt gactgggaaa accctggcgt tacccaactt aatcgccttg   6600
cagcacatcc ccctttcgcc agctggcgta atagcgaaga ggcccgcacc gatcgccctt   6660
cccaacagtt gcgcagcctg aatggcgaat ggtaaaaatt aaagaattac taagagagga   6720
ctttaagtat gcgtaacttc gaaaagatga ccaaacgttc taaccgtaat gctcgtgact   6780
tcgaggcaac caaaggtcgc aagttgaata agactaagcg tgaccgctct cacaagcgta   6840
gctgggaggg tcagtaagat gggacgttta tatagtggta atctggcagc attcaaggca   6900
gcaacaaaca agctgttcca gttagactta gcggtcattt atgatgactg gtatgatgcc   6960
tatacaagaa aagattgcat acggttacgt attgaggaca ggagtggaaa cctgattgat   7020
actagcacct tctaccacca cgacgaggac gttctgttca atatgtgtac tgattggttg   7080
aaccatatgt atgaccagtt gaaggactgg aagtaatacg actcagtata gggacaatgc   7140
```

ttaaggtcgc tctctaggag tggccttagt catttaacca ataggagata aacattatga 7200
tgaacattaa gactaacccg tttaaagccg tgtctttcgt agagtctgcc attaagaagg 7260
ctctggataa cgctgggtat cttatcgctg aaatcaagta cgatggtgta cgcgggaaca 7320
tctgcgtaga caatactgct aacagttact ggctctctcg tgtatctaaa acgattccgg 7380
cactggagca cttaaacggg tttgatgttc gctggaagcg tctactgaac gatgaccgtt 7440
gcttctacaa agatggcttt atgcttgatg gggaactcat ggtcaagggc gtagacttta 7500
acacagggtc cggcctactg cgtaccaaat ggactgacac gaagaaccaa gagttccatg 7560
aagagttatt cgttgaacca atccgtaaga aagataaagt tccctttaag ctgcacactg 7620
gacaccttca cataaaactg tacgctatcc tcccgctgca catcgtggag tctggagaag 7680
actgtgatgt catgacgttg ctcatgcagg aacacgttaa gaacatgctg cctctgctac 7740
aggaatactt ccctgaaatc gaatggcaag cggctgaatc ttacgaggtc tacgatatgg 7800
tagaactaca gcaactgtac gagcagaagc gagcagaagg ccatgagggt ctcattgtga 7860
aagacccgat gtgtatctat aagcgcggta agaaatctgg ctggtggaaa atgaaacctg 7920
agaacgaagc tgacggtatc attcagggtc tggtatgggg tacaaaaggt ctggctaatg 7980
aaggtaaagt gattggtttt gaggtgcttc ttgagagtgg tcgtttagtt aacgccacga 8040
atatctctcg cgccttaatg gatgagttca ctgagacagt aaaagaggcc accctaagtc 8100
aatggggatt ctttagccca tacggtattg gcgacaacga tgcttgtact attaaccctt 8160
acgatggctg ggcgtgtcaa attagctaca tggaggaaac acctgatggc tctttgcggc 8220
acccatcgtt cgtaatgttc cgtggcaccg aggacaaccc tcaagagaaa atgtaatcac 8280
actggctcac cttcgggtgg gcctttctgc gtttataagg agacacttta tgtttaagaa 8340
ggttggtaaa ttccttgcgg ctttggcagc tatcctgacg cttgcgtata ttcttgcggt 8400
ataccctcaa gtagcactag tagtagttgg cgcttgttac ttagcggcag tgtgtgcttg 8460
cgtgtggagt atagttaact ggtaatacga ctcactaaag gaggtacaca ccatgatgta 8520
cttaatgcca ttactcatcg tcattgtagg atgccttgcg ctccactgta gcgatgatga 8580
tatgccagat ggtcacgctt aatacgactc actaaaggag acactatatg tttcgacttc 8640
attacaacaa aagcgttaag aatttcacgg ttcgccgtgc tgaccgttca atcgtatgtg 8700
cgagcgagcg ccgagctaag atacctctta ttggtaacac agttcctttg gcaccgagcg 8760
tccacatcat tatcacccgt ggtgactttg agaaagcaat agacaagaaa cgtccggttc 8820
ttagtgtggc agtgacccgc ttcccgttcg tccgtctgtt actcaaacga atcaaggagg 8880
tgttctgatg ggactgttag atggtgaagc ctgggaaaaa gaaaacccgc cagtacaagc 8940
aactgggtgt atagcttgct tagagaaaga tgaccgttat ccacacacct gtaacaaagg 9000
agctaacgat atgaccgaac gtgaacaaga gatgatcatt aagttgatag acaataatga 9060
aggtcgccca gatgatttga atggctgcgg tattctctgc tccaatgtcc cttgccacct 9120
ctgccccgca aataacgatc aaaagataac cttaggtgaa atccgagcga tggacccacg 9180
taaaccacat ctgaataaac ctgaggtaac tcctacagat gaccagcctt ccgctgagac 9240
aatcgaaggt gtcactaagc cttcccacta catgctgttt gacgacattg aggctatcga 9300
agtgattgct cgttcaatga ccgttgagca gttcaaggga tactgcttcg gtaacatctt 9360
aaagtacaga ctacgtgctg gtaagaagtc agagttagcg tacttagaga aagacctagc 9420
gaaagcagac ttctataaag aactctttga gaaacataag gataaatgtt atgcataact 9480
tcaagtcaac cccacctgcc gacagcctat ctgatgactt cacatcttgc tcagagtggt 9540

-continued

```
gccgaaagat gtgggaagag acattcgacg atgcgtacat caagctgtat gaactttgga    9600
aatcgagagg tcaatgacta tgtcaaacgt aaatacaggt tcacttagtg tggacaataa    9660
gaagttttgg gctaccgtag agtcctcgga gcattccttc gaggttccaa tctacgctga    9720
gaccctagac gaagctctgg agttagccga atggcaatac gttccggctg gctttgaggt    9780
tactcgtgtg cgtccttgtg tagcaccgaa gtaatacgac tcactattag ggaagactcc    9840
ctctgagaaa ccaaacgaaa cctaaaggag attaacatta tggctaagaa gattttcacc    9900
tctgcgctgg gtaccgctga accttacgct tacatcgcca agccggacta cggcaacgaa    9960
gagcgtggct ttgggaaccc tcgtggtgtc tataaagttg acctgactat tcccaacaaa   10020
gacccgcgct gccagcgtat ggtcgatgaa atcgtgaagt gtcacgaaga ggcttatgct   10080
gctgccgttg aggaatacga agctaatcca cctgctgtag ctcgtggtaa gaaaccgctg   10140
aaaccgtatg agggtgacat gccgttcttc gataacggtg acggtacgac tacctttaag   10200
ttcaaatgct acgcgtcttt ccaagacaag aagaccaaag agaccaagca catcaatctg   10260
gttgtggttg actcaaaagg taagaagatg gaagacgttc cgattatcgg tggtggctct   10320
aagctgaaag ttaaatattc tctggttcca tacaagtgga acactgctgt aggtgcgagc   10380
gttaagctgc aactggaatc cgtgatgctg gtcgaactgg ctacctttgg tggcggtgaa   10440
gacgattggg ctgacgaagt tgaagagaac ggctatgttg cctctggttc tgccaaagcg   10500
agcaaaccac gcgacgaaga aagctgggac gaagacgacg aagagtccga ggaagcagac   10560
gaagacggag acttctaagt ggaactgcgg gagaaaatcc ttgagcgaat caaggtgact   10620
tcctctgggt gttgggagtg gcagggcgct acgaacaata aagggtacgg gcaggtgtgg   10680
tgcagcaata ccggaaaggt tgtctactgt catcgcgtaa tgtctaatgc tccgaaaggt   10740
tctaccgtcc tgcactcctg tgataatcca ttatgttgta accctgaaca cctatccata   10800
ggaactccaa aagagaactc cactgacatg gtaaataagg gtcgctcaca caaggggtat   10860
aaactttcag acgaagacgt aatggcaatc atggagtcca gcgagtccaa tgtatcctta   10920
gctcgcacct atggtgtctc ccaacagact atttgtgata tacgcaaagg gaggcgacat   10980
ggcaggttac ggcgctaaag gaatccgaaa ggttggagcg tttcgctctg gcctagagga   11040
caaggtttca aagcagttgg aatcaaaagg tattaaattc gagtatgaag agtggaaagt   11100
gccttatgta attccggcga gcaatcacac ttacactcca gacttcttac ttccaaacgg   11160
tatattcgtt gagacaaagg gtctgtggga aagcgatgat agaaagaagc acttattaat   11220
tagggagcag caccccgagc tagacatccg tattgtcttc tcaagctcac gtactaagtt   11280
atacaaaggt tctccaacgt cttatggaga gttctgcgaa aagcatggta ttaagttcgc   11340
tgataaactg atacctgctg agtggataaa ggaacccaag aaggaggtcc cctttgatag   11400
attaaaaagg aaaggaggaa agaaataatg gctcgtgtac agtttaaaca acgtgaatct   11460
actgacgcaa tctttgttca ctgctcggct accaagccaa gtcagaatgt tggtgtccgt   11520
gagattcgcc agtggcacaa agagcagggt tggctcgatg tgggatacca ctttatcatc   11580
aagcgagacg gtactgtgga ggcaggacga gatgagatgg ctgtaggctc tcacgctaag   11640
ggttacaacc acaactctat cggcgtctgc cttgttggtg gtatcgacga taaaggtaag   11700
ttcgacgcta actttacgcc agcccaaatg caatcccttc gctcactgct tgtcacactg   11760
ctggctaagt acgaaggcgc tgtgcttcgc gcccatcatg aggtggcgcc gaaggcttgc   11820
ccttcgttcg accttaagcg ttggtgggag aagaacgaac tggtcacttc tgaccgtgga   11880
```

-continued taattaattg aactcactaa agggagacca cagcggtttc cctttgttcg cattggaggt 11940
caaataatgc gcaagtctta taaacaattc tataaggctc cgaggaggca tatccaagtg 12000
tgggaggcag ccaatgggcc tataccaaaa ggttattata tagaccacat tgacggcaat 12060
ccactcaacg acgccttaga caatctccgt ctggctctcc caaaagaaaa ctcatggaac 12120
atgaagactc caaagagcaa tacctcagga ctaaagggac tgagttggag caaggaaagg 12180
gagatgtgga gaggcactgt aacagctgag ggtaaacagc ataactttcg tagtagagat 12240
ctattggaag tcgttgcgtg gatttataga actaggaggg aattgcatgg acaattcgca 12300
cgattccgat agtgtatttc tttaccacat tccttgtgac aactgtggga gtagtgatgg 12360
gaactcgctg ttctctgacg gacacacgtt ctgctacgta tgcgagaagt ggactgctgg 12420
taatgaagac actaaagaga gggcttcaaa acggaaaccc tcaggaggta aaccaatgac 12480
ttacaacgtg tggaacttcg gggaatccaa tggacgctac tccgcgttaa ctgcgagagg 12540
aatctccaag gaaacctgtc agaaggctgg ctactggatt gccaaagtag acggtgtgat 12600
gtaccaagtg gctgactatc gggaccagaa cggcaacatt gtgagtcaga aggttcgaga 12660
taaagataag aactttaaga ccactggtag tcacaagagt gacgctctgt tcgggaagca 12720
cttgtggaat ggtggtaaga agattgtcgt tacagaaggt gaaatcgaca tgcttaccgt 12780
gatggaactt caagactgta agtatcctgt agtgtcgttg ggtcacggtg cctctgccgc 12840
taagaagaca tgcgctgcca actacgaata ctttgaccag ttcgaacaga ttatcttaat 12900
gttcgatatg gacgaagcag ggcgcaaagc agtcgaagag gctgcacagg ttctacctgc 12960
tggtaaggta cgagtggcag ttcttccgtg taaggatgca aacgagtgtc acctaaatgg 13020
tcacgaccgt gaaatcatgg agcaagtgtg gaatgctggt ccttggattc ctgatggtgt 13080
ggtatcggct ctttcgttac gtgaacgaat ccgtgagcac ctatcgtccg aggaatcagt 13140
aggtttactt ttcagtggct gcactggtat caacgataag accttaggtg cccgtggtgg 13200
tgaagtcatt atggtcactt ccggttccgg tatgggtaag tcaacgttcg tccgtcaaca 13260
agctctacaa tggggcacag cgatgggcaa gaaggtaggc ttagcgatgc ttgaggagtc 13320
cgttgaggag accgctgagg accttatagg tctacacaac cgtgtccgac tgagacaatc 13380
cgactcacta aagagagaga ttattgagaa cggtaagttc gaccaatggt tcgatgaact 13440
gttcggcaac gatacgttcc atctatatga ctcattcgcc gaggctgaga cggatagact 13500
gctcgctaag ctggcctaca tgcgctcagg cttgggctgt gacgtaatca ttctagacca 13560
catctcaatc gtcgtatccg cttctggtga atccgatgag cgtaagatga ttgacaacct 13620
gatgaccaag ctcaaagggt tcgctaagtc aactggggtg gtgctggtcg taatttgtca 13680
ccttaagaac ccagacaaag gtaaagcaca tgaggaaggt cgccccgttt ctattactga 13740
cctacgtggt tctggcgcac tacgccaact atctgatact attattgccc ttgagcgtaa 13800
tcagcaaggc gatatgccta accttgtcct cgttcgtatt ctcaagtgcc gctttactgg 13860
tgatactggt atcgctggct acatggaata caacaaggaa accggatggc ttgaaccatc 13920
aagttactca ggggaagaag agtcacactc agagtcaaca gactggtcca acgacactga 13980
cttctgacag gattcttgat gactttccag acgactacga gaagtttcgc tggagagtcc 14040
cattctaata cgactcacta aaggagacac accatgttca aactgattaa gaagttaggc 14100
caactgctgg ttcgtatgta caacgtggaa gccaagcgac tgaacgatga ggctcgtaaa 14160
gaggccacac agtcacgcgc tctggcgatt cgctccaacg aactggctga cagtgcatcc 14220
actaaagtta ccgaggctgc ccgtgtggca aaccaagctc aacagctttc caaattcttt 14280

-continued gagtaatcaa acaggagaaa ccattatgtc taacgtagct gaaactatcc gtctatccga 14340
tacagctgac cagtggaacc gtcgagtcca catcaacgtt cgcaacggta aggcgactat 14400
ggtttaccgc tggaaggact ctaagtcctc taagaatcac actcagcgta tgacgttgac 14460
agatgagcaa gcactgcgtc tggtcaatgc gcttaccaaa gctgccgtga cagcaattca 14520
tgaagctggt cgcgtcaatg aagctatggc tatcctcgac aagattgata actaagagtg 14580
gtatcctcaa ggtcgccaaa gtggtggcct tcatgaatac tattcgactc actataggag 14640
atattaccat gcgtgaccct aaagttatcc aagcagaaat cgctaaactg gaagctgaac 14700
tggaggacgt taagtaccat gaagctaaga ctcgctccgc tgttcacatc ttgaagaact 14760
taggctggac ttggacaaga cagactggct ggaagaaacc agaagttacc aagctgagtc 14820
ataaggtgtt cgataaggac actatgaccc acatcaaggc tggtgattgg gttaaggttg 14880
acatgggagt tgttggtgga tacggctacg tccgctcagt tagtggcaaa tatgcacaag 14940
tgtcatacat cacaggtgtt actccacgcg gtgcaatcgt tgccgataag accaacatga 15000
ttcacacagg tttcttgaca gttgtttcat atgaagagat tgttaagtca cgataatcaa 15060
taggagaaat caatatgatc gtttctgaca tcgaagctaa cgccctctta gagagcgtca 15120
ctaagttcca ctgcggggtt atctacgact actccaccgc tgagtacgta agctaccgtc 15180
cgagtgactt cggtgcgtat ctggatgcgc tggaagccga ggttgcacga ggcggtctta 15240
ttgtgttcca caacggtcac aagtatgacg ttcctgcatt gaccaaactg gcaaagttgc 15300
aattgaaccg agagttccac cttcctcgtg agaactgtat tgacaccctt gtgttgtcac 15360
gtttgattca ttccaacctc aaggacaccg atatgggtct tctgcgttcc ggcaagttgc 15420
ccggaaaacg ctttgggtct cacgctttgg aggcgtgggg ttatcgctta ggcgagatga 15480
agggtgaata caaagacgac tttaagcgta tgcttgaaga gcagggtgaa gaatacgttg 15540
acggaatgga gtggtggaac ttcaacgaag agatgatgga ctataacgtt caggacgttg 15600
tggtaactaa agctctcctt gagaagctac tctctgacaa acattacttc cctcctgaga 15660
ttgactttac ggacgtagga tacactacgt tctggtcaga atcccttgag gccgttgaca 15720
ttgaacatcg tgctgcatgg ctgctcgcta aacaagagcg caacgggttc ccgtttgaca 15780
caaaagcaat cgaagagttg tacgtagagt tagctgctcg ccgctctgag ttgctccgta 15840
aattgaccga aacgttcggc tcgtggtatc agcctaaagg tggcactgag atgttctgcc 15900
atccgcgaac aggtaagcca ctacctaaat accctcgcat taagacacct aaagttggtg 15960
gtatctttaa gaagcctaag aacaaggcac agcgagaagg ccgtgagcct tgcgaacttg 16020
atacccgcga gtacgttgct ggtgctcctt acaccccagt tgaacatgtt gtgtttaacc 16080
cttcgtctcg tgaccacatt cagaagaaac tccaagaggc tgggtgggtc ccgaccaagt 16140
acaccgataa gggtgctcct gtggtggacg atgaggtact cgaaggagta cgtgtagatg 16200
accctgagaa gcaagccgct atcgacctca ttaaagagta cttgatgatt cagaagcgaa 16260
tcggacagtc tgctgaggga gacaaagcat ggcttcgtta tgttgctgag gatggtaaga 16320
ttcatggttc tgttaaccct aatggagcag ttacgggtcg tgcgacccat gcgttcccaa 16380
accttgcgca aattccgggt gtacgttctc cttatggaga gcagtgtcgc gctgcttttg 16440
gcgctgagca ccatttggat gggataactg gtaagccttg ggttcaggct ggcatcgacg 16500
catccggtct tgagctacgc tgcttggctc acttcatggc tcgctttgat aacggcgagt 16560
acgctcacga gattcttaac ggcgacatcc acactaagaa ccagatagct gctgaactac 16620

-continued ctacccgaga taacgctaag acgttcatct atgggttcct ctatggtgct ggtgatgaga 16680
agattggaca gattgttggt gctggtaaag agcgcggtaa ggaactcaag aagaaattcc 16740
ttgagaacac ccccgcgatt gcagcactcc gcgagtctat ccaacagaca cttgtcgagt 16800
cctctcaatg ggtagctggt gagcaacaag tcaagtggaa acgccgctgg attaaaggtc 16860
tggatggtcg taaggtacac gttcgtagtc ctcacgctgc cttgaatacc ctactgcaat 16920
ctgctggtgc tctcatctgc aaactgtgga ttatcaagac cgaagagatg ctcgtagaga 16980
aaggcttgaa gcatggctgg gatggggact ttgcgtacat ggcatgggta catgatgaaa 17040
tccaagtagg ctgccgtacc gaagagattg ctcaggtggt cattgagacc gcacaagaag 17100
cgatgcgctg ggttggagac cactggaact tccggtgtct tctggatacc gaaggtaaga 17160
tgggtcctaa ttgggcgatt tgccactgat acaggaggct actcatgaac gaaagacact 17220
taacaggtgc tgcttctgaa atgctagtag cctacaaatt taccaaagct gggtacactg 17280
tctattaccc tatgctgact cagagtaaag aggacttggt tgtatgtaag gatggtaaat 17340
ttagtaaggt tcaggttaaa acagccacaa cggttcaaac caacacagga gatgccaagc 17400
aggttaggct aggtggatgc ggtaggtccg aatataagga tggagacttt gacattcttg 17460
cggttgtggt tgacgaagat gtgcttattt tcacatggga cgaagtaaaa ggtaagacat 17520
ccatgtgtgt cggcaagaga aacaaaggca taaaactata ggagaaatta ttatggctat 17580
gacaaagaaa tttaaagtgt ccttcgacgt taccgcaaag atgtcgtctg acgttcaggc 17640
aatcttagag aaagatatgc tgcatctatg taagcaggtc ggctcaggtg cgattgtccc 17700
caatggtaaa cagaaggaaa tgattgtcca gttcctgaca cacggtatgg aaggattgat 17760
gacattcgta gtacgtacat catttcgtga ggccattaag gacatgcacg aagagtatgc 17820
agataaggac tctttcaaac aatctcctgc aacagtacgg gaggtgttct gatgtctgac 17880
tacctgaaag tgctgcaagc aatcaaaagt tgccctaaga ctttccagtc caactatgta 17940
cggaacaatg cgagcctcgt agcggaggcc gcttcccgtg gtcacatctc gtgcctgact 18000
actagtggac gtaacggtgg cgcttgggaa atcactgctt ccggtactcg ctttctgaaa 18060
cgaatgggag gatgtgtcta atgtctcgtg accttgtgac tattccacgc gatgtgtgga 18120
acgatataca gggctacatc gactctctgg aacgtgagaa cgatagcctt aagaatcaac 18180
taatggaagc tgacgaatac gtagcggaac tagaggagaa acttaatggc acttcttgac 18240
cttaaacaat tctatgagtt acgtgaaggc tgcgacgaca agggtatcct tgtgatggac 18300
ggcgactggc tggtcttcca agctatgagt gctgctgagt ttgatgcctc ttgggaggaa 18360
gagatttggc accgatgctg tgaccacgct aaggcccgtc agattcttga ggattccatt 18420
aagtcctacg agacccgtaa gaaggcttgg gcaggtgctc caattgtcct tgcgttcacc 18480
gatagtgtta actggcgtaa agaactggtt gacccgaact ataaggctaa ccgtaaggcc 18540
gtgaagaaac ctgtagggta ctttgagttc cttgatgctc tctttgagcg cgaagagttc 18600
tattgcatcc gtgagcctat gcttgagggt gatgacgtta tgggagttat tgcttccaat 18660
ccgtctgcct tcggtgctcg taaggctgta atcatctctt gcgataagga ctttaagacc 18720
atccctaact gtgacttcct gtggtgtacc actggtaaca tcctgactca gaccgaagag 18780
tccgctgact ggtggcacct cttccagacc atcaagggtg acatcactga tggttactca 18840
gggattgctg gatggggtga taccgccgag gacttcttga ataacccgtt cataaccgag 18900
cctaaaacgt ctgtgcttaa gtccggtaag aacaaaggcc aagaggttac taaatgggtt 18960
aaacgcgacc ctgagcctca tgagacgctt tgggactgca ttaagtccat tggcgcgaag 19020
gctggtatga ccgaagagga tattatcaag cagggccaaa tggctcgaat cctacggttc 19080
aacgagtaca actttattga caaggagatt tacctgtgga gaccgtagcg tatattggtc 19140
tgggtctttg tgttctcgga gtgtgcctca tttcgtgggg cctttgggac ttagccagaa 19200
taatcaagtc gttacacgac actaagtgat aaactcaagg tccctaaatt aatacgactc 19260
actataggga gataggggcc tttacgatta ttactttaag atttaactct aagaggaatc 19320
tttattatgt taacacctat taaccaatta cttaagaacc ctaacgatat tccagatgta 19380
cctcgtgcaa ccgctgagta tctacaggtt cgattcaact atgcgtacct cgaagcgtct 19440
ggtcatatag gacttatgcg tgctaatggt tgtagtgagg cccacatctt gggtttcatt 19500
cagggcctac agtatgcctc taacgtcatt gacgagattg agttacgcaa ggaacaacta 19560
agagatgatg gggaggattg acactatgtg tttctcaccg aaaattaaaa ctccgaagat 19620
ggataccaat cagattcgag ccgttgagcc agcgcctctg acccaagaag tgtcaagcgt 19680
ggagttcggt gggtcttctg atgagacgga taccgagggc accgaagtgt ctggacgcaa 19740
aggcctcaag gtcgaacgtg atgattccgt agcgaagtct aaagccagcg gcaatggctc 19800
cgctcgtatg aaatcttcca tccgtaagtc cgcatttgga ggtaagaagt gatgtctgag 19860
ttcacatgtg tggaggctaa gagtcgcttc cgtgcaatcc ggtggactgt ggaacacctt 19920
gggttgccta aaggattcga aggacacttt gtgggctaca gcctctacgt agacgaagtg 19980
atggacatgt ctggttgccg tgaagagtac attctggact ctaccggaaa acatgtagcg 20040
tacttcgcgt ggtgcgtaag ctgtgacatt caccacaaag gagacattct ggatgtaacg 20100
tccgttgtca ttaatcctga ggcagactct aagggcttac agcgattcct agcgaaacgc 20160
tttaagtacc ttgcggaact ccacgattgc gattgggtgt ctcgttgtaa gcatgaaggc 20220
gagacaatgc gtgtatactt taaggaggta taagttatgg gtaagaaagt taagaaggcc 20280
gtgaagaaag tcaccaagtc cgttaagaaa gtcgttaagg aaggggctcg tccggttaaa 20340
caggttgctg gcggtctagc tggtctggct ggtggtactg gtgaagcaca gatggtggaa 20400
gtaccacaag ctgccgcaca gattgttgac gtacctgaga aagaggtttc cactgaggac 20460
gaagcacaga cagaaagcgg acgcaagaaa gctcgtgctg gcggtaagaa atccttgagt 20520
gtagcccgta gctccggtgg cggtatcaac atttaatcag gaggttatcg tggaagactg 20580
cattgaatgg accggaggtg tcaactctaa gggttatggt cgtaagtggg ttaatggtaa 20640
acttgtgact ccacataggc acatctatga ggagacatat ggtccagttc caacaggaat 20700
tgtggtgatg catatctgcg ataaccctag gtgctataac ataaagcacc ttacgcttgg 20760
aactccaaag gataattccg aggacatggt taccaaaggt agacaggcta aaggagagga 20820
actaagcaag aaacttacag agtcagacgt tctcgctata cgctcttcaa ccttaagcca 20880
ccgctcctta ggagaactgt atggagtcag tcaatcaacc ataacgcgaa tactacagcg 20940
taagacatgg agacacattt aatggctgag aaacgaacag gacttgcgga ggatggcgca 21000
aagtctgtct atgagcgttt aaagaacgac cgtgctccct atgagacacg cgctcagaat 21060
tgcgctcaat ataccatccc atcattgttc cctaaggact ccgataacgc ctctacagat 21120
tatcaaactc cgtggcaagc cgtgggcgct cgtggtctga acaatctagc ctctaagctc 21180
atgctggctc tattccctat gcagacttgg atgcgactta ctatatctga atatgaagca 21240
aagcagttac tgagcgaccc cgatggactc gctaaggtcg atgagggcct ctcgatggta 21300
gagcgtatca tcatgaacta cattgagtct aacagttacc gcgtgactct ctttgaggct 21360

-continued

```
ctcaaacagt tagtcgtagc tggtaacgtc ctgctgtacc taccggaacc ggaagggtca  21420
aactataatc ccatgaagct gtaccgattg tcttcttatg tggtccaacg agacgcattc  21480
ggcaacgttc tgcaaatggt gactcgtgac cagatagctt ttggtgctct ccctgaggac  21540
atccgtaagg ctgtagaagg tcaaggtggt gagaagaaag ctgatgagac aatcgacgtg  21600
tacactcaca tctatctgga tgaggactca ggtgaatacc tccgatacga agaggtcgag  21660
ggtatggaag tccaaggctc cgatgggact tatcctaaag aggcttgccc atacatcccg  21720
attcggatgg tcagactaga tggtgaatcc tacggtcgtt cgtacattga ggaatactta  21780
ggtgacttac ggtcccttga aaatctccaa gaggctatcg tcaagatgtc catgattagc  21840
tctaaggtta tcggcttagt gaatcctgct ggtatcaccc agccacgccg actgaccaaa  21900
gctcagactg gtgacttcgt tactggtcgt ccagaagaca tctcgttcct ccaactggag  21960
aagcaagcag actttactgt agctaaagcc gtaagtgacg ctatcgaggc tcgccttttcg  22020
tttgccttta tgttgaactc tgcggttcag cgtacaggtg aacgtgtgac cgccgaagag  22080
attcggtatg tagcttctga acttgaagat actttaggtg gtgtctactc tatcctttct  22140
caagaattac aattgcctct ggtacgagtg ctcttgaagc aactacaagc cacgcaacag  22200
attcctgagt tacctaagga agccgtagag ccaaccatta gtacaggtct ggaagcaatt  22260
ggtcgaggac aagaccttga taagctggag cggtgtgtca ctgcgtgggc tgcactggca  22320
cctatgcggg acgaccctga tattaacctt gcgatgatta agttacgtat tgccaacgct  22380
atcggtattg acacttctgg tattctactc accgaagaac agaagcaaca gaagatggcc  22440
caacagtcta tgcaaatggg tatggataat ggtgctgctg cgctggctca aggtatggct  22500
gcacaagcta cagcttcacc tgaggctatg gctgctgccg ctgattccgt aggtttacag  22560
ccgggaattt aatacgactc actataggga gacctcatct ttgaaatgag cgatgacaag  22620
aggttggagt cctcggtctt cctgtagttc aactttaagg agacaataat aatggctgaa  22680
tctaatgcag acgtatatgc atcttttggc gtgaactccg ctgtgatgtc tggtggttcc  22740
gttgaggaac atgagcagaa catgctggct cttgatgttg ctgcccgtga tggcgatgat  22800
gcaatcgagt tagcgtcaga cgaagtggaa acagaacgtg acctgtatga caactctgac  22860
ccgttcggtc aagaggatga cgaaggccgc attcaggttc gtatcggtga tggctctgag  22920
ccgaccgatg tggacactgg agaagaaggc gttgagggca ccgaaggttc cgaagagttt  22980
accccactgg gcgagactcc agaagaactg gtagctgcct ctgagcaact tggtgagcac  23040
gaagagggct tccaagagat gattaacatt gctgctgagc gtggcatgag tgtcgagacc  23100
attgaggcta tccagcgtga gtacgaggag aacgaagagt tgtccgccga gtcctacgct  23160
aagctggctg aaattggcta cacgaaggct ttcattgact cgtatatccg tggtcaagaa  23220
gctctggtgg agcagtacgt aaacagtgtc attgagtacg ctggtggtcg tgaacgtttt  23280
gatgcactgt ataaccacct tgagacgcac aaccctgagg ctgcacagtc gctggataat  23340
gcgttgacca atcgtgactt agcgaccgtt aaggctatca tcaacttggc tggtgagtct  23400
cgcgctaagg cgttcggtcg taagccaact cgtagtgtga ctaatcgtgc tattccggct  23460
aaacctcagg ctaccaagcg tgaaggcttt gcggaccgta gcgagatgat taaagctatg  23520
agtgaccctc ggtatcgcac agatgccaac tatcgtcgtc aagtcgaaca gaaagtaatc  23580
gattcgaact tctgatagac ttcgaaatta atacgactca ctatagggag accacaacgg  23640
tttccctcta gaaataattt tgtttaactt taagaaggag atatacatat ggctagcatg  23700
actggtggac agcaaatggg tactaaccaa ggtaaaggtg tagttgctgc tggagataaa  23760
```

ctggcgttgt tcttgaaggt atttggcggt gaagtcctga ctgcgttcgc tcgtacctcc 23820
gtgaccactt ctcgccacat ggtacgttcc atctccagcg gtaaatccgc tcagttccct 23880
gttctgggtc gcactcaggc agcgtatctg gctccgggcg agaacctcga cgataaacgt 23940
aaggacatca aacacaccga gaaggtaatc accattgacg gtctcctgac ggctgacgtt 24000
ctgatttatg atattgagga cgcgatgaac cactacgacg ttcgctctga gtatacctct 24060
cagttgggtg aatctctggc gatggctgcg gatggtgcgg ttctggctga gattgccggt 24120
ctgtgtaacg tggaaagcaa atataatgag aacatcgagg gcttaggtac tgctaccgta 24180
attgagacca ctcagaacaa ggccgcactt accgaccaag ttgcgctggg taaggagatt 24240
attgcggctc tgactaaggc tcgtgcggct ctgaccaaga actatgttcc ggctgctgac 24300
cgtgtgttct actgtgaccc agatagctac tctgcgattc tggcagcact gatgccgaac 24360
gcagcaaact acgctgctct gattgaccct gagaagggtt ctatccgcaa cgttatgggc 24420
tttgaggttg tagaagttcc gcacctcacc gctggtggtg ctggtaccgc tcgtgagggc 24480
actactggtc agaagcacgt cttccctgcc aataaaggtg agggtaatgt caaggttgct 24540
aaggacaacg ttatcggcct gttcatgcac cgctctgcgg taggtactgt taagctgcgt 24600
gacttggctc tggagcgcgc tcgccgtgct aacttccaag cggaccagat tatcgctaag 24660
tacgcaatgg gccacggtgg tcttcgccca gaagctgctg gtgcagtggt tttcaaagtg 24720
gagtaatgct gggggtggcc tcaacggtcg ctgctagtcc cgaagaggcg agtgttactt 24780
caacagaaga aaccttaacg ccagcacagg aggccgcacg cacccgcgct gctaacaaag 24840
cccgaaagga agctgagttg gctgctgcca ccgctgagca ataactagca taaccccttg 24900
gggcctctaa acgggtcttg aggggttttt tgctgaaagg aggaactata tgcgctcata 24960
cgatatgaac gttgagactg ccgctgagtt atcagctgtg aacgacattc tggcgtctat 25020
cggtgaacct ccggtatcaa cgctggaagg tgacgctaac gcagatgcag cgaacgctcg 25080
gcgtattctc aacaagatta accgacagat tcaatctcgt ggatggacgt tcaacattga 25140
ggaaggcata acgctactac ctgatgttta ctccaacctg attgtataca gtgacgacta 25200
tttatcccta atgtctactt ccggtcaatc catctacgtt aaccgaggtg gctatgtgta 25260
tgaccgaacg agtcaatcag accgctttga ctctggtatt actgtgaaca ttattcgtct 25320
ccgcgactac gatgagatgc ctgagtgctt ccgttactgg attgtcacca aggcttcccg 25380
tcagttcaac aaccgattct ttggggcacc ggaagtagag ggtgtactcc aagaagagga 25440
agatgaggct agacgtctct gcatggagta tgagatggac tacggtgggt acaatatgct 25500
ggatggagat gcgttcactt ctggtctact gactcgctaa cattaataaa taaggaggct 25560
ctaatggcac tcattagcca atcaatcaag aacttgaagg gtggtatcag ccaacagcct 25620
gacatccttc gttatccaga ccaagggtca cgccaagtta acggttggtc ttcggagacc 25680
gagggcctcc aaaagcgtcc acctcttgtt ttcttaaata cacttggaga caacggtgcg 25740
ttaggtcaag ctccgtacat ccacctgatt aaccgagatg agcacgaaca gtattacgct 25800
gtgttcactg gtagcggaat ccgagtgttc gacctttctg gtaacgagaa gcaagttagg 25860
tatcctaacg gttccaacta catcaagacc gctaatccac gtaacgacct gcgaatggtt 25920
actgtagcag actatacgtt catcgttaac cgtaacgttg ttgcacagaa gaacacaaag 25980
tctgtcaact taccgaatta caaccctaat caagacggat tgattaacgt tcgtggtggt 26040
cagtatggta gggaactaat tgtacacatt aacggtaaag acgttgcgaa gtataagata 26100

-continued ccagatggta gtcaacctga acacgtaaac aatacggatg cccaatggtt agctgaagag 26160
ttagccaagc agatgcgcac taacttgtct gattggactg taaatgtagg gcaagggttc 26220
atccatgtga ccgcacctag tggtcaacag attgactcct tcacgactaa agatggctac 26280
gcagaccagt tgattaaccc tgtgacccac tacgctcagt cgttctctaa gctgccacct 26340
aatgctccta acggctacat ggtgaaaatc gtaggggacg cctctaagtc tgccgaccag 26400
tattacgttc ggtatgacgc tgagcggaaa gtttggactg agactttagg ttggaacact 26460
gaggaccaag ttctatggga aaccatgcca cacgctcttg tgcgagccgc tgacggtaat 26520
ttcgacttca agtggcttga gtggtctcct aagtcttgtg gtgacgttga caccaaccct 26580
tggccttctt ttgttggttc aagtattaac gatgtgttct tcttccgtaa ccgcttagga 26640
ttccttagtg gggagaacat catattgagt cgtacagcca aatacttcaa cttctaccct 26700
gcgtccattg cgaaccttag tgatgacgac cctatagacg tagctgtgag taccaaccga 26760
atagcaatcc ttaagtacgc cgttccgttc tcagaagagt tactcatctg gtccgatgaa 26820
gcacaattcg tcctgactgc ctcgggtact ctcacatcta agtcggttga gttgaaccta 26880
acgacccagt ttgacgtaca ggaccgagcg agaccttttg ggattgggcg taatgtctac 26940
tttgctagtc cgaggtccag cttcacgtcc atccacaggt actacgctgt gcaggatgtc 27000
agttccgtta agaatgctga ggacattaca tcacacgttc ctaactacat ccctaatggt 27060
gtgttcagta tttgcggaag tggtacggaa aacttctgtt cggtactatc tcacggggac 27120
cctagtaaaa tcttcatgta caaattcctg tacctgaacg aagagttaag gcaacagtcg 27180
tggtctcatt gggactttgg ggaaaacgta caggttctag cttgtcagag tatcagctca 27240
gatatgtatg tgattcttcg caatgagttc aatacgttcc tagctagaat ctctttcact 27300
aagaacgcca ttgacttaca gggagaaccc tatcgtgcct ttatggacat gaagattcga 27360
tacacgattc ctagtggaac atacaacgat gacacattca ctacctctat tcatattcca 27420
acaatttatg gtgcaaactt cgggaggggc aaaatcactg tattggagcc tgatggtaag 27480
ataaccgtgt ttgagcaacc tacggctggg tggaatagcg acccttggct gagactcagc 27540
ggtaacttgg agggacgcat ggtgtacatt gggttcaaca ttaacttcgt atatgagttc 27600
tctaagttcc tcatcaagca gactgccgac gacgggtcta cctccacgga agacattggg 27660
cgcttacagt tacgccgagc gtgggttaac tacgagaact ctggtacgtt tgacatttat 27720
gttgagaacc aatcgtctaa ctggaagtac acaatggctg gtgcccgatt aggctctaac 27780
actctgaggg ctgggagact gaacttaggg accggacaat atcgattccc tgtggttggt 27840
aacgccaagt tcaacactgt atacatcttg tcagatgaga ctacccctct gaacatcatt 27900
gggtgtggct gggaaggtaa ctacttacgg agaagttccg gtatttaatt aaatattctc 27960
cctgtggtgg ctcgaaatta atacgactca ctatagggag aacaatacga ctacgggagg 28020
gttttcttat gatgactata agacctacta aaagtacaga ctttgaggta ttcactccgg 28080
ctcaccatga cattcttgaa gctaaggctg ctggtattga gccgagtttc cctgatgctt 28140
ccgagtgtgt cacgttgagc ctctatgggt tccctctagc tatcggtggt aactgcgggg 28200
accagtgctg gttcgttacg agcgaccaag tgtggcgact tagtggaaag gctaagcgaa 28260
agttccgtaa gttaatcatg gagtatcgcg ataagatgct tgagaagtat gatactcttt 28320
ggaattacgt atgggtaggc aatacgtccc acattcgttt cctcaagact atcggtgcgg 28380
tattccatga agagtacaca cgagatggtc aatttcagtt atttacaatc acgaaaggag 28440
gataaccata tgtgttgggc agccgcaata cctatcgcta tatctggcgc tcaggctatc 28500
agtggtcaga acgctcaggc caaaatgatt gccgctcaga ccgctgctgg tcgtcgtcaa 28560
gctatggaaa tcatgaggca gacgaacatc cagaatgctg acctatcgtt gcaagctcga 28620
agtaaacttg aggaagcgtc cgccgagttg acctcacaga acatgcagaa ggtccaagct 28680
attgggtcta tccgagcggc tatcggagag agtatgcttg aaggttcctc aatggaccgc 28740
attaagcgag tcacagaagg acagttcatt cgggaagcca atatggtaac tgagaactat 28800
cgccgtgact accaagcaat cttcgcacag caacttggtg gtactcaaag tgctgcaagt 28860
cagattgacg aaatctataa gagcgaacag aaacagaaga gtaagctaca gatggttctg 28920
gacccactgg ctatcatggg gtcttccgct gcgagtgctt acgcatccgg tgcgttcgac 28980
tctaagtcca caactaaggc acctattgtt gccgctaaag gaaccaagac ggggaggtaa 29040
tgagctatga gtaaaattga atctgccctt caagcggcac aaccgggact ctctcggtta 29100
cgtggtggtg ctggaggtat gggctatcgt gcagcaacca ctcaggccga acagccaagg 29160
tcaagcctat tggacaccat tggtcggttc gctaaggctg gtgccgatat gtataccgct 29220
aaggaacaac gagcacgaga cctagctgat gaacgctcta acgagattat ccgtaagctg 29280
acccctgagc aacgtcgaga agctctcaac aacgggaccc ttctgtatca ggatgaccca 29340
tacgctatgg aagcactccg agtcaagact ggtcgtaacg ctgcgtatct tgtggacgat 29400
gacgttatgc agaagataaa agagggtgtc ttccgtactc gcgaagagat ggaagagtat 29460
cgccatagtc gccttcaaga gggcgctaag gtatacgctg agcagttcgg catcgaccct 29520
gaggacgttg attatcagcg tggtttcaac ggggacatta ccgagcgtaa catctcgctg 29580
tatggtgcgc atgataactt cttgagccag caagctcaga agggcgctat catgaacagc 29640
cgagtggaac tcaacggtgt ccttcaagac cctgatatgc tgcgtcgtcc agactctgct 29700
gacttctttg agaagtatat cgacaacggt ctggttactg gcgcaatccc atctgatgct 29760
caagccacac agcttataag ccaagcgttc agtgacgctt ctagccgtgc tggtggtgct 29820
gacttcctga tgcgagtcgg tgacaagaag gtaacactta acggagccac tacgacttac 29880
cgagagttga ttggtgagga acagtggaac gctctcatgg tcacagcaca acgttctcag 29940
tttgagactg acgcgaagct gaacgagcag tatcgcttga agattaactc tgcgctgaac 30000
caagaggacc caaggacagc ttgggagatg cttcaaggta tcaaggctga actagataag 30060
gtccaacctg atgagcagat gacaccacaa cgtgagtggc taatctccgc acaggaacaa 30120
gttcagaatc agatgaacgc atggacgaaa gctcaggcca aggctctgga cgattccatg 30180
aagtcaatga acaaacttga cgtaatcgac aagcaattcc agaagcgaat caacggtgag 30240
tgggtctcaa cggattttaa ggatatgcca gtcaacgaga acactggtga gttcaagcat 30300
agcgatatgg ttaactacgc caataagaag ctcgctgaga ttgacagtat ggacattcca 30360
gacggtgcca aggatgctat gaagttgaag taccttcaag cggactctaa ggacggagca 30420
ttccgtacag ccatcggaac catggtcact gacgctggtc aagagtggtc tgccgctgtg 30480
attaacggta agttaccaga acgaacccca gctatggatg ctctgcgcag aatccgcaat 30540
gctgaccctc agttgattgc tgcgctatac ccagaccaag ctgagctatt cctgacgatg 30600
gacatgatgg acaagcaggg tattgaccct caggttattc ttgatgccga ccgactgact 30660
gttaagcggt ccaaagagca acgctttgag gatgataaag cattcgagtc tgcactgaat 30720
gcatctaagg ctcctgagat tgcccgtatg ccagcgtcac tgcgcgaatc tgcacgtaag 30780
atttatgact ccgttaagta tcgctcgggg aacgaaagca tggctatgga gcagatgacc 30840

-continued

```
aagttcctta aggaatctac ctacacgttc actggtgatg atgttgacgg tgataccgtt  30900
ggtgtgattc ctaagaatat gatgcaggtt aactctgacc cgaaatcatg ggagcaaggt  30960
cgggatattc tggaggaagc acgtaaggga atcattgcga gcaacccttg gataaccaat  31020
aagcaactga ccatgtattc tcaaggtgac tccatttacc ttatggacac cacaggtcaa  31080
gtcagagtcc gatacgacaa agagttactc tcgaaggtct ggagtgagaa ccagaagaaa  31140
ctcgaagaga aagctcgtga gaaggctctg gctgatgtga acaagcgagc acctatagtt  31200
gccgctacga aggcccgtga agctgctgct aaacgagtcc gagagaaacg taaacagact  31260
cctaagttca tctacggacg taaggagtaa ctaaaggcta cataaggagg ccctaaatgg  31320
ataagtacga taagaacgta ccaagtgatt atgatggtct gttccaaaag gctgctgatg  31380
ccaacggggt ctcttatgac cttttacgta aagtcgcttg gacagaatca cgatttgtgc  31440
ctacagcaaa atctaagact ggaccattag gcatgatgca atttaccaag gcaaccgcta  31500
aggccctcgg tctgcgagtt accgatggtc cagacgacga ccgactgaac cctgagttag  31560
ctattaatgc tgccgctaag caacttgcag gtctggtagg gaagtttgat ggcgatgaac  31620
tcaaagctgc ccttgcgtac aaccaaggcg agggacgctt gggtaatcca caacttgagg  31680
cgtactctaa gggagacttc gcatcaatct ctgaggaggg acgtaactac atgcgtaacc  31740
ttctggatgt tgctaagtca cctatggctg gacagttgga aacttttggt ggcataaccc  31800
caaagggtaa aggcattccg gctgaggtag gattggctgg aattggtcac aagcagaaag  31860
taacacagga acttcctgag tccacaagtt ttgacgttaa gggtatcgaa caggaggcta  31920
cggcgaaacc attcgccaag gacttttggg agacccacgg agaaacactt gacgagtaca  31980
acagtcgttc aaccttcttc ggattcaaaa atgctgccga agctgaactc tccaactcag  32040
tcgctgggat ggctttccgt gctggtcgtc tcgataatgg ttttgatgtg tttaaagaca  32100
ccattacgcc gactcgctgg aactctcaca tctggactcc agaggagtta gagaagattc  32160
gaacagaggt taagaaccct gcgtacatca acgttgtaac tggtggttcc cctgagaacc  32220
tcgatgacct cattaaattg gctaacgaga actttgagaa tgactcccgc gctgccgagg  32280
ctggcctagg tgccaaactg agtgctggta ttattggtgc tggtgtggac ccgcttagct  32340
atgttcctat ggtcggtgtc actggtaagg gctttaagtt aatcaataag gctcttgtag  32400
ttggtgccga aagtgctgct ctgaacgttg catccgaagg tctccgtacc tccgtagctg  32460
gtggtgacgc agactatgcg ggtgctgcct taggtggctt tgtgtttggc gcaggcatgt  32520
ctgcaatcag tgacgctgta gctgctggac tgaaacgcag taaaccagaa gctgagttcg  32580
acaatgagtt catcggtcct atgatgcgat tggaagcccg tgagacagca cgaaacgcca  32640
actctgcgga cctctctcgg atgaacactg agaacatgaa gtttgaaggt gaacataatg  32700
gtgtccctta tgaggactta ccaacagaga gaggtgccgt ggtgttacat gatggctccg  32760
ttctaagtgc aagcaaccca atcaacccta agactctaaa agagttctcc gaggttgacc  32820
ctgagaaggc tgcgcgagga atcaaactgg ctgggttcac cgagattggc ttgaagacct  32880
tggggtctga cgatgctgac atccgtagag tggctatcga cctcgttcgc tctcctactg  32940
gtatgcagtc tggtgcctca ggtaagttcg gtgcaacagc ttctgacatc catgagagac  33000
ttcatggtac tgaccagcgt acttataatg acttgtacaa agcaatgtct gacgctatga  33060
aagaccctga gttctctact ggcggcgcta agatgtcccg tgaagaaact cgatacacta  33120
tctaccgtag agcggcacta gctattgagc gtccagaact acagaaggca ctcactccgt  33180
ctgagagaat cgttatggac atcattaagc gtcactttga caccaagcgt gaacttatgg  33240
```

-continued

```
aaaacccagc aatattcggt aacacaaagg ctgtgagtat cttccctgag agtcgccaca  33300
aaggtactta cgttcctcac gtatatgacc gtcatgccaa ggcgctgatg attcaacgct  33360
acggtgccga aggtttgcag gaagggattg cccgctcatg gatgaacagc tacgtctcca  33420
gacctgaggt caaggccaga gtcgatgaga tgcttaagga attacacggg gtgaaggaag  33480
taacaccaga gatggtagag aagtacgcta tggataaggc ttatggtatc tcccactcag  33540
accagttcac caacagttcc ataatagaag agaacattga gggcttagta ggtatcgaga  33600
ataactcatt ccttgaggca cgtaacttgt ttgattcgga cctatccatc actatgccag  33660
acggacagca attctcagtg aatgacctaa gggacttcga tatgttccgc atcatgccag  33720
cgtatgaccg ccgtgtcaat ggtgacatcg ccatcatggg gtctactggt aaaaccacta  33780
aggaacttaa ggatgagatt ttggctctca aagcgaaagc tgagggagac ggtaagaaga  33840
ctggcgaggt acatgcttta atggataccg ttaagattct tactggtcgt gctagacgca  33900
atcaggacac tgtgtgggaa acctcactgc gtgccatcaa tgacctaggg ttcttcgcta  33960
agaacgccta catgggtgct cagaacatta cggagattgc tgggatgatt gtcactggta  34020
acgttcgtgc tctagggcat ggtatcccaa ttctgcgtga tacactctac aagtctaaac  34080
cagtttcagc taaggaactc aaggaactcc atgcgtctct gttcgggaag gaggtggacc  34140
agttgattcg gcctaaacgt gctgacattg tgcagcgcct aagggaagca actgataccg  34200
gacctgccgt ggcgaacatc gtagggacct tgaagtattc aacacaggaa ctggctgctc  34260
gctctccgtg gactaagcta ctgaacggaa ccactaacta ccttctggat gctgcgcgtc  34320
aaggtatgct tggggatgtt attagtgcca ccctaacagg taagactacc cgctgggaga  34380
aagaaggctt ccttcgtggt gcctccgtaa ctcctgagca gatggctggc atcaagtctc  34440
tcatcaagga acatatggta cgcggtgagg acgggaagtt taccgttaag gacaagcaag  34500
cgttctctat ggacccacgg gctatggact tatggagact ggctgacaag gtagctgatg  34560
aggcaatgct gcgtccacat aaggtgtcct tacaggattc ccatgcgttc ggagcactag  34620
gtaagatggt tatgcagttt aagtctttca ctatcaagtc ccttaactct aagttcctgc  34680
gaaccttcta tgatggatac aagaacaacc gagcgattga cgctgcgctg agcatcatca  34740
cctctatggg tctcgctggt ggtttctatg ctatggctgc acacgtcaaa gcatacgctc  34800
tgcctaagga gaaacgtaag gagtacttgg agcgtgcact ggacccaacc atgattgccc  34860
acgctgcgtt atctcgtagt tctcaattgg gtgctccttt ggctatggtt gacctagttg  34920
gtggtgtttt agggttcgag tcctccaaga tggctcgctc tacgattcta cctaaggaca  34980
ccgtgaagga acgtgaccca aacaaaccgt acacctctag agaggtaatg ggcgctatgg  35040
gttcaaacct tctggaacag atgccttcgg ctggctttgt ggctaacgta ggggctacct  35100
taatgaatgc tgctggcgtg gtcaactcac ctaataaagc aaccgagcag gacttcatga  35160
ctggtcttat gaactccaca aaagagttag taccgaacga cccattgact caacagcttg  35220
tgttgaagat ttatgaggcg aacggtgtta acttgaggga gcgtaggaaa taatacgact  35280
cactataggg agaggcgaaa taatcttctc cctgtagtct cttagattta ctttaaggag  35340
gtcaaatggc taacgtaatt aaaaccgttt tgacttacca gttagatggc tccaatcgtg  35400
attttaatat cccgtttgag tatctagccc gtaagttcgt agtggtaact cttattggtg  35460
tagaccgaaa ggtccttacg attaatacag actatcgctt tgctacacgt actactatct  35520
ctctgacaaa ggcttggggt ccagccgatg gctacacgac catcgagtta cgtcgagtaa  35580
```

-continued

```
cctccactac cgaccgattg gttgacttta cggatggttc aatcctccgc gcgtatgacc  35640
ttaacgtcgc tcagattcaa acgatgcacg tagcggaaga ggcccgtgac ctcactacgg  35700
atactatcgg tgtcaataac gatggtcact tggatgctcg tggtcgtcga attgtgaacc  35760
tagcgaacgc cgtggatgac cgcgatgctg ttccgtttgg tcaactaaag accatgaacc  35820
agaactcatg gcaagcacgt aatgaagcct tacagttccg taatgaggct gagactttca  35880
gaaaccaagc ggagggcttt aagaacgagt ccagtaccaa cgctacgaac acaaagcagt  35940
ggcgcgatga gaccaagggt ttccgagacg aagccaagcg gttcaagaat acggctggtc  36000
aatacgctac atctgctggg aactctgctt ccgctgcgca tcaatctgag gtaaacgctg  36060
agaactctgc cacagcatcc gctaactctg ctcatttggc agaacagcaa gcagaccgtg  36120
cggaacgtga ggcagacaag ctggaaaatt acaatggatt ggctggtgca attgataagg  36180
tagatggaac caatgtgtac tggaaaggaa atattcacgc taacgggcgc ctttacatga  36240
ccacaaacgg ttttgactgt ggccagtatc aacagttctt tggtggtgtc actaatcgtt  36300
actctgtcat ggagtgggga gatgagaacg gatggctgat gtatgttcaa cgtagagagt  36360
ggacaacagc gataggcggt aacatccagt tagtagtaaa cggacagatc atcacccaag  36420
gtggagccat gaccggtcag ctaaaattgc agaatgggca tgttcttcaa ttagagtccg  36480
catccgacaa ggcgcactat attctatcta aagatggtaa caggaataac tggtacattg  36540
gtagagggtc agataacaac aatgactgta ccttccactc ctatgtacat ggtacgacct  36600
taacactcaa gcaggactat gcagtagtta acaaacactt ccacgtaggt caggccgttg  36660
tggccactga tggtaatatt caaggtacta agtggggagg taaatggctg gatgcttacc  36720
tacgtgacag cttcgttgcg aagtccaagg cgtggactca ggtgtggtct ggtagtgctg  36780
gcggtggggt aagtgtgact gtttcacagg atctccgctt ccgcaatatc tggattaagt  36840
gtgccaacaa ctcttggaac ttcttccgta ctggccccga tggaatctac ttcatagcct  36900
ctgatggtgg atggttacga ttccaaatac actccaacgg tctcggattc aagaatattg  36960
cagacagtcg ttcagtacct aatgcaatca tggtggagaa cgagtaattg gtaaatcaca  37020
aggaaagacg tgtagtccac ggatggactc tcaaggaggt acaaggtgct atcattagac  37080
tttaacaacg aattgattaa ggctgctcca attgttggga cgggtgtagc agatgttagt  37140
gctcgactgt tctttgggtt aagccttaac gaatggttct acgttgctgc tatcgcctac  37200
acagtggttc agattggtgc caaggtagtc gataagatga ttgactggaa gaaagccaat  37260
aaggagtgat atgtatggaa aaggataaga gccttattac attcttagag atgttggaca  37320
ctgcgatggc tcagcgtatg cttgcggacc tttcggacca tgagcgtcgc tctccgcaac  37380
tctataatgc tattaacaaa ctgttagacc gccacaagtt ccagattggt aagttgcagc  37440
cggatgttca catcttaggt ggccttgctg gtgctcttga agagtacaaa gagaaagtcg  37500
gtgataacgg tcttacggat gatgatattt acacattaca gtgatatact caaggccact  37560
acagatagtg gtctttatgg atgtcattgt ctatacgaga tgctcctacg tgaaatctga  37620
aagttaacgg gaggcattat gctagaattt ttacgtaagc taatcccttg ggttctcgct  37680
gggatgctat tcgggttagg atggcatcta gggtcagact caatggacgc taaatggaaa  37740
caggaggtac acaatgagta cgttaagaga gttgaggctg cgaagagcac tcaaagagca  37800
atcgatgcgg tatctgctaa gtatcaagaa gaccttgccg cgctggaagg gagcactgat  37860
aggattattt ctgatttgcg tagcgacaat aagcggttgc gcgtcagagt caaaactacc  37920
ggaacctccg atggtcagtg tggattcgag cctgatggtc gagccgaact tgacgaccga  37980
```

-continued gatgctaaac gtattctcgc agtgacccag aagggtgacg catggattcg tgcgttacag 38040
gatactattc gtgaactgca acgtaagtag gaaatcaagt aaggaggcaa tgtgtctact 38100
caatccaatc gtaatgcgct cgtagtggcg caactgaaag gagacttcgt ggcgttccta 38160
ttcgtcttat ggaaggcgct aaacctaccg gtgcccacta agtgtcagat tgacatggct 38220
aaggtgctgg cgaatggaga caacaagaag ttcatcttac aggctttccg tggtatcggt 38280
aagtcgttca tcacatgtgc gttcgttgtg tggtccttat ggagagaccc tcagttgaag 38340
atacttatcg tatcagcctc taaggagcgt gcagacgcta actccatctt tattaagaac 38400
atcattgacc tgctgccatt cctatctgag ttaaagccaa gacccggaca gcgtgactcg 38460
gtaatcagct ttgatgtagg cccagccaat cctgaccact ctcctagtgt gaaatcagta 38520
ggtatcactg gtcagttaac tggtagccgt gctgacatta tcattgcgga tgacgttgag 38580
attccgtcta acagcgcaac tatgggtgcc cgtgagaagc tatggactct ggttcaggag 38640
ttcgctgcgt tacttaaacc gctgccttcc tctcgcgtta tctaccttgg tacacctcag 38700
acagagatga ctctctataa ggaacttgag gataaccgtg ggtacacaac cattatctgg 38760
cctgctctgt acccaaggac acgtgaagag aacctctatt actcacagcg tcttgctcct 38820
atgttacgcg ctgagtacga tgagaaccct gaggcacttg ctgggactcc aacagaccca 38880
gtgcgctttg accgtgatga cctgcgcgag cgtgagttgg aatacggtaa ggctggcttt 38940
acgctacagt tcatgcttaa ccctaacctt agtgatgccg agaagtaccc gctgaggctt 39000
cgtgacgcta tcgtagcggc cttagactta gagaaggccc caatgcatta ccagtggctt 39060
ccgaaccgtc agaacatcat tgaggacctt cctaacgttg gccttaaggg tgatgacctg 39120
catacgtacc acgattgttc caacaactca ggtcagtacc aacagaagat tctggtcatt 39180
gaccctagtg gtcgcggtaa ggacgaaaca ggttacgctg tgctgtacac actgaacggt 39240
tacatctacc ttatggaagc tggaggtttc cgtgatggct actccgataa gacccttgag 39300
ttactcgcta agaaggcaaa gcaatgggga gtccagacgg ttgtctacga gagtaacttc 39360
ggtgacggta tgttcggtaa ggtattcagt cctatccttc ttaaacacca caactgtgcg 39420
atggaagaga ttcgtgcccg tggtatgaaa gagatgcgta tttgcgatac ccttgagcca 39480
gtcatgcaga ctcaccgcct tgtaattcgt gatgaggtca ttagggccga ctaccagtcc 39540
gctcgtgacg tagacggtaa gcatgacgtt aagtactcgt tgttctacca gatgacccgt 39600
atcactcgtg agaaaggcgc tctggctcat gatgaccgat tggatgccct tgcgttaggc 39660
attgagtatc tccgtgagtc catgcagttg gattccgtta aggtcgaggg tgaagtactt 39720
gctgacttcc ttgaggaaca catgatgcgt cctacggttg ctgctacgca tatcattgag 39780
atgtctgtgg gaggagttga tgtgtactct gaggacgatg agggttacgg tacgtctttc 39840
attgagtggt gatttatgca ttaggactgc atagggatgc actatagacc acggatggtc 39900
agttctttaa gttactgaaa agacacgata aattaatacg actcactata gggagaggag 39960
ggacgaaagg ttactatata gatactgaat gaatacttat agagtgcata aagtatgcat 40020
aatggtgtac ctagagtgac ctctaagaat ggtgattata ttgtattagt atcaccttaa 40080
cttaaggacc aacataaagg gaggagactc atgttccgct tattgttgaa cctactgcgg 40140
catagagtca cctaccgatt tcttgtggta ctttgtgctg cccttgggta cgcatctctt 40200
actggagacc tcagttcact ggagtctgtc gtttgctcta tactcacttg tagcgattag 40260
ggtcttcctg accgactgat ggctcaccga gggattcagc ggtatgattg catcacacca 40320

```
cttcatccct atagagtcaa gtcctaaggt atacccataa agagcctcta atggtctatc  40380

ctaaggtcta tacctaaaga taggccatcc tatcagtgtc acctaaagag ggtcttagag  40440

agggcctatg gagttcctat agggtccttt aaaatatacc ataaaaatct gagtgactat  40500

ctcacagtgt acggacctaa agttccccca tagggggtac ctaaagccca gccaatcacc  40560

taaagtcaac cttcggttga ccttgagggt tccctaaggg ttggggatga cccttgggtt  40620

tgtctttggg tgttaccttg agtgtctctc tgtgtccct                         40659


<210> SEQ ID NO 2
<211> LENGTH: 41369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

tctcacagtg tacggaccta aagttccccc atagggggta cctaaagccc agccaatcac     60

ctaaagtcaa ccttcggttg accttgaggg ttccctaagg gttggggatg acccttgggt    120

ttgtctttgg gtgttacctt gagtgtctct ctgtgtccct atctgttaca gtctcctaaa    180

gtatcctcct aaagtcacct cctaacgtcc atcctaaagc caacacctaa agcctacacc    240

taaagaccca tcaagtcaac gcctatctta aagtttaaac ataaagacca gacctaaaga    300

ccagacctaa agacactaca taaagaccag acctaaagac gccttgttgt tagccataaa    360

gtgataacct ttaatcattg tctttattaa tacaactcac tataaggaga gacaacttaa    420

agagacttaa aagattaatt taaaatttat caaaaagagt attgacttaa agtctaacct    480

ataggatact tacagccatc gagagggaca cggcgaatag ccatcccaat cgacaccggg    540

gtcaaccgga taagtagaca gcctgataag tcgcacgaaa aacaggtatt gacaacatga    600

agtaacatgc agtaagatac aaatcgctag gtaacactag cagcgtcaac cgggcgcaca    660

gtgccttcta ggtgacttaa gcgcaccacg gcacataagg tgaaacaaaa cggttgacaa    720

catgaagtaa acacggtacg atgtaccaca tgaaacgaca gtgagtcacc acactgaaag    780

gtgatgcggt ctaacgaaac ctgacctaag acgctcttta acaatctggt aaatagctct    840

tgagtgcatg actagcggat aactcaaggg tatcgcaagg tgccctttat gatattcact    900

aataactgca cgaggtaaca caagatggct atgtctaaca tgacttacaa caacgttttc    960

gaccacgctt acgaaatgct gaaagaaaac atccgttatg atgacatccg tgacactgat   1020

gacctgcacg atgctattca catggctgcc gataatgcag ttccgcacta ctacgctgac   1080

atctttagcg taatggcaag tgagggcatt gaccttgagt tcgaagactc tggtctgatg   1140

cctgacacca aggacgtaat ccgcatcctg caagcgcgta tctatgagca attaacgatt   1200

gacctctggg aagacgcaga agacttgctc aatgaatact tggaggaagt cgaggagtac   1260

gaggaggatg aagagtaatg tctactacca acgtgcaata cggtctgacc gctcaaactg   1320

tacttttcta tagcgacatg gtgcgctgtg gctttaactg gtcactcgca atggcacagc   1380

tcaaagaact gtacgaaaac aacaaggcaa tagctttaga atctgctgag tgatagactc   1440

aaggtcgctc ctagcgagtg gcctttatga ttatcacttt acttatgagg gagtaatgta   1500

tatgcttact atcggtctac tcaccgctct aggtctagct gtaggtgcat cctttgggaa   1560

ggctttaggt gtagctgtag gttcctactt taccgcttgc atcatcatag gaatcatcaa   1620

aggggcacta cgcaaatgat gaagcactac gttatgccaa tccacacgtc caacggggca   1680
```

-continued

```
accgtatgta cacctgatgg gttcgcaatg aaacaacgaa tcgaacgcct taagcgtgaa   1740
ctccgcatta accgcaagat taacaagata ggttccggct atgacagaac gcactgatgg   1800
cttaaagaaa ggttatatgc ccaatggcac actatacgct gcaaatcggc gaatagtgag   1860
aacttggcga gagaacaacc tcgaacgccg caaggacaag agagggcggc gtggcataga   1920
cgaaaggaaa aggttaaagc caagaaactc gccgcacttg aacaggcact agccaacaca   1980
ctgaacgcta tctcataacg aacataaagg acacaatgca atgaacatta ccgacatcat   2040
gaacgctatc gacgcaatca aagcactgcc aatctgtgaa cttgacaagc gtcaaggtat   2100
gcttatcgac ttactggtcg agatggtcaa cagcgagacg tgtgatggcg agctaaccga   2160
actaaatcag gcacttgagc atcaagattg gtggactacc ttgaagtgtc tcacggctga   2220
cgcagggttc aagatgctcg gtaatggtca cttctcggct gcttatagtc acccgctgct   2280
acctaacaga gtgattaagg tgggctttaa gaaagaggat tcaggcgcag cctataccgc   2340
attctgccgc atgtatcagg gtcgtcctgg tatccctaac gtctacgatg tacagcgcca   2400
cgctggatgc tatacggtgg tacttgacgc acttaaggat tgcgagcgtt tcaacaatga   2460
tgcccattat aaatacgctg agattgcaag cgacatcatt gattgcaatt cggatgagca   2520
tgatgagtta actggatggg atggtgagtt tgttgaaact tgtaaactaa tccgcaagtt   2580
ctttgagggc atcgcctcat tcgacatgca tagcgggaac atcatgttct caaatggaga   2640
cgtaccatac atcaccgacc cggtatcatt ctcgcagaag aaagacggtg gcgcattcag   2700
catcgaccct gaggaactca tcaaggaagt cgaggaagtc gcacgacaga aagaaattga   2760
ccgcgctaag gcccgtaaag aacgtcacga ggggcgctta gaggcacgca gattcaaacg   2820
tcgcaaccgc aaggcacgta aagcacacaa agctaagcgc gaaagaatgc ttgctgcgtg   2880
gcgatgggct gaacgtcaag aacggcgtaa ccatgaggta gctgtagatg tactaggaag   2940
aaccaataac gctatgctct gggtcaacat gttctctggg gactttaagg cgcttgagga   3000
acgaatcgcg ctgcactggc gtaatgctga ccggatggct atcgctaatg gtcttacgct   3060
caacattgat aagcaacttg acgcaatgtt aatgggctga tagtcttatc ttacaggtca   3120
tctgcgggtg gcctgaatag gtacgattta ctaactggaa gaggcactaa atgaacacga   3180
ttaacatcgc taagaacgac ttctctgaca tcgaactggc tgctatcccg ttcaacactc   3240
tggctgacca ttacggtgag cgtttagctc gcgaacagtt ggcccttgag catgagtctt   3300
acgagatggg tgaagcacgc ttccgcaaga tgtttgagcg tcaacttaaa gctggtgagg   3360
ttgcggataa cgctgccgcc aagcctctca tcactaccct actccctaag atgattgcac   3420
gcatcaacga ctggtttgag gaagtgaaag ctaagcgcgg caagcgcccg acagccttcc   3480
agttcctgca agaaatcaag ccggaagccg tagcgtacat caccattaag accactctgg   3540
cttgcctaac cagtgctgac aatacaaccg ttcaggctgt agcaagcgca atcggtcggg   3600
ccattgagga cgaggctcgc ttcggtcgta tccgtgacct tgaagctaag cacttcaaga   3660
aaaacgttga ggaacaactc aacaagcgcg tagggcacgt ctacaagaaa gcatttatgc   3720
aagttgtcga ggctgacatg ctctctaagg gtctactcgg tggcgaggcg tggtcttcgt   3780
ggcataagga agactctatt catgtaggag tacgctgcat cgagatgctc attgagtcaa   3840
ccggaatggt tagcttacac cgccaaaatg ctggcgtagt aggtcaagac tctgagacta   3900
tcgaactcgc acctgaatac gctgaggcta tcgcaacccg tgcaggtgcg ctggctggca   3960
tctctccgat gttccaacct tgcgtagttc ctcctaagcc gtggactggc attactggtg   4020
gtggctattg ggctaacggt cgtcgtcctc tggcgctggt gcgtactcac agtaagaaag   4080
```

cactgatgcg ctacgaagac gtttacatgc ctgaggtgta caaagcgatt aacattgcgc 4140
aaaacaccgc atggaaaatc aacaagaaag tcctagcggt cgccaacgta atcaccaagt 4200
ggaagcattg tccggtcgag gacatccctg cgattgagcg tgaagaactc ccgatgaaac 4260
cggaagacat cgacatgaat cctgaggctc tcaccgcgtg gaaacgtgct gccgctgctg 4320
tgtaccgcaa ggacaaggct cgcaagtctc gccgtatcag ccttgagttc atgcttgagc 4380
aagccaataa gtttgctaac cataaggcca tctggttccc ttacaacatg gactggcgcg 4440
gtcgtgttta cgctgtgtca atgttcaacc cgcaaggtaa cgatatgacc aaaggactgc 4500
ttacgctggc gaaaggtaaa ccaatcggta aggaaggtta ctactggctg aaaatccacg 4560
gtgcaaactg tgcgggtgtc gataaggttc cgttccctga gcgcatcaag ttcattgagg 4620
aaaaccacga gaacatcatg gcttgcgcta agtctccact ggagaacact tggtgggctg 4680
agcaagattc tccgttctgc ttccttgcgt tctgctttga gtacgctggg gtacagcacc 4740
acggcctgag ctataactgc tcccttccgc tggcgtttga cgggtcttgc tctggcatcc 4800
agcacttctc cgcgatgctc cgagatgagg taggtggtcg cgcggttaac ttgcttccta 4860
gtgaaaccgt tcaggacatc tacgggattg ttgctaagaa agtcaacgag attctacaag 4920
cagacgcaat caatgggacc gataacgaag tagttaccgt gaccgatgag aacactggtg 4980
aaatctctga gaaagtcaag ctgggcacta aggcactggc tggtcaatgg ctggcttacg 5040
gtgttactcg cagtgtgact aagcgttcag tcatgacgct ggcttacggg tccaaagagt 5100
tcggcttccg tcaacaagtg ctggaagata ccattcagcc agctattgat tccggcaagg 5160
gtctgatgtt cactcagccg aatcaggctg ctggatacat ggctaagctg atttgggaat 5220
ctgtgagcgt gacggtggta gctgcggttg aagcaatgaa ctggcttaag tctgctgcta 5280
agctgctggc tgctgaggtc aaagataaga agactggaga gattcttcgc aagcgttgcg 5340
ctgtgcattg ggtaactcct gatggtttcc ctgtgtggca ggaatacaag aagcctattc 5400
agacgcgctt gaacctgatg ttcctcggtc agttccgctt acagcctacc attaacacca 5460
acaaagatag cgagattgat gcacacaaac aggagtctgg tatcgctcct aactttgtac 5520
acagccaaga cggtagccac cttcgtaaga ctgtagtgtg ggcacacgag aagtacggaa 5580
tcgaatcttt tgcactgatt cacgactcct tcggtaccat tccggctgac gctgcgaacc 5640
tgttcaaagc agtgcgcgaa actatggttg acacatatga gtcttgtgat gtactggctg 5700
atttctacga ccagttcgct gaccagttgc acgagtctca attggacaaa atgccagcac 5760
ttccggctaa aggtaacttg aacctccgtg acatcttaga gtcggacttc gcgttcgcgt 5820
aacgccaaat caatacgact cactatagag ggacaaactc aaggtcattc gcaagagtgg 5880
cctttatgat tgaccttctt ccggttaata cgactcacta taggagaacc ttaaggttta 5940
actttaagac ccttaagtgt taattagaga tttaggagat tcaacatggt cttcacactc 6000
gaagatttcg ttggggactg gcgacagaca gccggctaca acctggacca agtccttgaa 6060
cagggaggtg tgtccagttt gtttcagaat ctcggggtgt ccgtaactcc gatccaaagg 6120
attgtcctga gcggtgaaaa tgggctgaag atcgacatcc atgtcatcat cccgtatgaa 6180
ggtctgagcg gcgaccaaat gggccagatc gaaaaaattt ttaaggtggt gtaccctgtg 6240
gatgatcatc actttaaggt gatcctgcac tatggcacac tggtaatcga cggggttacg 6300
ccgaacatga tcgactattt cggacggccg tatgaaggca tcgccgtgtt cgacggcaaa 6360
aagatcactg taacagggac cctgtggaac ggcaacaaaa ttatcgacga gcgcctgatc 6420

-continued

```
aaccccgacg gctccctgct gttccgagta accatcaacg gagtgaccgg ctggcggctg   6480
tgcgaacgca ttctggcgta aaggaggtaa acatatgacc atgattacgg attcactggc   6540
cgtcgtttta caacgtcgtg actgggaaaa ccctggcgtt acccaactta atcgccttgc   6600
agcacatccc cctttcgcca gctggcgtaa tagcgaagag gcccgcaccg atcgcccttc   6660
ccaacagttg cgcagcctga atggcgaatg gaaattaaag aattactaag agaggacttt   6720
aagtatgcgt aacttcgaaa agatgaccaa acgttctaac cgtaatgctc gtgacttcga   6780
ggcaaccaaa ggtcgcaagt tgaataagac taagcgtgac cgctctcaca agcgtagctg   6840
ggagggtcag taagatggga cgtttatata gtggtaatct ggcagcattc aaggcagcaa   6900
caaacaagct gttccagtta gacttagcgg tcatttatga tgactggtat gatgcctata   6960
caagaaaaga ttgcatacgg ttacgtattg aggacaggag tggaaacctg attgatacta   7020
gcaccttcta ccaccacgac gaggacgttc tgttcaatat gtgtactgat tggttgaacc   7080
atatgtatga ccagttgaag gactggaagt aatacgactc agtataggga caatgcttaa   7140
ggtcgctctc taggagtggc cttagtcatt taaccaatag gagataaaca ttatgatgaa   7200
cattaagact aacccgttta aagccgtgtc tttcgtagag tctgccatta agaaggctct   7260
ggataacgct gggtatctta tcgctgaaat caagtacgat ggtgtacgcg ggaacatctg   7320
cgtagacaat actgctaaca gttactggct ctctcgtgta tctaaaacga ttccggcact   7380
ggagcactta aacgggtttg atgttcgctg gaagcgtcta ctgaacgatg accgttgctt   7440
ctacaaagat ggctttatgc ttgatgggga actcatggtc aagggcgtag actttaacac   7500
agggtccggc ctactgcgta ccaaatggac tgacacgaag aaccaagagt tccatgaaga   7560
gttattcgtt gaaccaatcc gtaagaaaga taaagttccc tttaagctgc acactggaca   7620
ccttcacata aaactgtacg ctatcctccc gctgcacatc gtggagtctg gagaagactg   7680
tgatgtcatg acgttgctca tgcaggaaca cgttaagaac atgctgcctc tgctacagga   7740
atacttccct gaaatcgaat ggcaagcggc tgaatcttac gaggtctacg atatggtaga   7800
actacagcaa ctgtacgagc agaagcgagc agaaggccat gagggtctca ttgtgaaaga   7860
cccgatgtgt atctataagc gcggtaagaa atctggctgg tggaaaatga aacctgagaa   7920
cgaagctgac ggtatcattc agggtctggt atggggtaca aaaggtctgg ctaatgaagg   7980
taaagtgatt ggttttgagg tgcttcttga gagtggtcgt ttagttaacg ccacgaatat   8040
ctctcgcgcc ttaatggatg agttcactga gacagtaaaa gaggccaccc taagtcaatg   8100
gggattcttt agcccatacg gtattggcga caacgatgct tgtactatta acccttacga   8160
tggctgggcg tgtcaaatta gctacatgga ggaaacacct gatggctctt tgcggcaccc   8220
atcgttcgta atgttccgtg gcaccgagga caaccctcaa gagaaaatgt aatcacactg   8280
gctcaccttc gggtgggcct ttctgcgttt ataaggagac actttatgtt taagaaggtt   8340
ggtaaattcc ttgcggcttt ggcagctatc ctgacgcttg cgtatattct tgcggtatac   8400
cctcaagtag cactagtagt agttggcgct tgttacttag cggcagtgtg tgcttgcgtg   8460
tggagtatag ttaactggta atacgactca ctaaaggagg tacacaccat gatgtactta   8520
atgccattac tcatcgtcat tgtaggatgc cttgcgctcc actgtagcga tgatgatatg   8580
ccagatggtc acgcttaata cgactcacta aaggagacac tatatgtttc gacttcatta   8640
caacaaaagc gttaagaatt tcacggttcg ccgtgctgac cgttcaatcg tatgtgcgag   8700
cgagcgccga gctaagatac ctcttattgg taacacagtt cctttggcac cgagcgtcca   8760
catcattatc acccgtggtg actttgagaa agcaatagac aagaaacgtc cggttcttag   8820
```

-continued

```
tgtggcagtg acccgcttcc cgttcgtccg tctgttactc aaacgaatca aggaggtgtt   8880
ctgatgggac tgttagatgg tgaagcctgg gaaaaagaaa acccgccagt acaagcaact   8940
gggtgtatag cttgcttaga gaaagatgac cgttatccac acacctgtaa caaaggagct   9000
aacgatatga ccgaacgtga acaagagatg atcattaagt tgatagacaa taatgaaggt   9060
cgcccagatg atttgaatgg ctgcggtatt ctctgctcca atgtcccttg ccacctctgc   9120
cccgcaaata acgatcaaaa gataacctta ggtgaaatcc gagcgatgga cccacgtaaa   9180
ccacatctga ataaacctga ggtaactcct acagatgacc agccttccgc tgagacaatc   9240
gaaggtgtca ctaagccttc ccactacatg ctgtttgacg acattgaggc tatcgaagtg   9300
attgctcgtt caatgaccgt tgagcagttc aagggatact gcttcggtaa catcttaaag   9360
tacagactac gtgctggtaa gaagtcagag ttagcgtact tagagaaaga cctagcgaaa   9420
gcagacttct ataaagaact ctttgagaaa cataaggata aatgttatgc ataacttcaa   9480
gtcaacccca cctgccgaca gcctatctga tgacttcaca tcttgctcag agtggtgccg   9540
aaagatgtgg gaagagacat tcgacgatgc gtacatcaag ctgtatgaac tttggaaatc   9600
gagaggtcaa tgactatgtc aaacgtaaat acaggttcac ttagtgtgga caataagaag   9660
ttttgggcta ccgtagagtc ctcggagcat tccttcgagg ttccaatcta cgctgagacc   9720
ctagacgaag ctctggagtt agccgaatgg caatacgttc cggctggctt tgaggttact   9780
cgtgtgcgtc cttgtgtagc accgaagtaa tacgactcac tattagggaa gactccctct   9840
gagaaaccaa acgaaaccta aaggagatta acattatggc taagaagatt ttcacctctg   9900
cgctgggtac cgctgaacct tacgcttaca tcgccaagcc ggactacggc aacgaagagc   9960
gtggctttgg gaaccctcgt ggtgtctata aagttgacct gactattccc aacaaagacc  10020
cgcgctgcca gcgtatggtc gatgaaatcg tgaagtgtca cgaagaggct tatgctgctg  10080
ccgttgagga atacgaagct aatccacctg ctgtagctcg tggtaagaaa ccgctgaaac  10140
cgtatgaggg tgacatgccg ttcttcgata acggtgacgg tacgactacc tttaagttca  10200
aatgctacgc gtctttccaa gacaagaaga ccaaagagac caagcacatc aatctggttg  10260
tggttgactc aaaaggtaag aagatggaag acgttccgat tatcggtggt ggctctaagc  10320
tgaaagttaa atattctctg gttccataca agtggaacac tgctgtaggt gcgagcgtta  10380
agctgcaact ggaatccgtg atgctggtcg aactggctac ctttggtggc ggtgaagacg  10440
attgggctga cgaagttgaa gagaacggct atgttgcctc tggttctgcc aaagcgagca  10500
aaccacgcga cgaagaaagc tgggacgaag acgacgaaga gtccgaggaa gcagacgaag  10560
acggagactt ctaagtggaa ctgcgggaga aaatccttga gcgaatcaag gtgacttcct  10620
ctgggtgttg ggagtggcag ggcgctacga acaataaagg gtacgggcag gtgtggtgca  10680
gcaataccgg aaaggttgtc tactgtcatc gcgtaatgtc taatgctccg aaaggttcta  10740
ccgtcctgca ctcctgtgat aatccattat gttgtaaccc tgaacaccta tccataggaa  10800
ctccaaaaga gaactccact gacatggtaa ataagggtcg ctcacacaag gggtataaac  10860
tttcagacga agacgtaatg gcaatcatgg agtccagcga gtccaatgta tccttagctc  10920
gcacctatgg tgtctcccaa cagactattt gtgatatacg caaagggagg cgacatggca  10980
ggttacggcg ctaaaggaat ccgaaaggtt ggagcgtttc gctctggcct agaggacaag  11040
gtttcaaagc agttggaatc aaaaggtatt aaattcgagt atgaagagtg gaaagtgcct  11100
tatgtaattc cggcgagcaa tcacacttac actccagact tcttacttcc aaacggtata  11160
```

-continued

```
ttcgttgaga caaagggtct gtgggaaagc gatgatagaa agaagcactt attaattagg  11220
gagcagcacc ccgagctaga catccgtatt gtcttctcaa gctcacgtac taagttatac  11280
aaaggttctc caacgtctta tggagagttc tgcgaaaagc atggtattaa gttcgctgat  11340
aaactgatac ctgctgagtg gataaaggaa cccaagaagg aggtcccctt tgatagatta  11400
aaaaggaaag gaggaaagaa ataatggctc gtgtacagtt taaacaacgt gaatctactg  11460
acgcaatctt tgttcactgc tcggctacca agccaagtca gaatgttggt gtccgtgaga  11520
ttcgccagtg gcacaaagag cagggttggc tcgatgtggg ataccacttt atcatcaagc  11580
gagacggtac tgtggaggca ggacgagatg agatggctgt aggctctcac gctaagggtt  11640
acaaccacaa ctctatcggc gtctgccttg ttggtggtat cgacgataaa ggtaagttcg  11700
acgctaactt tacgccagcc caaatgcaat cccttcgctc actgcttgtc acactgctgg  11760
ctaagtacga aggcgctgtg cttcgcgccc atcatgaggt ggcgccgaag gcttgccctt  11820
cgttcgacct taagcgttgg tgggagaaga acgaactggt cacttctgac cgtggataat  11880
taattgaact cactaaaggg agaccacagc ggtttccctt tgttcgcatt ggaggtcaaa  11940
taatgcgcaa gtcttataaa caattctata aggctccgag gaggcatatc caagtgtggg  12000
aggcagccaa tgggcctata ccaaaaggtt attatataga ccacattgac ggcaatccac  12060
tcaacgacgc cttagacaat ctccgtctgg ctctcccaaa agaaaactca tggaacatga  12120
agactccaaa gagcaatacc tcaggactaa agggactgag ttggagcaag gaaagggaga  12180
tgtggagagg cactgtaaca gctgagggta aacagcataa ctttcgtagt agagatctat  12240
tggaagtcgt tgcgtggatt tatagaacta ggagggaatt gcatggacaa ttcgcacgat  12300
tccgatagtg tatttcttta ccacattcct tgtgacaact gtgggagtag tgatgggaac  12360
tcgctgttct ctgacggaca cacgttctgc tacgtatgcg agaagtggac tgctggtaat  12420
gaagacacta aagagagggc ttcaaaacgg aaaccctcag gaggtaaacc aatgacttac  12480
aacgtgtgga acttcgggga atccaatgga cgctactccg cgttaactgc gagaggaatc  12540
tccaaggaaa cctgtcagaa ggctggctac tggattgcca aagtagacgg tgtgatgtac  12600
caagtggctg actatcggga ccagaacggc aacattgtga gtcagaaggt tcgagataaa  12660
gataagaact ttaagaccac tggtagtcac aagagtgacg ctctgttcgg gaagcacttg  12720
tggaatggtg gtaagaagat tgtcgttaca gaaggtgaaa tcgacatgct taccgtgatg  12780
gaacttcaag actgtaagta tcctgtagtg tcgttgggtc acggtgcctc tgccgctaag  12840
aagacatgcg ctgccaacta cgaatacttt gaccagttcg aacagattat cttaatgttc  12900
gatatggacg aagcagggcg caaagcagtc gaagaggctg cacaggttct acctgctggt  12960
aaggtacgag tggcagttct tccgtgtaag gatgcaaacg agtgtcacct aaatggtcac  13020
gaccgtgaaa tcatggagca agtgtggaat gctggtcctt ggattcctga tggtgtggta  13080
tcggctcttt cgttacgtga acgaatccgt gagcacctat cgtccgagga atcagtaggt  13140
ttacttttca gtggctgcac tggtatcaac gataagacct taggtgcccg tggtggtgaa  13200
gtcattatgg tcacttccgg ttccggtatg ggtaagtcaa cgttcgtccg tcaacaagct  13260
ctacaatggg gcacagcgat gggcaagaag gtaggcttag cgatgcttga ggagtccgtt  13320
gaggagaccg ctgaggacct tataggtcta cacaaccgtg tccgactgag acaatccgac  13380
tcactaaaga gagagattat tgagaacggt aagttcgacc aatggttcga tgaactgttc  13440
ggcaacgata cgttccatct atatgactca ttcgccgagg ctgagacgga tagactgctc  13500
gctaagctgg cctacatgcg ctcaggcttg ggctgtgacg taatcattct agaccacatc  13560
```

tcaatcgtcg tatccgcttc tggtgaatcc gatgagcgta agatgattga caacctgatg 13620
accaagctca aagggttcgc taagtcaact ggggtggtgc tggtcgtaat ttgtcacctt 13680
aagaacccag acaaaggtaa agcacatgag gaaggtcgcc ccgtttctat tactgaccta 13740
cgtggttctg gcgcactacg ccaactatct gatactatta ttgcccttga gcgtaatcag 13800
caaggcgata tgcctaacct tgtcctcgtt cgtattctca agtgccgctt tactggtgat 13860
actggtatcg ctggctacat ggaatacaac aaggaaaccg gatggcttga accatcaagt 13920
tactcagggg aagaagagtc acactcagag tcaacagact ggtccaacga cactgacttc 13980
tgacaggatt cttgatgact ttccagacga ctacgagaag tttcgctgga gagtcccatt 14040
ctaatacgac tcactaaagg agacacacca tgttcaaact gattaagaag ttaggccaac 14100
tgctggttcg tatgtacaac gtggaagcca agcgactgaa cgatgaggct cgtaaagagg 14160
ccacacagtc acgcgctctg gcgattcgct ccaacgaact ggctgacagt gcatccacta 14220
aagttaccga ggctgcccgt gtggcaaacc aagctcaaca gctttccaaa ttctttgagt 14280
aatcaaacag gagaaaccat tatgtctaac gtagctgaaa ctatccgtct atccgataca 14340
gctgaccagt ggaaccgtcg agtccacatc aacgttcgca acggtaaggc gactatggtt 14400
taccgctgga aggactctaa gtcctctaag aatcacactc agcgtatgac gttgacagat 14460
gagcaagcac tgcgtctggt caatgcgctt accaaagctg ccgtgacagc aattcatgaa 14520
gctggtcgcg tcaatgaagc tatggctatc ctcgacaaga ttgataacta agagtggtat 14580
cctcaaggtc gccaaagtgg tggccttcat gaatactatt cgactcacta taggagatat 14640
taccatgcgt gaccctaaag ttatccaagc agaaatcgct aaactggaag ctgaactgga 14700
ggacgttaag taccatgaag ctaagactcg ctccgctgtt cacatcttga agaacttagg 14760
ctggacttgg acaagacaga ctggctggaa gaaaccagaa gttaccaagc tgagtcataa 14820
ggtgttcgat aaggacacta tgacccacat caaggctggt gattgggtta aggttgacat 14880
gggagttgtt ggtggatacg gctacgtccg ctcagttagt ggcaaatatg cacaagtgtc 14940
atacatcaca ggtgttactc cacgcggtgc aatcgttgcc gataagacca acatgattca 15000
cacaggtttc ttgacagttg tttcatatga agagattgtt aagtcacgat aatcaatagg 15060
agaaatcaat atgatcgttt ctgacatcga agctaacgcc ctcttagaga gcgtcactaa 15120
gttccactgc ggggttatct acgactactc caccgctgag tacgtaagct accgtccgag 15180
tgacttcggt gcgtatctgg atgcgctgga agccgaggtt gcacgaggcg gtcttattgt 15240
gttccacaac ggtcacaagt atgacgttcc tgcattgacc aaactggcaa agttgcaatt 15300
gaaccgagag ttccaccttc ctcgtgagaa ctgtattgac acccttgtgt tgtcacgttt 15360
gattcattcc aacctcaagg acaccgatat gggtcttctg cgttccggca agttgcccgg 15420
aaaacgcttt gggtctcacg ctttggaggc gtggggttat cgcttaggcg agatgaaggg 15480
tgaatacaaa gacgacttta agcgtatgct tgaagagcag ggtgaagaat acgttgacgg 15540
aatggagtgg tggaacttca acgaagagat gatggactat aacgttcagg acgttgtggt 15600
aactaaagct ctccttgaga agctactctc tgacaaacat tacttccctc ctgagattga 15660
ctttacggac gtaggataca ctacgttctg gtcagaatcc cttgaggccg ttgacattga 15720
acatcgtgct gcatggctgc tcgctaaaca agagcgcaac gggttcccgt ttgacacaaa 15780
agcaatcgaa gagttgtacg tagagttagc tgctcgccgc tctgagttgc tccgtaaatt 15840
gaccgaaacg ttcggctcgt ggtatcagcc taaaggtggc actgagatgt tctgccatcc 15900

-continued

```
gcgaacaggt aagccactac ctaaataccc tcgcattaag acacctaaag ttggtggtat  15960
ctttaagaag cctaagaaca aggcacagcg agaaggccgt gagccttgcg aacttgatac  16020
ccgcgagtac gttgctggtg ctccttacac cccagttgaa catgttgtgt ttaacccttc  16080
gtctcgtgac cacattcaga agaaactcca agaggctggg tgggtcccga ccaagtacac  16140
cgataagggt gctcctgtgg tggacgatga ggtactcgaa ggagtacgtg tagatgaccc  16200
tgagaagcaa gccgctatcg acctcattaa agagtacttg atgattcaga agcgaatcgg  16260
acagtctgct gagggagaca aagcatggct tcgttatgtt gctgaggatg gtaagattca  16320
tggttctgtt aaccctaatg gagcagttac gggtcgtgcg acccatgcgt tcccaaacct  16380
tgcgcaaatt ccgggtgtac gttctcctta tggagagcag tgtcgcgctg cttttggcgc  16440
tgagcaccat ttggatggga taactggtaa gccttgggtt caggctggca tcgacgcatc  16500
cggtcttgag ctacgctgct tggctcactt catggctcgc tttgataacg gcgagtacgc  16560
tcacgagatt cttaacggcg acatccacac taagaaccag atagctgctg aactacctac  16620
ccgagataac gctaagacgt tcatctatgg gttcctctat ggtgctggtg atgagaagat  16680
tggacagatt gttggtgctg gtaaagagcg cggtaaggaa ctcaagaaga aattccttga  16740
gaacaccccc gcgattgcag cactccgcga gtctatccaa cagacacttg tcgagtcctc  16800
tcaatgggta gctggtgagc aacaagtcaa gtggaaacgc cgctggatta aaggtctgga  16860
tggtcgtaag gtacacgttc gtagtcctca cgctgccttg aataccctac tgcaatctgc  16920
tggtgctctc atctgcaaac tgtggattat caagaccgaa gagatgctcg tagagaaagg  16980
cttgaagcat ggctgggatg ggactttgc gtacatggca tgggtacatg atgaaatcca  17040
agtaggctgc cgtaccgaag agattgctca ggtggtcatt gagaccgcac aagaagcgat  17100
gcgctgggtt ggagaccact ggaacttccg gtgtcttctg gataccgaag gtaagatggg  17160
tcctaattgg gcgatttgcc actgatacag gaggctactc atgaacgaaa gacacttaac  17220
aggtgctgct tctgaaatgc tagtagccta caaatttacc aaagctgggt acactgtcta  17280
ttaccctatg ctgactcaga gtaaagagga cttggttgta tgtaaggatg gtaaatttag  17340
taaggttcag gttaaaacag ccacaacggt tcaaaccaac acaggagatg ccaagcaggt  17400
taggctaggt ggatgcggta ggtccgaata taaggatgga gactttgaca ttcttgcggt  17460
tgtggttgac gaagatgtgc ttattttcac atgggacgaa gtaaaaggta agacatccat  17520
gtgtgtcggc aagagaaaca aaggcataaa actataggag aaattattat ggctatgaca  17580
aagaaattta aagtgtcctt cgacgttacc gcaaagatgt cgtctgacgt tcaggcaatc  17640
ttagagaaag atatgctgca tctatgtaag caggtcggct caggtgcgat tgtccccaat  17700
ggtaaacaga aggaaatgat tgtccagttc ctgacacacg gtatggaagg attgatgaca  17760
ttcgtagtac gtacatcatt tcgtgaggcc attaaggaca tgcacgaaga gtatgcagat  17820
aaggactctt tcaaacaatc tcctgcaaca gtacgggagg tgttctgatg tctgactacc  17880
tgaaagtgct gcaagcaatc aaaagttgcc ctaagacttt ccagtccaac tatgtacgga  17940
acaatgcgag cctcgtagcg gaggccgctt cccgtggtca catctcgtgc ctgactacta  18000
gtggacgtaa cggtggcgct tgggaaatca ctgcttccgg tactcgcttt ctgaaacgaa  18060
tgggaggatg tgtctaatgt ctcgtgacct tgtgactatt ccacgcgatg tgtggaacga  18120
tatacagggc tacatcgact ctctggaacg tgagaacgat agccttaaga atcaactaat  18180
ggaagctgac gaatacgtag cggaactaga ggagaaactt aatggcactt cttgacctta  18240
aacaattcta tgagttacgt gaaggctgcg acgacaaggg tatccttgtg atggacggcg  18300
```

```
actggctggt cttccaagct atgagtgctg ctgagtttga tgcctcttgg gaggaagaga  18360
tttggcaccg atgctgtgac cacgctaagg cccgtcagat tcttgaggat tccattaagt  18420
cctacgagac ccgtaagaag gcttgggcag gtgctccaat tgtccttgcg ttcaccgata  18480
gtgttaactg gcgtaaagaa ctggttgacc cgaactataa ggctaaccgt aaggccgtga  18540
agaaacctgt agggtacttt gagttccttg atgctctctt tgagcgcgaa gagttctatt  18600
gcatccgtga gcctatgctt gagggtgatg acgttatggg agttattgct tccaatccgt  18660
ctgccttcgg tgctcgtaag gctgtaatca tctcttgcga taaggacttt aagaccatcc  18720
ctaactgtga cttcctgtgg tgtaccactg gtaacatcct gactcagacc gaagagtccg  18780
ctgactggtg gcacctcttc cagaccatca agggtgacat cactgatggt tactcaggga  18840
ttgctggatg gggtgatacc gccgaggact tcttgaataa cccgttcata accgagccta  18900
aaacgtctgt gcttaagtcc ggtaagaaca aaggccaaga ggttactaaa tgggttaaac  18960
gcgaccctga gcctcatgag acgctttggg actgcattaa gtccattggc gcgaaggctg  19020
gtatgaccga agaggatatt atcaagcagg gccaaatggc tcgaatccta cggttcaacg  19080
agtacaactt tattgacaag gagatttacc tgtggagacc gtagcgtata ttggtctggg  19140
tctttgtgtt ctcggagtgt gcctcatttc gtggggcctt tgggacttag ccagaataat  19200
caagtcgtta cacgacacta agtgataaac tcaaggtccc taaattaata cgactcacta  19260
tagggagata ggggccttta cgattattac tttaagattt aactctaaga ggaatcttta  19320
ttatgttaac acctattaac caattactta agaaccctaa cgatattcca gatgtacctc  19380
gtgcaaccgc tgagtatcta caggttcgat tcaactatgc gtacctcgaa gcgtctggtc  19440
atataggact tatgcgtgct aatggttgta gtgaggccca catcttgggt ttcattcagg  19500
gcctacagta tgcctctaac gtcattgacg agattgagtt acgcaaggaa caactaagag  19560
atgatgggga ggattgacac tatgtgtttc tcaccgaaaa ttaaaactcc gaagatggat  19620
accaatcaga ttcgagccgt tgagccagcg cctctgaccc aagaagtgtc aagcgtggag  19680
ttcggtgggt cttctgatga gacggatacc gagggcaccg aagtgtctgg acgcaaaggc  19740
ctcaaggtcg aacgtgatga ttccgtagcg aagtctaaag ccagcggcaa tggctccgct  19800
cgtatgaaat cttccatccg taagtccgca tttggaggta agaagtgatg tctgagttca  19860
catgtgtgga ggctaagagt cgcttccgtg caatccggtg gactgtggaa caccttgggt  19920
tgcctaaagg attcgaagga cactttgtgg gctacagcct ctacgtagac gaagtgatgg  19980
acatgtctgg ttgccgtgaa gagtacattc tggactctac cggaaaacat gtagcgtact  20040
tcgcgtggtg cgtaagctgt gacattcacc acaaaggaga cattctggat gtaacgtccg  20100
ttgtcattaa tcctgaggca gactctaagg gcttacagcg attcctagcg aaacgcttta  20160
agtaccttgc ggaactccac gattgcgatt gggtgtctcg ttgtaagcat gaaggcgaga  20220
caatgcgtgt atactttaag gaggtataag ttatgggtaa gaaagttaag aaggccgtga  20280
agaaagtcac caagtccgtt aagaaagtcg ttaaggaagg ggctcgtccg gttaaacagg  20340
ttgctggcgg tctagctggt ctggctggtg gtactggtga agcacagatg gtggaagtac  20400
cacaagctgc cgcacagatt gttgacgtac ctgagaaaga ggtttccact gaggacgaag  20460
cacagacaga aagcggacgc aagaaagctc gtgctggcgg taagaaatcc ttgagtgtag  20520
cccgtagctc cggtggcggt atcaacattt aatcaggagg ttatcgtgga agactgcatt  20580
gaatggaccg gaggtgtcaa ctctaagggt tatggtcgta agtgggttaa tggtaaactt  20640
```

-continued

```
gtgactccac ataggcacat ctatgaggag acatatggtc cagttccaac aggaattgtg  20700
gtgatgcata tctgcgataa ccctaggtgc tataacataa agcaccttac gcttggaact  20760
ccaaaggata attccgagga catggttacc aaaggtagac aggctaaagg agaggaacta  20820
agcaagaaac ttacagagtc agacgttctc gctatacgct cttcaacctt aagccaccgc  20880
tccttaggag aactgtatgg agtcagtcaa tcaaccataa cgcgaatact acagcgtaag  20940
acatggagac acatttaatg gctgagaaac gaacaggact tgcggaggat ggcgcaaagt  21000
ctgtctatga gcgtttaaag aacgaccgtg ctccctatga gacacgcgct cagaattgcg  21060
ctcaatatac catcccatca ttgttcccta aggactccga taacgcctct acagattatc  21120
aaactccgtg gcaagccgtg ggcgctcgtg gtctgaacaa tctagcctct aagctcatgc  21180
tggctctatt ccctatgcag acttggatgc gacttactat atctgaatat gaagcaaagc  21240
agttactgag cgaccccgat ggactcgcta aggtcgatga gggcctctcg atggtagagc  21300
gtatcatcat gaactacatt gagtctaaca gttaccgcgt gactctcttt gaggctctca  21360
aacagttagt cgtagctggt aacgtcctgc tgtacctacc ggaaccggaa gggtcaaact  21420
ataatcccat gaagctgtac cgattgtctt cttatgtggt ccaacgagac gcattcggca  21480
acgttctgca aatggtgact cgtgaccaga tagcttttgg tgctctccct gaggacatcc  21540
gtaaggctgt agaaggtcaa ggtggtgaga agaaagctga tgagacaatc gacgtgtaca  21600
ctcacatcta tctggatgag gactcaggtg aatacctccg atacgaagag gtcgagggta  21660
tggaagtcca aggctccgat gggacttatc ctaaagaggc ttgcccatac atcccgattc  21720
ggatggtcag actagatggt gaatcctacg gtcgttcgta cattgaggaa tacttaggtg  21780
acttacggtc ccttgaaaat ctccaagagg ctatcgtcaa gatgtccatg attagctcta  21840
aggttatcgg cttagtgaat cctgctggta tcacccagcc acgccgactg accaaagctc  21900
agactggtga cttcgttact ggtcgtccag aagacatctc gttcctccaa ctggagaagc  21960
aagcagactt tactgtagct aaagccgtaa gtgacgctat cgaggctcgc ctttcgtttg  22020
cctttatgtt gaactctgcg gttcagcgta caggtgaacg tgtgaccgcc gaagagattc  22080
ggtatgtagc ttctgaactt gaagatactt taggtggtgt ctactctatc ctttctcaag  22140
aattacaatt gcctctggta cgagtgctct tgaagcaact acaagccacg caacagattc  22200
ctgagttacc taaggaagcc gtagagccaa ccattagtac aggtctggaa gcaattggtc  22260
gaggacaaga ccttgataag ctggagcggt gtgtcactgc gtgggctgca ctggcaccta  22320
tgcgggacga ccctgatatt aaccttgcga tgattaagtt acgtattgcc aacgctatcg  22380
gtattgacac ttctggtatt ctactcaccg aagaacagaa gcaacagaag atggcccaac  22440
agtctatgca aatgggtatg gataatggtg ctgctgcgct ggctcaaggt atggctgcac  22500
aagctacagc ttcacctgag gctatggctg ctgccgctga ttccgtaggt ttacagccgg  22560
gaatttaata cgactcacta tagggagacc tcatctttga aatgagcgat gacaagaggt  22620
tggagtcctc ggtcttcctg tagttcaact ttaaggagac aataataatg gctgaatcta  22680
atgcagacgt atatgcatct tttggcgtga actccgctgt gatgtctggt ggttccgttg  22740
aggaacatga gcagaacatg ctggctcttg atgttgctgc ccgtgatggc gatgatgcaa  22800
tcgagttagc gtcagacgaa gtggaaacag aacgtgacct gtatgacaac tctgacccgt  22860
tcggtcaaga ggatgacgaa ggccgcattc aggttcgtat cggtgatggc tctgagccga  22920
ccgatgtgga cactggagaa gaaggcgttg agggcaccga aggttccgaa gagtttaccc  22980
cactgggcga gactccagaa gaactggtag ctgcctctga gcaacttggt gagcacgaag  23040
```

```
agggcttcca agagatgatt aacattgctg ctgagcgtgg catgagtgtc gagaccattg  23100
aggctatcca gcgtgagtac gaggagaacg aagagttgtc cgccgagtcc tacgctaagc  23160
tggctgaaat tggctacacg aaggctttca ttgactcgta tatccgtggt caagaagctc  23220
tggtggagca gtacgtaaac agtgtcattg agtacgctgg tggtcgtgaa cgttttgatg  23280
cactgtataa ccaccttgag acgcacaacc ctgaggctgc acagtcgctg gataatgcgt  23340
tgaccaatcg tgacttagcg accgttaagg ctatcatcaa cttggctggt gagtctcgcg  23400
ctaaggcgtt cggtcgtaag ccaactcgta gtgtgactaa tcgtgctatt ccggctaaac  23460
ctcaggctac caagcgtgaa ggctttgcgg accgtagcga gatgattaaa gctatgagtg  23520
accctcggta tcgcacagat gccaactatc gtcgtcaagt cgaacagaaa gtaatcgatt  23580
cgaacttctg atagacttcg aaattaatac gactcactat agggagacca caacggtttc  23640
cctctagaaa taattttgtt taactttaag aaggagatat acatatggag gagattcaac  23700
atggtcttca cactcgaaga tttcgttggg gactggcgac agacagccgg ctacaacctg  23760
gaccaagtcc ttgaacaggg aggtgtgtcc agtttgtttc agaatctcgg ggtgtccgta  23820
actccgatcc aaaggattgt cctgagcggt gaaaatgggc tgaagatcga catccatgtc  23880
atcatcccgt atgaaggtct gagcggcgac caaatgggcc agatcgaaaa aatttttaag  23940
gtggtgtacc ctgtggatga tcatcacttt aaggtgatcc tgcactatgg cacactggta  24000
atcgacgggg ttacgccgaa catgatcgac tatttcggac ggccgtatga aggcatcgcc  24060
gtgttcgacg gcaaaaagat cactgtaaca gggaccctgt ggaacggcaa caaaattatc  24120
gacgagcgcc tgatcaaccc cgacggctcc ctgctgttcc gagtaaccat caacggagtg  24180
accggctggc ggctgtgcga acgcattctg gcgtaaagga ggtaaacata tgaccatgat  24240
tacggattca ctggccgtcg ttttacaacg tcgtgactgg gaaaaccctg gcgttaccca  24300
acttaatcgc cttgcagcac atcccccttt cgccagctgg cgtaatagcg aagaggcccg  24360
caccgatcgc ccttcccaac agttgcgcag cctgaatggc gaatggcatg actggtggac  24420
agcaaatggg tactaaccaa ggtaaaggtg tagttgctgc tggagataaa ctggcgttgt  24480
tcttgaaggt atttggcggt gaagtcctga ctgcgttcgc tcgtacctcc gtgaccactt  24540
ctcgccacat ggtacgttcc atctccagcg gtaaatccgc tcagttccct gttctgggtc  24600
gcactcaggc agcgtatctg gctccgggcg agaacctcga cgataaacgt aaggacatca  24660
aacacaccga gaaggtaatc accattgacg gtctcctgac ggctgacgtt ctgatttatg  24720
atattgagga cgcgatgaac cactacgacg ttcgctctga gtatacctct cagttgggtg  24780
aatctctggc gatggctgcg gatggtgcgg ttctggctga gattgccggt ctgtgtaacg  24840
tggaaagcaa atataatgag aacatcgagg gcttaggtac tgctaccgta attgagacca  24900
ctcagaacaa ggccgcactt accgaccaag ttgcgctggg taaggagatt attgcggctc  24960
tgactaaggc tcgtgcggct ctgaccaaga actatgttcc ggctgctgac cgtgtgttct  25020
actgtgaccc agatagctac tctgcgattc tggcagcact gatgccgaac gcagcaaact  25080
acgctgctct gattgaccct gagaagggtt ctatccgcaa cgttatgggc tttgaggttg  25140
tagaagttcc gcacctcacc gctggtggtg ctggtaccgc tcgtgagggc actactggtc  25200
agaagcacgt cttccctgcc aataaaggtg agggtaatgt caaggttgct aaggacaacg  25260
ttatcggcct gttcatgcac cgctctgcgg taggtactgt taagctgcgt gacttggctc  25320
tggagcgcgc tcgccgtgct aacttccaag cggaccagat tatcgctaag tacgcaatgg  25380
```

-continued

```
gccacggtgg tcttcgccca gaagctgctg gtgcagtggt tttcaaagtg gagtaatgct  25440
gggggtggcc tcaacggtcg ctgctagtcc cgaagaggcg agtgttactt caacagaaga  25500
aaccttaacg ccagcacagg aggccgcacg cacccgcgct gctaacaaag cccgaaagga  25560
agctgagttg gctgctgcca ccgctgagca ataactagca taaccccttg gggcctctaa  25620
acgggtcttg aggggttttt tgctgaaagg aggaactata tgcgctcata cgatatgaac  25680
gttgagactg ccgctgagtt atcagctgtg aacgacattc tggcgtctat cggtgaacct  25740
ccggtatcaa cgctggaagg tgacgctaac gcagatgcag cgaacgctcg gcgtattctc  25800
aacaagatta accgacagat tcaatctcgt ggatggacgt tcaacattga ggaaggcata  25860
acgctactac ctgatgttta ctccaacctg attgtataca gtgacgacta tttatcccta  25920
atgtctactt ccggtcaatc catctacgtt aaccgaggtg gctatgtgta tgaccgaacg  25980
agtcaatcag accgctttga ctctggtatt actgtgaaca ttattcgtct ccgcgactac  26040
gatgagatgc ctgagtgctt ccgttactgg attgtcacca aggcttcccg tcagttcaac  26100
aaccgattct ttggggcacc ggaagtagag ggtgtactcc aagaagagga agatgaggct  26160
agacgtctct gcatggagta tgagatggac tacggtgggt acaatatgct ggatggagat  26220
gcgttcactt ctggtctact gactcgctaa cattaataaa taaggaggct ctaatggcac  26280
tcattagcca atcaatcaag aacttgaagg gtggtatcag ccaacagcct gacatccttc  26340
gttatccaga ccaagggtca cgccaagtta acggttggtc ttcggagacc gagggcctcc  26400
aaaagcgtcc acctcttgtt ttcttaaata cacttggaga caacggtgcg ttaggtcaag  26460
ctccgtacat ccacctgatt aaccgagatg agcacgaaca gtattacgct gtgttcactg  26520
gtagcggaat ccgagtgttc gacctttctg gtaacgagaa gcaagttagg tatcctaacg  26580
gttccaacta catcaagacc gctaatccac gtaacgacct gcgaatggtt actgtagcag  26640
actatacgtt catcgttaac cgtaacgttg ttgcacagaa gaacacaaag tctgtcaact  26700
taccgaatta caaccctaat caagacggat tgattaacgt tcgtggtggt cagtatggta  26760
gggaactaat tgtacacatt aacggtaaag acgttgcgaa gtataagata ccagatggta  26820
gtcaacctga acacgtaaac aatacggatg cccaatggtt agctgaagag ttagccaagc  26880
agatgcgcac taacttgtct gattggactg taaatgtagg gcaagggttc atccatgtga  26940
ccgcacctag tggtcaacag attgactcct tcacgactaa agatggctac gcagaccagt  27000
tgattaaccc tgtgacccac tacgctcagt cgttctctaa gctgccacct aatgctccta  27060
acggctacat ggtgaaaatc gtaggggacg cctctaagtc tgccgaccag tattacgttc  27120
ggtatgacgc tgagcggaaa gtttggactg agactttagg ttggaacact gaggaccaag  27180
ttctatggga aaccatgcca cacgctcttg tgcgagccgc tgacggtaat ttcgacttca  27240
agtggcttga gtggtctcct aagtcttgtg gtgacgttga caccaaccct tggccttctt  27300
ttgttggttc aagtattaac gatgtgttct tcttccgtaa ccgcttagga ttccttagtg  27360
gggagaacat catattgagt cgtacagcca aatacttcaa cttctaccct gcgtccattg  27420
cgaaccttag tgatgacgac cctatagacg tagctgtgag taccaaccga atagcaatcc  27480
ttaagtacgc cgttccgttc tcagaagagt tactcatctg gtccgatgaa gcacaattcg  27540
tcctgactgc ctcgggtact ctcacatcta agtcggttga gttgaaccta acgacccagt  27600
ttgacgtaca ggaccgagcg agaccttttg ggattgggcg taatgtctac tttgctagtc  27660
cgaggtccag cttcacgtcc atccacaggt actacgctgt gcaggatgtc agttccgtta  27720
agaatgctga ggacattaca tcacacgttc ctaactacat ccctaatggt gtgttcagta  27780
```

tttgcggaag tggtacggaa aacttctgtt cggtactatc tcacggggac cctagtaaaa 27840
tcttcatgta caaattcctg tacctgaacg aagagttaag gcaacagtcg tggtctcatt 27900
gggactttgg ggaaaacgta caggttctag cttgtcagag tatcagctca gatatgtatg 27960
tgattcttcg caatgagttc aatacgttcc tagctagaat ctctttcact aagaacgcca 28020
ttgacttaca gggagaaccc tatcgtgcct ttatggacat gaagattcga tacacgattc 28080
ctagtggaac atacaacgat gacacattca ctacctctat tcatattcca acaatttatg 28140
gtgcaaactt cgggaggggc aaaatcactg tattggagcc tgatggtaag ataaccgtgt 28200
ttgagcaacc tacggctggg tggaatagcg acccttggct gagactcagc ggtaacttgg 28260
agggacgcat ggtgtacatt gggttcaaca ttaacttcgt atatgagttc tctaagttcc 28320
tcatcaagca gactgccgac gacgggtcta cctccacgga agacattggg cgcttacagt 28380
tacgccgagc gtgggttaac tacgagaact ctggtacgtt tgacatttat gttgagaacc 28440
aatcgtctaa ctggaagtac acaatggctg gtgcccgatt aggctctaac actctgaggg 28500
ctgggagact gaacttaggg accggacaat atcgattccc tgtggttggt aacgccaagt 28560
tcaacactgt atacatcttg tcagatgaga ctacccctct gaacatcatt gggtgtggct 28620
gggaaggtaa ctacttacgg agaagttccg gtatttaatt aaatattctc cctgtggtgg 28680
ctcgaaatta atacgactca ctatagggag aacaatacga ctacgggagg gttttcttat 28740
gatgactata agacctacta aaagtacaga ctttgaggta ttcactccgg ctcaccatga 28800
cattcttgaa gctaaggctg ctggtattga gccgagtttc cctgatgctt ccgagtgtgt 28860
cacgttgagc ctctatgggt tccctctagc tatcggtggt aactgcgggg accagtgctg 28920
gttcgttacg agcgaccaag tgtggcgact tagtggaaag gctaagcgaa agttccgtaa 28980
gttaatcatg gagtatcgcg ataagatgct tgagaagtat gatactcttt ggaattacgt 29040
atgggtaggc aatacgtccc acattcgttt cctcaagact atcggtgcgg tattccatga 29100
agagtacaca cgagatggtc aatttcagtt atttacaatc acgaaaggag gataaccata 29160
tgtgttgggc agccgcaata cctatcgcta tatctggcgc tcaggctatc agtggtcaga 29220
acgctcaggc caaaatgatt gccgctcaga ccgctgctgg tcgtcgtcaa gctatggaaa 29280
tcatgaggca gacgaacatc cagaatgctg acctatcgtt gcaagctcga agtaaacttg 29340
aggaagcgtc cgccgagttg acctcacaga acatgcagaa ggtccaagct attgggtcta 29400
tccgagcggc tatcggagag agtatgcttg aaggttcctc aatggaccgc attaagcgag 29460
tcacagaagg acagttcatt cgggaagcca atatggtaac tgagaactat cgccgtgact 29520
accaagcaat cttcgcacag caacttggtg gtactcaaag tgctgcaagt cagattgacg 29580
aaatctataa gagcgaacag aaacagaaga gtaagctaca gatggttctg gacccactgg 29640
ctatcatggg gtcttccgct gcgagtgctt acgcatccgg tgcgttcgac tctaagtcca 29700
caactaaggc acctattgtt gccgctaaag gaaccaagac ggggaggtaa tgagctatga 29760
gtaaaattga atctgccctt caagcggcac aaccgggact ctctcggtta cgtggtggtg 29820
ctggaggtat gggctatcgt gcagcaacca ctcaggccga acagccaagg tcaagcctat 29880
tggacaccat tggtcggttc gctaaggctg gtgccgatat gtataccgct aaggaacaac 29940
gagcacgaga cctagctgat gaacgctcta acgagattat ccgtaagctg acccctgagc 30000
aacgtcgaga agctctcaac aacgggaccc ttctgtatca ggatgaccca tacgctatgg 30060
aagcactccg agtcaagact ggtcgtaacg ctgcgtatct tgtggacgat gacgttatgc 30120
agaagataaa agagggtgtc ttccgtactc gcgaagagat ggaagagtat cgccatagtc 30180
gccttcaaga gggcgctaag gtatacgctg agcagttcgg catcgaccct gaggacgttg 30240
attatcagcg tggtttcaac ggggacatta ccgagcgtaa catctcgctg tatggtgcgc 30300
atgataactt cttgagccag caagctcaga agggcgctat catgaacagc cgagtggaac 30360
tcaacggtgt ccttcaagac cctgatatgc tgcgtcgtcc agactctgct gacttctttg 30420
agaagtatat cgacaacggt ctggttactg gcgcaatccc atctgatgct caagccacac 30480
agcttataag ccaagcgttc agtgacgctt ctagccgtgc tggtggtgct gacttcctga 30540
tgcgagtcgg tgacaagaag gtaacactta acggagccac tacgacttac cgagagttga 30600
ttggtgagga acagtggaac gctctcatgg tcacagcaca acgttctcag tttgagactg 30660
acgcgaagct gaacgagcag tatcgcttga agattaactc tgcgctgaac caagaggacc 30720
caaggacagc ttgggagatg cttcaaggta tcaaggctga actagataag gtccaacctg 30780
atgagcagat gacaccacaa cgtgagtggc taatctccgc acaggaacaa gttcagaatc 30840
agatgaacgc atggacgaaa gctcaggcca aggctctgga cgattccatg aagtcaatga 30900
acaaacttga cgtaatcgac aagcaattcc agaagcgaat caacggtgag tgggtctcaa 30960
cggattttaa ggatatgcca gtcaacgaga acactggtga gttcaagcat agcgatatgg 31020
ttaactacgc caataagaag ctcgctgaga ttgacagtat ggacattcca gacggtgcca 31080
aggatgctat gaagttgaag taccttcaag cggactctaa ggacggagca ttccgtacag 31140
ccatcggaac catggtcact gacgctggtc aagagtggtc tgccgctgtg attaacggta 31200
agttaccaga acgaacccca gctatggatg ctctgcgcag aatccgcaat gctgaccctc 31260
agttgattgc tgcgctatac ccagaccaag ctgagctatt cctgacgatg gacatgatgg 31320
acaagcaggg tattgaccct caggttattc ttgatgccga ccgactgact gttaagcggt 31380
ccaaagagca acgctttgag gatgataaag cattcgagtc tgcactgaat gcatctaagg 31440
ctcctgagat tgcccgtatg ccagcgtcac tgcgcgaatc tgcacgtaag atttatgact 31500
ccgttaagta tcgctcgggg aacgaaagca tggctatgga gcagatgacc aagttcctta 31560
aggaatctac ctacacgttc actggtgatg atgttgacgg tgataccgtt ggtgtgattc 31620
ctaagaatat gatgcaggtt aactctgacc cgaaatcatg ggagcaaggt cgggatattc 31680
tggaggaagc acgtaaggga atcattgcga gcaacccttg gataaccaat aagcaactga 31740
ccatgtattc tcaaggtgac tccatttacc ttatggacac cacaggtcaa gtcagagtcc 31800
gatacgacaa agagttactc tcgaaggtct ggagtgagaa ccagaagaaa ctcgaagaga 31860
aagctcgtga gaaggctctg gctgatgtga acaagcgagc acctatagtt gccgctacga 31920
aggcccgtga agctgctgct aaacgagtcc gagagaaacg taaacagact cctaagttca 31980
tctacggacg taaggagtaa ctaaaggcta cataaggagg ccctaaatgg ataagtacga 32040
taagaacgta ccaagtgatt atgatggtct gttccaaaag gctgctgatg ccaacggggt 32100
ctcttatgac cttttacgta aagtcgcttg gacagaatca cgatttgtgc ctacagcaaa 32160
atctaagact ggaccattag gcatgatgca atttaccaag gcaaccgcta aggccctcgg 32220
tctgcgagtt accgatggtc cagacgacga ccgactgaac cctgagttag ctattaatgc 32280
tgccgctaag caacttgcag gtctggtagg gaagtttgat ggcgatgaac tcaaagctgc 32340
ccttgcgtac aaccaaggcg agggacgctt gggtaatcca caacttgagg cgtactctaa 32400
gggagacttc gcatcaatct ctgaggaggg acgtaactac atgcgtaacc ttctggatgt 32460
tgctaagtca cctatggctg gacagttgga aacttttggt ggcataaccc caaagggtaa 32520

```
aggcattccg gctgaggtag gattggctgg aattggtcac aagcagaaag taacacagga  32580
acttcctgag tccacaagtt ttgacgttaa gggtatcgaa caggaggcta cggcgaaacc  32640
attcgccaag gacttttggg agacccacgg agaaacactt gacgagtaca acagtcgttc  32700
aaccttcttc ggattcaaaa atgctgccga agctgaactc tccaactcag tcgctgggat  32760
ggctttccgt gctggtcgtc tcgataatgg ttttgatgtg tttaaagaca ccattacgcc  32820
gactcgctgg aactctcaca tctggactcc agaggagtta gagaagattc gaacagaggt  32880
taagaaccct gcgtacatca acgttgtaac tggtggttcc cctgagaacc tcgatgacct  32940
cattaaattg gctaacgaga actttgagaa tgactcccgc gctgccgagg ctggcctagg  33000
tgccaaactg agtgctggta ttattggtgc tggtgtggac ccgcttagct atgttcctat  33060
ggtcggtgtc actggtaagg gctttaagtt aatcaataag gctcttgtag ttggtgccga  33120
aagtgctgct ctgaacgttg catccgaagg tctccgtacc tccgtagctg gtggtgacgc  33180
agactatgcg ggtgctgcct taggtggctt tgtgtttggc gcaggcatgt ctgcaatcag  33240
tgacgctgta gctgctggac tgaaacgcag taaaccagaa gctgagttcg acaatgagtt  33300
catcggtcct atgatgcgat tggaagcccg tgagacagca cgaaacgcca actctgcgga  33360
cctctctcgg atgaacactg agaacatgaa gtttgaaggt gaacataatg gtgtccctta  33420
tgaggactta ccaacagaga gaggtgccgt ggtgttacat gatggctccg ttctaagtgc  33480
aagcaaccca atcaacccta agactctaaa agagttctcc gaggttgacc ctgagaaggc  33540
tgcgcgagga atcaaactgg ctgggttcac cgagattggc ttgaagacct tggggtctga  33600
cgatgctgac atccgtagag tggctatcga cctcgttcgc tctcctactg gtatgcagtc  33660
tggtgcctca ggtaagttcg gtgcaacagc ttctgacatc catgagagac ttcatggtac  33720
tgaccagcgt acttataatg acttgtacaa agcaatgtct gacgctatga aagaccctga  33780
gttctctact ggcggcgcta agatgtcccg tgaagaaact cgatacacta tctaccgtag  33840
agcggcacta gctattgagc gtccagaact acagaaggca ctcactccgt ctgagagaat  33900
cgttatggac atcattaagc gtcactttga caccaagcgt gaacttatgg aaaacccagc  33960
aatattcggt aacacaaagg ctgtgagtat cttccctgag agtcgccaca aaggtactta  34020
cgttcctcac gtatatgacc gtcatgccaa ggcgctgatg attcaacgct acggtgccga  34080
aggtttgcag gaagggattg cccgctcatg gatgaacagc tacgtctcca gacctgaggt  34140
caaggccaga gtcgatgaga tgcttaagga attacacggg gtgaaggaag taacaccaga  34200
gatggtagag aagtacgcta tggataaggc ttatggtatc tcccactcag accagttcac  34260
caacagttcc ataatagaag agaacattga gggcttagta ggtatcgaga ataactcatt  34320
ccttgaggca cgtaacttgt ttgattcgga cctatccatc actatgccag acggacagca  34380
attctcagtg aatgacctaa gggacttcga tatgttccgc atcatgccag cgtatgaccg  34440
ccgtgtcaat ggtgacatcg ccatcatggg gtctactggt aaaaccacta aggaacttaa  34500
ggatgagatt ttggctctca aagcgaaagc tgagggagac ggtaagaaga ctggcgaggt  34560
acatgcttta atggataccg ttaagattct tactggtcgt gctagacgca atcaggacac  34620
tgtgtgggaa acctcactgc gtgccatcaa tgacctaggg ttcttcgcta agaacgccta  34680
catgggtgct cagaacatta cggagattgc tgggatgatt gtcactggta acgttcgtgc  34740
tctagggcat ggtatcccaa ttctgcgtga tacactctac aagtctaaac cagtttcagc  34800
taaggaactc aaggaactcc atgcgtctct gttcgggaag gaggtggacc agttgattcg  34860
```

-continued

```
gcctaaacgt gctgacattg tgcagcgcct aagggaagca actgataccg gacctgccgt  34920
ggcgaacatc gtagggacct tgaagtattc aacacaggaa ctggctgctc gctctccgtg  34980
gactaagcta ctgaacggaa ccactaacta ccttctggat gctgcgcgtc aaggtatgct  35040
tggggatgtt attagtgcca ccctaacagg taagactacc cgctgggaga aagaaggctt  35100
ccttcgtggt gcctccgtaa ctcctgagca gatggctggc atcaagtctc tcatcaagga  35160
acatatggta cgcggtgagg acgggaagtt taccgttaag gacaagcaag cgttctctat  35220
ggacccacgg gctatggact tatggagact ggctgacaag gtagctgatg aggcaatgct  35280
gcgtccacat aaggtgtcct tacaggattc ccatgcgttc ggagcactag gtaagatggt  35340
tatgcagttt aagtctttca ctatcaagtc ccttaactct aagttcctgc gaaccttcta  35400
tgatggatac aagaacaacc gagcgattga cgctgcgctg agcatcatca cctctatggg  35460
tctcgctggt ggtttctatg ctatggctgc acacgtcaaa gcatacgctc tgcctaagga  35520
gaaacgtaag gagtacttgg agcgtgcact ggacccaacc atgattgccc acgctgcgtt  35580
atctcgtagt tctcaattgg gtgctccttt ggctatggtt gacctagttg gtggtgtttt  35640
agggttcgag tcctccaaga tggctcgctc tacgattcta cctaaggaca ccgtgaagga  35700
acgtgaccca aacaaaccgt acacctctag agaggtaatg ggcgctatgg gttcaaacct  35760
tctggaacag atgccttcgg ctggctttgt ggctaacgta ggggctacct taatgaatgc  35820
tgctggcgtg gtcaactcac ctaataaagc aaccgagcag gacttcatga ctggtcttat  35880
gaactccaca aaagagttag taccgaacga cccattgact caacagcttg tgttgaagat  35940
ttatgaggcg aacggtgtta acttgaggga gcgtaggaaa taatacgact cactataggg  36000
agaggcgaaa taatcttctc cctgtagtct cttagattta ctttaaggag gtcaaatggc  36060
taacgtaatt aaaaccgttt tgacttacca gttagatggc tccaatcgtg attttaatat  36120
cccgtttgag tatctagccc gtaagttcgt agtggtaact cttattggtg tagaccgaaa  36180
ggtccttacg attaatacag actatcgctt tgctacacgt actactatct ctctgacaaa  36240
ggcttggggt ccagccgatg gctacacgac catcgagtta cgtcgagtaa cctccactac  36300
cgaccgattg gttgacttta cggatggttc aatcctccgc gcgtatgacc ttaacgtcgc  36360
tcagattcaa acgatgcacg tagcggaaga ggcccgtgac ctcactacgg atactatcgg  36420
tgtcaataac gatggtcact tggatgctcg tggtcgtcga attgtgaacc tagcgaacgc  36480
cgtggatgac cgcgatgctg ttccgtttgg tcaactaaag accatgaacc agaactcatg  36540
gcaagcacgt aatgaagcct tacagttccg taatgaggct gagactttca gaaaccaagc  36600
ggagggcttt aagaacgagt ccagtaccaa cgctacgaac acaaagcagt ggcgcgatga  36660
gaccaagggt ttccgagacg aagccaagcg gttcaagaat acggctggtc aatacgctac  36720
atctgctggg aactctgctt ccgctgcgca tcaatctgag gtaaacgctg agaactctgc  36780
cacagcatcc gctaactctg ctcatttggc agaacagcaa gcagaccgtg cggaacgtga  36840
ggcagacaag ctggaaaatt acaatggatt ggctggtgca attgataagg tagatggaac  36900
caatgtgtac tggaaaggaa atattcacgc taacgggcgc ctttacatga ccacaaacgg  36960
ttttgactgt ggccagtatc aacagttctt tggtggtgtc actaatcgtt actctgtcat  37020
ggagtgggga gatgagaacg gatggctgat gtatgttcaa cgtagagagt ggacaacagc  37080
gataggcggt aacatccagt tagtagtaaa cggacagatc atcacccaag gtggagccat  37140
gaccggtcag ctaaaattgc agaatgggca tgttcttcaa ttagagtccg catccgacaa  37200
ggcgcactat attctatcta aagatggtaa caggaataac tggtacattg gtagagggtc  37260
```

```
agataacaac aatgactgta ccttccactc ctatgtacat ggtacgacct taacactcaa  37320
gcaggactat gcagtagtta acaaacactt ccacgtaggt caggccgttg tggccactga  37380
tggtaatatt caaggtacta agtggggagg taaatggctg gatgcttacc tacgtgacag  37440
cttcgttgcg aagtccaagg cgtggactca ggtgtggtct ggtagtgctg gcggtggggt  37500
aagtgtgact gtttcacagg atctccgctt ccgcaatatc tggattaagt gtgccaacaa  37560
ctcttggaac ttcttccgta ctggccccga tggaatctac ttcatagcct ctgatggtgg  37620
atggttacga ttccaaatac actccaacgg tctcggattc aagaatattg cagacagtcg  37680
ttcagtacct aatgcaatca tggtggagaa cgagtaattg gtaaatcaca aggaaagacg  37740
tgtagtccac ggatggactc tcaaggaggt acaaggtgct atcattagac tttaacaacg  37800
aattgattaa ggctgctcca attgttggga cgggtgtagc agatgttagt gctcgactgt  37860
tctttgggtt aagccttaac gaatggttct acgttgctgc tatcgcctac acagtggttc  37920
agattggtgc caaggtagtc gataagatga ttgactggaa gaaagccaat aaggagtgat  37980
atgtatggaa aaggataaga gccttattac attcttagag atgttggaca ctgcgatggc  38040
tcagcgtatg cttgcggacc tttcggacca tgagcgtcgc tctccgcaac tctataatgc  38100
tattaacaaa ctgttagacc gccacaagtt ccagattggt aagttgcagc cggatgttca  38160
catcttaggt ggccttgctg gtgctcttga agagtacaaa gagaaagtcg gtgataacgg  38220
tcttacggat gatgatattt acacattaca gtgatatact caaggccact acagatagtg  38280
gtctttatgg atgtcattgt ctatacgaga tgctcctacg tgaaatctga aagttaacgg  38340
gaggcattat gctagaattt ttacgtaagc taatcccttg ggttctcgct gggatgctat  38400
tcgggttagg atggcatcta gggtcagact caatggacgc taaatggaaa caggaggtac  38460
acaatgagta cgttaagaga gttgaggctg cgaagagcac tcaaagagca atcgatgcgg  38520
tatctgctaa gtatcaagaa gaccttgccg cgctggaagg gagcactgat aggattattt  38580
ctgatttgcg tagcgacaat aagcggttgc gcgtcagagt caaaactacc ggaacctccg  38640
atggtcagtg tggattcgag cctgatggtc gagccgaact tgacgaccga gatgctaaac  38700
gtattctcgc agtgacccag aagggtgacg catggattcg tgcgttacag gatactattc  38760
gtgaactgca acgtaagtag gaaatcaagt aaggaggcaa tgtgtctact caatccaatc  38820
gtaatgcgct cgtagtggcg caactgaaag gagacttcgt ggcgttccta ttcgtcttat  38880
ggaaggcgct aaacctaccg gtgcccacta agtgtcagat tgacatggct aaggtgctgg  38940
cgaatggaga caacaagaag ttcatcttac aggctttccg tggtatcggt aagtcgttca  39000
tcacatgtgc gttcgttgtg tggtccttat ggagagaccc tcagttgaag atacttatcg  39060
tatcagcctc taaggagcgt gcagacgcta actccatctt tattaagaac atcattgacc  39120
tgctgccatt cctatctgag ttaaagccaa gacccggaca gcgtgactcg gtaatcagct  39180
ttgatgtagg cccagccaat cctgaccact ctcctagtgt gaaatcagta ggtatcactg  39240
gtcagttaac tggtagccgt gctgacatta tcattgcgga tgacgttgag attccgtcta  39300
acagcgcaac tatgggtgcc cgtgagaagc tatggactct ggttcaggag ttcgctgcgt  39360
tacttaaacc gctgccttcc tctcgcgtta tctaccttgg tacacctcag acagagatga  39420
ctctctataa ggaacttgag gataaccgtg ggtacacaac cattatctgg cctgctctgt  39480
acccaaggac acgtgaagag aacctctatt actcacagcg tcttgctcct atgttacgcg  39540
ctgagtacga tgagaaccct gaggcacttg ctgggactcc aacagaccca gtgcgctttg  39600
```

accgtgatga cctgcgcgag cgtgagttgg aatacggtaa ggctggcttt acgctacagt 39660
tcatgcttaa ccctaacctt agtgatgccg agaagtaccc gctgaggctt cgtgacgcta 39720
tcgtagcggc cttagactta gagaaggccc caatgcatta ccagtggctt ccgaaccgtc 39780
agaacatcat tgaggacctt cctaacgttg gccttaaggg tgatgacctg catacgtacc 39840
acgattgttc caacaactca ggtcagtacc aacagaagat tctggtcatt gaccctagtg 39900
gtcgcggtaa ggacgaaaca ggttacgctg tgctgtacac actgaacggt tacatctacc 39960
ttatggaagc tggaggtttc cgtgatggct actccgataa gacccttgag ttactcgcta 40020
agaaggcaaa gcaatgggga gtccagacgg ttgtctacga gagtaacttc ggtgacggta 40080
tgttcggtaa ggtattcagt cctatccttc ttaaacacca caactgtgcg atggaagaga 40140
ttcgtgcccg tggtatgaaa gagatgcgta tttgcgatac ccttgagcca gtcatgcaga 40200
ctcaccgcct tgtaattcgt gatgaggtca ttagggccga ctaccagtcc gctcgtgacg 40260
tagacggtaa gcatgacgtt aagtactcgt tgttctacca gatgacccgt atcactcgtg 40320
agaaaggcgc tctggctcat gatgaccgat tggatgccct tgcgttaggc attgagtatc 40380
tccgtgagtc catgcagttg gattccgtta aggtcgaggg tgaagtactt gctgacttcc 40440
ttgaggaaca catgatgcgt cctacggttg ctgctacgca tatcattgag atgtctgtgg 40500
gaggagttga tgtgtactct gaggacgatg agggttacgg tacgtctttc attgagtggt 40560
gatttatgca ttaggactgc atagggatgc actatagacc acggatggtc agttctttaa 40620
gttactgaaa agacacgata aattaatacg actcactata gggagaggag ggacgaaagg 40680
ttactatata gatactgaat gaatacttat agagtgcata aagtatgcat aatggtgtac 40740
ctagagtgac ctctaagaat ggtgattata ttgtattagt atcaccttaa cttaaggacc 40800
aacataaagg gaggagactc atgttccgct tattgttgaa cctactgcgg catagagtca 40860
cctaccgatt tcttgtggta ctttgtgctg cccttgggta cgcatctctt actggagacc 40920
tcagttcact ggagtctgtc gtttgctcta tactcacttg tagcgattag ggtcttcctg 40980
accgactgat ggctcaccga gggattcagc ggtatgattg catcacacca cttcatccct 41040
atagagtcaa gtcctaaggt atacccataa agagcctcta atggtctatc ctaaggtcta 41100
tacctaaaga taggccatcc tatcagtgtc acctaaagag ggtcttagag agggcctatg 41160
gagttcctat agggtccttt aaaatatacc ataaaaatct gagtgactat ctcacagtgt 41220
acggacctaa agttccccca tagggggtac ctaaagccca gccaatcacc taaagtcaac 41280
cttcggttga ccttgagggt tccctaaggg ttggggatga cccttgggtt tgtctttggg 41340
tgttaccttg agtgtctctc tgtgtccct 41369

<210> SEQ ID NO 3
<211> LENGTH: 1044
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
caacgtcgtg ccatgaagaa accttctgca tcttctgcgt aaagaggaga tatacaatgg 60
tcttcacact cgaagatttc gttggggact ggcgacagac agccggctac aacctggacc 120
aagtccttga acagggaggt gtgtccagtt tgtttcagaa tctcggggtg tccgtaactc 180
cgatccaaag gattgtcctg agcggtgaaa atgggctgaa gatcgacatc catgtcatca 240

-continued

```
tcccgtatga aggtctgagc ggcgaccaaa tgggccagat cgaaaaaatt tttaaggtgg    300

tgtaccctgt ggatgatcat cactttaagg tgatcctgca ctatggcaca ctggtaatcg    360

acggggttac gccgaacatg atcgactatt tcggacggcc gtatgaaggc atcgccgtgt    420

tcgacggcaa aaagatcact gtaacaggga ccctgtggaa cggcaacaaa attatcgacg    480

agcgcctgat caaccccgac ggctccctgc tgttccgagt aaccatcaac ggagtgaccg    540

gctggcggct gtgcgaacgc attctggcgt aagcaggtta atatcttagt ataaacaagg    600

gcagacttag gtttgtcctt agtgtattcc aaaggaggta acatgctgaa agatggttgg    660

gtttcatatg accctacaga ccctaagaat tggctacagg ttatcgctat agcttgtgca    720

ggtagcctat tggctgccct gatgtattca ttatggatgt acacaaagta accaaagtca    780

aaattttgat gtaggcgtgt gtcagctctc tcgccctcgc cctcgccggg ttgtccccat    840

agggtggcct gagggaatcc gtcttcgacg ggcagggctg atgtactcct tgtctagtac    900

aagggaggcg gagggaacgc ctagggaggc ctaggaatgg cttagtggtg gacaaggtga    960

ttaccttagt gaagcctctt agtgcattcc tgaggccatt cagggcgttt atgagggatt   1020

gacagggtgt gagggcgtgg gcta                                          1044
```

```
<210> SEQ ID NO 4
<211> LENGTH: 44915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

tcgccctcgc cctcgccggg ttgtccccat agggtggcct gagggaatcc gtcttcgacg     60

ggcagggctg atgtactcct tgtctagtac aagggaggcg gagggaacgc ctagggaggc    120

ctaggaatgg cttagtggtg gacaaggtga ttaccttagt gaagcctctt agtgcattcc    180

tgaggccatt cagggcgttt atgagggatt gacagggtgt gagggcgtgg gctatctgtt    240

cctttgctcc tcacttcgtt cgtcgctgcg gtagcctgat gtgtacctta ggttattcct    300

tgatggatag cttaggttag ccttagtgga ttaccttagt taaagcctta gtgcttcact    360

tagtatcagc ttagtagtgt accttagtaa gtcttagtgt cttctcttag tgattgcaca    420

tgcaagcatg taagatgcta ataggtcgcg gtcggcagac cgctaaagaa agagaatggt    480

aataagatgc agtaggagga acaccagaag cctagccaac ctaagctatc ctagctctat    540

atctattgct tttccttagt ctaacacgtt agacaaccta tcttattctt agtgatggta    600

acttagtgtt gacaagataa tcttagtgta atactatgca tcacgtaggc ggtgctgagg    660

cacctagtag ccagctagta aggcatacga agagactagc gcttacattg ctctttaaca    720

atttgcttag tgtaacctat gtatgccgtg gttaactact tattgaatga ggtattaact    780

atgacattaa ataaccgtga actgtccgtt ctcttcactc tgttgtgcta catgattcgt    840

aacaacgaat tacttacaga tgatgagtta gccttgtatc accgctttct taacgaaggt    900

tggaccgata cagttaatca ataccgtaac atgatagatg agttgaggga gggtaaataa    960

tgtatcaaca tgaggtattc tttgaatcag ctagcgaagc tattcgcttc cgtgatgata   1020

tgatgcaagc tggtgtaggc gttgatgtgt atcactattt gatagattac gacactgaat   1080

atcaccgagt taccttagta tctgagtatg acaaccaagt cattactgag tatctaggca   1140

gtgaagatta cgattacgat gaagtaatca cgacaaatct ctaaattaac tgttgacagc   1200
```

-continued

```
cacggcatac aaggttacat taagcatcaa gacggcgacg tctttaaaca tcccgctctt   1260
taacaatacg gtttgtgtct tgataggcta actaactaac taaggtaatt atcatgaaag   1320
ggttaatttg tgtagaacgt atggtcaatg gtaaacttga aatattacca ctggaaaacc   1380
aatctagctt caaagagtgg tatggctgtt tctcactgat ttaaggtaaa ggctggcact   1440
agtcagccta tcaaggcgca aaccaagctc tttaacaatt tggatggtag cttcttagtc   1500
tggataggtt aaacctagga gattctcttg agtctcctat aatgtaacct aactaactaa   1560
atgaggatta aatcatggaa cgcaatgcta acgcttacta caaccttctg gctgcaactg   1620
ttgaagcatt caacgagcgt attcagtttg atgagattcg cgaaggtgat gattactctg   1680
atgcactaca tgaggttgta gacagcaatg ttccagttta ttacagcgaa atctttacag   1740
tgatggctgc tgatggtatt gatgttgatt ttgaggatgc tggtttgatt cctgacacga   1800
aggatgtaac caagattcta caagctcgca tctatgaagc tctttataat gatgtaccaa   1860
atgacagcga tgtagtttgg tgtgaaggcg aagaagagga agaataagga tggaaaagca   1920
atataacttt atcttttcag acggtgtaac cctgaagtgt tccctacgat tcgcacaaat   1980
tcgtgaggaa gtactaggca ctacatacaa actatttagc tgacactata agagaaggct   2040
taacaaggcg ttactaaggt agcgcctgat taaactttca cttactagga gttgagatta   2100
tgaaaacctt gattggatgc ttcttgttgg cttctcttgc tctggcattt accgctaaag   2160
ctggttatga cgcttataaa gtagaacaag cccagcaaga ctgggccaaa aaaaagttca   2220
acttgtgcag caagagcaac acctacgagt actgcaacaa aacactaaga cacttatgga   2280
aagagtaact agcctatagc ccacctgagt gggctatgtg atatttactt aacactatat   2340
aaggtgatta ctatgactac tgaaaacacc ctcgtgtctg tccgtgaagc tgcaaccgct   2400
gaaatcaagc aacatttaga caatatcggc acttcttaca tcaaagtagg ggcttgtctg   2460
aatgagttac gcggagactt tgaaggtcaa aaagagtttt tagcctatgt tgaagcagag   2520
tttgccatta agaaggcaca atgttacaag ctgatgagtg tagcccgtgt ctttgaaggc   2580
gatgatcgct ttaaaggcgt ggcgatgcgt gtaatgctgg cgcttgttcc tttcgctgat   2640
gaaaatataa tcatggagaa ggccgcagaa ctcgccgcaa atggcaagct ggacactaat   2700
gccgtaaacg ccctgattga acctaagaaa gagtcaaagg ccgaaacggt acaatctaag   2760
gctgagacag taaaaccgca ggagaacgcg actgagtccg cagaatcaca tgaaatgcaa   2820
gcgccgcagg tagtgccacc cgcgagcgag caggagtccg acgaatcagc accttgggaa   2880
gaggaaagca aaccggaagc gccaaaggca gctccgatgg ataacacggc taatactgag   2940
aatgccgcta ttgctggtct gctggcacaa attaaagcac tgactgagca attacaggca   3000
gccaatgacc gcatcgcctc cttaagtagc gcacgcgaaa gcaagaaggc atccgcacct   3060
atgctgccgc agttcaaatc ttcctgcttc tacgctcgct taggcttgag cgcggaggag   3120
gcaacgaaga aaacagcagt taacaaggca cgccgcgaac tggttaagct gggatacggt   3180
gaaggccatg aggcatggcc cttaatctct gaggcagtag aagagttgac taagtaacct   3240
tatcggtggc atcttcttag gtgtcaccta ttaaggtttc tttcactagg agtaaacaag   3300
atgcaaggcc tacacgctat tcaacttcaa cttgaagaag aaatgtttaa cggcggtatc   3360
cgtcgctttg aagcggacca acaacgccag attgcatccg gtaatgaatc agacacggca   3420
tggaatcgcc gcttattgtc cgagttaatc gcgccaatgg ctgaaggtat tcaggcatac   3480
aaggaagagt atgaaggtaa aagaggccgt gcaccgcgtg cattagcttt cattaactgc   3540
gtagaaaacg aagtggcagc atatatcacg atgaaaatcg ttatggatat gctgaacacg   3600
```

-continued gatgtaacct tgcaggctat agccatgaat gtagctgacc gcattgagga ccaagtacgt 3660
tttagcaagc tggaaggtca cgccgccaaa tactttgaaa aagttaagaa gtcacttaag 3720
gcaagtaaga ctaaatcata tcgccatgcg cacaacgtag cggtagtggc tgagaagtca 3780
gtagctgacc gtgacgctga tttctcccgc tgggaggcat ggcctaaaga caccttgctg 3840
caaattggga tgaccttgct tgaaatctta gagaatagcg tattcttcaa cgggcaacct 3900
gtcttcctcc gcaccttgcg cactaatggc ggcaaacatg gtgtttacta cctacagact 3960
agtgaacacg taggtgagtg gataactgca ttcaaagagc acgtagcgca actgagtcct 4020
gcctatgctc cttgcgtcat ccctccgcgt ccgtgggtat caccttttaa cggcggtttc 4080
cacactgaga aagtagcaag ccgtattcgt ctggtaaaag gaaaccgcga acacgtccgc 4140
aagctgacca aaaagcaaat gccagaggtt tacaaggctg ttaacgcgtt gcaggcgact 4200
aaatggcagg ttaacaagga agttttacag gttgtggaag acgtcatccg tctagaccta 4260
ggttatggtg taccttcctt taaaccactc attgaccgcg agaacaagcc agctaatcca 4320
gtgccgctag aatttcagca cctacggggc cgtgaactga aagaaatgct tacgccggaa 4380
caatggcaag cctttatcaa ctggaaaggt gaatgtacta agctgtacac cgctgaaact 4440
aagcgcggaa gcaaatcggc ggcaaccgtt cgcatggttg gtcaggcccg taaatatagc 4500
cagttcgacg caatctactt cgtgtatgca ctggacagcc gcagccgcgt ctacgcgcaa 4560
tctagcacac tctcaccgca atcaaatgac ttgggcaagg ccttgctccg ttttaccgaa 4620
gggcagcgtc ttgatagcgc tgaggcgctt aagtggtttt tggtgaacgg ggctaataac 4680
tggggttggg ataagaaaac ttttgacgtg cgcaccgcta acgtgctgga tagtgaattt 4740
caagacatgt gccgcgacat tgcagcggat ccgctgacct tcactcaatg ggtaaatgcc 4800
gactcccctt acggcttcct tgcatggtgc tttgaatatg cgcgttatct ggatgcactg 4860
gatgaaggca cgcaagacca attcatgacg cacctcccag tccatcaaga tggtagttgt 4920
tctggtatcc agcactacag tgctatgcta cgcgatgcag taggtgcgaa agcagtaaac 4980
cttaagccct ctgactctcc tcaagatatt tatggtgccg ttgcgcaggt agtaattcag 5040
aagaattatg catacatgaa tgcagaggat gcggaaacct tcacttctgg cagcgtgact 5100
ttaacaggtg cggagctgcg tagtatggct agtgcgtggg atatgatagg aatcactcgc 5160
ggcctgacca aaaagcccgt aatgacacta ccttatggca gcacacgtct aacctgccgt 5220
gagtcagtga ttgattatat cgttgattta gaagaaaaag aggcccaacg ggctattgcg 5280
gaagggcgta ccgccaatcc tgtacaccct tttgataatg accgtaaaga cagcctgaca 5340
cctagcgcag cttataacta tatgacagct ttaatctggc cttctatttc ggaagtggtt 5400
aaagccccta tagtggcaat gaaaatgatt cgtcagcttg cccgtttcgc agctaaaagg 5460
aatgaaggct tagagtatac cctgcctact ggcttcatct tgcaacaaaa gattatggct 5520
actgatatgc tccgcgtatc tacttgcttg atgggagaaa tcaagatgag tctacagatt 5580
gaaacagacg tagtggatga aacggcaatg atgggcgctg ctgctcctaa ctttgtgcat 5640
ggtcatgatg ccagccacct tatcttaaca gtctgcgacc ttgttgataa agggattaca 5700
tctatcgcag ttattcatga ctcttttggc actcatgcag gccgtacagc cgaccttcgt 5760
gatagcttaa gggcagaaat ggtgaagatg tatcaaggcc gtaatgcact gcaaagcctg 5820
ctagatgagc acgaagaacg ctggttagtt gataccggaa tacaagtacc agagcaaggg 5880
gagtttgacc ttaacgaaat cttagtttca gactattgct tcgcataata ttaataggcc 5940

-continued attccttcgg gagtggcctt tcttttacct actacctgta acatttcatt aacataaaag 6000
tgtctcacat gtgagactta tttaccggac actataggat agccgtcgga gacgggaaag 6060
aaagggaaga taaaggatat aaaggaagta ataggtatta aaggttatat aggttatcta 6120
ggaataccta ttaccttctt ccttcctctt attaccactc agaggaaggg cagacctagg 6180
ttgtctcaca tgtgagactt cgtatttacc ggacagtata gataagatta actcactttg 6240
gagatttaac catgcgcaac tttgagaaga tggcccgtaa agctaaccgt tttgacatgg 6300
aagaggggca gaagaaaggc aagaagctga ataagcctgt ccgtgaccgt gcatctaaac 6360
gcgctgcgtg ggagttctaa gttatggcta ttattcagaa tgtaccgtgt cctgcctgtc 6420
aaaagaatgg acatgatatt actggcaacc atctcatgat atttgatgat ggtgccggct 6480
actgtaatcg tggacacttt catgataatg gtagacctta ctatcacaag ccggaaggtg 6540
gcatcgagat aaccgagtta tctattactg gcaatatcaa atatacacct tctcaattca 6600
aagaaatgga gaaggaaggg aagataagcg accctaaatt acgtgccatc gcacttggtg 6660
gtatgcgtat gaaagaccgt tgggaggtca tgaatgaaca agaaagggca gagcaagaag 6720
cagagtggaa acttgatgtt gaatggttcc tcacgcttaa gcgtaagaac cttgtttcca 6780
ggcacattcg cggcgacatt tgcgcattgt atgatgtacg tgttgggcac gatgaagagg 6840
gtagagtctc acggcattac tatccgcgct tcgaaaaagg tgagctagta ggcgctaagt 6900
gtcgcacatt acctaaagat tttaagtttg gtcatttagg taaactcttt ggtatgcaag 6960
atcttttcgg tatgaatact ttgtctcacg tgttagacaa gggaagacga aaggattgct 7020
tgctcattgt cggcggcgaa ctggatgcac tagcagcgca gcagatgctc cttgattctg 7080
ccaagggtac taagtgggaa ggccagccat accatgtatg gtctgtcaac aaaggcgagt 7140
cttgccttga agagatagtg cagaaccgtg agcatatcgc ccaattcaag aagattatat 7200
ggggttttga tggagatgag gtagggcaga agcagaatca gcaagcggct cgcctgtttc 7260
ctggtaaatc ctatatcctt gaatacccct ctggttgcaa agatgctaac aaggcattga 7320
tggctggcaa ggctaaagaa tttgtagatg catggtttaa tgccaagtca tctgatgaag 7380
tctttggtag ccagattaaa tctatcgcat ctcaaaggga taagctcaag gctgcacgtc 7440
cagagcaagg actgtcatgg ccttggccta agctgaacaa ggtaacgcta ggtattcgta 7500
agaaccagct tatcattgta ggtgcagggt ctggtgtagg taagactgag ttccttcgtg 7560
aagtagttaa gcacctcatt gaagaacacg gtgaatctgt aggcatcatt tctacagaag 7620
acccgatggt caaggtgtcc cgtgctttta tcggcaagtg gattgataag cgtattgagt 7680
tacctccaac caacgacccg aaagaagacg gataccgtga ggtgttcgac tataccgagg 7740
aagaagctaa cgccgccatt gattatgtag ctgatacagg taagctgttt gtagctgacc 7800
tagagggtga ctattcgatg gaaaaggtag agcaaacttg cctagagttt gaggctatgg 7860
gtatttctaa tatcatcatt gataacttaa cggggattaa attagatgag cgtgcttttg 7920
gtgggaaggt tggtgcactt gatgaatgcg tcaagcggat tggtactatc aaagaccgac 7980
acccggttac tatattcctt gtatcacacc ttacacgtcc tccggcaaac cgtacccaac 8040
acgaagaagg tggcgaagtt atcctttctg acttccgagg ctcaggcgct atcggattct 8100
gggcatctta cgccttgggg attgagcgta atacaagagc tgaaacgctt gacgaaagga 8160
ctaccacgta catctcatgt gtcaaagacc gcgaccaagg tatctacact ggaaccaagg 8220
tcatgcttaa gggtgacatt caaaccggac gtttaatgga accacaagcc cgtactaagt 8280
catttgatac aggtgaagca aggcaacaag aagtaccaga tttaccggat actatagaag 8340

-continued

```
agactacctt cgatgaagaa agtgagttct gattagtgta tttatcaggc ttgtctcaca   8400
tgtgagacag gctcttatta agtacattaa ataactggag attgattatg tataacttag   8460
tgttgaatgt aggtgacttt gtacgcaaca tcaagaaaga ttcaagtcgc tatctttgcc   8520
gtggtgttgt aacctttgta ggtgagaacc tgtattatgt agaatatcgc agtggtgtta   8580
agcaatatta ccacaagaag acagcacata aatatcttga aaagattgta gagataaaca   8640
atcaatgtaa gtgcatacat gatgaggttt gcgataaatg tgctcgccag atgcttaaga   8700
atttcctagc tcctctttat tatggtgctg gtcctcaaac actagcagag tgcatggcag   8760
aaaagaaaac cacactcaag aaagagcgtc gcaatgtaat cactggtaag actcaaagtg   8820
agatgattaa gcaatgtggc actgcattag gtgttacaca gtttaatact cgtgcattgg   8880
gtaaatccac aggacaagct atggtaaaga ttggagaagc catgatgcat ccaaatgtac   8940
ctgtgcgaat catggatgtt gaccatgcaa tcacagaaca aggtacgcaa cgacgtgtaa   9000
ttaataagca ttttgccgac actatagaag gcattattcg taagcaaggg ttgaaaggtc   9060
ttcacatctt aaatggtgaa gaattactgt acctacctat cgttactgaa gaaacatacg   9120
tgaatatcta aggagttaat catgactaag gtattaattt atatgcgtgg acctcataaa   9180
tgctatgcag ttgtagcacc aaatggtgtt aagccttatc gtacttcaaa aagattggca   9240
ttaataggtg ctagtagtag tgcaagtttc caaatggaac tttttggtca ttggactgaa   9300
aggcaattcc gtgaggattt taaagtcatt ggcagcttca tggtgaaata tgcagaataa   9360
acatagtctt agaatgttcg atggtcatga aaacctgcaa gccaagatta ctaaccaagc   9420
cttcctgttc gcacagttaa ctatggctga ggctaagaag aatagtctca ctcgtgaaca   9480
ggttatcaag gaggccactt gggaaccaca ccaaggtaaa tatatgggcc acaaattaac   9540
tgtaacacgc agtcgataag tcaagggttg tccaacgtgt tggacagcct ttcatcatat   9600
tgattgggag gtattaaatg actaagttta ctatgcaaga cctcattaaa ttacgtgatg   9660
aaatagaatc accggaagtt aatacagagt ttcactacat tgatccacga gataaacgag   9720
agattcctga ttatcagatt gagacggagt taatgtatga agattattga ttggaagaag   9780
gaagcagaag gccgtatcct agtgatggat gcggaggcta aaggcctgct gggtgctatc   9840
cgctacggtc atcgtgaaga tgtacacatt atttgctgca tggacttgct caccactgag   9900
gagttcctct tcttcgaccc atatgagatg cgtgaccctg aagcaaggga acacttgaaa   9960
gagtgggaag gccatcaaga tggaccttg gttgatggtg ttaacttcct aaagcactgt  10020
gaagccatcg tctcacagaa cttcctaggc tatgacgggc ttctctttga gaaagccttc  10080
cctgacatct ggaagggatt taactacacc gagaggcgcg gcaagggcag actacgtgct  10140
gacttgtgtc cggtacgcgt catggatacg ctggtcatga gtcgcctgtt aaacccagat  10200
agacgccttc ctccgcaagc atatgccaaa ggtatgggta acgttgcccc tcactcaatt  10260
gaggcgcacg gcattcgtat aggccgttat aagccggaga acgaggattg gtctaaacta  10320
actgaccaca tggtacatcg tgtacgcgag gacgtggcga taggccgtga cctattcctc  10380
tggctattta acggagaatg gacggagcac aaacgccgtg gcgtgaataa acgcactggc  10440
ctaggtattg agacagcctt ccacatggag tccattgtga cgctggagat gagccgtcag  10500
gccgagcgtg gattccgtct ggatatagat aaagcattag cacgatgcga ggaattggac  10560
gctaagattg atgagacagt cgcagcgttc cgtccgcaca tgcctatgcg tatcaagtct  10620
aaacctttta aaccggaaga aaagaatgaa gtatgccaac gcgcaaatga gtatggagct  10680
```

agcaacaata tacctactgt ccttgacccc tctcactttc ttcacgcaga gagacgagga 10740
gatcgcaaga cagtatggag tgtcactact aagtctggtg attggtcggc tagcgtcaag 10800
aaagactttc ctcaccttag aggaaaccgt aatgacacgc caagtgtcaa gtggattggc 10860
gcttactcgc ctgttacttt cgaagagatt cccttgggta acagggatac agttaagcaa 10920
gtgctctatg attatggatg gaaaggtgtt gaatttaacg ataccgagca agcgcatctc 10980
gatgagcatg gcgtattacc caagccttgg agtgggaaga taaatgaaaa gtcccttact 11040
ttatggcaag agagagccgc acgtgaaggt aaaacagtcc ctgattggtg cttgggtatc 11100
gctgcatggt acatactcgt atcccgtcgt ggtcagatcc tcaaccgtgg tgacgttgaa 11160
gccttcgacc agaagggggt gtggccttcg caagctggta tacgaaagtg tcgcggcctt 11220
gtacctgtag catttaacaa ggagttagga atcaatgcgc agcaatacta cgaaaggtac 11280
ggatgctggc ctacgtcaga caaggatgac ggagaatggc gtgtgccagc tattgctatt 11340
agtattggaa cttctacgtt ccgtatgcgt catcgtaacg tggttaatat tcctgcccgt 11400
ggcttgtatc ctttacgtga tttattcata gcagggaaag gcaagctaat ccttggttgt 11460
gacggtgcag gtcttgaact gcgtgtcctg tctcacttca tgaatgaccc tgagtaccaa 11520
gagattgtac tgcacggtga tattcatacg cataaccaga tgaaggctgg tcttcctaag 11580
cgtgatatgg cgaagacatt tatatatgcc ttcctatatg ggtctggtat agctaacctt 11640
gcagcagtat gtggtgttac tgaggaagaa atggaggaag ttgtggcaag atttgaggtt 11700
gaactaccat ctcttgcacg tcttcgtgag aatgttatcg cacaaggtaa caagtttggc 11760
tacctacaag cacctgatgg tcattggggt cgcatccgta tgtctggtgg tgaacttaaa 11820
gaacacacta tgcttaacgt actactccag atgactggtt ctctgtgtat gaaatacgca 11880
ttggtcagag cgtttgcagt gatgcgcaag gaaggtgtgg ccttagatag catgggaaac 11940
ccttgcggta tagctaacgt gcacgatgaa atccagatgg aagtccctga agatgaggtc 12000
ttgtatctca actacgactt gcctttcacc ttagaagggt tcgaaacaga gaaggctgct 12060
gtgaaagcag tgttcgatgc agaggagaaa cgtgttcatg tggattctga aggacgtatg 12120
tggtctgctg caaatctcgt tagtgttgat gctggtgtac ttcattgcca gcgtcgttat 12180
caccgtgcag ggcatatcat tgccgacgca atgacctggg cgggtcagta cctgaagatg 12240
cgttgtccga tggcaggtga gtataagatt ggtgcaagtt ggaaggaaac acactgatgg 12300
acaggtttga tattgtttgc ctattctcta ccttctttct tatattcctt atgcttgctt 12360
gctatggaag tatgcgatta gatatacctg atgaagagga gggttacgat tgatgcaggc 12420
atcttttatt attcttggag tcatattatt tatggtagta ttctgggctt tctctggcat 12480
tgacccagat tgtgatggta actacgactg agttatactc aaggtcactt acgagtggcc 12540
tttatgaata acttattcct acttattttg tctaacatga tttactggac actatagaag 12600
gaaagcatag gtaatctagg tttataaggt agtataggta attaagtaaa tataggagat 12660
ataaatatgt ctatggtaac tactctggta ttcgtggctc aatactttcg tggtcttgct 12720
aataagttca agtccaaggc tatcaaagct attgaggctc gcatcgaagc agtacaggca 12780
gagcaagtta aagttgaaga acatcgtagt tctcaaatga ttgactgtca taaccgctac 12840
tatgcatctc gtgatgaact aaatgcacgt caagtcaaag aggtagaaga tatgctggca 12900
cgtcaccagc aagagcgtga cagcctgaaa gctgaatttg aagagaacaa ggcatcaatt 12960
gctcttgtac atcaagctgc atctgacagt ctgaagaaag agattgttat gctggaaatc 13020
gaactggata acctgaccaa ataagggggg gttatgatgg aagaagtaat tcaagctaaa 13080

```
catgtaggta ttatctttcg cgatctagag cagcgtaaag ttgcaggtca tactcgtctg  13140
gctaaagagg aagacaccgc aatcactact gtagaacaag cagatgccta tcgtggacca  13200
gagttcactc aaggtgaaac ttgtcaccaa ttgagcctat caatttgtga cactatggct  13260
attgtaaatg tgcaagaagt cgaagagggt gagtgtgtca gttacatcta ccctttagat  13320
actattgcac gcattaaggt aatccataag taattactag acactataga acaataggtc  13380
ggcttagttc ggcctatgat tgtaaagtgt tgttgatgtt gaaccattgt gcatcttgca  13440
caacccgata ccgtataggg ctttctagtg agtacatgct tgtgctcagt acaaagctaa  13500
ctgacaatag gagactaaat aaatggcacg tggtgatttt gattttggtg ctcaggttac  13560
taaatctgaa ggtaaagtct ttaagaatcc agaagtaggt gatcatgaag cagtaatctc  13620
tggcatcatt catgttggtt ccttccaaga catctttaag aaaggtaata ccactgaagt  13680
taagaagcca gcaaactttg ttctggttaa gattgtcctg atgggtgacg atgacaagaa  13740
cgaagatggt tctcgcatgg aacaatggat ggctgtgcct ctgaagtctg gtgataaggc  13800
aacactgact aagttcctga atgcagttga ccctaaagag ttgctgggtg gcttcgatga  13860
tttcattggt gaatgcctga ctgcaacgat ggtcggttct ggtgataaga atgacgatgg  13920
ctcattcaag tatgttaact ggaagggatt tggtggtatg ccggacaagc tgaagaaact  13980
ggtcattgct caggttgaag aggaaggtct gtctatgaca ggtcacatta ccttcgacaa  14040
gctgaccaaa gaaatccttg atgacatccc agccaacttg gtgcgtcaat acttcctgaa  14100
cgagacgcct cgtggtaaga acctgtctgt tgctggttct cacgtagaag caatcattaa  14160
agctgctcgt gaagaagacc cagaatggaa gaaggctaag aagaaagacg aggaagatgc  14220
taccccagct aatcgtaaat ctctggatac tggtgagtct gttccacagg aagtacctga  14280
agcagaagat actcctgcac cggagatgga tgaggacgcg gaatattaag gagaaaggat  14340
gaaagtacaa atcgtaaccc tgcactgcaa gaaaggaatt acaactcttg gcggcaacac  14400
ttttcactcc ttctctgaag gggacacata tgccgacctg cactacatct ggcgcgacgg  14460
acagcacgtg gtgaactaca gcgacccagc tacggggaaa cgccacggcg tatcgcttcc  14520
ggcgcatgac attgctcagg tgaacacagt tttataaagt ctcacgtgtg agacaaatcg  14580
gtgtccggta tttactggac actatagaag agaagaattt taatcggcga taatgccata  14640
accaacaaaa ggagaattta atatgttcaa gattgaaact atcgtaaacc gtgttgttaa  14700
aggtgctgct ctggtatccg ttgagtcttt cattatcgtc gatgaaactg atcaactggt  14760
agctggtact aaggcttacg atacccgtga agaagctcag gctaagattg acagcatggg  14820
taacttcgct gctggtctgg agttcgctcg tgcttgcttc cctgagcagg ctgacaaagc  14880
tcagattggt aaggctaata tcgtagctga atatctggat tgggttgctg ctggtaaacc  14940
agtgaaagaa gttaaggctg ctgaagaagc tgaagctcca gcagaagaag tagctgcacc  15000
ggaaactccg gtaagtgaag aggaagaatt ttgataatag caggtgttgc ctctgttagt  15060
cctagctgac tatcacgctc acctcatcta atgccctgtc tgccttagtg taggcagggt  15120
cttttgcgta atagttattg gagaatgaat tatgccgact attgaatctc gaattgaact  15180
ggacattagc tacaatgcaa tcaccagaca gtatattggg gttgcctatg attacaaaac  15240
tggtgagaag ctagtggagg tgagacaatg ggatgactat tggttaagac agaacctcca  15300
tgatgcggtg tcctccttcc tgaaggagtg gcctacatgc gaccaaactt cgacttcgga  15360
gctacagtat cggaagacaa taacctgttg ctgtggccaa ctgaaggtaa tcgaatcgct  15420
```

```
ttaatagatg ctgatatgtt accttacatc atagggtata caatcagtga tatgacttat  15480
gtacgagcca caactcgtgt taagtcaggg caagtcccct caatcaaaga tacacctgag  15540
tgtaagcaag cgtgtgaccg tgtgaactcc ttgcttaact cttgggtgta tgcagcagaa  15600
tgtgatgcag ctaagttgtt catgacgaaa tcagaagcta acttccgtgt ccgcctagca  15660
ttcaccaagc cttataaagg tcaacgtaag accgagaagc ctccattctt ctatgaattg  15720
cgagagcatc tcttagaggt tcacggtgca atcttggcag atggagagga agcagatgac  15780
ctcatgagta tcgcacaatg ggacagccac cgccgcttcc agcaagatac aggtaacgag  15840
ttccctatcg gtagtccaga gcataaagca ttctctgata cttgcatcgt ttccttggat  15900
aaggatttga tgattgttcc cggttggcat ctacagccgg gtcaagagaa gaaatgggta  15960
gagcctatgg gttggcttga gctacgccgt aaggctaatg ggcaagtcaa agatctaaaa  16020
ggtgctggcc tcatgttcca ctatgcacag atgattatcg gtgatgatat tgataactat  16080
gctggcatac caggtcgtgg tgctaaatat gcctatgatc ttctcaaaga ttgtaagaca  16140
gagaaagagt tgtacatggc agtgctgggt gcttacaagg ctaagttcgg gcatggacaa  16200
gttaaaatta agaattaccg aggtggttat cgtatcggca aagcctttga cctaatgctt  16260
gagtgtggtc gcttatctca catggcaaga ttcaagggtg atatatggcg agccgataag  16320
aacccaatct tgtggggaga tgatgcggaa tggttagcaa attaaaatca tcggaggtgg  16380
cagcttataa gaaggaattg ctagataagc aaggatggaa atgccctctg tgtggcggca  16440
gtctcaaagc tgtcacacct gtaaaccgtg tacttgacca tgaccatgag acaggattct  16500
gccgcgctgt tgtatgccga ggctgcaatg gtgcggaagg gaagattaag ggtgttatct  16560
ctggttatgg taaggctggt aacaaccgtt acttccagct tcaatggtta gagcgactat  16620
atgaatactg gaagttacat agtacgcctc agacagataa gttatatcac aaacatcaaa  16680
cggaggcaga gaagcgcgag gctaagaacc gtaaggcacg ccttgcttat gcaagaaaga  16740
aggaggttaa agttgggtaa gctgcgcagc ttgtacaaag actccgaggt acttgatgca  16800
atcgagcaag ctaccgacga gaaaggtaat gttaactaca atgagatggc acgtgtatta  16860
tcgtgtcata ctgtgggtaa gaagattacc cgccagttgg ctcgatactg gcatggtcaa  16920
ttcaagaaga ccaagaagaa tggtgattac taccagaccc ttctgcaaga agataagcgt  16980
atcaaagaag agcgtaagct caggactcct gaccgctacg aggatttggc tattgtgcca  17040
ttgcctgact cgcctcatcg aagtgtactg gtgatccctg atactcatgc accttatgag  17100
cacccagata ccctagagtt ccttgcagcc gtggcagcac gttaccgtcc agacacagtg  17160
gtacacctag gagatgaggc agacaaacat gccctgtcat tccacgattc ggacccaaat  17220
ctggatagtg ctggcatgga gttagagaag gctcgtatct tcatgcacaa attgcacaag  17280
atgttccctg tgatgcgcct gtgtcactct aaccacggct ctatgcactt ccgtaaggca  17340
agcgccaaag gcatccctgt gcaatacctg cgcacctatc gtgaagtctt cttcccgcag  17400
ggaggtggcg accagtggga ttggcaacat acgcacgtcc ttgagttgcc gaatggtgaa  17460
caagtggcat tcaagcatca acctgctggc tctgtcctag cagatgcagc gcatgagcgt  17520
atgaaccttg tgtgtggtca cttgcacggt aagatgtctg tggagtacgc acgtaataca  17580
catgaacagt attgggctgt gcaaggtggc tgcttaattg atgagtcatc ccgtgcattt  17640
gcctatggtc gtgagtctaa atacaagcca gcattaggtt gtgtggtcat tctggagggt  17700
gtgcctcaca ttgtcccgat gcaaaccaat agcgacaacc gttggattgg caagatttag  17760
ttgacactat agaacaaagg gctaggtaag actttatcgg ctggcgtatc caaatgatat  17820
```

tgcactagcc cttgattgta tagtgaatgg aggattcaat atgtcacact atgaatgtaa 17880
gaagtgtcat aagcgttatg attactgtac ttgtggtcaa gagaaaacat cttttaaagt 17940
tggagacaag gtatttcgta atgaaaaaga ttcgattcct tggaatcaat actgcaaaga 18000
agctggtatt gaccctgata gccctgtaac catagatgat attgatggca ttaacttgtg 18060
ctttcgtgag gtgaggggta caggttggga ttccaaaaaa ttcaaacttg catctgataa 18120
gttagacaac aatatggtaa ttaagcctaa gcactacgag ttctttgatg gcgtagaggc 18180
aatcactatc attgcccgca gtatgaccga gaagcaattc gctggctatt gcatgggtaa 18240
tgctttgaag taccgtctac gtgcaggtaa gaagttcaac actgaagaag acctgaagaa 18300
agcagattac tacaaagagt tattccagaa gcatcgtcac gaatgtattg atgaggatat 18360
ttgatatgaa tatctttgag ttcctaggtc ttccagaaga ccaccgcaat cacccattca 18420
tgctggtgaa gcatcgcggt gaagttcctg agaagaaatt aacttttcca tgttatgcac 18480
aggtgaaacg agatggtatc ttttctgctg ttgttgttcg cactgatggt gtcgttggca 18540
tttttggtcg cactggtaag aaattggcaa acactgaagg actcgaacaa gcctttgcta 18600
cctttccggt tggcatttat cttggtgagc ttcagtctat ggccattgat atctaccttg 18660
aggcaatctc tggggttgtg aaccccaatc gcactgagcc acttgatttc ataggccagc 18720
agattaaaga caacctgtat atcgacttct tcgatatgtt aactattaag gcattccatg 18780
atggattcac tgatgtttct tatctcaaac gttacgatgc tttacatcgt cgtatcggcg 18840
ctcatcttag cgggtgcaac gctatccttc ctatcactcc ttgccataat gagcgagaag 18900
ttgaagcgtt tgcgcaagag caaatagatg caggacgtga gggtgctgta ttcaaactgg 18960
actgcgatta tgaagcagga cacaaaggtt atcgtcagac taaagaagtc cgtaaggtaa 19020
cctatgacct tacttgtatt ggctttgaag aaggtaaagg caaatacaaa ggtaaggtag 19080
ctaacctcat tttcaaatgg aaaggaggca agacaatcaa agctatgtta ggtaaggggt 19140
ggactcatgc agatgcagag cagatgttcc acgacattaa acatggtgga cgattgaatg 19200
tcattggtaa aatctttgaa gtcaaaggtc ttcaggattc aagcaagggc aacattcgtc 19260
tgcccaaagc gggagaatta agacatgaca aagatgaacc agatttcttt tgatagcatg 19320
aaggcaactc gtgcagttga ggtagcagaa gctatcttcg aaactttatc ctgtggcatg 19380
gaagtgccat atactttact tgctgatgca gaagaacttg gtctttctgt agaagctatc 19440
caagagaagg ttgacgaatt atatggtaca gacgaagaag aaaccgacga tttcatttga 19500
aggaatggag atgcttgaga tgattctcaa gccttcttct cctaaggtga ctaagactca 19560
tgaagagtta atcgttgatg aagttaagcg ttacatcatg gattgtgtca gagcacaact 19620
ggtggtccaa tgatacgtcc agcctccttc ctagatattc ctgagattat aaaccttggg 19680
aataaatatg tggaagagga agtcaaggtt gtagcccacc actcagcctc atggaatgca 19740
gaacaaagtg ccataacctt tgtgcatctc ttaatagaga cccaccactc agcctcatgg 19800
aatgcagaac aaagtgcaca taacctttgt gcatctctta gtagagaaga tttatcccta 19860
tgggttgctg tagatgaagg gcagattgta gggttcctgt gggctggcta tcacgagttg 19920
gccccttgga cacctgtaag agttgcctct gacattctct tttatattat accagagagg 19980
cgaggaacac tacttggtat gcgtctcatc aaagccctaa agcaatgggc tagtgataat 20040
gaatgctctg aggttcgcct gtctatcgcc tctggtatta atgaagaacg tgtcggacgt 20100
atgtataagc gacttggctt tgaaccgttt ggcactgtgt ataacctgaa gttctaagga 20160

-continued

```
gataacatgg gtgttgtaaa gaaagcattt aaggctatcg gtcttgctca agatgcacca  20220
cgtattgaag ccaaagtccc agcacagcag cttgagcgta agcctgagac tgaagctgaa  20280
gatattcaaa ttggtgcagg ggatgatgct actgcatctg caaaaggtaa gcgtggcctt  20340
gtccgtccgg tagcttctag cttgaaggtg taatatgaaa cagagcatag atttggagta  20400
tggaggtaag cggtctaaga tacctaagct atgggagaag ttctccaata aacgtagctc  20460
tttccttgat agggcgaagc attactccaa attaaccttg ccctatctga tgaatgacaa  20520
aggtgataac gagacttcgc agaatggatg gcaaggtgta ggtgctcagg caaccaacca  20580
tctagccaac aagctagcgc aagtactatt ccctgcacag cgttccttct tccgtgtaga  20640
cttaactgca caaggtgaga aggttcttaa tcagcgtggc ctgaagaaga cagagctagc  20700
taccatcttc gctcaagtgg aaacacgggc aatgaaagag ttagagcaac gtcaattccg  20760
gcctgctgta gtagaagcat ttaagcatct tattgttgct ggcagctgta tgctatacaa  20820
gccgagcaaa ggtgcaatca gtgctatccc aatgcatcac tacgtagtta accgtgatac  20880
caatggcgac ctgttagaca ttatcttgct acaagagaaa gccttacgta cctttgaccc  20940
agctacacgt gcggtagtag aggttggcct gaaaggtaag aagtgcaagg aagatgacag  21000
cgttaagctg tacacacatg ctaagtatct tggtgatgga ttttgggaac tcaagcaatc  21060
tgctgatgat atccctgtgg gtaaggtgag taaaatcaaa tcagaaaagc tacctttcat  21120
cccattaact tggaagcgaa gctatggtga ggattggggt cgacctcttg cagaggatta  21180
ctccggtgat ttattcgtta tccaattctt atctgaagcg gttgcccgtg gtgctgcgct  21240
gatggcagat atcaagtacc tgattcgtcc tggtgctcaa actgatgttg accactttgt  21300
taactctggc actggtgagg ttgtcactgg tgtagaagaa gacatccata ttgtacagtt  21360
aggtaagtac gcagacctca cacctattag cgcggttcta gaggtataca ctcgccgtat  21420
cggtgttgtc ttcatgatgg agacaatgac acgccgtgac gccgaacgtg ttactgctgt  21480
agaaatccag cgagatgcgt tagagattga gcagaacatg ggtggtgtat actccctctt  21540
tgctactact atgcaatcgc cagtagcgat gtggggtctg ctggaggcag gggagtcctt  21600
cactagtgac ttagtggacc ctgtgattat cacaggtatt gaagctttag gacgcatggc  21660
tgagttggat aaactggcta actttgctca gtatatgtca ctgccattac aatggcctga  21720
gcctgtccta gctgctgtga aatggcctga ctatatggat tgggtgcgtg gtcaaatctc  21780
tgctgaactg ccgttcctta aatcggctga agagatggca caagaacagg aagcacagat  21840
gcaagcacag caagcacaga tgcttgaaga aggtgtggct aaggccgtgc cgggtgtaat  21900
tcaacaagaa cttaaggagg cgtaatgtct ttctcattta ctgaaccgtc aaccactcac  21960
cctactgctg aagagggtcc ggtagaaacc aaggaggtaa caactgatgc tgctactact  22020
gatgctcctg ctgacgctgg cacttctgta caagatgaca atgctggtgc acaacctact  22080
gaagacaccg gaggagaagc ttctggacag ccttcagaaa aaggagacaa tggcggagag  22140
aatggtgaac ctaagccaga tgataccgcg accgacactg aggaagtgca atacttcttc  22200
ggagaacatg aagtaacagt agacatccca caggatgtaa ctgacagcct taaagagaaa  22260
ggcattgatg ccaagcaggt tgccaaggaa ctctattcca aaggtggcaa gtttgaactg  22320
tcagatgcaa ccaagcagaa attgtatgat gcttttggca agtttgcggt agatgcttac  22380
ctatcaggtc taaaggctca aaatgaagcc ttcttcctga aagaagccaa cgcagctaaa  22440
gagttggaag cagctaacac ccaacgcttc tctgatgttt ctaaggaaat tggtggcgaa  22500
gaaggttggt cccgtcttga ggagtgggca cttgaagcgc tgtctgatga cgaactaatg  22560
```

gcattcaatg cggtgatgga atctggcaac cagtacctgc aacaatatgc tgttcgtgaa 22620
ctggagggtc gtcgtaagca ggcacagggg gatgataagc catccctgat tgagccatca 22680
gcacctgcta aggctaatga agagaatggc ccactgacgc gagatcagta cgttcaagca 22740
atcgcaactc ttagccagaa gtacggcaat gaccgtaaag ctatggcaga agctcaggct 22800
aaactggacg cccgtcgccg tgctggcatg gctcgcggta tctaattcag tatttactgg 22860
acactataga agggagaaaa gttctcccta gttatcaatt tgatttataa ggagattata 22920
atacatgtct acaccgaata ctctgactaa cgttgctgta tctgcgtccg gtgaggttga 22980
cagccttctc attgagaagt ttaatggtaa ggtcaatgag cagtacctga aaggtgagaa 23040
cattctgtcc tactttgatg tacaaactgt tactggcact aacacagtga gcaacaaata 23100
tttgggcgaa actgagttgc aggtgctagc accgggtcag tcccctaatg ccacccctac 23160
tcaggcggat aaaaaccagt tggtaattga taccactgtc attgctcgta acactgtggc 23220
tcacatccac gatgtacaag gtgacatcga tagcctgaaa ccaaaactgg ctatgaacca 23280
agccaagcaa ctgaaacgtc tggaagacca gatggcaatt cagcagatgc tgttaggcgg 23340
tattgctaac accaaggccg aacgtaacaa gccgcgtgtt aaagggcatg gcttctctat 23400
caacgttaac gtaactgaga gtgaagcact ggctaaccct cagtatgtta tggctgcggt 23460
agagtatgct ctggagcaac agcttgagca ggaagtggac atctctgatg tagctatcat 23520
gatgccgtgg aagttcttca atgctttgcg tgatgcagac cgaattgtag ataagactta 23580
cactatcagc cagtctggtg caaccattaa tggcttcgtt ctctcttctt ataactgccc 23640
tgtgatcccg tctaaccgat tccctacctt cgctcaggat caggctcacc acctgttgtc 23700
taatgaagat aacggctatc gttatgaccc tatcgcagag atgaatggtg cagttgctgt 23760
tctgttcact tccgacgcac tgctggtggg tcgtaccatt gaagtgactg gtgacatctt 23820
ctatgagaag aaagagaaga cttattacat tgacaccttc atggctgagg gtgcaatccc 23880
tgaccgttgg gaagcagtgt ctgtagttac cactaaacgt gatgcaacta ctggtgatgc 23940
tggaggtcct ggtgatgatc acgcaaccgt actggctcgt gcacagcgta aggctgtata 24000
tgtcaaaacc gaaggtgctg cggctgcatt ctctgctgcc ccagcaggta tccaagcgga 24060
agaccttgta gcggcggtac gtgctgtaat ggcaaatgac attaagccga ctgcaatgaa 24120
acctactgag taacacctat gccctatcta ccttgcgtag gtagggttct tttgttagg 24180
aggattcatg cctgtaatta gacaaaccag taaattagga catatgatgg aagatgtggc 24240
cttccagatt attgatagta agctggaagc ggtaaacttg tgtatgcgag ctattggtcg 24300
tgagggtgtg gattccctcg actcagggga cttggacgca gaagatgcaa gcaaaatgat 24360
cgacatcgta tcccagcggt tccagtacaa caaaggaggt ggctggtggt tcaatcgtga 24420
accaaactgg caacttgcac cagacactaa cggtgaagtt aatttaccta acaactgcct 24480
agcagtattg cagtgttatg ctttaggtga aaagaaagta cctatgacta tgcgagcagg 24540
taagctctac tctacttgga gtcacacctt tgatatgcgt aagcatgtta atgctaatgg 24600
tatgattcgt cttaccttac tcaccttact accctacgag catctaccta caagtgtaat 24660
gcaggctatt gcctatcaag ctgctgtaga gtttattgtg tctaaggatg cagatcagac 24720
taagctagcc actgcgcagc agatagccac tcagcttctt atggatgtac aatctgagca 24780
aatgtcacag aagcgattaa acatgctggt acataaccct actcagcgtc agtttggtat 24840
catggctggt ggctctcaga atgtacctgc ttactctcat tcaccttatg agagttgggc 24900

-continued

```
gctccgtccg tgggaggatc gttaatggaa gtacaaggtt cattaggtag acaaatccaa  24960
gggattagcc agcagccgcc agcggtacgc ttggatggtc agtgcacagc tatggttaat  25020
atgatacctg atgtagtgaa tggtactcaa tcacgcatgg gtacaactca tattgcaaag  25080
atacttgatg cggggactga tgacatggct actcatcatt atcgcagagg tgatggtgat  25140
gaagagtatt tcttcacgtt gaagaaagga caagttcctg agatatttga taagtatggg  25200
cgcaaatgta atgtgacttc acaagatgca cctatgacct acctctctga ggttgttaat  25260
ccaagggaag atgtgcaatt catgacgata gctgatgtta ctttcatgct taatcgtagg  25320
aaagtagtta aagctagtag caggaagtca cctaaagttg gaaacaaagc cattgtgttt  25380
tgtgcgtatg gtcaatatgg tacatcttat tccattgtaa ttaatggggc caacgctgct  25440
agttttaaaa caccggatgg tggaagtgca gaccatgttg aacaaattcg aactgaacgt  25500
atcacttctg aattgtactc taagttgcag caatggagcg gtgtgagtga ctatgaaata  25560
caaagagacg gtactagtat atttatcgag agacgggatg gtgctagctt tacaataaca  25620
accaccgatg gtgcaaaagg taaggactta gtggctatca agaataaagt tagctctact  25680
gacctactcc cttctcgtgc gcctgctggt tataaagtac aagtgtggcc tactggcagc  25740
aaacctgagt ctcgttactg gctgcaagct gagcctaaag agggaaacct tgtgtcttgg  25800
aaagaaacaa tagctgctga tgtattactt gggtttgata aaggcacaat gccttacatt  25860
attgaacgta cagatatcat caacggcata gctcaattca agataagaca aggtgattgg  25920
gaagatcgta aagtagggga tgacttgact aaccctatgc cctcttttat tgatgaggaa  25980
gtaccccaga caataggtgg aatgttcatg gtgcagaacc gcctatgctt tacagcaggt  26040
gaagcggtta ttgcttctcg tacatcatac ttcttcgatt tctttcgtta tacggttatc  26100
tctgcattgg caactgaccc ctttgatatt ttctcagatg ctagtgaagt ctaccagcta  26160
aaacatgcag tgaccttaga tggcgctacc gtgttgttct ctgataagtc acaattcata  26220
ctgccaggcg ataagccttt agagaagtca aatgcactgc ttaagcctgt tacaacattt  26280
gaagtgaaca ataaagtgaa gccagtagta actggtgaat cggtaatgtt tgccactaat  26340
gatggttctt actctggtgt acgagagttc tatacagact cttatagtga cactaagaag  26400
gcacaagcaa tcacaagtca tgtgaataaa ctcatcgaag gtaacattac caacatggca  26460
gcaagcacca atgtcaacag gttacttgtc actaccgata agtatcgtaa cataatctac  26520
tgctacgatt ggttatggca aggaacagac cgtgtacaat cagcatggca tgtatggaag  26580
tggcctatag gtacaaaggt gcgaggtatg ttttattctg gtgaattact ttacctgctc  26640
cttgagcgag gagatggcgt gtatctggag aagatggaca tgggtgatgc actaacctac  26700
ggtttgaatg accgcatcag aatggatagg caagcagagt tagtcttcaa gcatttcaaa  26760
gcagaagatg aatgggtatc tgagccgctc ccttgggttc ctactaaccc agaactttta  26820
gattgcatct taatcgaggg ttgggattca tatattggcg gctctttctt attcaagtac  26880
aaccctagtg acaatacttt gtctacaacc tttgatatgt atgatgacag ccatgtaaaa  26940
gcgaaggtta ttgttggtca gatttaccct caagagtttg aacctacgcc tgtggttatc  27000
agagacaatc aagaccgtgt atcctacatt gatgtaccag ttgtaggatt ggttcacctt  27060
aatcttgaca tgtaccccga tttctccgta gaagttaaga atgtgaagag tggtaaagta  27120
cgtagagtat tagcgtcaaa ccgtataggt ggtgctctca ataatacagt aggctatgtt  27180
gaaccgagag aaggtgtctt cagatttcca ctgagagcta agagcacgga tgttgtttat  27240
cgtattattg tagagtcacc tcacacattc cagcttcgtg atattgagtg ggaagggagc  27300
```

```
tacaatccaa ccaaaaggag ggtctaatgg ctataggttc agccgttatg gctggtatgt  27360
cttctattgg tagcatgttt gcaggcagtg gtgcagcagc cgctgctgga ggtgctgccg  27420
caggtggcgg aggtttgcta ggttcactag gtggattcct aagtggctct actgctggtt  27480
tctctaatgc tggccttctt ggtgctggcc ttcaagggtt aggcttgatt ggtgatctat  27540
ttggtggaag tgatgaagcc aaggcgatga agaaagcaca agaagagcaa tggcggcagc  27600
agcttattgc tacacaagag gcgtacaaga cagtggcaga cgcagaacgt tctgctgcta  27660
aacaatatca tgcagatgca atcagtaatc aggcttcact gctacagcag cgagcacagg  27720
ttgcattact tgctggggct actggtactg gtggtaattc tgtgtcctct atgcttaatg  27780
acttagcagc agatggcggc aggaaccaga gtactatcat tgataactat gagaatcaga  27840
agattaattt caccaaccag cttaagtcta tccaacgtgg tggtcagatg cagatgcgtg  27900
agtttaagaa gccttctgct atgaatacct tggttaaagg tattccaagt ctggcatctg  27960
cctatgtaac tggtagtaag tctggcaagg cattgggtaa agccttaact gattctcgca  28020
catattcatc tggaacaaga ggtatttaat ggcaattgag cgacaagcag tacaaggtct  28080
gccacaagtg caggccactt ctcctaatgt catgaccttt gcacctcaac aagtgggagg  28140
tgtggaggct ggcgtggctt ctacctccgg tagtaggttt atcgaagacc ttattcgtgc  28200
agcaagcagc gtggctgatg ttaccactgg tatccttaat cagaagattg aggaagataa  28260
ggttgttcaa atggaacggg catataacgg attaatgcct tctgaggatg caactcgtgg  28320
tggcgctcgt gctaacatgc ttgtcaaagc tcaactgcta gctaatgatg aagcagcacg  28380
aatgaaagac atggctactc gtttccaagg aacggatgac gaatggacac aacttatggt  28440
tgactctcgt aatgagatgc agaataagct gttccagcaa taccctgagt tgcaaggtga  28500
caaagatact atgcgtatgg tcactaatgt cttccaagaa cagcagcctc agatttgggc  28560
tacacgaacc cagcataaac ttgaccgtga acaagcagac cgtgaggata cctttgacgg  28620
gcgagtggct tctacttggg attctaatat tgaccctgaa gcctctggct atgctttaca  28680
ggaacgaatc cgcgaaggtc ttactcaagg attactacct gaacagatgt acaagaagtt  28740
agtccagcga gcaatttcac ttgcacaagg cggtgatgtt agcatggctg aagccctgaa  28800
gtatgtgaag gacgataagg gtgtttctgt ttatgctaag aatccacagc ttatcacagc  28860
catcactagt ggtaatgcag tttgggctag gaataatgta gctgatgtaa ctcgtatgtc  28920
tttcgaagtt aaagaatcct accttgcagg tgatttaact gatgaagaat tgttggaacg  28980
agcacagcac attaataatc tgacaggtaa ctctgtcttc tctaatccag aactagaggc  29040
actgatgcgc caacgggcta agcagaatgc agagctaggt gcaatgcagg atatgcgacg  29100
tgagctttac tccgaccgcc tgactggctt ccaaggtaag actgataaag agaagaaggc  29160
ttacattgat gttatcaaac aggatagcca actttatgca gaccagcaaa tcaaacaacg  29220
tggcttggac ccttacagtc aagaggctga agctattcgt ggtgcagtgg aagtgcagcg  29280
cctgcaattc atgaactcca aaggcttagt ggatgatacc tttgagtctc gtatcaaagc  29340
catggaatct atgctatcgc ctgagcactt tgccaagggc gaaccacagg agttgatgac  29400
tattcgccag ttgtgggaac agttaccaga agagagccga ggtgtctttg gtgacacggt  29460
gaatggctac atggataact acaacactgc actacaaatg ggagagacac ctttgcaggc  29520
tgcaaggttt gcgcgtaaag cacagcagaa attctctcgt actgagaagg aaaccaagaa  29580
gttcaactca gctattggag atgcactgga tgaggtatct ggtgctggct ggtttgatgg  29640
```

-continued taaaaccgaa gtgtcagact taggtaaagc tattgcggaa gaagagttac gagctaaggc 29700
caatatgttg tggtctagtg gtatgcgtaa catggattcc atcaagaagg ctttaattac 29760
ttggggcaat aaacgctaca ctcaatcaga ggatgcaaag acttccggtg gctatttcat 29820
taaaggtgat tacacttctg catctgatat gcttatgtca gttgggaaag gcgtaaaccc 29880
taccgatgta cctctggcgc ttggtaggta tgtagaaaca cagatgccag aattgaagaa 29940
ggagcttcaa gagggggaaa ctaaagatga tatatacatt gattacaatg aacagaaagg 30000
tactttcgtg attcgtgctg gtgcagcagg tcgccctctt tctggagtaa tccctgtaac 30060
ctctttagat accacttcac tactagattc tgcctatcag aagaaagtag aggaacgaga 30120
taaaggcgag tatgttcacc cgtatcgtac agatattggt gcacaagagc ctatgccagc 30180
taaaccaact gccaaagata ttggtaaatt tggactagct aacttcctca tgtcttctgc 30240
ttttgcttct ggtgagaatc tgccttctaa cttcgagatt aactatcgag gtaatatgca 30300
acaattctat gacaagctag ctatggatga gaataaagat aaagttggct ttaataaggc 30360
aactggaacc tttactccat ataaagacgc tcacggtgag tctatcggtt acggtcattt 30420
cttaacggaa gaagagaagc gaaacgggta tattaagatt ggcgatgaac tagttcccta 30480
tcgagggtct atgtctcagc ttacagagag caaggctcgc gctcttatgg agcaagatgc 30540
taagaagcat gtgcctccta ctcgtgactg gaagattccg tttgaccaga tgcaccctgc 30600
acagcaacgt ggcttgatgg atttaagcta caatttaggt aaaggtggaa tccagaactc 30660
accgcgtgct cttgctgcat tcaaagctgg taagcttacg gagggcttta tcgaaatgct 30720
gggcactgca tcaagtgaag gtaagcgtat tcctggccta ctgaagcgac gcgctgaggc 30780
atacaatatg gcatctgctg gtggtgtgcc taagattacc gaagtggaga ctcgtgaaga 30840
tggctccatg tgggttaggt ttggtggacc tatgccagca ggttctgtct cggcatggac 30900
tcataaacgt attggcgcgg atggttggta tcaggtttat gaggctgcac ctaccaagtt 30960
agctaaagat tctaaggtag gtaaagttaa gttgtagtac ctaactcaag gcttgtctca 31020
catgtgagac aggtctttat gataggcact atggaggaat tatggaacaa gacattaaga 31080
ctaattgggc tggatatgtc cagtctactc ctgagccgtt ttctattgag gcggctccgg 31140
tatcggctcc tacgatacgc cagcgtaatg agttacaaga gcaagttctt gaagctaaag 31200
ctgacgctga tatcttaggt gctgtaggtg ctgccttcca gaatgagtgg ttggcattcg 31260
gaggcaagcg gtggtatgac cgtgccactg ctgatttcac acctcaacca gactttgaga 31320
tacaacctga gcaacgtgaa gcactacgtt tcaaatatgg tacggatatg atgcagacaa 31380
tcactgaggg tgttcgttct gaggatgaat tgaacttccg tattcagaat gcggatgaag 31440
accttgagcg caataagcgc attgctcagg ctggctgggt tggctctgtg gcgacgattg 31500
gcgctgctgt gcttgaccct gtgggatggg ttgcctctat tccaaccggt ggtgccgcta 31560
aagttggact cgtaggccgt gctgtgcgtg gcgctatcgc cgctggcgtg agtaatgccg 31620
ctattgaatc cgtattggtc caaggtgaca tgactcgtga tttagatgac attatggtag 31680
cactgggttc cggtatggct atgggtggcg ttattggcgc tgtagcgcgt ggtagggcca 31740
ctaagctcag tgagcaaggt gatgacaggg ctgctagcat tgtgcgcagt gcagacgcag 31800
gggaccgcta tgttcgtgct gttgccgatg acagtatcgg tgcgatgcgt gttaagggcg 31860
cagaggttct cactgagggt gtattcgata tctccagtaa gagtgaagac ctactgaaaa 31920
ccttgcaacg agaaggtaat gcgattgata tgacacctcg ccgttgggct ggaactatgt 31980
ctgccctcgg tactgtcgtg cactcatcta aagatgcaag tatccgaggc cttggtgctc 32040
gtctgtttga atccccacaa ggtctaggta tgcagaaggc atctgctagt cttatgcaga 32100
atactaactt aaatcgcctg aaatctgctg atatgaaccg cttcaatgat gggtttgatt 32160
tgtggcttaa agagaataat atcaatccag tagcagggca taccaactct cattatgtac 32220
agcaatacaa tgaaaaggtg tgggaggcag tgcgtattgg catggatgag tctacaccta 32280
aatctatccg catggctgct gagggacaac aggctatgta cagagaggcg ctggctttac 32340
gtcaacgttc tggtgaagcg ggatttgaaa aggtaaaagc cgacaacaaa tatatgcctg 32400
atatctttga tagtatgaaa gccagacgtc aattcgatat gcacgataaa gaagacatca 32460
tcgaactttt ctctcgtgcc taccagaatg gcgctcgtaa gattccaaag gaagcagcag 32520
atgagattgc acgagcacag gtaaatcgcg ttgctgatgc taccttaact ggaaagctta 32580
gttttgaaaa ggcaatgtca ggtcagacta aggcagagta tgaagctatc atgcgtaagg 32640
caggcttcag tgatgaagaa attgaaaaga tgatagaagc tctggataac aaagaaacca 32700
gagataacat ctctaaccga gctaaaatga gtttaggatt agatgttact caagaataca 32760
atggcattcg tatgcgtgac ttcatgaata ccaacgtgga agagctaaca gataactata 32820
tgaaggaagc agcaggtggc gctgcattgg ctcgccaagg cttctctacc tatcaggctg 32880
cacttaatgc aattgacctt gtagagcgaa atgcacgaaa cgcggctaag gatagcaagg 32940
ctagtttggc attagatgaa gagattcgtc agatgcgaga aggtcttcgc ctgattatgg 33000
gcaagtcgat tgatgcagac cccacaggcta tatctactaa gatgatgcgt cgtggtcgtg 33060
atatcacagg tgtgcttcgc ttaggtcaaa tgggcttcgc acagctaggt gaacttgcca 33120
actttatggg tgaatttggt attgctgcaa ctactatggc tttaggtaag caattccgct 33180
tcacctctaa ggcgttgcgt aatggcgatg gcttcttccg agataagaac ttagctgagg 33240
ttgagagaat ggtggggtac attggtgagg ataactggct aacaactaag ggtgcacgtc 33300
ctgatgaatt tggtgatgta accacagtaa gagggatgat ggctcacttt gaccaatcca 33360
tgaactcaat acgtcgtgct caaaccaacc tatcactctt ccgcatggca cagggttctc 33420
tggagcgaat gactaatagg caaatagctt tgtctttcat tgaccacctt gaaggcaaga 33480
agattattcc tcagaagaaa ctggaggaac ttggtcttac tcaggagttc atgactaacc 33540
tacagaagca ctatgatgct aactctaaag gttctggctt gcttggcttt gatacaatgc 33600
cttatgccat gggtgaaact ttagctaatg ctattcgtcg taagtcaggt ctaatcatcc 33660
aacgtaactt cattggtgat gaaggtatct ggatgaacaa agcactaggt aagacatttg 33720
cacagcttaa gtcattctct cttgtatctg gtgagaagca atttggtcga gggattcgcc 33780
acgataaaat tggtcttgct aagaagacag cttacgggtt tgctttgggt tcaatagtgt 33840
atgcggcaaa agcctatgtg aactctattg ggcgagaaga ccaagatgaa tatttggaag 33900
agaagttatc gcctaaaggg ttggcctttg gtgcaatggg tatgatgagt acaactgctg 33960
tatttagtct aggtggagat ttcttaggtg gcctaggtgt tctaccttcc gaactcattc 34020
aatcacgcta tgaagcaggt ttccaaagta agggtctgat tgaccaaata cctctggttg 34080
gcgttggtgc agatgcagta aatctggcta actcaatcaa gaagtatgca gaaggtgaca 34140
cagaaggtgt agatatcgct aagcgagcac tccgtcttgt gccacttacc aatataatag 34200
gtgtccaaaa cgcattgcgt tatggcttag atgaactgga ggattgatga gttatacttt 34260
cacagaacat acagccaatg gtacgcaagt cacctatcct tttagctttg ctggtaggga 34320
taaaggttat cttcgtgcct cagatgtgat agtggagtct cttcaaggta acacttggat 34380

-continued

```
tgaagttaca tctggctggc aactaactgg cacgcaccag attacttttg atgtagcacc  34440
agttgcaggt ttgaagttcc gtattcgaag ggaagtacaa aaagaatatc catacgctga  34500
gtttgaccgt ggtgttacct tggatatgaa gtctttaaat ggttctttca ttcatatact  34560
ggagattaca caggagttac ttgacgggtt ttatccagaa ggatacttca ttaaacagaa  34620
tgtaagctgg ggcggcaata agattactga tttggctgat ggcacaaatc cgggagatgc  34680
agtaaataaa gggcagcttg atgccatcga caagaagcat acagattgga acgccaaaca  34740
ggacattgag attgctggcc ttaaggctgg tatgacttct ggtattgcgc acagaactgt  34800
tccttggtac acgatagccc aaggtggtga gatttccgta aaaccacctt atgaatttca  34860
agatgcacta gttttcctta atggggtatt gcagcaccaa attgtaggcg catactctat  34920
aagcaacaac actatcactt tcgcagagcc gcttgtggct ggtacagagg tgtatgtgct  34980
gattggtagt cgtgtggcta catctgaacc taatattcag ttggagttga actttgactt  35040
agtagaaggc caacaagtag tacagattgg ctctgcattt aagtacattg aggtctacct  35100
tgatggatta ttacaaccta aacttgctta tcaggtagac ggtgacattg ttactttctc  35160
agaaagagta ccagaatgcc ggatgactgc taagattatc acagcataag gaggtgggat  35220
gattaactcc gaactggtag atagtggtgt gaagcttgcg ccacctgcac tcatatcagg  35280
tgggtacttc ctcggtatca gttgggataa ttgggtgtta atagcaacat tcatttatac  35340
cgtgttgcaa attggggact ggttttataa taagttcaag atttggaggg agaagcgtga  35400
gcgtacacaa taaacatgca gctacagagg acgaggttgg cattctgcat ggtgctatta  35460
ccaaaatctt caataagaaa gcacaggcaa tactggacac tatagaagaa gaccctgatg  35520
cagcattaca tttagtgtct ggtaaggata ttggtgcgat gtgtaagtgg gttcttgata  35580
acggcattac cgccacacct gctgcacagc aggaagagtc caagttatct aagcgcctca  35640
aggctatccg agaggcatcc agtggtaaga taattcaatt cactaaggag gattgatggc  35700
taaggcaaga gaatcacaag cggaggctct tgccagatgg gagatgctac aggagttaca  35760
gcagaccttt ccttacaccg cggaaggttt gcttctcttt gcagatacag ttattcataa  35820
cttaattgca ggcaaccctc atctgattcg tatgcaggcg gatatcttga agttcctatt  35880
ttacggacac aagtaccgcc tcatcgaagc gcctcgtggt atcgctaaga caacactatc  35940
agcaatctat acggtattcc gtattattca tgaaccgcat aagcgtatca tggttgtgtc  36000
ccaaaacgcc aagcgagcag aggaaatcgc aggttgggta gttaaaatct tccgtggctt  36060
agactttctt gagtttatgc tgccggatat ctacgctggg gaccgtgcat ccgttaaggc  36120
gtttgagatt cattacaccc tacgtggtag tgataagtct ccttctgtat cctgttactc  36180
aatcgaagca ggtatgcagg gtgctcgtgc tgatattatt ctagcggatg acgtagagtc  36240
gatgcagaat gctcgtacgg cagcgggccg tgccttgctt gaggagctga ctaaggagtt  36300
tgaatctatc aaccagtttg gggatatcat ttaccttggt acacctcaga acgtaaactc  36360
tatctacaac aacctacctg ctcgtggtta ctctgttcgt atctggactg cgcgttaccc  36420
ttcagtagag caagagcaat gttatggcga cttccttgca cctatgattg ttcaagatat  36480
gaaggacaac ccagcacttc gctcagggta cgggttggat ggtaatagtg gtgcaccttg  36540
tgcccctgaa atgtatgatg atgaagtcct gattgagaag gaaatctctc agggtgctgc  36600
taagttccag cttcagttca tgcttaacac tcgcatgatg gatgctgaca gatacccatt  36660
acgcctgaac aatctaatct tcacctcgtt tggtacagag gaagtccctg tgatgcctac  36720
gtggagtaat gattccataa acatcattgg tgatgcacct aagtatggta acaagcctac  36780
```

-continued ggatttcatg tacagacctg tagctcgccc atatgaatgg ggtgctgtct cccgcaagat 36840
tatgtatatt gaccctgcgg gtggtggtaa gaacggagat gagacgggtg tagccatcgt 36900
attcctgcac ggcacattca tttatgtgta tcagtgcttt ggtgtacctg gcggataccg 36960
agagtcgtcc ctgaatcgca ttgtgcaggc cgcaaagcag gcgggtgtta aagaggtatt 37020
cattgagaag aactttggtc atggcgcgtt tgaggcggta attaagccgt actttgaacg 37080
agagtggcct gtaactctgg aagaggatta cgccaccgga cagaaagagt tgcgtatcat 37140
tgagacgctg gagccgctca tggcagccca taggcttatc ttcaatgcag agatggtgaa 37200
gtcagacttt gagtcggtac agcactatcc gcttgaacta cgcatgtcct acagtctttt 37260
caatcaaatg tcgaacataa cgattgagaa gaacagcctc cggcacgatg accgcctaga 37320
cgccctgtat ggcgctatac ggcaattaac ttctcagata gactatgacg aggttacacg 37380
gattaatcgc ctcagagcgc aggagatgcg cgattacatc catgctatga acacacctca 37440
tctacgcagg gcaatgctat atggagatta cggtactgag cgaagagtga ccaacacttc 37500
cgtagcgatg cagcagcgag tttacgggca gaactaccga aataaatcgg caagcagaaa 37560
tacactttct gcaaggattt caaggactta ttaattactg gacactatag aaggaaggcc 37620
cagataataa gagaaaataa taggtaatat atatataggt taacctaggt tatataggta 37680
tgccttagta tgggtgtact cctgtacacc ctattcctta ctaccttact atatttacat 37740
aataggagag agacaatggc taatgattat agtagtcaac cattaacagg taagtctaag 37800
agaaagcagg tacaacctgt aagtgaagaa ctaatgcttc cggtgctcaa aaaagaggaa 37860
gttagtaaga aaagcaatgt tattaatgat gccaccaaat caggtaaaca gaaaggggcc 37920
atggtgtgcc ttgaagtgaa aggtggtgta ttgaagattg ctatcgcggt tgatggcaaa 37980
gaagattcag agtggaagtt agtaacagtg gaaccaactg ttaacccagt ttaagataag 38040
gaggaagatt acatggctaa atatggtact acaggttctg ttactggtca ggcttttcga 38100
gtaaaagcag tacaaactat tgcaacggca atcccgatgc ctgttgttaa agaagaagac 38160
cttaagagta aagaccaccc tatcaacatc aaacatttat caggtaaaca gaaaggtgca 38220
atggttgctc ttgagaaagg tgacacaacc ttacatattg ctgttgcacg tggtagtgaa 38280
cccacagacc cttgggatgt aactggtatg gaaaaggacg ctgttactcc agcaggggta 38340
taataatgct taataaatac ttcaagcgta aagagtttgc ttgccgttgt gggtgcggta 38400
catccactgt tgatgctgaa ttactacagg tagtcacaga tgtgcgtgag cactttggtt 38460
ctcctgtagt tatcacttcg ggtcatcgct gtgctaagca caatgccaat gtaggtggcg 38520
ctaagaactc catgcatctt actggtaagg ctgctgacat taaagtgtct ggcatattac 38580
cttctgaagt gcataagtat cttactagca aataccaagg caagtatggt ataggtaagt 38640
ataactcctt cactcacatc gatgtacggg atggttgtgc gcgatggtaa gatgtgttga 38700
atggtgtgag cgtatggttg cccaagctgc cgaggatggc aactatgatg actggaagaa 38760
ctactctgac ttgttagctc aatggaaagg gagatgcaat gaaaaagctg tttaagtcta 38820
agaaggttgt aggtgcactg gttgcacttg ttattgctct tgtttctgta ggtcttggtg 38880
tagaccttgg ctctggcacg gaatcctctg tgacagatgt ggtctgccaa gtgatcacct 38940
gtgaataagt ttctagaagt tctggcaggt cttattggcc tgcttgtctc tgctaagaag 39000
aaacaagaag agaaggaggc acaaagtgaa gcgaatcatg ttagtgacaa cccttctgat 39060
tggttcgctg accacttccg ggtgtcagca ggcgttacca gagaaagcaa tggtgaaacc 39120

-continued

```
tctgaggccg acgctgacgg cagtttacga ggtagacgat aaggtctgct ttagtaagcc  39180
tgacgctaca aaacttggtt tgtacattct ctcgctagaa cgcggataca attaatacat  39240
agctttatgt atcagtgtct tacgatttac tggacactat agaagaggta agatagcgcc  39300
gttcttttga gcggcctatt actagccaat cttcataggg agggttggaa agtaatagga  39360
gatagcatgg ctaaattaac caaacctaat actgaaggaa tcttgcataa aggacaatct  39420
ttgtatgagt accttgatgc gagagtttta acatcaaagc cgtttggtgc tgcaggtgac  39480
gccactactg atgatacgga ggttatagct gcttcattaa actctcagaa agctgtcaca  39540
gtctcagatg gtgtattctc tagctctggt attaacagta attactgtaa cttagacggc  39600
aggggtagtg gcgtgctaag tcaccgttca agtacaggta actacttagt atttaacaat  39660
ctacgtgcag gtcgcttaag taatattacg gtagaaagta ataaggcgac tgatacaact  39720
cagggacagc aggtatccct tgctggtgga agtgatgtta ctgtaagtga cgttaacttc  39780
tcaaacgtta aaggtactgg tttcagttta atcgcatacc ctaatgatgc gccacctgat  39840
ggacttatga ttaaaggcat tcgaggtagc tattccggct atgctactaa taaggcagcc  39900
ggatgcgtac ttgctgattc ctcagttaac tccctcatag ataacgtcat tgctaagaac  39960
taccctcagt tcggagcagt agagttgaaa ggtacagcca gttacaacat agtcagtaat  40020
gttataggga cagattgcca gcatgtaact tacaacggca ctgaagggcc aatagctcct  40080
tctaataacc ttatcaaggg ggtgatggct aataacccta agtatgcagc ggttgttgca  40140
ggcaaaggaa gtacgaactt aatctcagac gtgctcgtag attactcaac ttctgatgct  40200
aggcaggctc atggtgttac agtagagggt tctgataacg tcataaataa tgtgcttatg  40260
tcaggatgtg atggtactaa ctctttagga caagggcaga ctgctacaat tgcacgcttt  40320
ataggtacag ctaataacaa ctatgcgtct gtatttccta gctacagtgc tacaggtgtt  40380
attactttcg aatccggctc tacccgtaac ttcgtagagg taaagcaccc tggcaggaga  40440
aacgaccttc tcagttctgc tagtactatt gacggtgcag ctactattga cggcactagt  40500
aatagtaacg tagtgcacgc acctgcctta gggcagtaca taggtagtat gtcaggtagg  40560
ttcgaatggc ggattaagtc catgtcactc ccttcaggcg ttcttacttc tgctgataag  40620
tacagaatgc ttggagatgg tgctgtgtca ttagctgtag gtgggggcac ttcttctcaa  40680
gttcgcctat ttacttctga tggtacttct cggacagtgt ccctcaccaa cggtaacgtg  40740
cgtctttcta ccagtagcac aggctttttg cagttaggtg ctgatgcaat gaccccagac  40800
agtactggta catacgcatt aggttccgcc agccgagcat ggtctggcgg ttttactcaa  40860
gcagcattca ctgttacctc agatgctcgg tgtaaaacag aacctcttac tatctcagat  40920
gccttactgg atgcttggtc tgaagttgac tttgtgcagt ttcagtattt ggatcgtgtt  40980
gaggagaagg gtgcagactc agctagatgg cacttcggta tcatcgctca gcgagctaag  41040
gaggctttcg aacgtcacgg tatagatgca catcgctatg gcttcttgtg cttcgacagt  41100
tgggatgatg tatacgagga agatgccaat ggctctcgta aactgattac accagcaggt  41160
tcccgctacg gtattcgtta cgaggaagta ctgatattag aggctgcgtt gatgcggcgg  41220
actattaagc gtatgcagga agcactagct tccctgccta agtaagcaac aggcagtgcg  41280
taagcactgc ttttagcgca acttttctta aaggttatca cggtggtagc ctttcagaaa  41340
aggaggttac atgattcaaa gactaggttc ttcattagtt aaattcaaga gtaaaatagc  41400
aggtgcaatc tggcgtaact tggatgacaa gctcaccgag gttgtatcgc ttaaagattt  41460
tggagccaaa ggtgatggta agacaaacga ccaagatgca gtaaatgcag cgatggcttc  41520
```

```
aggtaagaga attgacggtg ctggtgctac ttacaaagta tcatctttac ctgatatgga  41580
gcgattctat aacacccgct tcgtatggga acgtttagca ggtcaacctc tttactatgt  41640
gagtaaaggt tttatcaatg gtgaactata taaaatcacg gataaccctt attacaatgc  41700
ttggcctcaa gacaaagcgt ttgtatatga gaacgtgata tatgcacctt acatgggtag  41760
tgaccgtcat ggtgttagtc gtctgcatgt atcatgggtt aagtctggtg acgatggtca  41820
aacatggtct actccagagt ggttaactga tctgcatcca gattacccta cagtgaacta  41880
tcattgtatg agtatgggtg tatgtcgcaa ccgtctgttt gccatgattg aaacacgtac  41940
tttagccaag aacaaactaa ccaattgtgc attgtgggat cgccctatgt ctcgtagtct  42000
gcatcttact ggtggtatca ctaaggctgc aaatcagcaa tatgcaacaa tacatgtacc  42060
agatcacgga ctattcgtgg gcgattttgt taacttctct aattctgcgg taacaggtgt  42120
atcaggtgat atgactgttg caacggtaat agataaggac aacttcacgg ttcttacacc  42180
taaccagcag acttcagatt tgaataacgc tggaaagagt tggcacatgg gtacttcttt  42240
ccataagtct ccatggcgta agacagatct tggtctaatc cctagtgtca cagaggtgca  42300
tagctttgct actattgata acaatggctt tgttatgggc tatcatcaag gtgatgtagc  42360
tccacgagaa gttggtcttt tctacttccc tgatgctttc aatagcccat ctaattatgt  42420
tcgtcgtcag ataccatctg agtatgaacc agatgcgtca gagccatgca tcaagtacta  42480
tgacggtgta ttatacctta tcactcgtgg cactcttggt gacagacttg gaagctcttt  42540
gcatcgtagt agagatatag gtcagacttg ggagtcactg agatttccac ataatgttca  42600
tcatactacc ctacctttg ctaaagtagg agatgacctt attatgtttg gttcagaacg  42660
tgcagaaaat gaatgggaag caggtgcacc agatgatcgt tacaaggcat cttatcctcg  42720
taccttctat gcacgattga atgtaaacaa ttggaatgca gatgatattg aatgggttaa  42780
catcacagac caaatctatc aaggtgacat tgtgaactct agtgtaggtg taggttcggt  42840
agtagttaaa gacagctaca tttactatat ctttggtggc gaaaaccatt tcaacccaat  42900
gacttatggt gacaacaaag gtaaagaccc atttaaaggt catggacacc ctactgatat  42960
atactgctat aagatgcaga ttgcaaatga caatcgtgta tctcgtaagt ttacatatgg  43020
tgcaactccg ggtcaagcta tacctacttt catgggtact gatggaatac gaaatatccc  43080
tgcacctttg tatttctcag ataacattgt tacagaggat actaaagttg gacacttaac  43140
acttaaagca agcacaagtt ccaatatacg atctgaagtg cagatggaag gtgaatatgg  43200
ctttattggc aagtctgttc caaaggacaa cccaactggt caacgtttga ttatttgtgg  43260
tggagaagag acttcgtcct cttcaggtgc acagataact ttgcacggct ctaattcaag  43320
taaggctaat cgtatcactt ataacggaaa tgagcaccta ttccaaggtg caccaatcat  43380
gcctgctgta gataaccagt ttgctgctgg tggacctagt aaccgattca ctaccatcta  43440
cctaggtagt gaccctgtta caacttcaga tgctgaccac aagtacagta tctctagtat  43500
taataccaag gtgttaaagg cttggagcag ggttggtttt aaacagtatg gtttgaatag  43560
tgaagcagag agggaccttg atagcataca cttcggtgtc ttggctcagg atattgtagc  43620
tgcttttgaa gctgaagggt tggatgccat taagtatgga attgtgtcct tcgaagaagg  43680
taggtacggt gtgaggtata gtgaagttct aatactagag gctgcttata ctcgttatcg  43740
tttagacaag ttagaggaga tgtatgccac taataaaatc agttaagcaa gctgctgtac  43800
tccagaacac agaagagctt attcaatcag gacgtgaccc taagcaggct tatgccattg  43860
```

-continued ccaaggatgt tcaacgtcgt gccatgaaga aaccttctgc atcttctgcg taaagaggag 43920
atatacaatg gtcttcacac tcgaagattt cgttggggac tggcgacaga cagccggcta 43980
caacctggac caagtccttg aacagggagg tgtgtccagt ttgtttcaga atctcggggt 44040
gtccgtaact ccgatccaaa ggattgtcct gagcggtgaa aatgggctga agatcgacat 44100
ccatgtcatc atcccgtatg aaggtctgag cggcgaccaa atgggccaga tcgaaaaaat 44160
ttttaaggtg gtgtaccctg tggatgatca tcactttaag gtgatcctgc actatggcac 44220
actggtaatc gacggggtta cgccgaacat gatcgactat ttcggacggc cgtatgaagg 44280
catcgccgtg ttcgacggca aaaagatcac tgtaacaggg accctgtgga acggcaacaa 44340
aattatcgac gagcgcctga tcaaccccga cggctccctg ctgttccgag taaccatcaa 44400
cggagtgacc ggctggcggc tgtgcgaacg cattctggcg taagcaggtt aatatcttag 44460
tataaacaag ggcagactta ggtttgtcct tagtgtattc caaaggaggt aacatgctga 44520
aagatggttg ggtttcatat gaccctacag accctaagaa ttggctacag gttatcgcta 44580
tagcttgtgc aggtagccta ttggctgccc tgatgtattc attatggatg tacacaaagt 44640
aaccaaagtc aaaattttga tgtaggcgtg tgtcagctct ctcgccctcg ccctcgccgg 44700
gttgtcccca tagggtggcc tgagggaatc cgtcttcgac gggcagggct gatgtactcc 44760
ttgtctagta caagggaggc ggagggaacg cctagggagg cctaggaatg gcttagtggt 44820
ggacaaggtg attaccttag tgaagcctct tagtgcattc ctgaggccat tcagggcgtt 44880
tatgagggat tgacagggtg tgagggcgtg ggcta 44915

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
gcttacgcag aagatgcaga 20

<210> SEQ ID NO 6
<211> LENGTH: 814
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
cctctagaaa taattttgtt taactttaag aaggagatat acatatggtc ttcacactcg 60
aagatttcgt tggggactgg cgacagacag ccggctacaa cctggaccaa gtccttgaac 120
agggaggtgt gtccagtttg tttcagaatc tcggggtgtc cgtaactccg atccaaagga 180
ttgtcctgag cggtgaaaat gggctgaaga tcgacatcca tgtcatcatc ccgtatgaag 240
gtctgagcgg cgaccaaatg ggccagatcg aaaaaatttt taaggtggtg taccctgtgg 300
atgatcatca ctttaaggtg atcctgcact atggcacact ggtaatcgac ggggttacgc 360
cgaacatgat cgactatttc ggacggccgt atgaaggcat cgccgtgttc gacggcaaaa 420
agatcactgt aacagggacc ctgtggaacg gcaacaaaat tatcgacgag cgcctgatca 480
accccgacgg ctccctgctg ttccgagtaa ccatcaacgg agtgaccggc tggcggctgt 540
gcgaacgcat tctggcgtaa aggaggtaaa catatgacca tgattacgga ttcactggcc 600

```
gtcgttttac aacgtcgtga ctgggaaaac cctggcgtta cccaacttaa tcgccttgca    660

gcacatcccc ctttcgccag ctggcgtaat agcgaagagg cccgcaccga tcgcccttcc    720

caacagttgc gcagcctgaa tggcgaatgg taaaaagagg aggtatacaa tggctagcat    780

gactggtgga cagcaaatgg gtactaacca aggt                                814


<210> SEQ ID NO 7
<211> LENGTH: 796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

ctttaagacc cttaagtgtt aattagagat ttaaggagat tcaacatggt cttcacactc     60

gaagatttcg ttggggactg gcgacagaca gccggctaca acctggacca agtccttgaa    120

cagggaggtg tgtccagttt gtttcagaat ctcggggtgt ccgtaactcc gatccaaagg    180

attgtcctga gcggtgaaaa tgggctgaag atcgacatcc atgtcatcat cccgtatgaa    240

ggtctgagcg gcgaccaaat gggccagatc gaaaaaattt ttaaggtggt gtaccctgtg    300

gatgatcatc actttaaggt gatcctgcac tatggcacac tggtaatcga cggggttacg    360

ccgaacatga tcgactattt cggacggccg tatgaaggca tcgccgtgtt cgacggcaaa    420

aagatcactg taacagggac cctgtggaac ggcaacaaaa ttatcgacga gcgcctgatc    480

aaccccgacg gctccctgct gttccgagta accatcaacg gagtgaccgg ctggcggctg    540

tgcgaacgca ttctggcgta aaggaggtaa acatatgacc atgattacgg attcactggc    600

cgtcgtttta caacgtcgtg actgggaaaa ccctggcgtt acccaactta atcgccttgc    660

agcacatccc cctttcgcca gctggcgtaa tagcgaagag gcccgcaccg atcgcccttc    720

ccaacagttg cgcagcctga atggcgaatg gtaaaaatta aagaattact aagagaggac    780

tttaagtatg cgtaac                                                    796


<210> SEQ ID NO 8
<211> LENGTH: 1109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

aaatgccagc acttccggct aaaggtaact tgaacctccg tgacatctta gagtcggact     60

tcgcgttcgc gtaacgccaa atcaatacga ctcactatag agggacaaac tcaaggtcat    120

tcgcaagagt ggcctttatg attgaccttc ttccggttaa tacgactcac tataggagaa    180

ccttaaggtt taactttaag acccttaagt gttaattaga gatttaagga gattcaacat    240

ggtcttcaca ctcgaagatt tcgttgggga ctggcgacag acagccggct acaacctgga    300

ccaagtcctt gaacagggag gtgtgtccag tttgtttcag aatctcgggg tgtccgtaac    360

tccgatccaa aggattgtcc tgagcggtga aaatgggctg aagatcgaca tccatgtcat    420

catcccgtat gaaggtctga gcggcgacca aatgggccag atcgaaaaaa tttttaaggt    480

ggtgtaccct gtggatgatc atcactttaa ggtgatcctg cactatggca cactggtaat    540

cgacggggtt acgccgaaca tgatcgacta tttcggacgg ccgtatgaag gcatcgccgt    600
```

-continued

```
gttcgacggc aaaaagatca ctgtaacagg gaccctgtgg aacggcaaca aaattatcga    660

cgagcgcctg atcaaccccg acggctccct gctgttccga gtaaccatca acggagtgac    720

cggctggcgg ctgtgcgaac gcattctggc gtaaaggagg taaacatatg accatgatta    780

cggattcact ggccgtcgtt ttacaacgtc gtgactggga aaaccctggc gttacccaac    840

ttaatcgcct tgcagcacat ccccctttcg ccagctggcg taatagcgaa gaggcccgca    900

ccgatcgccc ttcccaacag ttgcgcagcc tgaatggcga atggtaaaaa ttaaagaatt    960

actaagagag gactttaagt atgcgtaact tcgaaaagat gaccaaacgt tctaaccgta   1020

atgctcgtga cttcgaggca accaaaggtc gcaagttgaa taagactaag cgtgaccgct   1080

ctcacaagcg tagctgggag ggtcagtaa                                     1109


<210> SEQ ID NO 9
<211> LENGTH: 988
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

cggtatcgca cagatgccaa ctatcgtcgt caagtcgaac agaaagtaat cgattcgaac     60

ttctgataga cttcgaaatt aatacgactc actataggga gaccacaacg gtttccctct    120

agaaataatt ttgtttaact ttaagaagga gatatacata tggtcttcac actcgaagat    180

ttcgttgggg actggcgaca gacagccggc tacaacctgg accaagtcct tgaacaggga    240

ggtgtgtcca gtttgtttca gaatctcggg gtgtccgtaa ctccgatcca aaggattgtc    300

ctgagcggtg aaaatgggct gaagatcgac atccatgtca tcatcccgta tgaaggtctg    360

agcggcgacc aaatgggcca gatcgaaaaa atttttaagg tggtgtaccc tgtggatgat    420

catcacttta aggtgatcct gcactatggc acactggtaa tcgacggggt tacgccgaac    480

atgatcgact atttcggacg gccgtatgaa ggcatcgccg tgttcgacgg caaaaagatc    540

actgtaacag ggaccctgtg gaacggcaac aaaattatcg acgagcgcct gatcaacccc    600

gacggctccc tgctgttccg agtaaccatc aacggagtga ccggctggcg gctgtgcgaa    660

cgcattctgg cgtaaaggag gtaaacatat gaccatgatt acggattcac tggccgtcgt    720

tttacaacgt cgtgactggg aaaaccctgg cgttacccaa cttaatcgcc ttgcagcaca    780

tccccctttc gccagctggc gtaatagcga agaggcccgc accgatcgcc cttcccaaca    840

gttgcgcagc ctgaatggcg aatggtaaaa agaggaggta tacaatggct agcatgactg    900

gtggacagca aatgggtact aaccaaggta aaggtgtagt tgctgctgga gataaactgg    960

cgttgttctt gaaggtattt ggcggtga                                      988
```

BACTERIOPHAGE ENGINEERING METHODS

CROSS-REFERENCE TO RELATED APPLICATIONS

This application claims the benefit of and priority to U.S. Application No. 62/314,163, filed Mar. 28, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 5, 2017, is named 102590-0560_SL.txt and is 173,292 bytes in size.

TECHNICAL FIELD

The present technology relates generally to methods and kits for generating recombinant bacteriophage genomes.

BACKGROUND

The following description of the background of the present technology is provided simply as an aid in understanding the present technology and is not admitted to describe or constitute prior art to the present technology.

Model phages have been engineered using molecular biology techniques to deliver heterologous protein products to bacterial cells. E.g., US 2009/0155215; M. J. Loessner et. al., *Applied and Environmental Microbiology*, Vol. 62, No. 4, pp. 1133-40 (1996)). The natural host range of model phage engineered to date is limited. Methods for creating variations in phage genomes and engineering new phage genomes may lead to the identification of phages with varied properties (e.g., varied host ranges) that are useful for diagnostic and therapeutic purposes.

Engineering diverse phage is generally made more difficult by the properties of phage genomes. For example, phage genomes have relatively few restriction sites and are heavily modified, making use of traditional cloning techniques with phage challenging. Phages also have compact genomes with very little non-coding DNA, which can make it challenging to find sites within the genome that are compatible with traditional engineering. Many existing phage engineering technologies that rely on in vitro strategies are generally inefficient and challenging to scale up. Further, engineering phages within bacteria can be problematic due to toxicity of phages to bacteria as well as the difficulty in maintaining the stability of large engineered genomes.

SUMMARY OF THE PRESENT TECHNOLOGY

In one aspect, the present disclosure provides a method for generating a recombinant bacteriophage genome comprising: (a) contacting a non-recombinant bacteriophage genome with a sgRNA-CRISPR enzyme conjugate in vitro under conditions where the sgRNA-CRISPR enzyme conjugate cleaves a protospacer sequence within the non-recombinant bacteriophage genome to produce a cleaved non-recombinant bacteriophage genome; and (b) recombining in vitro the cleaved non-recombinant bacteriophage genome with a heterologous nucleic acid in the presence of a recombination system under conditions to produce a recombinant bacteriophage genome (a.k.a., "Break and Recombine 3.0" (BAR 3.0) method). The cleaved non-recombinant bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment. In some embodiments, the protospacer sequence is 5' GCTTACGCAGAAGATGCAGA 3' (SEQ ID NO: 5).

Additionally or alternatively, in some embodiments, the method further comprises propagating the recombinant bacteriophage genome in a bacterial host. The bacterial host may be a non-natural bacterial host cell or a natural bacterial host cell.

Additionally or alternatively, in some embodiments, the CRISPR enzyme is a Cas protein selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. In certain embodiments, the CRISPR enzyme is Cas9.

In certain embodiments of the method, the non-recombinant bacteriophage genome corresponds to K1-5 phage. The nucleic acid sequence of the recombinant bacteriophage genome may comprise SEQ ID NO: 3 or SEQ ID NO: 4.

In another aspect, the present disclosure provides a method for generating a recombinant bacteriophage genome comprising: (a) contacting a non-recombinant bacteriophage genome comprising a single first recognition site with a first restriction enzyme in vitro under conditions where the first restriction enzyme cleaves the first recognition site to produce a cleaved non-recombinant bacteriophage genome; and (b) recombining in vitro the cleaved non-recombinant bacteriophage genome with a heterologous nucleic acid in the presence of a recombination system under conditions to produce a recombinant bacteriophage genome (a.k.a., BAR 4.0 method). The cleaved non-recombinant bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments, the method further comprises propagating the recombinant bacteriophage genome in a bacterial host. The bacterial host may be a non-natural bacterial host cell or a natural bacterial host cell.

In some embodiments, the first restriction enzyme is SwaI. In other embodiments, the first restriction enzyme is NheI.

In certain embodiments of the method, the non-recombinant bacteriophage genome corresponds to *Escherichia coli* (a.k.a., *E. coli*) T7. The nucleic acid sequence of the recombinant bacteriophage genome may comprise SEQ ID NO: 1, SEQ ID NO: 2, SEQ ID NO: 6 or SEQ ID NO: 7.

Additionally or alternatively, in some embodiments of the BAR 3.0 and BAR 4.0 methods disclosed herein, the recombination system comprises a 5'-3' exonuclease, a DNA polymerase, and a DNA ligase.

In one aspect, the present disclosure provides a method for generating a recombinant bacteriophage genome comprising: (a) contacting a non-recombinant bacteriophage genome with (i) a sgRNA-CRISPR enzyme conjugate in vitro under conditions where the sgRNA-CRISPR enzyme conjugate cleaves a protospacer sequence within the non-recombinant bacteriophage genome to produce a cleaved non-recombinant bacteriophage genome; or (ii) a restriction enzyme in vitro under conditions where the restriction enzyme cleaves a unique recognition site within the non-recombinant bacteriophage genome to produce a cleaved non-recombinant bacteriophage genome; (b) transforming the cleaved non-recombinant bacteriophage genome into a bacterial host cell, wherein the bacterial host cell comprises a vector that expresses a heterologous nucleic acid; and (c) recombining in vivo the cleaved non-recombinant bacteriophage genome with the heterologous nucleic acid in the presence of a non-endogenous recombination system under conditions to produce a recombinant bacteriophage genome (a.k.a., BARner method). The cleaved non-recombinant bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment.

The cleaved non-recombinant bacteriophage genome may be transformed into the bacterial host cell via electroporation. The bacterial host cell may be a non-natural bacterial host cell or a natural bacterial host cell. In some embodiments, the non-endogenous recombination system is induced in the bacterial host cell. In certain embodiments, the non-endogenous recombination system is induced by the addition of arabinose.

Additionally or alternatively, in some embodiments, the CRISPR enzyme is a Cas protein selected from the group consisting of Cast, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

Additionally or alternatively, in some embodiments, the restriction enzyme is AclI, HindIII, SspI, MluCI Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, BssSI, BssSαI, Nb.BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI, PaeR7I, TliI, EarI, AcuI, PstI, BpmI, DdeI, SfcI, AflII, BpuEI, SmlI, AvaI, BsoBI, MboII, BbsI, XmnI, BsmI, Nb.BsmI, EcoRI, HgaI, AatII, ZraI, Tth111I, PflFI, PshAI, AhdI, DrdI, Eco53kI, SacI, BseRI, PleI, Nt.BstNBI, MlyI, HinfI, EcoRV, MboI, Sau3AI, DpnII, BfuCI, DpnI, BsaBI, TfiI, BsrDI, Nb.BsrDI, BbvI, BtsI, BtsαI, Nb.BtsI, BstAPI, SfaNI, SphI, SrfI, NmeAIII, NaeI, NgoMIV, BglI, AsiSI, BtgZI, HinP1I, HhaI, BssHII, NotI, Fnu4HI, Cac8I, MwoI, NheI, BmtI, SapI, BspQI, Nt.BspQI, BlpI, TseI, ApeKI, Bsp1286I, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpy166II, Tsp45I, HpaI, PmeI, HincII, BsiHKAI, ApoI, NspI, BsrFI, BsrFαI, BstYI, HaeII, CviKI-1, EcoO109I, PpuMI, I-CeuI, SnaBI, I-SceI, BspHI, BspEI, MmeI, TaqαI, NruI, Hpy188I, Hpy188III, XbaI, BclI, HpyCH4V, FspI, PI-PspI, MscI, BsrGI, MseI, PacI, PsiI, BstBI, DraI, PspXI, BsaWI, BsaAI, and EaeI.

In another aspect, the present disclosure provides a method for generating a recombinant bacteriophage genome comprising: (a) transforming an intact non-recombinant bacteriophage genome into a bacterial host cell, wherein the bacterial host cell comprises a vector that expresses a heterologous nucleic acid; and (b) recombining in vivo the intact non-recombinant bacteriophage genome with the heterologous nucleic acid in the presence of a non-endogenous recombination system under conditions to produce a recombinant bacteriophage genome (a.k.a., BREDner method). In some embodiments, the heterologous nucleic acid comprises a 5' flanking region that is homologous to a first region within the intact non-recombinant bacteriophage genome, and a 3' flanking region that is homologous to a second region within the intact non-recombinant bacteriophage genome, wherein the first region of the intact non-recombinant bacteriophage genome is located 5' to the second region of the intact non-recombinant bacteriophage genome. The intact non-recombinant bacteriophage genome may be transformed into the bacterial host cell via electroporation. The bacterial host cell may be a non-natural bacterial host cell or a natural bacterial host cell. In some embodiments, the non-endogenous recombination system is induced in the bacterial host cell. In certain embodiments, the non-endogenous recombination system is induced by the addition of arabinose.

Additionally or alternatively, in some embodiments of the BREDner and BARner methods disclosed herein, the recombination system comprises lambda Red proteins Gam, Exo, and Beta operably linked to an inducible promoter (e.g., araB promoter).

In any of the above embodiments of the methods of the present technology, the heterologous nucleic acid is about 500-1050 base pairs or 1050 base pairs to 5 kb in length. The heterologous nucleic acid may comprise an open reading frame that encodes a bioluminescent protein, a fluorescent protein, a chemiluminescent protein, or any combination thereof. Examples of bioluminescent protein include Aequorin, firefly luciferase, *Renilla* luciferase, red luciferase, luxAB, or nanoluciferase. Examples of chemiluminescent protein include β-galactosidase, horseradish peroxidase (HRP), or alkaline phosphatase. Examples of fluorescent protein include TagBFP, Azurite, EBFP2, mKalamal, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherryl, PATagRFP, Kaede (green), Kaede (red), KikGR1 (green), KikGR1 (red), PS-CFP2, PS-CFP2, mEos2 (green), mEos2 (red), PSmOrange, or Dronpa.

Additionally or alternatively, in some embodiments of the methods disclosed herein, the open reading frame of the heterologous nucleic acid is operably linked to an expression control sequence that is capable of directing expression of the bioluminescent protein, the fluorescent protein, the chemiluminescent protein, or any combination thereof. The expression control sequence may be an inducible promoter or a constitutive promoter.

Also provided herein are recombinant bacteriophages comprising a genome having a nucleic acid sequence comprising any one of SEQ ID NOs: 1-4 or 6. Also disclosed herein are kits for integrating a heterologous nucleic acid sequence into a bacteriophage genome.

BRIEF DESCRIPTION OF THE DRAWINGS

FIG. 4 discloses SEQ ID NO: 8.

FIG. 7 discloses SEQ ID NO: 9.

FIG. 10 shows the complete genome sequence of the recombinant NanoLuc® T7 phage strain DLPECO1, which contains a single insertion of the NanoLuc® reporter gene (SEQ ID NO: 1).

FIG. 11 shows the complete genome sequence of the recombinant NanoLuc® T7 phage strain DLPECO2, which contains a double insertion of the NanoLuc® reporter gene (SEQ ID NO: 2).

FIG. 15 shows the heterologous nucleic acid sequence that was inserted into K1-5 phage using the BAR 3.0 method disclosed herein (SEQ ID NO: 3).

FIG. 16 shows the complete genome sequence of the recombinant NanoLuc® K1-5 phage. (SEQ ID NO: 4).

FIG. 17 shows the heterologous nucleic acid sequence that was inserted near the NheI site in T7 phage using the BAR 4.0 method disclosed herein (SEQ ID NO: 6).

FIG. 18 shows the heterologous nucleic acid sequence that was inserted near the SwaI site in T7 phage using the BAR 4.0 method disclosed herein (SEQ ID NO: 7).

DETAILED DESCRIPTION

Figure 1:
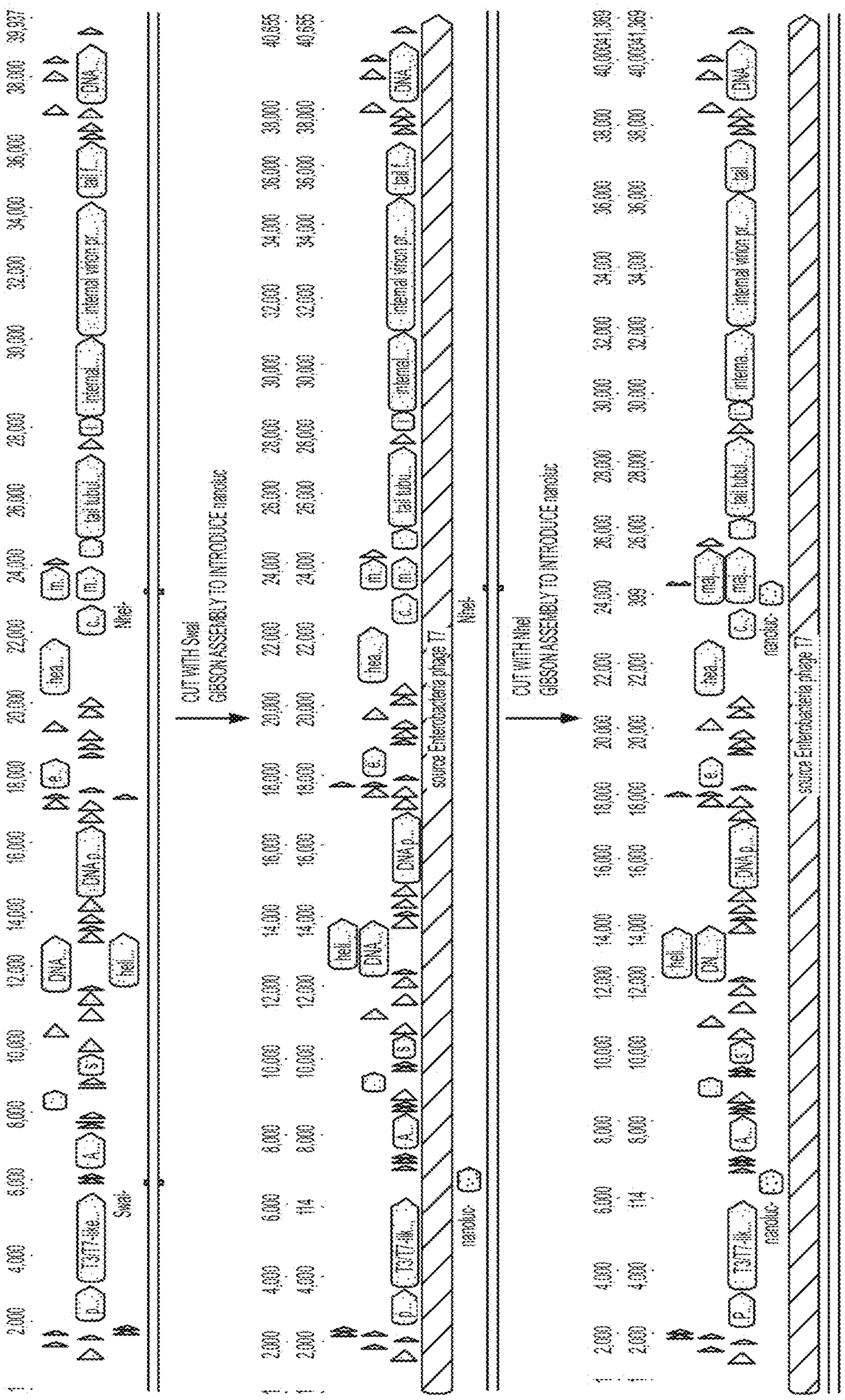
FIG. 1 outlines the BAR 4.0 method of the present technology that was used to generate the DLPECO2 phage strain, which contains a double insertion of the nanoluciferase (NanoLuc®) reporter gene.

It is to be appreciated that certain aspects, modes, embodiments, variations and features of the present methods are described below in various levels of detail in order to provide a substantial understanding of the present technology.

One of the most commonly used and well-established methods for engineering phage genomes is homologous recombination in their bacterial hosts, which can occur between two homologous DNA sequences as short as 23 bp (Alberts B et al., Molecular biology of the cell, 5th ed. Garland Science, New York, N.Y. (2007); Snyder L et al., Molecular genetics of bacteria, 4th ed. ASM Press, Washington, D.C. (2013)). Homologous recombination occurs between the plasmid and the phage genome, allowing the heterologous gene to be integrated into the phage genome and eventually packaged within the phage particle. However, homologous recombination only yields a small fraction of recombination progeny phage. Reported recombination rates range from $10^{-10}$ to $10^{-4}$ (Loessner M. et al., *Appl Environ Microbiol* 62:1133-1140 (1996); Le S. et al., *PLoS One* 8:e68562 (2013); Mahichi F. et al., *FEMS Microbiol Lett* 295:211-217 (2009)). One of the major challenges of generating recombinant bacteriophages is that the recombinant processes used to create such bacteriophages are inefficient, and often result in a low yield of recombinant bacteriophage genomes. Transformation of large bacteriophage genomes (e.g., about or greater than 40-48 kb) is prohibitive in many bacterial strains and species, making it difficult to isolate viable bacteriophage particles post-transformation. See e.g., Chauthaiwale et al., *Microbiological Reviews* 56 (4): 577-592 (1992); see also Vaughan et al., *Nature Biotechnology* 14:309-314 (1996). Thus, finding the desired clone using conventional phage screening methods is labor-intensive and unpredictable.

The present disclosure provides methods for integrating a heterologous nucleic acid sequence into a bacteriophage genome, and isolating recombinant bacteriophages that express the heterologous nucleic acid sequence. The methods disclosed herein permit higher recovery of recombinant bacteriophage genomes that express the phenotypic properties associated with the heterologous nucleic acid sequence relative to that observed with conventional phage engineering methods, such as bacteriophage recombineering of electroporated DNA (BRED) (Marinelli L J et al., *PLoS One* 3:e3957 (2008)). For example, the overall yield of recombinant bacteriophage genomes was about 44%-69% with the BAR 4.0 method of the present technology, and 2.78% with the BAR 3.0 method of the present technology. In contrast, no recombinant bacteriophages were generated using BRED (i.e., 0% recovery of recombinant bacteriophage genomes).

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization; Anderson* (1999) *Nucleic Acid Hybridization*; Hames and Higgins eds. (1984) *Transcription and Translation; Immobilized Cells and Enzymes* (IRL Press (1986)); Perbal (1984)*A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60, expect=10; Matrix=BLOSUM62; Descriptions=50 sequences; sort by=HIGH SCORE; Databases=non-redundant, GenBank+EMBL+DDBJ+

PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to the nucleic acid of interest to initiate, regulate or otherwise control transcription of the nucleic acid of interest.

As used herein, a "phage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion and an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, the terms "restriction endonucleases" and "restriction enzymes" refer to bacterial enzymes each of which cleave double-stranded DNA at or near a specific nucleotide sequence known as a "restriction site", "recognition site", or "double-stranded recognition site."

As used herein, the term "sample" refers to clinical samples obtained from a subject or isolated microorganisms.

In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

In some embodiments, a phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 375 kb, at least 400 kb, at least 425 kb, at least 450 kb, at least 475 kb, or at least 500 kb of nucleic acids.

Phage Engineering Methods of the Present Technology

BAR 3.0

In one aspect, the present disclosure provides a method for generating a recombinant bacteriophage genome comprising: (a) contacting a non-recombinant bacteriophage genome with a sgRNA-CRISPR enzyme conjugate in vitro under conditions where the sgRNA-CRISPR enzyme conjugate cleaves a protospacer sequence within the non-recombinant bacteriophage genome to produce a cleaved non-recombinant bacteriophage genome; and (b) recombining in vitro the cleaved non-recombinant bacteriophage genome with a heterologous nucleic acid in the presence of a recombination system under conditions to produce a recombinant bacteriophage genome. The cleaved non-recombinant bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment. In some embodiments, the protospacer sequence is 5' GCTTACGCAGAAGATGCAGA 3' (SEQ ID NO: 5).

In some embodiments of the BAR 3.0 method, the homologous 5' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the BAR 3.0 method, the homologous 3' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments, the BAR 3.0 method further comprises propagating the recombinant bacteriophage genome in a bacterial host. For example, the bacterial host may be transformed with the recombinant bacteriophage genome via electroporation. The bacterial host may be a non-natural bacterial host cell or a natural bacterial host cell.

Additionally or alternatively, in some embodiments of the BAR 3.0 method, the non-recombinant bacteriophage genome corresponds to T3, T7, M6, K11, F92, K1-5, and K1F. In certain embodiments of the BAR 3.0 method, the non-recombinant bacteriophage genome corresponds to K1-5 phage. In certain embodiments of the BAR 3.0 method, the non-recombinant bacteriophage genome corresponds to a phage group selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae. The nucleic acid sequence of the recombinant bacteriophage genome may comprise SEQ ID NO: 3 or SEQ ID NO: 4.

BAR 4.0

In another aspect, the present disclosure provides a method for generating a recombinant bacteriophage genome comprising: (a) contacting a non-recombinant bacteriophage genome comprising a single first recognition site with a first restriction enzyme in vitro under conditions where the first restriction enzyme cleaves the first recognition site to produce a cleaved non-recombinant bacteriophage genome; and (b) recombining in vitro the cleaved non-recombinant bacteriophage genome with a heterologous nucleic acid in the presence of a recombination system under conditions to produce a recombinant bacteriophage genome. The cleaved non-recombinant bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment.

In some embodiments of the BAR 4.0 method, the homologous 5' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the BAR 4.0 method, the homologous 3' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments, the BAR 4.0 method further comprises propagating the recombinant bacteriophage genome in a bacterial host. For example, the bacterial host may be transformed with the recombinant bacteriophage genome via electroporation. The bacterial host may be a non-natural bacterial host cell or a natural bacterial host cell.

Additionally or alternatively, in some embodiments of the BAR 4.0 method, the non-recombinant bacteriophage genome corresponds to T3, T7, M6, K11, F92, K1-5, and K1F. In certain embodiments of the BAR 4.0 method, the non-recombinant bacteriophage genome corresponds to *E. coli* T7. In certain embodiments of the BAR 4.0 method, the non-recombinant bacteriophage genome corresponds to a phage group selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae. The nucleic acid sequence of the recombinant bacteriophage genome may comprise SEQ ID NO: 1, SEQ ID NO: 2, SEQ ID NO: 6, or SEQ ID NO: 7.

BARner

In one aspect, the present disclosure provides a method for generating a recombinant bacteriophage genome comprising: (a) contacting a non-recombinant bacteriophage genome with (i) a sgRNA-CRISPR enzyme conjugate in vitro under conditions where the sgRNA-CRISPR enzyme conjugate cleaves a protospacer sequence within the non-recombinant bacteriophage genome to produce a cleaved non-recombinant bacteriophage genome; or (ii) a restriction enzyme in vitro under conditions where the restriction enzyme cleaves a unique recognition site within the non-recombinant bacteriophage genome to produce a cleaved non-recombinant bacteriophage genome; (b) transforming the cleaved non-recombinant bacteriophage genome into a bacterial host cell, wherein the bacterial host cell comprises a vector that expresses a heterologous nucleic acid; and (c) recombining in vivo the cleaved non-recombinant bacteriophage genome with the heterologous nucleic acid in the presence of a non-endogenous recombination system under conditions to produce a recombinant bacteriophage genome. The cleaved non-recombinant bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment. The cleaved non-recombinant bacteriophage genome may be transformed into the bacterial host cell via electroporation. The bacterial host cell may be a non-natural bacterial host cell or a natural bacterial host cell. In some embodiments, the non-endogenous recombination system is induced in the bacterial host cell. In certain embodiments, the non-endogenous recombination system is induced by the addition of arabinose.

In some embodiments of the BARner method, the homologous 5' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the BARner method, the homologous 3' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the BARner method, the non-recombinant bacteriophage genome corresponds to T3, T7, M6, K11, F92, K1-5, and K1F. In certain embodiments of the BARner method, the non-recombinant bacteriophage genome corresponds to a phage group selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae.

BREDner

In another aspect, the present disclosure provides a method for generating a recombinant bacteriophage genome comprising: (a) transforming an intact non-recombinant bacteriophage genome into a bacterial host cell, wherein the bacterial host cell comprises a vector that expresses a heterologous nucleic acid; and (b) recombining in vivo the intact non-recombinant bacteriophage genome with the heterologous nucleic acid in the presence of a non-endogenous recombination system under conditions to produce a recombinant bacteriophage genome. In some embodiments, the heterologous nucleic acid comprises a 5' flanking region that is homologous to a first region within the intact non-recombinant bacteriophage genome, and a 3' flanking region that is homologous to a second region within the intact non-recombinant bacteriophage genome, wherein the first region of the intact non-recombinant bacteriophage genome is located 5' to the second region of the intact non-recombinant bacteriophage genome. The intact non-recombinant bacteriophage genome may be transformed into the bacterial host cell via electroporation. The bacterial host cell may be a non-natural bacterial host cell or a natural bacterial host cell. In some embodiments, the non-endogenous recombination system is induced in the bacterial host cell. In certain embodiments, the non-endogenous recombination system is induced by the addition of arabinose.

In some embodiments of the BREDner method, the homologous 5' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the BREDner method, the homologous 3' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the BREDner method, the intact non-recombinant bacteriophage genome corresponds to T3, T7, M6, K11, F92, K1-5, and K1F. In certain embodiments of the BREDner method, the non-recombinant bacteriophage genome corresponds to a phage group selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae.

Additionally or alternatively, in any of the above embodiments of the methods disclosed herein (BAR 3.0, BAR 4.0, BARner and BREDner), the recombination system comprises a 5'-3' exonuclease, a DNA polymerase, and a DNA ligase. In one embodiment, the 5'-3' exonuclease is T5 exonuclease, the DNA polymerase is Phusion® DNA polymerase, and the DNA ligase is Taq ligase. In other embodiments of the methods disclosed herein, the recombination system comprises lambda Red proteins Gam, Exo, and Beta operably linked to an inducible promoter (e.g., araB promoter). In certain embodiments of the methods disclosed herein, the recombination system comprises RecET (RecE, RecT) operons. In other embodiments of the methods disclosed herein, the recombination system comprises RecA recombinase, or a RecA gain-of-function variant.

Accurate identification of bacterial species within a biological sample informs the selection of suitable therapies for treating bacterial infections. Recombinant bacteriophage generated using the methods disclosed herein, may be used to identify bacteria present within a biological sample (e.g., whole blood, plasma, serum). Such methods entail contacting the biological sample with a recombinant bacteriophage generated using the methods disclosed herein, and detecting the presence of bacterial host cells infected by the recombinant phage, wherein the recombinant phage comprises a heterologous nucleic acid that encodes a detectable gene product, thereby leading to the identification of bacteria present within the biological sample.

Additionally or alternatively, recombinant bacteriophage generated using the methods disclosed herein, may be used in methods for profiling antibiotic susceptibility of bacteria present within a biological sample (e.g., whole blood, plasma, serum). These methods include (a) contacting the biological sample with an antibiotic and a recombinant bacteriophage generated using the methods disclosed herein, (b) detecting the presence of bacterial host cells infected by the recombinant phage, wherein the recombinant phage comprises a heterologous nucleic acid that encodes a detectable gene product, and (c) determining that the antibiotic is effective in inhibiting the bacteria present in the biological sample when the number of recombinant phage infected bacterial host cells is reduced relative to that observed in an untreated control sample.

CRISPR Enzymes

A variety of CRISPR enzymes are available for use in conjunction with the disclosed BAR 3.0 and BARner methods of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any variants, homologs or orthologs thereof. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or variants thereof. In some embodiments, the CRISPR enzyme cleaves both strands of the target nucleic acid at the Protospacer Adjacent Motif (PAM) site. In certain embodiments of the BAR 3.0 method, the CRISPR enzyme is Cas9.

Restriction Enzymes

A variety of restriction enzymes are available for use in conjunction with the disclosed BAR 4.0 and BARner methods of the present disclosure. Non-limiting examples of restriction enzymes include AclI, HindIII, SspI, MluCI Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, BssSI, BssSαI, Nb.BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI, PaeR7I, TliI, EarI, AcuI, PstI, BpmI, DdeI, SfcI, AflII, BpuEI, SmlI, AvaI, BsoBI, MboII, BbsI, XmnI, BsmI, Nb.BsmI, EcoRI, HgaI, AatII, ZraI, Tth111I, PflFI, PshAI, AhdI, DrdI, Eco53kI, SacI, BseRI, PleI, Nt.BstNBI, MlyI, HinfI, EcoRV, MboI, Sau3AI, DpnII, BfuCI, DpnI, BsaBI, TfiI, BsrDI, Nb.BsrDI, BbvI, BtsI, BtsαI, Nb.BtsI, BstAPI, SfaNI, SphI, SrfI, NmeAIII, NaeI, NgoMIV, BglI, AsiSI, BtgZI, HinP1I, HhaI, BssHII, NotI, Fnu4HI, Cac8I, MwoI, NheI, BmtI, SapI, BspQI, Nt.BspQI, BlpI, TseI, ApeKI, Bsp1286I, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpy166II, Tsp45I, HpaI, PmeI, HincII, BsiHKAI, ApoI, NspI, BsrFI, BsrFαI, BstYI, HaeII, CviKI-1, EcoO109I, PpuMI, I-CeuI, SnaBI, I-SceI, BspHI, BspEI, MmeI, TaqαI, NruI, Hpy188I, Hpy188III, XbaI, HpyCH4V, FspI, PI-PspI, MscI, BsrGI, MseI, Pad, PsiI, BstBI, DraI, PspXI, BsaWI, BsaAI, and EaeI. In some embodiments of the BAR 4.0 method, the first restriction enzyme is SwaI. In other embodiments of the BAR 4.0 method, the first restriction enzyme is NheI.

Heterologous Nucleic Acids

In some embodiments of the methods disclosed herein, the heterologous nucleic acid comprises an open reading frame that encodes a bioluminescent protein, a fluorescent protein, a chemiluminescent protein, or any combination thereof. In some embodiments, the encoded gene product(s) produces a detectable signal upon exposure to the appropriate stimuli, and the resulting signal permits detection of bacterial host cells infected by the recombinant phage. In certain embodiments, the open reading frame encodes a protein that serves as a marker that can be identified by screening bacterial host cells infected by a recombinant phage comprising a heterologous nucleic acid sequence comprising the open reading frame. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments, the length of the heterologous nucleic acid sequence is at least 100 bases, at least 200 based, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the phage genome with no loss of endogenous phage genomic sequence. In some embodiments, the heterologous nucleic acid sequence replaces an endogenous phage genomic sequence. In some embodiments, the heterologous nucleic acid sequence includes an endogenous phage genomic sequence that was previously excised from the phage genome.

In certain embodiments, the heterologous nucleic acid sequence replaces an endogenous phage genomic sequence that is less than the length of the heterologous nucleic acid sequence. Accordingly, in some embodiments, the length of the recombinant phage genome is longer than the length of the wild-type phage genome. In some embodiments, the heterologous nucleic acid sequence replaces an endogenous phage genomic sequence that is greater than the length of the heterologous nucleic acid sequence. Thus, in some embodiments, the length of the recombinant phage genome is shorter than the length of the wild-type phage genome. In certain embodiments, the heterologous nucleic acid sequence replaces an endogenous phage genomic sequence that is equal to the length of the heterologous nucleic acid sequence.

In certain embodiments, the open reading frame of the heterologous nucleic acid encodes a protein that confers a phenotype of interest on a host cell infected by a recombinant phage expressing the heterologous nucleic acid. In some embodiments, the phenotype of interest is the expression of the gene product encoded by the open reading frame of the heterologous nucleic acid.

In certain embodiments, the open reading frame of the heterologous nucleic acid is operably linked to an expression control sequence that is capable of directing expression of the open reading frame, wherein the open reading frame encodes a bioluminescent protein, a fluorescent protein, a chemiluminescent protein, or any combination thereof. In some embodiments, the expression control sequence is located within the heterologous nucleic acid sequence. In other embodiments, the expression control sequence is located in the endogenous phage genome sequence. For example, the open reading frame may be inserted into the phage genome downstream of or in the place of an endogenous phage open reading frame sequence. In some embodiments, the expression control sequence is an inducible promoter or a constitutive promoter. See e.g., Djordjevic & Klaenhammer, *Methods in Cell Science* 20(1):119-126 (1998). The inducible promoter or constitutive promoter may be an endogenous phage promoter sequence, a non-endogenous phage promoter sequence, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include but are not limited to blue/UV fluorescent proteins (for example, TagBFP, Azurite, EBFP2, mKalamal, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherryl, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type bacteriophage and the bacterial host cell. Accordingly, detection of the epitope in a sample demonstrates the presence of a bacterial host cell infected by a recombinant phage comprising a heterologous nucleic acid, wherein the open reading frame of the heterologous nucleic acid comprises the epitope.

In other embodiments, the open reading frame of the heterologous nucleic acid comprises a polypeptide tag sequence, such that the expression product of the open reading frame comprises the tag fused to a polypeptide or protein encoded by the open reading frame (e.g., polyhistidine, FLAG, Glutathione S-transferase (GST) etc.).

Kits

The present technology provides kits for integrating a heterologous nucleic acid sequence into a bacteriophage genome. Also provided herein are recombinant bacteriophages comprising a genome having a nucleic acid sequence comprising any one of SEQ ID NOs: 1-4 or 6.

In one aspect, the kits of the present technology comprise (a) one or more coded/labeled vials that contain a plurality of bacteriophage genomes, (b) a recombination system, and (c) at least one CRISPR enzyme, or restriction enzyme.

In some embodiments, each coded/labeled vial containing a plurality of bacteriophage genomes corresponds to a different bacteriophage type. In other embodiments, each coded/labeled vial containing a plurality of bacteriophage genomes corresponds to the same bacteriophage type. In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

In some embodiments, the kits comprise a recombination system that includes a 5'-3' exonuclease, a DNA polymerase, and a DNA ligase. For example, in one embodiment, the 5'-3' exonuclease is T5 exonuclease, the DNA polymerase is Phusion® DNA polymerase, and the DNA ligase is Taq ligase. In other embodiments of the kits, the recombination system comprises lambda Red proteins Gam, Exo, and Beta operably linked to an inducible promoter (e.g., araB promoter). In certain embodiments of the kits, the recombination system comprises RecET (RecE, RecT) operons. In other embodiments, the recombination system comprises RecA recombinase or variants thereof.

Additionally or alternatively, in some embodiments, the kits comprise one or more CRISPR enzymes selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The one or more CRISPR enzymes may be coupled to a sgRNA. In certain embodiments, the sgRNA targets the protospacer sequence 5' GCTTACGCAGAAGATGCAGA 3' (SEQ ID NO: 5).

Additionally or alternatively, in some embodiments, the kits comprise one or more restriction enzymes selected from the group consisting of AclI, HindIII, SspI, MluCI Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, BssSI, BssSαI, Nb.BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI, PaeR7I, TliI, EarI, AcuI, PstI, BpmI, DdeI, SfcI, AflII, BpuEI, SmlI, AvaI, BsoBI, MboII, BbsI, XmnI, BsmI, Nb.BsmI, EcoRI, HgaI, AatII, ZraI, Tth111I, PflFI, PshAI, AhdI, DrdI, Eco53kI, SacI, BseRI, PleI, Nt.BstNBI, MlyI, HinfI, EcoRV, MboI, Sau3AI, DpnII, BfuCI, DpnI, BsaBI, TfiI, BsrDI, Nb.BsrDI, BbvI, BtsI, BtsαI, Nb.BtsI, BstAPI, SfaNI, SphI, SrfI, NmeAIII, NaeI, NgoMIV, BglI, AsiSI, BtgZI, HinP1I, HhaI, BssHII, NotI, Fnu4HI, Cac8I, MwoI, NheI, BmtI, SapI, BspQI, Nt.BspQI, BlpI, TseI, ApeKI, Bsp12861, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpyl66II, Tsp45I, HpaI, PmeI, HincII, BsiHKAI, ApoI, NspI, BsrFI, BsrFαI, BstYI, HaeII, CviKI-1, EcoO109I, PpuMI, I-CeuI, SnaBI, I-SceI, BspHI, BspEI, MmeI, TaqαI, NruI, Hpyl881, Hpyl88III, XbaI, BclI, HpyCH4V, FspI, PI-PspI, MscI, BsrGI, MseI, Pad, PsiI, BstBI, DraI, PspXI, BsaWI, BsaAI, and EaeI.

Additionally or alternatively, in some embodiments, the kits further comprise vials containing natural or non-natural bacterial host cells. In some embodiments, the bacterial host cells are *E. coli*. In certain embodiments, the bacterial host cells are *E. coli* strain DH10B.

In some embodiments, the kits further comprise positive control heterologous nucleic acid sequences to correct for any variability in the recombination systems between experimental runs. The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics.

EXAMPLES

Example 1: BAR 4.0 Phage Engineering Methods of the Present Technology in T7 Phage This Example demonstrates that the BAR 4.0 methods of the present technology are useful for integrating a heterologous nucleic acid into a bacteriophage genome (e.g., T7 phage genome) and for isolating recombinant bacteriophages that express the heterologous nucleic acid sequence.

Transformation of large DNA inserts into bacteria has traditionally been prohibitive in many bacterial strains and species. Piers D. et al., *Microbiol Mol Biol Rev.* 80(3):523-43 (2016). Previous attempts to generate recombinant NanoLuc® T3 bacteriophage and recombinant NanoLuc® T7 bacteriophage in $RecA^+$ or $RecA^-$ K12 *E. coli* strains via conventional methods such as BRED were unsuccessful. Indeed, no recombinant phages were obtained using BRED.

BAR 4.0 is an in vitro recombination method and permits the transformation of large DNA inserts into bacterial cells. FIG. 1 outlines the BAR 4.0 method of the present technology that was used to generate the recombinant T7 phage strains DLPECO1 and DLPECO2, which contain a single and a double insertion of the NanoLuc® reporter gene, respectively. The complete genome sequences of the DLPECO1 and DLPECO2 phage strains are shown in FIG. 10 and FIG. 11, respectively. FIG. 17 shows the heterologous nucleic acid sequence that was inserted near the NheI site in T7 phage using the BAR 4.0 method disclosed herein (SEQ ID NO: 6). FIG. 18 shows the heterologous nucleic acid sequence that was inserted near the SwaI site in T7 phage using the BAR 4.0 method disclosed herein (SEQ ID NO: 7).

T7 bacteriophage DNA was extracted from a clarified phage lysate using the Zymo ZR Viral DNA Kit (Cat no. D3015) (Zymo Research, Irvine, Calif.). About 100 ng of T7 phage DNA was digested with the restriction enzyme SwaI (NEB R0604) (New England Biolabs, Ipswich, Mass.) according to the manufacturer's specifications. A gBlock (synthesized by Integrated DNA Technologies, Coralville, Iowa) containing the NanoLuc® gene surrounded by 60 bp of homology to the viral genome was inserted into the SwaI cut site by Gibson Assembly® (New England Biolabs, Ipswich, Mass.).

Figure 2:
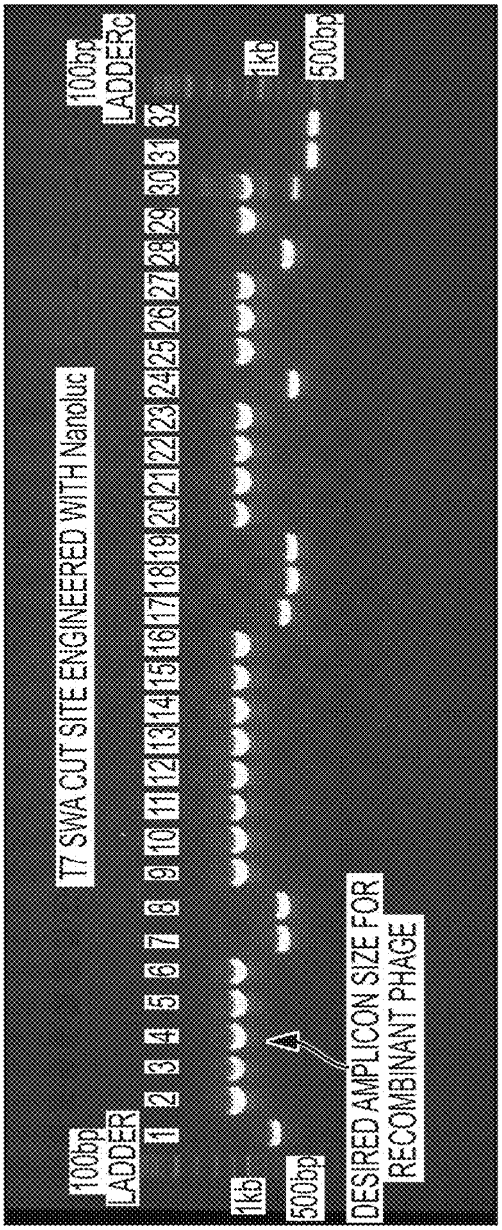
FIG. 2 shows the recovery of recombinant NanoLuc® T7 phages that contain a single insertion of the NanoLuc® reporter gene using the BAR 4.0 method disclosed herein. Isolated plaques were selected and screened for NanoLuc® insertion via PCR using primers that flanked the NanoLuc® insertion site. A 700 bp increase in amplicon size correlated with the successful insertion of the NanoLuc® reporter gene within the T7 genome at the SwaI restriction site.
Figure 3:
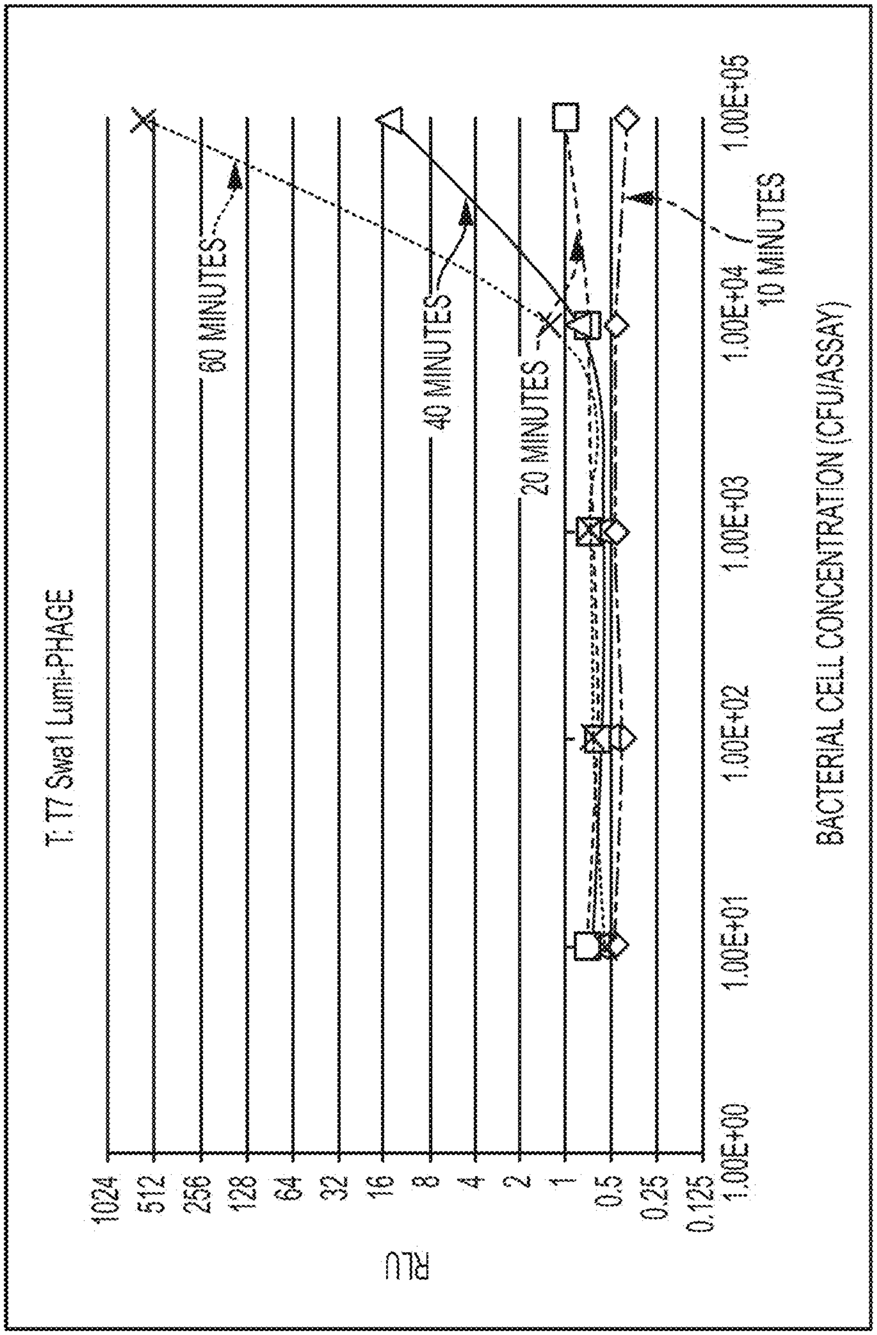
FIG. 3 shows the luminescence activity profile of the DLPECO1 phage strain, which contains a single insertion of the NanoLuc® reporter gene.

2 μl of the resulting T7/NanoLuc® fusion product was electroporated into NEB10β cells (NEB C3030K) (New England Biolabs, Ipswich, Mass.). Cells were plated on LB agar with a 0.65% soft agar overlay. After incubation at 37° C. overnight, isolated plaques were selected and screened for NanoLuc® insertion via PCR using primers that flanked the NanoLuc® insertion site (FIG. 2). A 700 bp increase in amplicon size correlated with the successful insertion of the NanoLuc® reporter gene within the T7 genome at the SwaI restriction site. See FIG. 2. NanoLuc® production was evaluated by infecting bacterial host cells with recombinant phage strain DLPECO1 and measuring luminescence between 10-60 minutes at different bacterial host cell concentrations. FIG. 3 demonstrates that the intensity of the NanoLuc® signal produced by a recombinant T7 phage strain containing a single NanoLuc® insertion was dependent on bacterial cell concentration and time.

Figure 4:
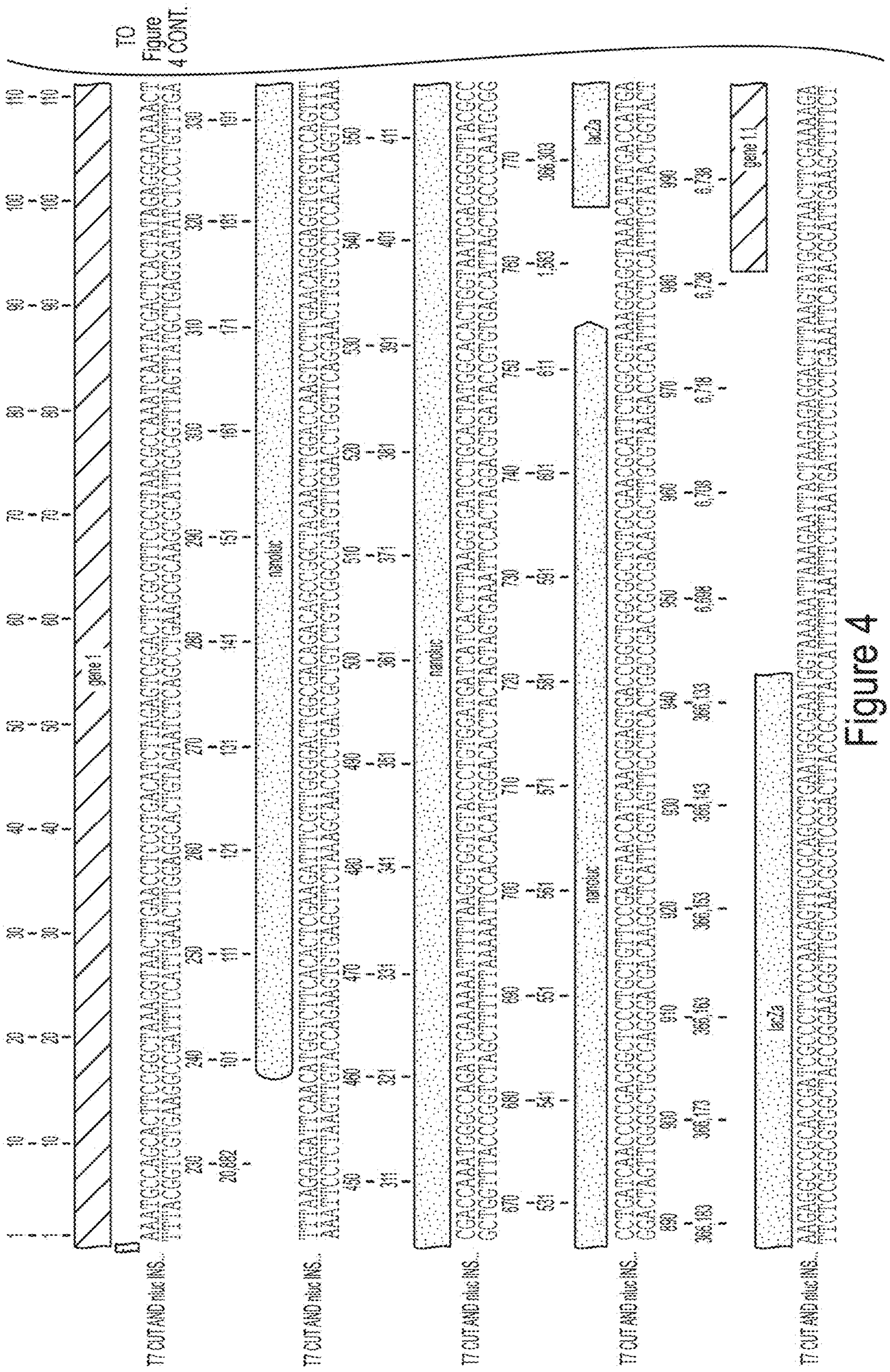
FIG. 4 shows a schematic of the NanoLuc® insertion into the T7 genome at the SwaI restriction site.
Figure 4:
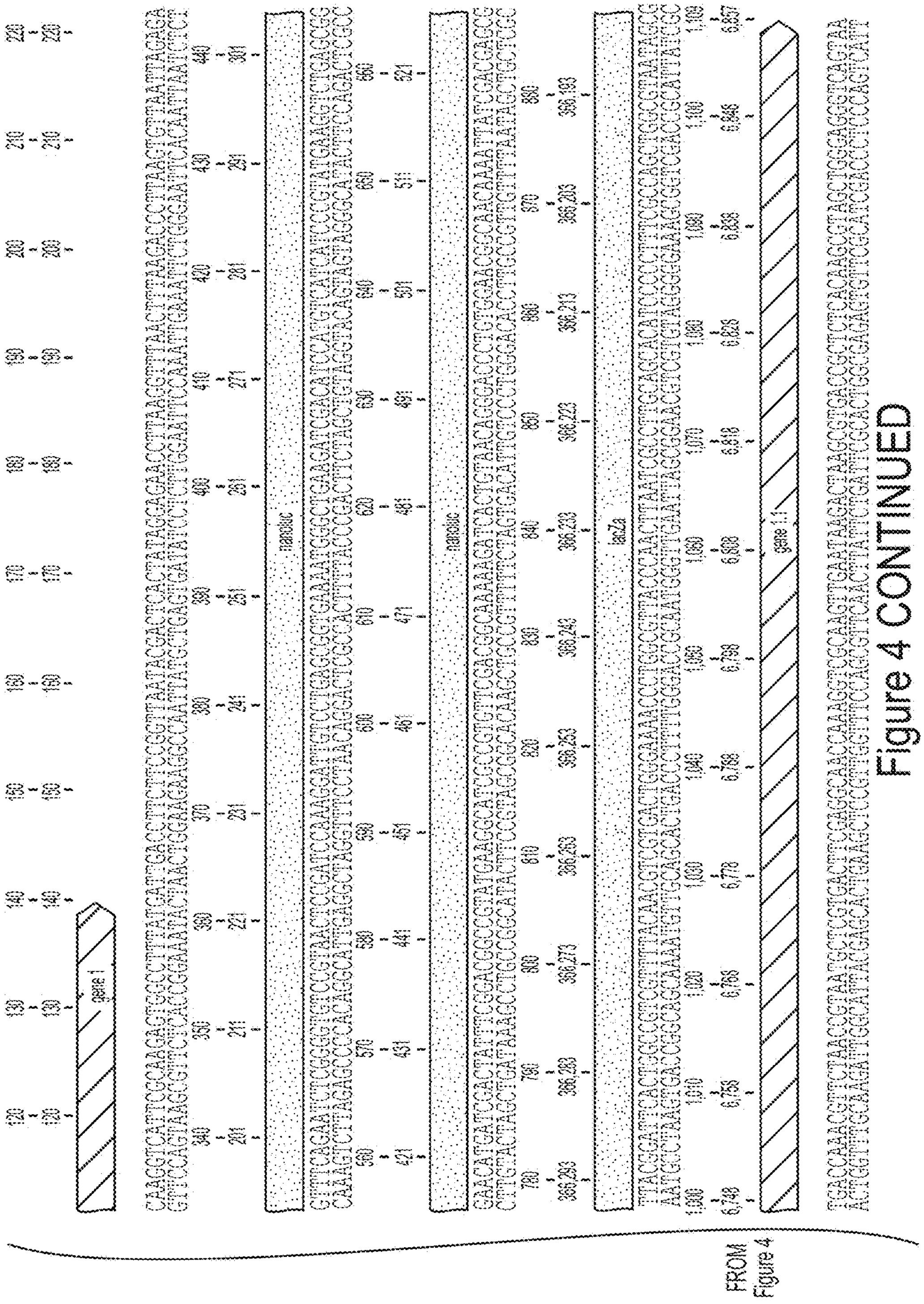
Figure 5:
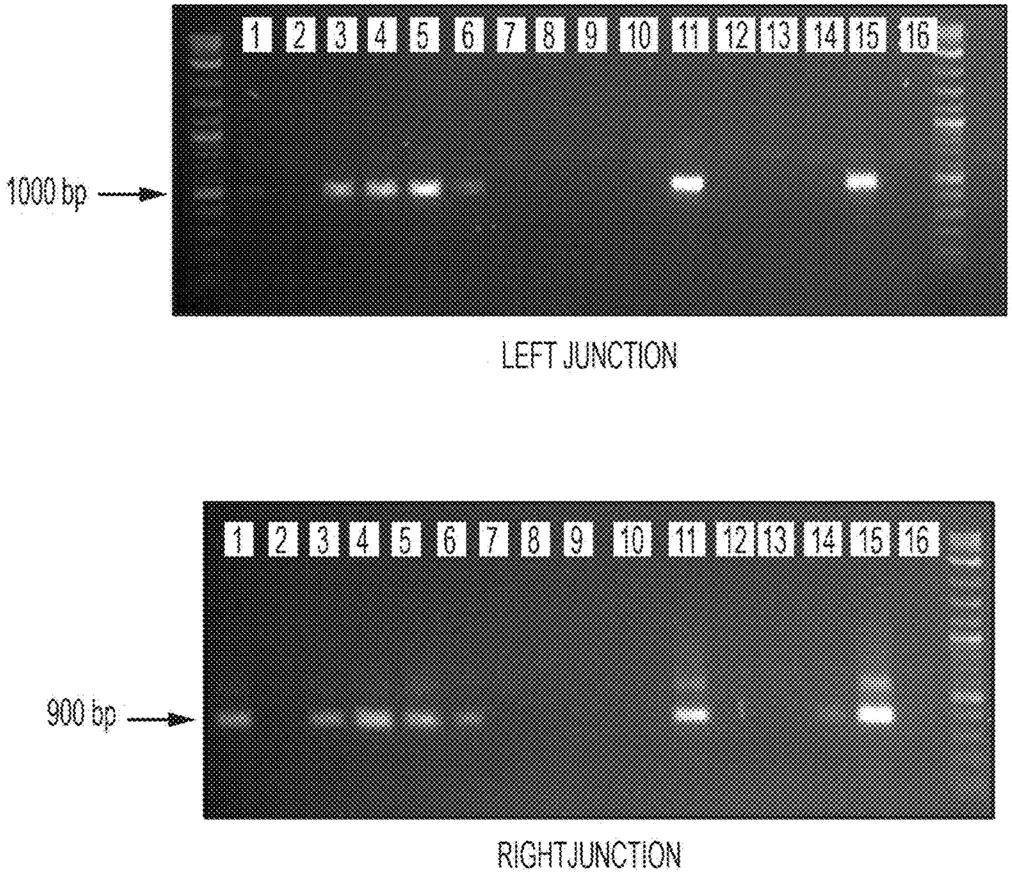
FIG. 5 shows the recovery of recombinant NanoLuc® T7 phages that contain a second insertion of the NanoLuc® reporter gene using the BAR 4.0 method disclosed herein. Isolated plaques were selected and screened for NanoLuc® insertion within the T7 genome at the NheI restriction site via PCR. A PCR product of approximately 1 kb correlated with the successful insertion of the NanoLuc® reporter gene within the T7 genome at the NheI restriction site.
Figure 7:
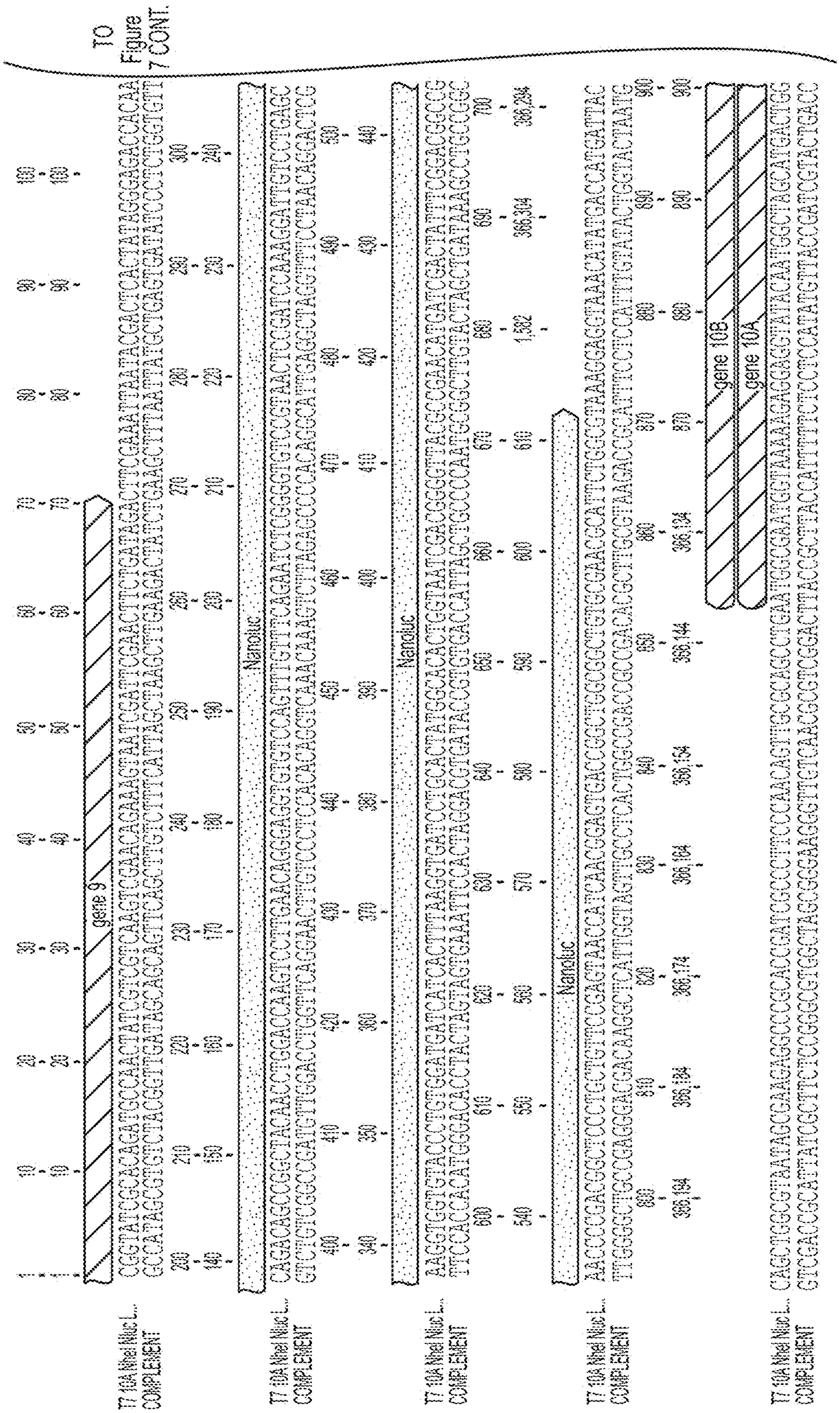
FIG. 7 shows a schematic of the NanoLuc® insertion into the T7 genome at the NheI restriction site.
Figure 7:
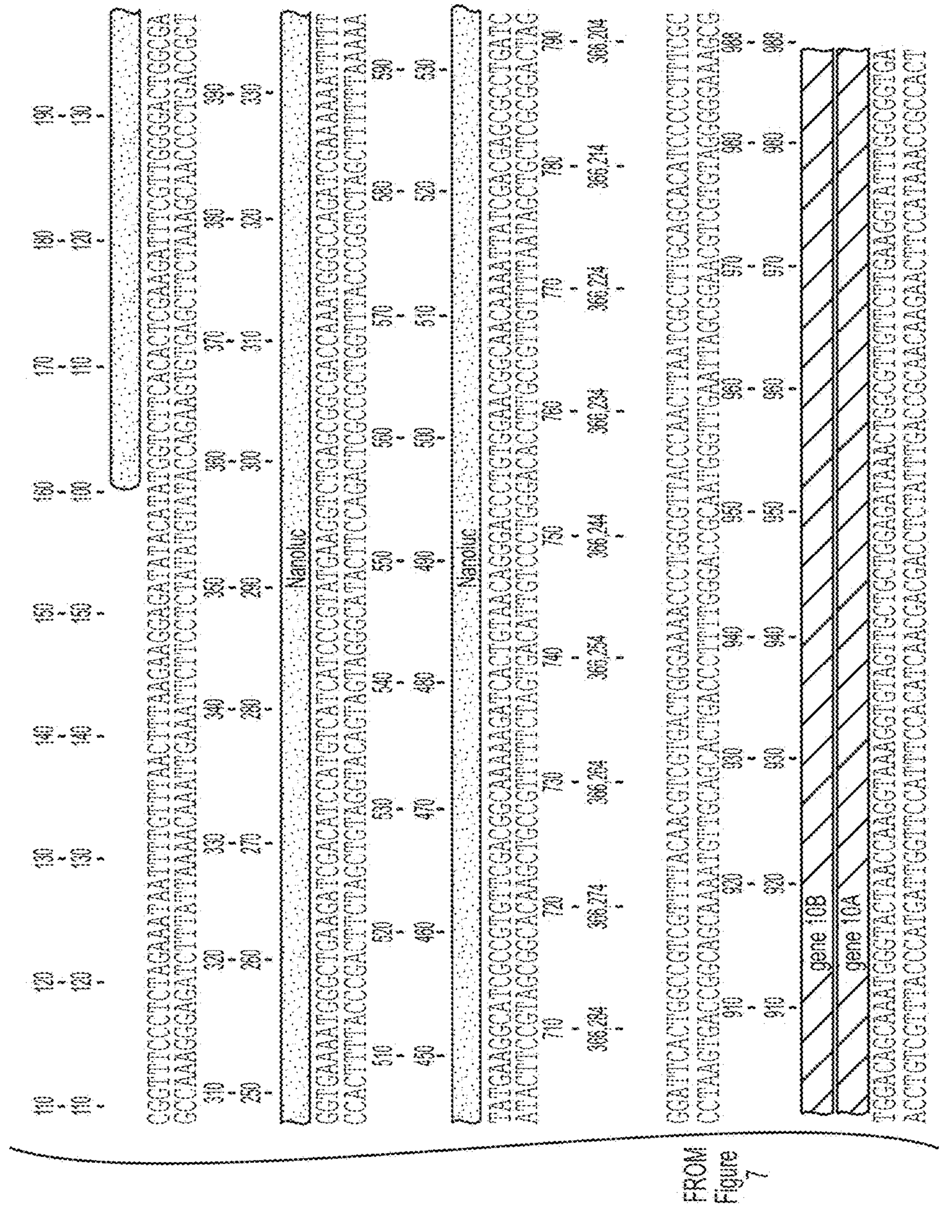

After a recombinant T7 phage with a single NanoLuc® insertion at the SwaI site (see FIG. 4) was isolated, a second NanoLuc® insertion was made at the NheI restriction site (NEB R0131) (New England Biolabs, Ipswich, Mass.) using the cloning protocol outlined above. After incubation at 37° C. overnight, isolated plaques were selected and screened for the second NanoLuc® insertion via PCR using primers that flanked the second NanoLuc® insertion site (i.e., spanned the junction between NanoLuc® and phage genomic DNA). A PCR product of approximately 1 kb correlated with the successful insertion of the NanoLuc® reporter gene within the T7 genome at the NheI restriction site. See FIG. 5 and FIG. 7. Thus, the overall yield of recombinant T7 phage genomes obtained using the BAR 4.0 technique was about 44% to about 69%.

Figure 6:
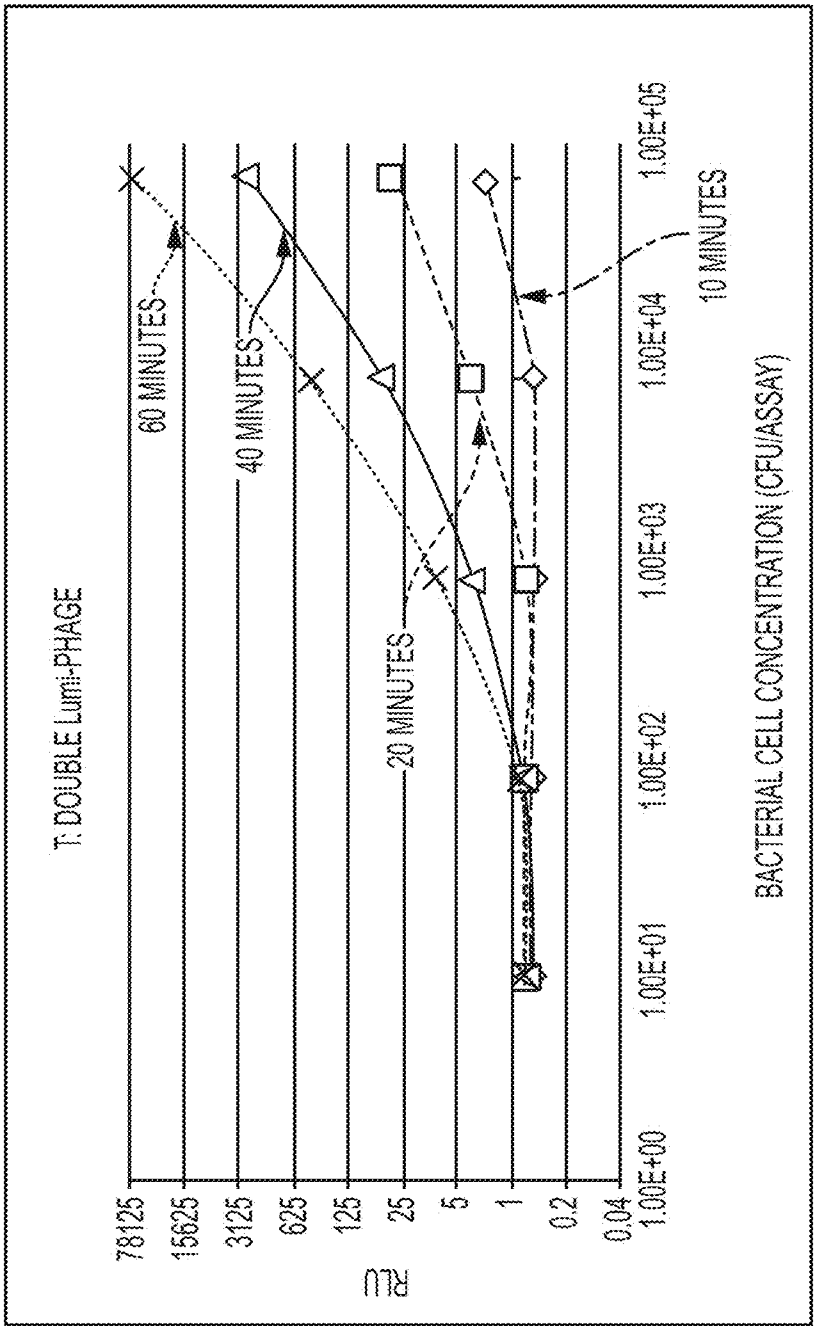
FIG. 6 shows the luminescence activity profile of the DLPECO2 phage strain, which contains a double insertion of the NanoLuc® reporter gene.
Figure 8:
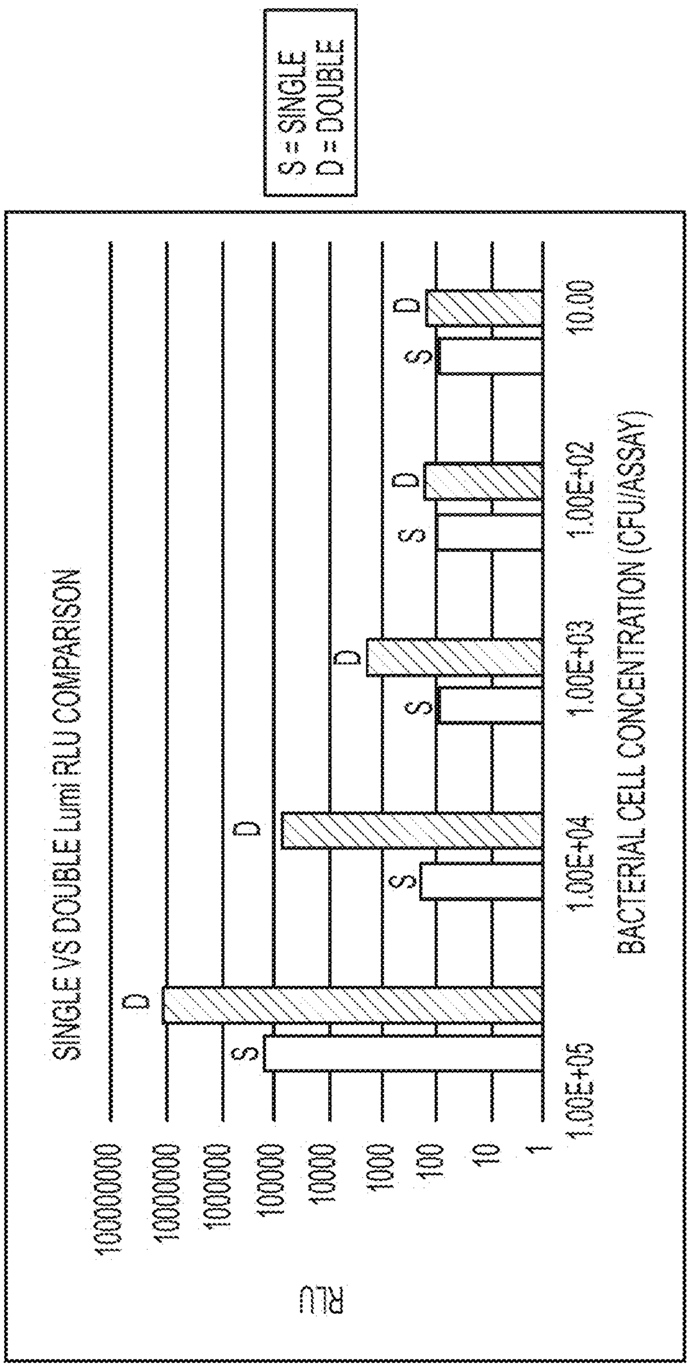
FIG. 8 shows a comparison of the relative luminescence units (RLU) between the DLPECO1 (S) and the DLPECO2 (D) phage strains. Phage infection at different bacterial host cell concentrations was carried out for 60 minutes before measuring luminescence. The DLPECO2 phage strain exhibited increases in both luminescence levels and sensitivity relative to that observed with the DLPECO1 phage strain.

NanoLuc® production was evaluated by infecting bacterial host cells with recombinant phage strain DLPECO2 and measuring luminescence between 10-60 minutes at different bacterial host cell concentrations. FIG. 6 demonstrates that the intensity of the NanoLuc® signal produced by a recombinant T7 phage strain containing a double NanoLuc® insertion was dependent on bacterial cell concentration and time. FIG. 8 demonstrates that the recombinant T7 phage strain containing a double NanoLuc® insertion exhibited significantly higher luminescence, along with significantly increased sensitivity relative to that observed with the recombinant T7 phage strain containing a single NanoLuc® insertion.

Figure 9:
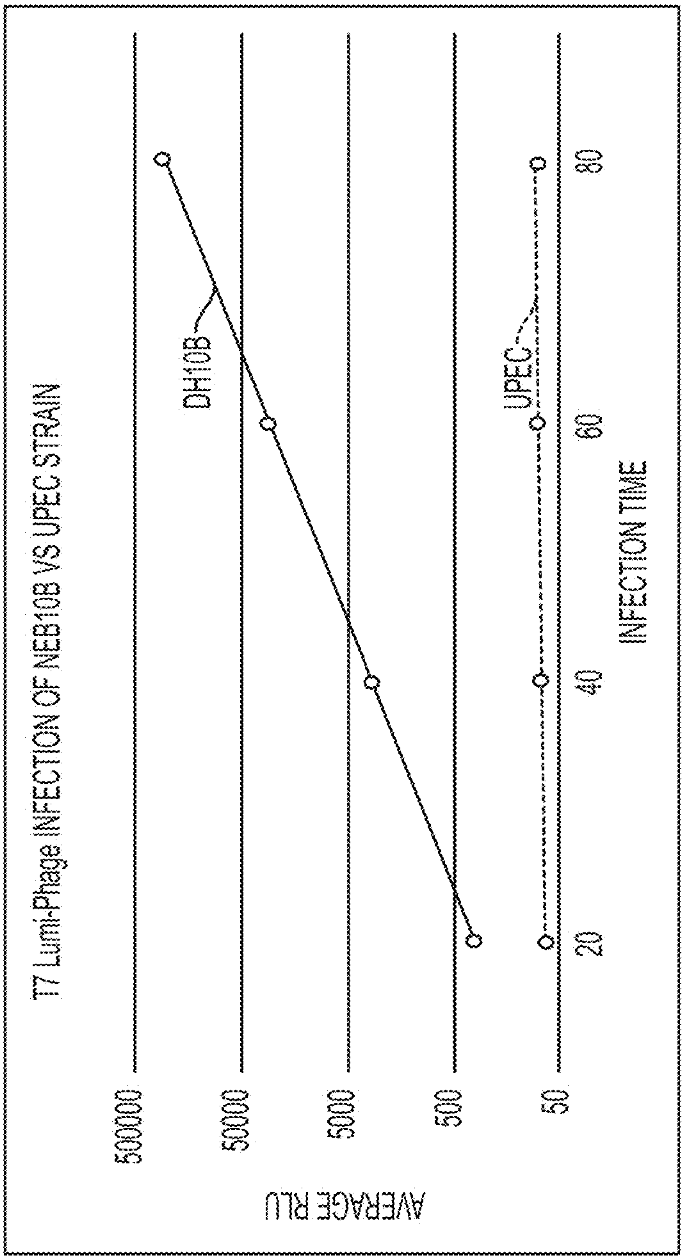
FIG. 9 shows the specific host range of the recombinant NanoLuc® T7 phages that contain a double insertion of the NanoLuc® reporter gene.

To ensure that NanoLuc® production was specific to a bacterial host cell that could be infected by T7 phage, DH10B cells (which are the normal T7 host) were infected in parallel with the uropathogenic *E. coli* strain UPEC, which cannot be infected by T7. FIG. 9 shows that luminescence was detected in the infected DH10B cells, whereas no luminescence was detected in UPEC.

TABLE 1

| Strain Name | Phage Type | Phage Family | Heterologous reporter | Host Range | Modifications to Phage Genomes |
|---|---|---|---|---|---|
| DLPECO1 | T7 | Podoviridae | Nanoluciferase | K12 *E. coli* | SwaI insertion contains lacZ alpha fragment with ribosomal binding site |
| DLPECO2 | T7 | Podoviridae | Nanoluciferase | K12 *E. coli* | NheI insertion into DLPECO1 |

These results demonstrate that the methods of the present technology generate recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for generating recombinant bacteriophage genomes.

Example 2: BAR 3.0 Phage Engineering Methods of the Present Technology in K1-5 Phage This Example demonstrates that the BAR 3.0 methods of the present technology are useful for integrating a heterologous nucleic acid into a bacteriophage genome (e.g., K1-5 phage genome) and for isolating recombinant bacteriophages that express the heterologous nucleic acid sequence.

K1-5 phage is a 44,385 bp, terminally redundant, lytic bacteriophage that infects numerous strain of *E. coli* with either the K1 or K5 capsule type. The NanoLuc® luciferase gene (with an upstream ribosome binding site (RBS)) was inserted towards the 3' end of the K1-5 genome using the BAR 3.0 methods disclosed herein. The intended genomic insertion site for the NanoLuc® reporter was between nucleotide positions 43,913 and 43,914. A sgRNA-Cas9 conjugate that targets the protospacer sequence 5' GCTTACGCAGAAGATGCAGA 3' (SEQ ID NO: 5) was designed so as to induce cleavage between nucleotide positions 43,898 and 43,899 of the K1-5 genome. The RBS/NanoLuc® cassette also contained the nucleic acid sequence present at the 3' end of K1-5 genome that would be excised by the sgRNA-Cas9 conjugate. Thus, the heterologous nucleic acid insert comprised: 5' (nucleotide positions 43,872 to 43,913 of K1-5 genome)+(RBS)+(NanoLuc®)+(nucleotide positions 43,914 to 44,385 of K1-5 genome) 3'. FIG. 15 shows the heterologous nucleic acid sequence that was inserted into K1-5 phage using the BAR 3.0 method disclosed herein (SEQ ID NO: 3). FIG. 16 shows the complete genome sequence of the recombinant NanoLuc® K1-5 phage. (SEQ ID NO: 4).

To generate the sgRNA, a target specific DNA oligonucleotide was synthesized and used as a template for the EnGen® sgRNA Synthesis Kit, *S. pyogenes* (New England Biolabs, Ipswich, Mass.). The target specific DNA oligonucleotide contains the T7 promoter sequence, the target protospacer sequence, and a 14 nucleotide overlap sequence complementary to the *S. pyogenes* Cas9 Scaffold Oligo supplied in the EnGen® sgRNA reaction mix. The target specific DNA oligonucleotide was mixed with the EnGen 2× sgRNA Reaction Mix (NTPs, dNTPs, *S. pyogenes* Cas9 Scaffold Oligo) and the EnGen sgRNA Enzyme Mix (DNA and RNA polymerases) at room temperature. The DNA synthesis and transcription reactions occurred at 37° C. during a 30 minute incubation period. The resulting sgRNA contained the target-specific/crRNA sequence as well as the tracrRNA. DNA contaminants were subsequently removed with DNase I treatment and the sgRNA was purified with an RNA cleanup kit.

*S. pyogenes* Cas9 nuclease (New England Biolabs, Ipswich, Mass.) was co-incubated with the purified sgRNA according to the supplier's protocol, and was subsequently used to cleave approximately 2.4 μg of purified K1-5 genomic DNA. Cleaved K1-5 genomic DNA was purified using phenol: chloroform: isoamyl alcohol extraction, followed by ethanol precipitation.

Approximately 2 μg of cleaved K1-5 genomic DNA and 200 ng of the insert DNA were combined in a Gibson assembly reaction using NEBuilder® HiFi DNA Assembly Cloning Kit (New England Biolabs, Ipswich, Mass.). The reaction occurred at 50° C. for 1 hour, and was subsequently purified using phenol: chloroform: isoamyl alcohol extraction, followed by ethanol precipitation.

Approximately 440 ng of total DNA from this purified reaction was transformed into NEB® 10-beta Electrocompetent *E. coli* (New England Biolabs, Ipswich, Mass.), a non-natural bacterial host, via electroporation (2.4 kV, 600Ω, 25 μF) and was recovered in 950 μl of SOC medium (2% tryptone, 0.5% yeast extract, 10 mM NaCl, 2.5 mM KCl, 10 mM $MgCl_2$, 10 mM $MgSO_4$, and 20 mM glucose) for approximately 2 hours at 37° C. The transformation reaction was centrifuged such that the supernatant (containing phage particles) could be used to infect a native host. About 100 μl of the supernatant was used to infect 100 μl of K5 *E. coli*. The infection was plated in 3 mL of 0.65% LB top agar and incubated at 37° C. overnight to allow plaque development.

Phenotypic Analysis.

Figure 12:
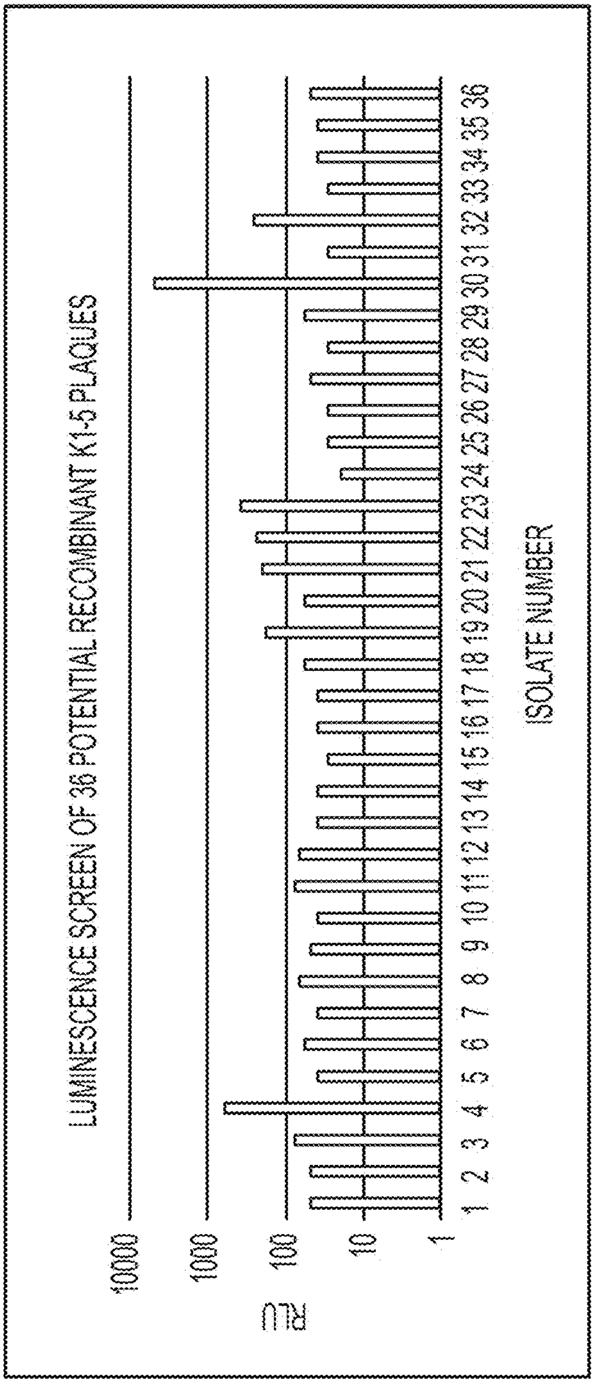
FIG. 12 shows the luminescence activity profile of 36 resulting plaques that were isolated after subjecting the non-recombinant bacteriophage K1-5 to the BAR 3.0 method disclosed herein.
Figure 13:
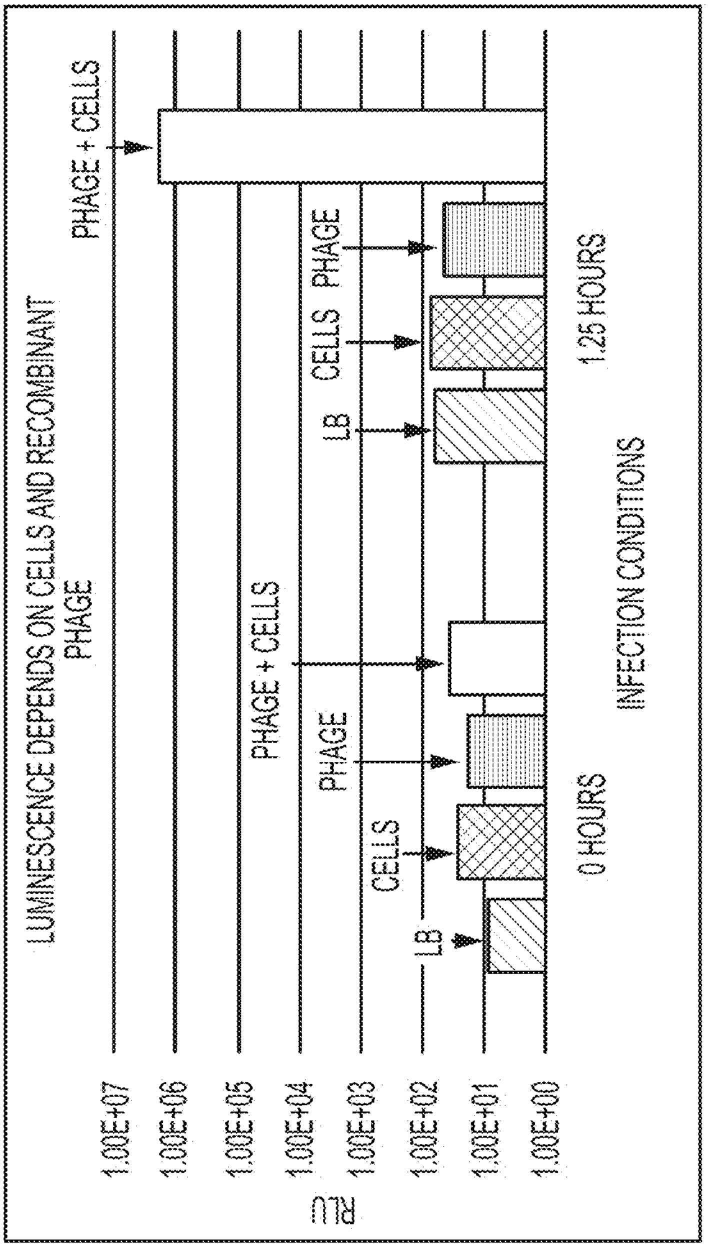
FIG. 13 shows that K5 *E. coli* infected with bacteriophage derived from isolate #30 exhibit a high degree of luminescence.

Hundreds of plaques were observed after overnight incubation. A total of 36 plaques were picked into 20 μL 10 mM Tris-HCl+10 mM $MgSO_4$. These isolates were used to infect 100 μL of log-phase K5 *E. coli* for approximately 1 hour in the presence of $MgSO_4$. FIG. 12 shows that the RLU generated by isolate #30 was several times higher than any other isolate. Isolate #30 was further analyzed by infecting larger K5 *E. coli* cultures with isolate #30 for a longer duration to determine if the high RLU value was actually indicative of a recombinant phage or merely a technical error. The remainder of the isolate #30 infection was used to re-infect 5 mL cultures of log-phase K5 *E. coli*. FIG. 13 shows that only the sample containing both bacterial cells and phage (derived from isolate #30) produced higher RLUs relative to samples that only contained phage or bacterial cells after 1.25 hours. The overall yield of recombinant K1-5 phage genomes obtained using the BAR 3.0 technique was about 2.78%. Thus, FIG. 13 demonstrates that the BAR 3.0 methods disclosed herein yielded recombinant NanoLuc® K1-5 phage genomes.

Genotypic Analysis.

Figure 14:
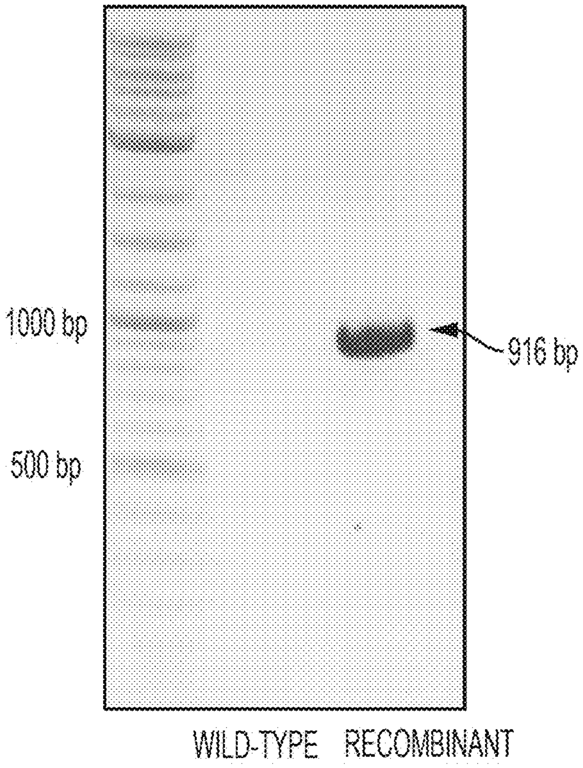
FIG. 14 shows that a recombinant junction is present in a putative recombinant K1-5 phage, but not in wild-type K1-5 phage. A PCR product of approximately 916 bp correlated with the successful insertion of the NanoLuc® reporter gene.

The isolate #30 plaque was used as a template for PCR to screen for the presence of a recombinant junction spanning from inside the NanoLuc® reporter insert to the phage genome. FIG. 14 shows that a recombinant junction was detected in the recombinant K1-5 phage derived from isolate #30, but not in wild-type K1-5 phage. A PCR product of approximately 916 bp correlated with the successful insertion of the NanoLuc® reporter gene. Thus, FIG. 14 demonstrates that the BAR 3.0 methods disclosed herein yielded recombinant NanoLuc® K1-5 phage genomes.

These results demonstrate that the methods of the present technology generate recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for generating recombinant bacteriophage genomes.

Example 3: BREDner Phage Engineering Methods of the Present Technology

This Example demonstrates that the BREDner methods of the present technology are useful for generating recombinant bacteriophage genomes.

The BREDner protocol takes advantage of the increased homologous recombination rate conferred by the λ Red recombinase system of the pKD46 plasmid (GenBank Acc. No.: AY048746.1). The expression of λ Red recombinase genes (gam-bet-exo) are operably linked to the araB promoter. Bacterial host cells are transformed with the pKD46 plasmid and a second plasmid that comprises a nanoluciferase sequence (e.g., NanoLuc®) that is flanked on both sides by 100-500 bp of homologous phage sequence. The homologous recombination system is induced in the transformed bacterial host cells that contain the pKD46 plasmid and the second plasmid by adding 10 mM arabinose.

After growing the bacterial host cells containing both pKD46 and the second plasmid to mid-log phase in the presence of arabinose, cells are washed and concentrated 100× in 1M sorbitol for use in electroporation. Approximately 100 ng of phage DNA is electroporated into the bacterial host cells containing both pKD46 and the second plasmid. The electroporated cells are then allowed to recover for 1 hour before plating in 0.65% top agar containing the corresponding phage host strain. Plates are incubated overnight and the resulting plaques are screened by PCR, or for NanoLuc® production to select for recombinant luminescent phages.

These results will demonstrate that the methods of the present technology generate recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for generating recombinant bacteriophage genomes.

Example 4: BARner Phage Engineering Methods of the Present Technology

This Example demonstrates that the BARner methods of the present technology are useful for generating recombinant bacteriophage genomes.

The BARner protocol is a modification of the BREDner protocol which uses a restriction enzyme to introduce a double strand break in the phage DNA surrounding the desired insertion site for a heterologous nucleic acid sequence of interest.

The BARner protocol takes advantage of the increased homologous recombination rate conferred by the λ Red recombinase system of the pKD46 plasmid (GenBank Acc. No.: AY048746.1). The expression of the λ Red recombinase genes (gam-bet-exo) is operably linked to the araB promoter. Bacterial host cells are transformed with the pKD46 plasmid and a second plasmid that comprises a nanoluciferase sequence (e.g., NanoLuc®) that is flanked on both sides by 100-500 bp of homologous phage sequence. The homologous recombination system is induced in the transformed bacterial host cells that contain the pKD46 plasmid and the second plasmid by adding 10 mM arabinose. After growing the bacterial host cells containing both pKD46 and the second plasmid to mid-log phase in the presence of arabinose, the cells are washed and concentrated 100× in 1M sorbitol. Approximately 100 ng of phage DNA is cleaved with the appropriate restriction enzyme and purified using phenol/chloroform before being electroporated into the cells. Electroporated cells are recovered for one hour and plated on 0.65% top agar containing the appropriate host strain. Plates are incubated overnight and the resulting plaques are screened by PCR, or for NanoLuc® production to select for recombinant luminescent phages.

These results will demonstrate that the methods of the present technology generate recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for generating recombinant bacteriophage genomes.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for generating a recombinant bacteriophage genome comprising:

(a) contacting a first bacteriophage genome comprising a unique first recognition site with a first restriction enzyme in vitro under conditions where the first restriction enzyme cleaves the first recognition site to produce a cleaved first bacteriophage genome; and (b) recombining in vitro the cleaved first bacteriophage genome with a heterologous nucleic acid in the presence of a recombination system under conditions to produce a recombinant bacteriophage genome, wherein the cleaved first bacteriophage genome comprises a first cleaved bacteriophage genomic fragment and a second cleaved bacteriophage genomic fragment, wherein the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment, and wherein the homologous 5 ‘ flanking region of the heterologous nucleic acid, and the homologous 3’ flanking region of the heterologous nucleic acid, each has a length of 20-70 base pairs (bps);

wherein the heterologous nucleic acid encodes a non-endogenous protein; and wherein the recombinant bacteriophage genome is capable of producing non-endogenous protein that is functionally active when transformed into a bacterial host cell.

2. The method of claim 1, wherein the first bacteriophage genome corresponds to *E. coli* T7.

3. The method of claim 1, further comprising propagating the recombinant bacteriophage genome in a bacterial host cell.

4. The method of claim 3, wherein the bacterial host cell is a natural host of a bacteriophage comprising the first bacteriophage genome.

5. The method of claim 1, wherein the first restriction enzyme is SwaI.

6. The method of claim 1, wherein the first restriction enzyme is NheI.

7. The method of claim 1, wherein the heterologous nucleic acid is about 500-1050 base pairs in length.

8. The method of claim 1, wherein the recombination system comprises a 5'-3' exonuclease, a DNA polymerase, and a DNA ligase.

9. The method of claim 1, wherein the heterologous nucleic acid comprises an open reading frame that encodes a bioluminescent protein, a fluorescent protein, a chemiluminescent protein, or any combination thereof.

10. The method of claim 9, wherein the open reading frame of the heterologous nucleic acid is operably linked to an expression control sequence that is capable of directing expression of the bioluminescent protein, the fluorescent protein, the chemiluminescent protein, or any combination thereof.

11. The method of claim 9, wherein the bioluminescent protein is Aequorin, firefly luciferase, *Renilla* luciferase, red luciferase, luxAB, or nanoluciferase.

12. The method of claim 9, wherein the chemiluminescent protein is β-galactosidase, horseradish peroxidase (HRP), or alkaline phosphatase.

13. The method of claim 9, wherein the fluorescent protein is TagBFP, Azurite, EBFP2, mKalamal, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherryl, PATagRFP, Kaede (green), Kaede (red), KikGR1 (green), KikGR1 (red), PS-CFP2, PS-CFP2, mEos2 (green), mEos2 (red), PSmOrange, or Dronpa.

14. The method of claim 10, wherein the expression control sequence is an inducible promoter or a constitutive promoter.

15. The method of claim 1, wherein the nucleic acid sequence of the recombinant bacteriophage genome comprises SEQ ID NO: 2.

16. The method of claim 1, wherein the nucleic acid sequence of the recombinant bacteriophage genome comprises SEQ ID NO: 1.

17. The method of claim 1, wherein the nucleic acid sequence of the recombinant bacteriophage genome comprises one or more of SEQ ID NO: 6 or SEQ ID NO: 7.

* * * * *